United States Patent
Gray et al.

(10) Patent No.: US 10,787,461 B2
(45) Date of Patent: Sep. 29, 2020

(54) PYRIMIDO-DIAZEPINONE COMPOUNDS AND METHODS OF TREATING DISORDERS

(71) Applicant: DANA-FARBER CANCER INSTITUTE, INC., Boston, MA (US)

(72) Inventors: Nathanael S. Gray, Boston, MA (US); David Waller, Somerville, MA (US); Hwan Guen Choi, Seoul (KR); Jinhua Wang, Boston, MA (US); Xianming Deng, Brookline, MA (US)

(73) Assignee: Dana-Farber Cancer Institute, Inc., Boston, MA (US)

(*) Notice: Subject to any disclaimer, the term of this patent is extended or adjusted under 35 U.S.C. 154(b) by 0 days.

(21) Appl. No.: 16/570,490

(22) Filed: Sep. 13, 2019

(65) Prior Publication Data

US 2020/0071340 A1 Mar. 5, 2020

Related U.S. Application Data

(60) Continuation of application No. 16/195,983, filed on Nov. 20, 2018, now Pat. No. 10,457,692, which is a continuation of application No. 15/581,702, filed on Apr. 28, 2017, now Pat. No. 10,189,861, which is a division of application No. 14/775,897, filed as application No. PCT/US2014/030760 on Mar. 17, 2014, now Pat. No. 9,676,792.

(60) Provisional application No. 61/802,075.

(51) Int. Cl.
| | |
|---|---|
| *C07D 401/14* | (2006.01) |
| *C07D 403/12* | (2006.01) |
| *C07D 403/14* | (2006.01) |
| *C07D 405/14* | (2006.01) |
| *C07D 513/04* | (2006.01) |
| *C07D 487/14* | (2006.01) |
| *C07D 471/18* | (2006.01) |
| *C07D 487/16* | (2006.01) |
| *C07D 495/14* | (2006.01) |
| *C07D 498/04* | (2006.01) |
| *C07D 498/18* | (2006.01) |
| *C07F 5/02* | (2006.01) |
| *C07D 487/12* | (2006.01) |
| *C07D 487/04* | (2006.01) |
| *C07D 487/18* | (2006.01) |

(52) U.S. Cl.
CPC ......... *C07D 513/04* (2013.01); *C07D 471/18* (2013.01); *C07D 487/04* (2013.01); *C07D 487/12* (2013.01); *C07D 487/14* (2013.01); *C07D 487/16* (2013.01); *C07D 487/18* (2013.01); *C07D 495/14* (2013.01); *C07D 498/04* (2013.01); *C07D 498/18* (2013.01); *C07F 5/022* (2013.01)

(58) Field of Classification Search
CPC .. C07D 401/14; C07D 403/12; C07D 403/14; C07D 405/14
See application file for complete search history.

(56) References Cited

FOREIGN PATENT DOCUMENTS

| | | |
|---|---|---|
| WO | 20007095188 A2 | 8/2007 |
| WO | 2008113711 | 9/2008 |
| WO | 2009040556 | 4/2009 |
| WO | 2010080712 | 7/2010 |
| WO | 2013144632 | 10/2013 |

OTHER PUBLICATIONS

Deng, et al., "Discovery of a benzo[e]pyrimido-[5,4-b][1,4]diazepin-6(11H0-one as a Potent and Selective Inhibitor of Big MAP Kinase 1", Medicinal Chemistry Letters, 2(3): 195-200 (2011).
Deng, et al., Xianming, "Structural Determinants for ERK5 (MAPK7) and Leucine Rich Repeat Kinase 2 Activities of benzo[e]pyrimido-[5,4-b]diazepine-6(11H)-ones", European Journal of Medicinal Chemistry, vol. 70, pp. 758-767, XP028794198 (P-document), (2011).
Elkins, et al., Jonathan M., "X-Ray Crystal Structure of ERK5 (MAP7) in Complex with a Specific Inhibitor", Journal of Medicinal Chemistry, vol. 56, No. 11, Jun. 13, 2013 (Jun. 13, 2013), pp. 4413-4421, XP055282012 (P-document).
Kwiatkowski, et al., "Selective Aurora Kinase Inhibitors Identified Using a Taxol-Induced Checkpoint Sensitivity Screen", Chemical Biology. 7(1): 185-196 (2012).
Miduturu, et al., "High-Throughput Kinase Profiling: A More Efficient Approach Towards the Discovery of New Kinase Inhibitors", Chemistry & Biology, 18(7): 868-879 (2011).
Tandon, M. et al. "Emerging Strategies for EPHA2 Receptor Targeting for Cancer Therapeutics", Expert Opin. Ther. Targets, 2001, vol. 15, No. 1, pp. 31-51.

*Primary Examiner* — Bruck Kifle
(74) *Attorney, Agent, or Firm* — Burns & Levinson, LLP; Daniel W. Clarke

(57) ABSTRACT

The present invention relates to novel pyrimido-diazepinone compounds, methods of modulating protein kinases, including MPS1 (TTK), ERK5 (BMK1, MAPK7), LRKK2, EphA2, polo kinase 1, 2, 3, or 4, Ack1, Ack2, Abl, DCAMKL1, ABL1, Abl mutants, DCAMKL2, ARK5, BRK, MKNK2, FGFR4, TNK1, PLK1, ULK2, PLK4, PRKD1, PRKD2, PRKD3, ROS1, RPS6KA6, TAOK1, TAOK3, TNK2, Bcr-Abl, GAK, cSrc, TPR-Met, Tie2, MET, FGFR3, Aurora, Axl, Bmx, BTK, c-kit, CHK2, Flt3, MST2, p70S6K, PDGFR, PKB, PKC, Raf, ROCK-H, Rsk1, SGK, TrkA, TrkB and TrkC, and the use of such compounds in the treatment of various diseases, disorders or conditions.

12 Claims, 4 Drawing Sheets

PYRIMIDO-DIAZEPINONE COMPOUNDS AND METHODS OF TREATING DISORDERS

RELATED APPLICATIONS

This application is a continuation application of U.S. application Ser. No. 16/195,983, filed Nov. 20, 2018, which is a continuation application of U.S. application Ser. No. 15/581,702, filed Apr. 28, 2017 (now U.S. Pat. No. 10,189,861, issued Jan. 29, 2019), which is a divisional application of U.S. application Ser. No. 14/775,897, filed Sep. 14, 2015, (now U.S. Pat. No. 9,676,792, issued Jun. 13, 2017), which is a national stage application, filed under 35 U.S.C. § 371 of International Application No. PCT/US2014/030760, filed on Mar. 17, 2014, which claims the benefit of and priority to U.S. Provisional Application No. 61/802,075, filed Mar. 15, 2013, the contents of which are incorporated herein by reference in their entireties.

GOVERNMENT SUPPORT

This invention was made with government support under Grant No. GM079575, CA079871, and CA114059 awarded by the National Institutes of Health. The government has certain rights in the invention.

TECHNICAL FIELD

The present invention relates to novel pyrimido-diazepinone compounds which are able to modulate protein kinases, including MPS1 (TTK), ERK5 (BMK1, MAPK7), polo kinase 1, 2, 3, or 4, Ack1, Ack2, Abl, DCAMKL1, ABL1, Abl mutants, DCAMKL2, ARK5, BRK, MKNK2, FGFR4, TNK1, PLK1, ULK2, PLK4, PRKD1, PRKD2, PRKD3, ROS1, RPS6KA6, TAOK1, TAOK3, TNK2, Bcr-Abl, GAK, cSrc, TPR-Met, Tie2, MET, FGFR3, Aurora, Axl, Bmx, BTK, c-kit, CHK2, Flt3, MST2, p70S6K, PDGFR, PKB, PKC, Raf, ROCK-H, Rsk1, SGK, TrkA, TrkB and TrkC, and the use of such compounds in the treatment of various diseases, disorders or conditions.

BACKGROUND OF THE INVENTION

Protein kinases represent a large family of proteins, which play a central role in the regulation of a wide variety of cellular processes and maintaining control over cellular function. Protein kinases constitute a large family of structurally related enzymes that are responsible for the control of a variety of signal transduction processes within the cell (see Hardie, G and Hanks, S. The Protein Kinase Facts Book, I and II, Academic Press, San Diego, Calif.: 1995). Protein kinases are thought to have evolved from a common ancestral gene due to the conservation of their structure and catalytic function. Almost all kinases contain a similar 250-300 amino acid catalytic domain. The kinases may be categorized into families by the substrates they phosphorylate (e.g., protein-tyrosine, protein-serine/threonine, lipids etc).

In general, protein kinases mediate intracellular signaling by catalyzing a phosphoryl transfer from a nucleoside triphosphate to a protein acceptor that is involved in a signaling pathway. These phosphorylation events act as molecular on/off switches that can modulate or regulate the target protein biological function. These phosphorylation events are ultimately triggered in response to a variety of extracellular and other stimuli. Examples of such stimuli include environmental and chemical stress signals (e.g., shock, heat shock, ultraviolet radiation, bacterial endotoxin, and H2O2), cytokines (e.g., interleukin-1 (IL-I) and tumor necrosis factor alpha (TNF-a), and growth factors (e.g., granulocyte macrophage-colony stimulating factor (GM-CSF), and fibroblast growth factor (FGF)). An extracellular stimulus may affect one or more cellular responses related to cell growth, migration, differentiation, secretion of hormones, activation of transcription factors, muscle contraction, glucose metabolism, control of protein synthesis, survival and regulation of the cell cycle.

A partial, non-limiting, list of these kinases include: receptor tyrosine kinases such as platelet-derived growth factor receptor kinase (PDGF-R), the nerve growth factor receptor, Trk-A, -B and -C, and the fibroblast growth factor receptor, FGFR3; non-receptor tyrosine kinases such Abl and the fusion kinase BCR-Abl, Lck, Csk, Fes, BTK, Bmx and c-src; and serine/threonine kinases such as Aurora, c-RAF, SGK, MAP kinases (e.g., MKK4, MKK6, etc.) and SAPK2α and SAPK2β. Aberrant kinase activity has been observed in many disease states including benign and malignant proliferative disorders as well as diseases resulting from inappropriate activation of the immune and nervous systems.

The novel compounds of this invention inhibit the activity of one or more protein kinases and are, therefore, expected to be useful in the treatment of kinase-associated diseases.

SUMMARY OF THE INVENTION

In one aspect, the invention provides a compound of formula I:

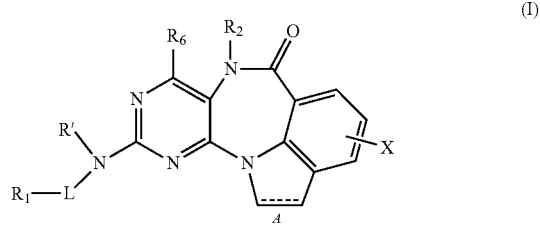

or a pharmaceutically acceptable salt, ester or prodrug thereof,
wherein,
A is a single bond or double bond;
R' is H or alkyl;
L is absent, S, SO, $SO_2$, or CO;
X is an optional substituent (for example, halogen, —OH, —$NO_2$, —CN, —$NH_2$, protected amino, —NH—$C_1$-$C_{12}$-alkyl, —NH—$C_2$-$C_{12}$-alkenyl, —NH—$C_2$-$C_{12}$-alkenyl, —NH—$C_3$-$C_{12}$-cycloalkyl, —NH-aryl, —NH-heteroaryl, —NH-heterocycloalkyl, -dialkylamino, -diarylamino, -diheteroarylamino, —O—$C_1$-$C_{12}$-alkyl, —O—$C_2$-$C_{12}$-alkenyl, —O—$C_2$-$C_{12}$-alkenyl, —O—$C_3$-$C_{12}$-cycloalkyl, —O-aryl, —O-heteroaryl, —O-heterocycloalkyl, —C(O)—$C_1$-$C_{12}$-alkyl, —C(O)—$C_2$-$C_{12}$-alkenyl, —C(O)—$C_2$-$C_{12}$-alkenyl, —C(O)—$C_3$-$C_{12}$-cycloalkyl, —C(O)-aryl, —C(O)-heteroaryl, —C(O)-heterocycloalkyl, —$CONH_2$, —CONH—$C_1$-$C_{12}$-alkyl, —CONH—$C_2$-$C_{12}$-alkenyl, —CONH—$C_2$-$C_{12}$-alkenyl, —CONH—$C_3$-$C_{12}$-cycloalkyl, —CONH-aryl, —CONH-heteroaryl, —CONH-heterocycloalkyl, —$OCO_2$—$C_1$-$C_{12}$-alkyl, —$OCO_2$—$C_2$-$C_{12}$-alkenyl, —$OCO_2$—$C_2$-$C_{12}$-alkenyl, —$OCO_2$—$C_3$-$C_{12}$-cycloalkyl, —$OCO_2$-aryl, —$OCO_2$-heteroaryl, —$OCO_2$- heterocycloalkyl, —OCONH₂, —OCONH—C₁-C₁₂-alkyl, —OCONH—C₂-C₁₂-alkenyl, —OCONH—C₂-C₁₂-alkenyl, —OCONH—C₃-C₁₂-cycloalkyl, —OCONH-aryl, —OCONH-heteroaryl, —OCONH-heterocycloalkyl, —NHC(O)—C₁-C₁₂-alkyl, —NHC(O)—C₂-C₁₂-alkenyl, —NHC(O)—C₂-C₁₂-alkenyl, —NHC(O)—C₃-C₁₂-cycloalkyl, —NHC(O)-aryl, —NHC(O)-heteroaryl, —NHC(O)-heterocycloalkyl, —NHCO₂—C₁-C₁₂-alkyl, —NHCO₂—C₂-C₁₂-alkenyl, —NHCO₂—C₂-C₁₂-alkenyl, —NHCO₂—C₃-C₁₂-cycloalkyl, —NHCO₂-aryl, —NHCO₂-heteroaryl, —NHCO₂-heterocycloalkyl, —NHC(O)NH₂, —NHC(O)NH—C₁-C₁₂-alkyl, —NHC(O)NH—C₂-C₁₂-alkenyl, —NHC(O)NH—C₂-C₁₂-alkenyl, —NHC(O)NH—C₃-C₁₂-cycloalkyl, —NHC(O)NH-aryl, —NHC(O)NH-heteroaryl, —NHC(O)NH-heterocycloalkyl, NHC(S)NH₂, —NHC(S)NH—C₁-C₁₂-alkyl, —NHC(S)NH—C₂-C₁₂-alkenyl, —NHC(S)NH—C₂-C₁₂-alkenyl, —NHC(S)NH—C₃-C₁₂-cycloalkyl, —NHC(S)NH-aryl, —NHC(S)NH-heteroaryl, —NHC(S)NH-heterocycloalkyl, —NHC(NH)NH₂, —NHC(NH)NH—C₁-C₁₂-alkyl, —NHC(NH)NH—C₂-C₁₂-alkenyl, —NHC(NH)NH—C₂-C₁₂-alkenyl, —NHC(NH)NH—C₃-C₁₂-cycloalkyl, —NHC(NH)NH-aryl, —NHC(NH)NH-heteroaryl, —NHC(NH)NH-heterocycloalkyl, —NHC(NH)—C₁-C₁₂-alkyl, —NHC(NH)—C₂-C₁₂-alkenyl, —NHC(NH)—C₂-C₁₂-alkenyl, —NHC(NH)—C₃-C₁₂-cycloalkyl, —NHC(NH)-aryl, —NHC(NH)-heteroaryl, —NHC(NH)-heterocyclalkyl, —C(NH)NH—C₁-C₁₂-alkyl, —C(NH)NH—C₂-C₁₂-alkenyl, —C(NH)NH—C₂-C₁₂-alkenyl, —C(NH)NH—C₃-C₁₂-cycloalkyl, —C(NH)NH-aryl, —C(NH)NH-heteroaryl, —C(NH)NH-heterocycloalkyl, —S(O)—C₁-C₁₂-alkyl, —S(O)—C₂-C₁₂-alkenyl, —S(O)—C₂-C₁₂-alkenyl, —S(O)—C₃-C₁₂-cycloalkyl, —S(O)-aryl, —S(O)-heteroaryl, —S(O)-heterocycloalkyl-SO₂NH₂, —SO₂NH—C₁-C₁₂-alkyl, —SO₂NH—C₂-C₁₂-alkenyl, —SO₂NH—C₂-C₁₂-alkenyl, —SO₂NH—C₃-C₁₂-cycloalkyl, —SO₂NH-aryl, —SO₂NH-heteroaryl, —SO₂NH-heterocycloalkyl, —NHS₂—C₁-C₁₂-alkyl, —NHSO₂—C₂-C₁₂-alkenyl, —NHSO₂—C₂-C₁₂-alkenyl, —NHSO₂—C₃-C₁₂-cycloalkyl, —NHSO₂-aryl, —NHSO₂-heteroaryl, —NHSO₂-heterocycloalkyl, —CH₂NH₂, —CH₂SO₂CH₃, aryl, arylalkyl, heteroaryl, heteroarylalkyl, heterocycloalkyl, —C₃-C₁₂-cycloalkyl, polyalkoxyalkyl, polyalkoxy, -methoxymethoxy, -methoxyethoxy, —SH, —S—C₁-C₁₂-alkyl, —S—C₂-C₁₂-alkenyl, —S—C₂-C₁₂-alkenyl, —S—C₃-C₁₂-cycloalkyl, —S-aryl, —S-heteroaryl, —S-heterocycloalkyl, or methylthiomethyl);

$R_1$ is H, alkyl, alkenyl, alkynyl, each containing 0, 1, 2, or 3 heteroatoms selected from O, S, or N; or $R_1$ is aryl, arylalkyl, heteroaryl, heterocyclic, or carbocyclic; wherein $R_1$ may be optionally substituted;

$R_2$ is hydrogen, optionally substituted alkyl (including aralkyl), optionally substituted cycloalkyl, and optionally substituted heterocyclyl; and $R_6$ is hydrogen or optionally substituted alkyl.

In another aspect, the invention provides a compound of formula II:

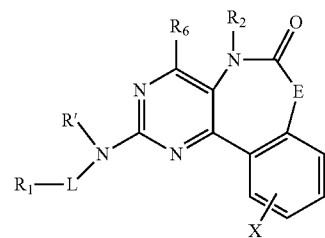

(II)

or a pharmaceutically acceptable salt, ester or prodrug thereof, wherein,

R' is H or alkyl;

L is absent, S, SO, SO₂, or CO;

X is an optional substituent as defined for formula I;

E is $NR_2$ or $CHR_2$;

$R_1$ is H, alkyl, alkenyl, alkynyl, each containing 0, 1, 2, or 3 heteroatoms selected from O, S, or N; or $R_1$ is aryl, arylalkyl, heteroaryl, heterocyclic, or carbocyclic; wherein $R_1$ may be optionally substituted;

$R_2$ is, independently for each occurrence, hydrogen, optionally substituted alkyl (including aralkyl), optionally substituted cycloalkyl, and optionally substituted heterocyclyl; and $R_6$ is hydrogen or optionally substituted alkyl.

In certain embodiments, E is $NR_2$. In certain embodiments, $R_2$ is H or —CH₃.

In another aspect, the invention provides a compound of formula III:

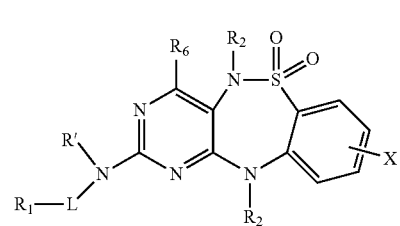

(III)

or a pharmaceutically acceptable salt, ester or prodrug thereof, wherein,

R' is H or alkyl;

L is absent, S, SO, SO₂, or CO;

X is an optional substituent as defined for formula I;

$R_1$ is H, alkyl, alkenyl, alkynyl, each containing 0, 1, 2, or 3 heteroatoms selected from O, S, or N; or $R_1$ is aryl, arylalkyl, heteroaryl, heterocyclic, or carbocyclic; wherein $R_1$ may be optionally substituted;

$R_2$ is, independently for each occurrence, hydrogen, optionally substituted alkyl (including aralkyl), optionally substituted cycloalkyl, and optionally substituted heterocyclyl; and $R_6$ is hydrogen or optionally substituted alkyl.

In another aspect, the invention provides a compound of formula IV:

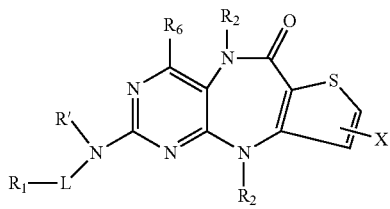
(IV)

or a pharmaceutically acceptable salt, ester or prodrug thereof,
wherein,
R' is H or alkyl;
L is absent, S, SO, SO$_2$, or CO;
R$_1$ is H, alkyl, alkenyl, alkynyl, each containing 0, 1, 2, or 3 heteroatoms selected from O, S, or N; or R$_1$ is aryl, arylalkyl, heteroaryl, heterocyclic, or carbocyclic; wherein R$_1$ may be optionally substituted;
R$_2$ is, independently for each occurrence, hydrogen, optionally substituted alkyl (including aralkyl), optionally substituted cycloalkyl, and optionally substituted heterocyclyl; and
R$_6$ is hydrogen or optionally substituted alkyl.

In another aspect, the invention provides a compound of formula V:

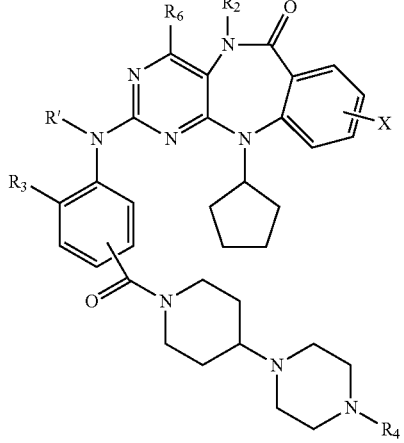
(V)

or a pharmaceutically acceptable salt, ester or prodrug thereof,
wherein,
R$_2$ is hydrogen or optionally substituted alkyl;
R$_3$ is —OH or —O-(optionally substituted alkyl);
R$_4$ is hydrogen or optionally substituted alkyl; and
R$_6$ is hydrogen or optionally substituted alkyl.

In another aspect, the invention provides a compound of Formula VI:

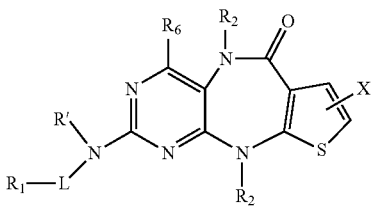

or a pharmaceutically acceptable salt, ester or prodrug thereof,
wherein,
R' is H or alkyl;
L is absent, S, SO, SO$_2$, or CO;
X is an optional substituent as defined for formula I;
R$_1$ is H, alkyl, alkenyl, alkynyl, each containing 0, 1, 2, or 3 heteroatoms selected from O, S, or N; or R$_1$ is aryl, arylalkyl, heteroaryl, heterocyclic, or carbocyclic; wherein R$_1$ may be optionally substituted;
R$_2$ is, independently for each occurrence, hydrogen, optionally substituted alkyl, optionally substituted cycloalkyl, and optionally substituted heterocyclyl; or
two X moieties on adjacent atoms of the thiophene ring can form, together with the atoms to which they are attached, a phenyl ring; and
R$_6$ is hydrogen or optionally substituted alkyl.

In another aspect, the invention provides a compound of Formula VII:

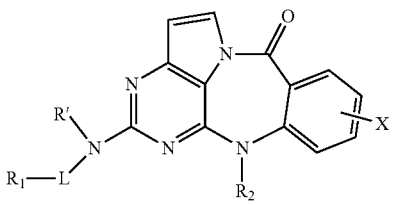

or a pharmaceutically acceptable salt, ester or prodrug thereof,
wherein,
R' is H or alkyl;
L is absent, S, SO, SO$_2$, or CO;
X is an optional substituent as defined for formula I;
R$_1$ is H, alkyl, alkenyl, alkynyl, each containing 0, 1, 2, or 3 heteroatoms selected from O, S, or N; or R$_1$ is aryl, arylalkyl, heteroaryl, heterocyclic, or carbocyclic; wherein R$_1$ may be optionally substituted;
R$_2$ is hydrogen, optionally substituted alkyl, optionally substituted cycloalkyl, and optionally substituted heterocyclyl; and
R$_6$ is hydrogen or optionally substituted alkyl.

In another aspect, the invention provides a compound of Formula VIII:

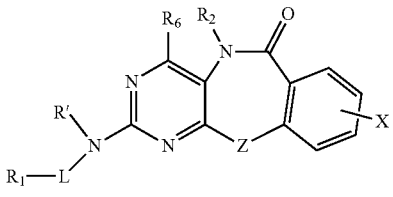

or a pharmaceutically acceptable salt, ester or prodrug thereof,
wherein,
R' is H or alkyl;
L is absent, S, SO, $SO_2$, or CO;
X is an optional substituent as defined for formula I;
Z is O or S;
$R_1$ is H, alkyl, alkenyl, alkynyl, each containing 0, 1, 2, or 3 heteroatoms selected from O, S, or N; or $R_1$ is aryl, arylalkyl, heteroaryl, heterocyclic, or carbocyclic; wherein $R_1$ may be optionally substituted;
$R_2$ is hydrogen, optionally substituted alkyl, optionally substituted cycloalkyl, and optionally substituted heterocyclyl; and
$R_6$ is hydrogen or optionally substituted alkyl.
In another aspect, the invention provides a compound of Formula IX:

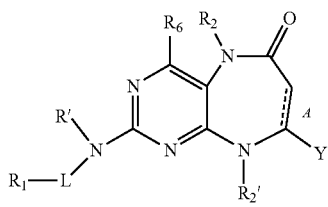

or a pharmaceutically acceptable salt, ester or prodrug thereof,
wherein,
A is a single bond or double bond;
R' is H or alkyl;
L is absent, S, SO, $SO_2$, or CO;
Y is hydrogen, optionally substituted alkyl, optionally substituted cycloalkyl, and optionally substituted heterocyclyl;
$R_1$ is H, alkyl, alkenyl, alkynyl, each containing 0, 1, 2, or 3 heteroatoms selected from O, S, or N; or $R_1$ is aryl, arylalkyl, heteroaryl, heterocyclic, or carbocyclic; wherein $R_1$ may be optionally substituted;
$R_2$ and $R_2'$ are each independently hydrogen, optionally substituted alkyl, optionally substituted cycloalkyl, and optionally substituted heterocyclyl;
or Y and $R_2'$ can form, together with the atoms to which they are attached, a five-membered ring; and
$R_6$ is hydrogen or optionally substituted alkyl.
In another aspect, the invention provides a method of treating a disease in a subject comprising administering to the subject a compound, pharmaceutically acceptable salt, ester or prodrug of formulae I-IX (or formulae A or F).
In another aspect, the invention provides a method of treating a kinase-mediated disorder in a subject comprising: administering to the subject identified as in need thereof a compound, pharmaceutically acceptable salt, ester or prodrug of formulae I-IX (or formulae A or F).
In another aspect, the invention provides a method for reducing kinase-dependent cell growth comprising contacting a cell with a kinase inhibitor compound of formulae I-IX (or formulae A or F).
In other aspects, the invention provides a method of inhibiting a kinase in a cell or in a subject identified as in need of such treatment, comprising administering a compound of formulae I-IX (or formulae A or F).
In another aspect, the invention provides a kit comprising a compound capable of inhibiting kinase activity selected from one or more compounds of formulae I-IX (or formulae A or F), and instructions for use in treating cancer.
In another aspect, the invention provides a pharmaceutical composition comprising a compound of formulae I-IX (or formulae A or F), or a pharmaceutically acceptable ester, salt, or prodrug thereof, together with a pharmaceutically acceptable carrier.
In one aspect, the invention provides a method of synthesizing a compound of formulae I-IX (or formulae A or F).

DESCRIPTION OF THE DRAWINGS

In FIG. 2A, HEK293 cells stably expressing wild-type GFP-LRRK2, GFP-LRRK2[G2019S], GFP-LRRK2[G2019S+A2016T], and GFP-LRRK2[A2016T] were treated with DMSO or increasing concentrations of compound 24 for 90 min. Cell lysates were subjected to immunoblotting for detection of LRRK2 phosphorylated at Ser910 and Ser935 and for total LRRK2. FIG. 2B shows similar results as in FIG. 2A except 26 was used at the indicated concentration.

DETAILED DESCRIPTION OF THE INVENTION

Definitions

Figure 1:
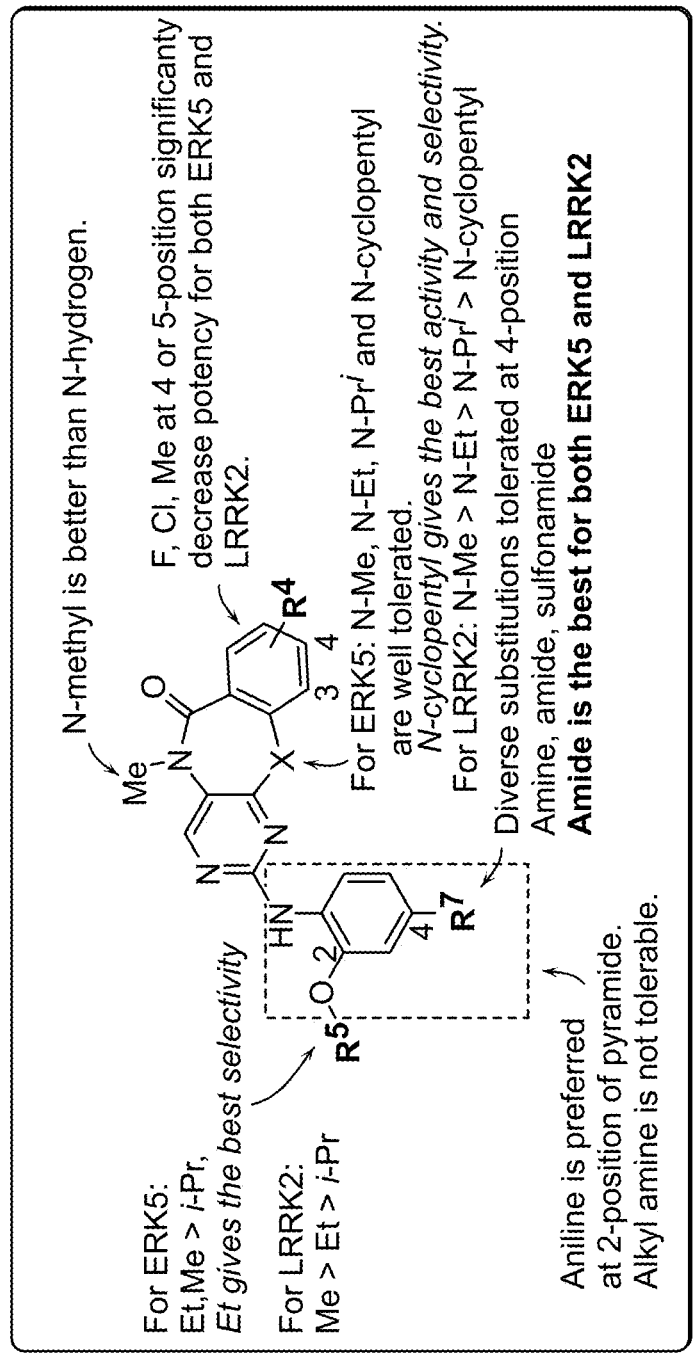
FIG. 1. Summary of SAR for benzo[e]pyrimido-[5,4-b]diazepine-6(11H)-ones as ERK5 inhibitors and LRRK2 inhibitors.
Figure 1:
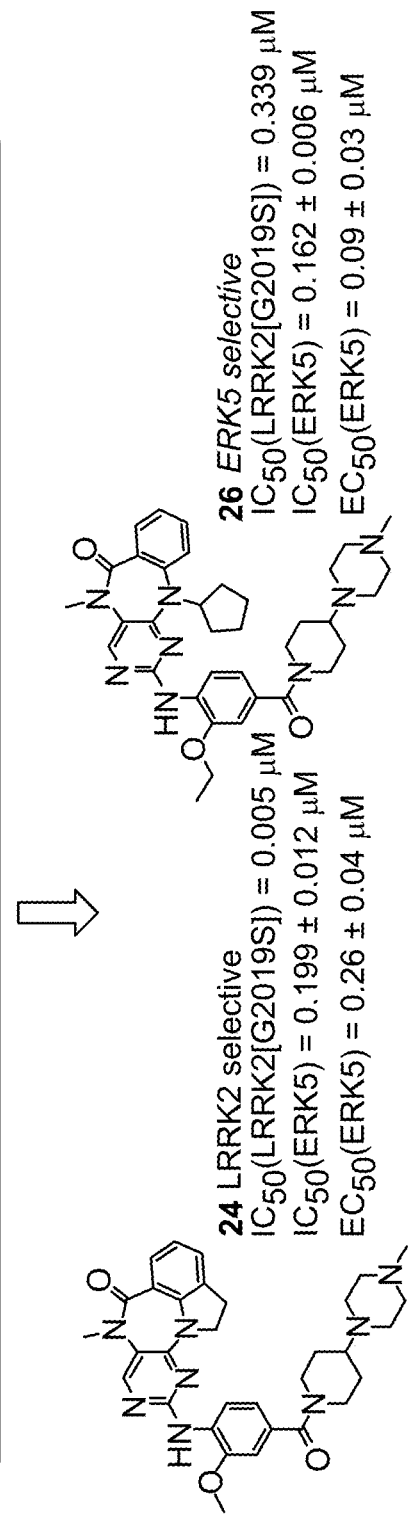

Listed below are definitions of various terms used to describe this invention. These definitions apply to the terms as they are used throughout this specification and claims, unless otherwise limited in specific instances, either individually or as part of a larger group.

The term "alkyl," as used herein, refers to saturated, straight- or branched-chain hydrocarbon radicals containing, in certain embodiments, between one and six, or one and eight carbon atoms, respectively. Examples of $C_1$-$C_6$ alkyl radicals include, but are not limited to, methyl, ethyl, propyl, isopropyl, n-butyl, tert-butyl, neopentyl, n-hexyl radicals; and examples of $C_1$-$C_8$ alkyl radicals include, but are not limited to, methyl, ethyl, propyl, isopropyl, n-butyl, tert-butyl, neopentyl, n-hexyl, heptyl, octyl radicals.

The term "alkenyl," as used herein, denotes a monovalent group derived from a hydrocarbon moiety containing, in certain embodiments, from two to six, or two to eight carbon atoms having at least one carbon-carbon double bond. The double bond may or may not be the point of attachment to another group. Alkenyl groups include, but are not limited to, for example, ethenyl, propenyl, butenyl, 1-methyl-2-buten-1-yl, heptenyl, octenyl and the like.

The term "alkynyl," as used herein, denotes a monovalent group derived from a hydrocarbon moiety containing, in certain embodiments, from two to six, or two to eight carbon atoms having at least one carbon-carbon triple bond. The alkynyl group may or may not be the point of attachment to another group. Representative alkynyl groups include, but are not limited to, for example, ethynyl, 1-propynyl, 1-butynyl, heptynyl, octynyl and the like.

The term "alkoxy" refers to an —O-alkyl radical.

The term "aryl," as used herein, refers to a mono- or poly-cyclic carbocyclic ring system having one or more aromatic rings, fused or non-fused, including, but not limited to, phenyl, naphthyl, tetrahydronaphthyl, indanyl, idenyl and the like.

The term "aralkyl," as used herein, refers to an alkyl residue attached to an aryl ring. Examples include, but are not limited to, benzyl, phenethyl and the like.

The term "cycloalkyl," as used herein, denotes a monovalent group derived from a monocyclic or polycyclic saturated or partially unsaturated carbocyclic ring compound. Examples of $C_3$-$C_8$-cycloalkyl include, but not limited to, cyclopropyl, cyclobutyl, cyclopentyl, cyclohexyl, cyclopentyl and cyclooctyl; and examples of $C_3$-$C_{12}$-cycloalkyl include, but not limited to, cyclopropyl, cyclobutyl, cyclopentyl, cyclohexyl, bicyclo[2.2.1]heptyl, and bicyclo[2.2.2] octyl. Also contemplated are a monovalent group derived from a monocyclic or polycyclic carbocyclic ring compound having at least one carbon-carbon double bond by the removal of a single hydrogen atom. Examples of such groups include, but are not limited to, cyclopropenyl, cyclobutenyl, cyclopentenyl, cyclohexenyl, cycloheptenyl, cyclooctenyl, and the like.

The term "heteroaryl," as used herein, refers to a mono- or poly-cyclic (e.g., bi-, or tri-cyclic or more) fused or non-fused, radical or ring system having at least one aromatic ring, having from five to ten ring atoms of which one ring atoms is selected from S, O and N; zero, one or two ring atoms are additional heteroatoms independently selected from S, O and N; and the remaining ring atoms are carbon. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzoxazolyl, quinoxalinyl, and the like.

The term "heteroaralkyl," as used herein, refers to an alkyl residue residue attached to a heteroaryl ring. Examples include, but are not limited to, pyridinylmethyl, pyrimidinylethyl and the like.

The term "heterocycloalkyl," as used herein, refers to a non-aromatic 3-, 4-, 5-, 6- or 7-membered ring or a bi- or tri-cyclic group fused of non-fused system, where (i) each ring contains between one and three heteroatoms independently selected from oxygen, sulfur and nitrogen, (ii) each 5-membered ring has 0 to 1 double bonds and each 6-membered ring has 0 to 2 double bonds, (iii) the nitrogen and sulfur heteroatoms may optionally be oxidized, (iv) the nitrogen heteroatom may optionally be quaternized, and (iv) any of the above rings may be fused to a benzene ring. Representative heterocycloalkyl groups include, but are not limited to, [1,3]dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The term "alkylamino" refers to a group having the structure —NH($C_1$-$C_{12}$ alkyl) where $C_1$-$C_{12}$ alkyl is as previously defined.

The term "acyl" includes residues derived from acids, including but not limited to carboxylic acids, carbamic acids, carbonic acids, sulfonic acids, and phosphorous acids. Examples include aliphatic carbonyls, aromatic carbonyls, aliphatic sulfonyls, aromatic sulfinyls, aliphatic sulfinyls, aromatic phosphates and aliphatic phosphates. Examples of aliphatic carbonyls include, but are not limited to, acetyl, propionyl, 2-fluoroacetyl, butyryl, 2-hydroxy acetyl, and the like.

In accordance with the invention, any of the aryls, substituted aryls, heteroaryls and substituted heteroaryls described herein, can be any aromatic group. Aromatic groups can be substituted or unsubstituted.

The terms "halo" and "halogen," as used herein, refer to an atom selected from fluorine, chlorine, bromine and iodine.

As described herein, compounds of the invention may optionally be substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. The terms "optionally substituted", "optionally substituted alkyl," "optionally substituted "optionally substituted alkenyl," "optionally substituted alkynyl", "optionally substituted cycloalkyl," "optionally substituted cycloalkenyl," "optionally substituted aryl", "optionally substituted heteroaryl," "optionally substituted aralkyl", "optionally substituted heteroaralkyl," "optionally substituted heterocycloalkyl," and any other optionally substituted group as used herein, refer to groups that are substituted or unsubstituted by independent replacement of one, two, or three or more of the hydrogen atoms thereon with substituents including, but not limited to:

—F, —Cl, —Br, —I,

—OH, protected hydroxy,

—$NO_2$, —CN,

—$NH_2$, protected amino, —NH—$C_1$-$C_{12}$-alkyl, —NH—$C_2$-$C_{12}$-alkenyl, —NH—$C_2$-$C_{12}$-alkenyl, —NH—$C_3$-$C_{12}$-cycloalkyl, —NH-aryl, —NH-heteroaryl, —NH-heterocycloalkyl, -dialkylamino, -diarylamino, -diheteroarylamino, —O—$C_1$-$C_{12}$-alkyl, —O—$C_2$-$C_{12}$-alkenyl, —O—$C_2$-$C_{12}$-alkenyl, —O—$C_3$-$C_{12}$-cycloalkyl, —O-aryl, —O-heteroaryl, —O-heterocycloalkyl, —C(O)—$C_1$-$C_{12}$-alkyl, —C(O)—$C_2$-$C_{12}$-alkenyl, —C(O)—$C_2$-$C_{12}$-alkenyl, —C(O)—$C_3$-$C_{12}$-cycloalkyl, —C(O)-aryl, —C(O)-heteroaryl, —C(O)-heterocycloalkyl, —$CONH_2$, —CONH—$C_1$-$C_{12}$-alkyl, —CONH—$C_2$-$C_{12}$-alkenyl, —CONH—$C_2$-$C_{12}$-alkenyl, —CONH—$C_3$-$C_{12}$-cycloalkyl, —CONH-aryl, —CONH-heteroaryl, —CONH-heterocyclalkyl, —$OCO_2$—$C_1$-$C_{12}$-alkyl, —$OCO_2$—$C_2$-$C_{12}$-alkenyl, —$OCO_2$—$C_2$-$C_{12}$-alkenyl, —$OCO_2$—$C_3$-$C_{12}$-cycloalkyl, —$OCO_2$-aryl, —$OCO_2$-heteroaryl, —$OCO_2$-heterocycloalkyl, —$OCONH_2$, —OCONH—$C_1$-$C_{12}$-alkyl, —OCONH—$C_2$-$C_{12}$-alkenyl, —OCONH—$C_2$-$C_{12}$-alkenyl, —OCONH—$C_3$-$C_{12}$-cycloalkyl, —OCONH-aryl, —OCONH-heteroaryl, —OCONH-heterocycloalkyl, —NHC(O)—$C_1$-$C_{12}$-alkyl, —NHC(O)—$C_2$-$C_{12}$-alkenyl, —NHC(O)—$C_2$-$C_{12}$-alkenyl, —NHC(O)—$C_3$-$C_{12}$-cycloalkyl, —NHC(O)-aryl, —NHC(O)-heteroaryl, —NHC(O)-heterocycloalkyl, —NHCO$_2$—$C_1$-$C_{12}$-alkyl, —NHCO$_2$—$C_2$-$C_{12}$-alkenyl, —NHCO$_2$—$C_2$-$C_{12}$-alkenyl, —NHCO$_2$—$C_3$-$C_{12}$-cycloalkyl, —NHCO$_2$-aryl, —NHCO$_2$-heteroaryl, —NHCO$_2$-heterocycloalkyl, —NHC(O)NH$_2$, —NHC(O)NH—$C_1$-$C_{12}$-alkyl, —NHC(O)NH—$C_2$-$C_{12}$-alkenyl, —NHC(O)NH—$C_2$-$C_{12}$-alkenyl, —NHC(O)NH—$C_3$-$C_{12}$-cycloalkyl, —NHC(O)NH-aryl, —NHC(O)NH-heteroaryl, —NHC(O)NH-heterocycloalkyl, NHC(S)NH$_2$, —NHC(S)NH—$C_1$-$C_{12}$-alkyl, —NHC(S)NH—$C_2$-$C_{12}$-alkenyl, —NHC(S)NH—$C_2$-$C_{12}$-alkenyl, —NHC(S)NH—$C_3$-$C_{12}$-cycloalkyl, —NHC(S)NH-aryl, —NHC(S)NH-heteroaryl, —NHC(S)NH-heterocycloalkyl, —NHC(NH)NH$_2$, —NHC(NH)NH—$C_1$-$C_{12}$-alkyl, —NHC(NH)NH—$C_2$-$C_{12}$-alkenyl, —NHC(NH)NH—$C_2$-$C_{12}$-alkenyl, —NHC(NH)NH—$C_3$-$C_{12}$-cycloalkyl, —NHC(NH)NH-aryl, —NHC(NH)NH-heteroaryl, —NHC(NH)NH-heterocycloalkyl, —NHC(NH)—$C_1$-$C_{12}$-alkyl, —NHC(NH)—$C_2$-$C_{12}$-alkenyl, —NHC(NH)—$C_2$-$C_{12}$-alkenyl, —NHC(NH)—$C_3$-$C_{12}$-cycloalkyl, —NHC(NH)-aryl, —NHC(NH)-heteroaryl, —NHC(NH)-heterocycloalkyl, —(NH)NH—$C_1$-$C_{12}$-alkyl, —C(NH)NH—$C_2$-$C_{12}$-alkenyl, —C(NH)NH—$C_2$-$C_{12}$-alkenyl, —C(NH)NH—$C_3$-$C_{12}$-cycloalkyl, —C(NH)NH-aryl, —C(NH)NH-heteroaryl, —C(NH)NH-heterocycloalkyl, —S(O)—$C_1$-$C_{12}$-alkyl, —S(O)—$C_2$-$C_{12}$-alkenyl, —S(O)—$C_2$-$C_{12}$-alkenyl, —S(O)—$C_3$-$C_{12}$-cycloalkyl, —S(O)-aryl, —S(O)-heteroaryl, —S(O)-heterocycloalkyl-SO$_2$NH$_2$, —SO$_2$NH—$C_1$-$C_{12}$-alkyl, —SO$_2$NH—$C_2$-$C_{12}$-alkenyl, —SO$_2$NH—$C_2$-$C_{12}$-alkenyl, —SO$_2$NH—$C_3$-$C_{12}$-cycloalkyl, —SO$_2$NH-aryl, —SO$_2$NH-heteroaryl, —SO$_2$NH-heterocycloalkyl, —NHSO$_2$—$C_1$-$C_{12}$-alkyl, —NHSO$_2$—$C_2$-$C_{12}$-alkenyl, —NHSO$_2$—$C_2$-$C_{12}$-alkenyl, —NHSO$_2$—$C_3$-$C_{12}$-cycloalkyl, —NHSO$_2$-aryl, —NHSO$_2$-heteroaryl, —NHSO$_2$-heterocycloalkyl, —CH$_2$NH$_2$, —CH$_2$SO$_2$CH$_3$, -aryl, -arylalkyl, -heteroaryl, -heteroarylalkyl, -heterocycloalkyl, $C_3$-$C_{12}$-cycloalkyl, polyalkoxyalkyl, polyalkoxy, -methoxymethoxy, -methoxyethoxy, —SH, —S—$C_1$-$C_{12}$-alkyl, —S—$C_2$-$C_{12}$-alkenyl, —S—$C_2$-$C_{12}$-alkenyl, —S—$C_3$-$C_{12}$-cycloalkyl, —S-aryl, —S-heteroaryl, —S-heterocycloalkyl, or methylthiomethyl.

It is understood that the aryls, heteroaryls, alkyls, and the like can be further substituted.

The term "cancer" includes, but is not limited to, the following cancers: epidermoid Oral: buccal cavity, lip, tongue, mouth, pharynx; Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell or epidermoid, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, larynx, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel or small intestines (adenocarcinoma, lymphoma, carcinoid tumors, Karposi's sarcoma, leiomyoma, hemangioma, lipoma, neurofibroma, fibroma), large bowel or large intestines (adenocarcinoma, tubular adenoma, villous adenoma, hamartoma, leiomyoma), colon, colon-rectum, colorectal; rectum, Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma, biliary passages; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma), breast; Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma] hairy cell; lymphoid disorders; Skin: malignant melanoma, basal cell carcinoma, squamous cell carcinoma, Karposi's sarcoma, keratoacanthoma, moles dysplastic nevi, lipoma, angioma, dermatofibroma, keloids, psoriasis, Thyroid gland: papillary thyroid carcinoma, follicular thyroid carcinoma; medullary thyroid carcinoma, undifferentiated thyroid cancer, multiple endocrine neoplasia type 2A, multiple endocrine neoplasia type 2B, familial medullary thyroid cancer, pheochromocytoma, paraganglioma; and Adrenal glands: neuroblastoma. Thus, the term "cancerous cell" as provided herein, includes a cell afflicted by any one of the above-identified conditions.

The term "Kinase Panel" is a list of kinases comprising MPS1 (TTK), ERK5 (BMK1, MAPK7), polo kinase 1, 2, 3, or 4, Ack1, Ack2, Abl, DCAMKL1, ABL1, Abl mutants, DCAMKL2, ARK5, BRK, MKNK2, FGFR4, TNK1, PLK1, ULK2, PLK4, PRKD1, PRKD2, PRKD3, ROS1, RPS6KA6, TAOK1, TAOK3, TNK2, Bcr-Abl, GAK, cSrc, TPR-Met, Tie2, MET, FGFR3, Aurora, Axl, Bmx, BTK, c-kit, CHK2, Flt3, MST2, p70S6K, PDGFR, PKB, PKC, Raf, ROCK-H, Rsk1, SGK, TrkA, TrkB, TrkC, AAK1, ABL1, ABL1(E255K), ABL1(F317I), ABL1(F317L), ABL1 (H396P), ABL1(M351T), ABL1(Q252H), ABL1(T315I), ABL1(Y253F), ABL2, ACVR1, ACVR1B, ACVR2A, ACVR2B, ACVRL1, ADCK3, ADCK4, AKT1, AKT2, AKT3, ALK, AMPK-alpha1, AMPK-alpha2, ANKK1, ARK5, ASK1, ASK2, AURKA, AURKB, AURKC, AXL, BIKE, BLK, BMPR1A, BMPR1B, BMPR2, BMX, BRAF, BRAF(V600E), BRK, BRSK1, BRSK2, BTK, CAMK1, CAMK1D, CAMK1G, CAMK2A, CAMK2D, CAMK2G, CAMK4, CAMKK1, CAMKK2, CDC2L1, CDC2L2, CDK11, CDK2, CDK3, CDK5, CDK7, CDK8, CDK9, CDKL2, CDKL3, CDKL5, CHECK1, CHEK2, CIT, CLK1, CLK2, CLK3, CLK4, CSF1R, CSK, CSNK1A1L, CSNK1D, CSNK1E, CSNK1G1, CSNK1G3, CSNK2A1, CSNK2A2, CTK, DAPK1, DAPK2, DAPK3, DCAMKL1, DCAMKL2, DCAMKL3, DDR1, DDR2, DLK, DMPK, DMPK2, DRAK1, DRAK2, DYRK1A, DYRK1B, DYRK2, EGFR, EGFR (E746-A750DEL), EGFR (G719C), EGFR (G719S), EGFR(L747-E749del, A750P), EGFR(L747-S752del, P753S), EGFR(L747-T751del, Sins), EGFR (L858R), EGFR(L858R, T790M), EGFR(L861Q), EGFR (S752-1759del), EPHAL EPHA2, EPHA3, EPHA4, EPHA5, EPHA6, EPHA7, EPHA8, EPHB1, EPHB2, EPHB3, EPHB4, EPHB6, ERBB2, ERBB3, ERBB4, ERK1, ERK2, ERK3, ERK4, ERK5, ERK8, ERN1, FAK, FER, FES, FGFR1, FGFR2, FGFR3, FGFR3(G697C), FGFR4, FGR, FLT1, FLT3, FLT3(D835H), FLT3(D835Y), FLT3 (ITD), FLT3(K663Q), FLT3(N841I), FLT4, FRK, FYN, GAK, GCN2(Kin.Dom.2, S808G), GRK1, GRK4, GRK7, GSK3A, GSK3B, HCK, HIPK1, HIPK2, HIPK3, HIPK4, HPK1, HUNK, ICK, IGF1R, IKK-ALPHA, IKK-BETA, IKK-EPSILON, INSR, INSRR, IRAK1, IRAK3, ITK, JAK1(JH1domain-catalytic), JAK1(JH2domain-pseudokinase), JAK2(JH1domain-catalytic), JAK3(JH1domain-catalytic), JNK1, JNK2, JNK3, KIT, KIT(D816V), KIT(L576P), KIT(V559D), KIT(V559D, T6701), KIT(V559D, V654A), LATS1, LATS2, LCK, LIMK1, LIMK2, LKB1, LOK, LTK, LYN, LZK, MAK, MAP3K1, MAP2K15, MAP3K2, MAP3K3, MAP3K4, MAP4K2, MAP4K3, MAP4K5, MAPKAPK2, MAPKAPK5, MARK1, MARK2, MARK3, MARK4, MAST1, MEK1, MEK2, MEK3, MEK4, MEK6, MELK, MERTK, MET, MET(M1250T), MET(Y1235D), MINK, MKNK1, MKNK2, MLCK, MLK1, MLK2, MLK3, MRCKA, MRCKB, MST1, MST1R, MST2, MST3, MST4, MUSK, MYLK, MYLK2, MYO3A, MYO3B, NDR1, NDR2, NEK1, NEK2, NEK5, NEK6, NEK7, NEK9, NIM1, NLK, OSR1, p38-alpha, p38-beta, p38-delta, p38-gamma, PAK1, PAK2, PAK3, PAK4, PAK6, PAK7, PCTK1, PCTK2, PCTK3, PDGFRA, PDGFRB, PDPK1, PFTAIRE2, PFTK1, PHKG1, PHKG2, PIK3C2B, PIK3C2G, PIK3CA, PIK3CA (C420R), PIK3CA(E542K), PIK3CA(E545A), PIK3CA (E545K), PIK3CA(H1047L), PIK3CA(H1047Y), PIK3CA (M1043I), PIK3CA(Q546K), PIK3CB, PIK3CD, PIK3CG, PIK4CB, PIM1, PIM2, PIM3, PIP5K1A, PIP5K2B, PKAC-ALPHA, PKAC-BETA, PKMYT1, PKN1, PKN2, PLK1, PLK2, PLK3, PLK4, PRKCD, PRKCE, PRKCH, PRKCQ, PRKD1, PRKD3, PRKG1, PRKG2, PRKR, PRKX, PRP4, PYK2, QSK, RAF1, RET, RET(M918T), RET(V804L), RET(V804M), RIOK1, RIOK2, RIOK3, RIPK1, RIPK2, RIPK4, ROCK1, ROCK2, ROS1, RPS6KA1(Kin.Dom. 1-N-terminal), RPS6KA1(Kin. Dom. 2-C-terminal), RPS6KA2(Kin.Dom.1-N-terminal), RPS6KA2(Kin.Dom.2-C-terminal), RPS6KA3(Kin.Dom.1-N-terminal), RPS6KA4 (Kin.Dom.1-N-terminal), RPS6KA4(Kin.Dom.2-C-terminal), RPS6KA5(Kin.Dom.1-N-terminal), RPS6KA5 (Kin.Dom.2-C-terminal), RPS6KA6(Kin.Dom.1-N-terminal), RPS6KA6(Kin.Dom.2-C-terminal), SBK1, SgK085, SgK110, SIK, SIK2, SLK, SNARK, SRC, SRMS, SRPK1, SRPK2, SRPK3, STK16, STK33, STK39, SYK, TAK1, TAO1, TAOK2, TAOK3, TBK1, TEC, TESK1, TGFBR1, TGFBR2, TIE1, TIE2, TLK1, TLK2, TNIK, TNK1, TNK2, TNNI3K, TRKA, TRKB, TRKC, TSSK1B, TTK, TXK, TYK2(JH1domain-catalytic), TYK2 (JH2domain-pseudokinase), TYRO3, ULK1, ULK2, ULK3, VEGFR2, WEE1, WEE2, YANK2, YANK3, YES, YSK1, YSK4, ZAK and ZAP70. Compounds of the invention are screened against the kinase panel (wild type and/or mutation thereof) and inhibit the activity of at least one of said panel members. In certain embodiments, the kinase is selected from ERK5, LRRK2, or EphA2.

Mutant forms of a kinase means single or multiple amino acid changes from the wild-type sequence.

The term "subject" as used herein refers to a mammal. A subject therefore refers to, for example, dogs, cats, horses, cows, pigs, guinea pigs, and the like. Preferably the subject is a human. When the subject is a human, the subject may be referred to herein as a patient.

Treat", "treating" and "treatment" refer to a method of alleviating or abating a disease and/or its attendant symptoms.

As used herein, the term "pharmaceutically acceptable salt" refers to those salts of the compounds formed by the process of the present invention which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1-19 (1977). The salts can be prepared in situ during the final isolation and purification of the compounds of the invention, or separately by reacting the free base function with a suitable organic acid. Examples of pharmaceutically acceptable include, but are not limited to, nontoxic acid addition salts are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, the term "pharmaceutically acceptable ester" refers to esters of the compounds formed by the process of the present invention which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The term "pharmaceutically acceptable prodrugs" as used herein refers to those prodrugs of the compounds formed by the process of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present invention. "Prodrug", as used herein means a compound which is convertible in vivo by metabolic means (e.g. by hydrolysis) to afford any compound delineated by the formulae of the instant invention. Various forms of prodrugs are known in the art, for example, as discussed in Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development, Chapter 5, 113-191 (1991); Bundgaard, et al., Journal of Drug Deliver Reviews, 8:1-38(1992); Bundgaard, J. of Pharmaceutical Sciences, 77:285 et seq. (1988); Higuchi and Stella (eds.) Prodrugs as Novel Drug Delivery Systems, American Chemical Society (1975); and Bernard Testa & Joachim Mayer, "Hydrolysis In Drug And Prodrug Metabolism: Chemistry, Biochemistry And Enzymology," John Wiley and Sons, Ltd. (2002).

This invention also encompasses pharmaceutical compositions containing, and methods of treating disorders through administering, pharmaceutically acceptable prodrugs of compounds of the invention. For example, compounds of the invention having free amino, amido, hydroxy or carboxylic groups can be converted into prodrugs. Prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of the invention. The amino acid residues include but are not limited to the 20 naturally occurring amino acids commonly designated by three letter symbols and also includes 4-hydroxyproline, hydroxyysine, demosine, isodemosine, 3-methylhistidine, norvalin, beta-alanine, gamma-aminobutyric acid, citrulline, homocysteine, homoserine, ornithine and methionine sulfone. Additional types of prodrugs are also encompassed. For instance, free carboxyl groups can be derivatized as amides or alkyl esters. Free hydroxy groups may be derivatized using groups including but not limited to hemisuccinates, phosphate esters, dimethylaminoacetates, and phosphoryloxymethyloxy carbonyls, as outlined in Advanced Drug Delivery Reviews, 1996, 19, 1 15. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in J. Med. Chem. 1996, 39, 10. Free amines can also be derivatized as amides, sulfonamides or phosphonamides. All of these prodrug moieties may incorporate groups including but not limited to ether, amine and carboxylic acid functionalities Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

Compounds of the Invention

In certain aspects, the invention provides a compound of formulae I-IX (or formulae A or F).

In one aspect, the invention provides a compound of formula I:

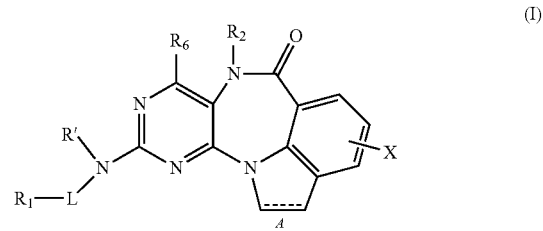

or a pharmaceutically acceptable salt, ester or prodrug thereof,
wherein,
A is a single bond or double bond;
R' is H or alkyl;
L is absent, S, SO, SO$_2$, or CO;
X is an optional substituent (for example, halogen, —OH, —NO$_2$, —CN, —NH$_2$, protected amino, —NH—C$_1$-C$_{12}$-alkyl, —NH—C$_2$-C$_{12}$-alkenyl, —NH—C$_2$-C$_{12}$-alkenyl, —NH—C$_3$-C$_{12}$-cycloalkyl, —NH-aryl, —NH-heteroaryl, —NH-heterocycloalkyl, -dialkylamino, -diarylamino, -diheteroarylamino, —O—C$_1$-C$_{12}$-alkyl, —O—C$_2$-C$_{12}$-alkenyl, —O—C$_2$-C$_{12}$-alkenyl, —O—C$_3$-C$_{12}$-cycloalkyl, —O-aryl, —O-heteroaryl, —O-heterocycloalkyl, —C(O)—C$_1$-C$_{12}$-alkyl, —C(O)—C$_2$-C$_{12}$-alkenyl, —C(O)—C$_2$-C$_{12}$-alkenyl, —C(O)—C$_3$-C$_{12}$-cycloalkyl, —C(O)-aryl, —C(O)-heteroaryl, —C(O)-heterocycloalkyl, —CONH$_2$, —CONH—C$_1$-C$_{12}$-alkyl, —CONH—C$_2$-C$_{12}$-alkenyl, —CONH—C$_2$-C$_{12}$-alkenyl, —CONH—C$_3$-C$_{12}$-cycloalkyl, —CONH-aryl, —CONH-heteroaryl, —CONH-heterocycloalkyl, —OCO$_2$—C$_1$-C$_{12}$-alkyl, —OCO$_2$—C$_2$-C$_{12}$-alkenyl, —OCO$_2$—C$_2$-C$_{12}$-alkenyl, —OCO$_2$—C$_3$-C$_{12}$-cycloalkyl, —OCO$_2$-aryl, —OCO$_2$-heteroaryl, —OCO$_2$-heterocycloalkyl, —OCONH$_2$, —OCONH—C$_1$-C$_{12}$-alkyl, —OCONH—C$_2$-C$_{12}$-alkenyl, —OCONH—C$_2$-C$_{12}$-alkenyl, —OCONH—C$_3$-C$_{12}$-cycloalkyl, —OCONH-aryl, —OCONH-heteroaryl, —OCONH-heterocycloalkyl, —NHC(O)—C$_1$-C$_{12}$-alkyl, —NHC(O)—C$_2$-C$_{12}$-alkenyl, —NHC(O)—C$_2$-C$_{12}$-alkenyl, —NHC(O)—C$_3$-C$_{12}$-cycloalkyl, —NHC(O)-aryl, —NHC(O)-heteroaryl, —NHC(O)-heterocycloalkyl, —NHCO$_2$—C$_1$-C$_{12}$-alkyl, —NHCO$_2$—C$_2$-C$_{12}$-alkenyl, —NHCO$_2$—C$_2$-C$_{12}$-alkenyl, —NHCO$_2$—C$_3$-C$_{12}$-cycloalkyl, —NHCO$_2$-aryl, —NHCO$_2$-heteroaryl, —NHCO$_2$-heterocycloalkyl, —NHC(O)NH$_2$, —NHC(O)NH—C$_1$-C$_{12}$-alkyl, —NHC(O)NH—C$_2$-C$_{12}$-alkenyl, —NHC(O)NH—C$_2$-C$_{12}$-alkenyl, —NHC(O)NH—C$_3$-C$_{12}$-cycloalkyl, —NHC(O)NH-aryl, —NHC(O)NH-heteroaryl, —NHC(O)NH-heterocycloalkyl, NHC(S)NH$_2$, —NHC(S)NH—C$_1$-C$_{12}$-alkyl, —NHC(S)NH—C$_2$-C$_{12}$-alkenyl, —NHC(S)NH—C$_2$-C$_{12}$-alkenyl, —NHC(S)NH—C$_3$-C$_{12}$-cycloalkyl, —NHC(S)NH-aryl, —NHC(S)NH-heteroaryl, —NHC(S)NH-heterocycloalkyl, —NHC(NH)NH$_2$, —NHC(NH)NH—C$_1$-C$_{12}$-alkyl, —NHC(NH)

NH—$C_2$-$C_{12}$-alkenyl, —NHC(NH)NH—$C_2$-$C_{12}$-alkenyl, —NHC(NH)NH—$C_3$-$C_{12}$-cycloalkyl, —NHC(NH)NH-aryl, —NHC(NH)NH-heteroaryl, —NHC(NH)NH-heterocycloalkyl, —NHC(NH)—$C_1$-$C_{12}$-alkyl, —NHC(NH)—$C_2$-$C_{12}$-alkenyl, —NHC(NH)—$C_2$-$C_{12}$-alkenyl, —NHC(NH)—$C_3$-$C_{12}$-cycloalkyl, —NHC(NH)-aryl, —NHC(NH)-heteroaryl, —NHC(NH)-heterocycloalkyl, —C(NH)NH—$C_1$-$C_{12}$-alkyl, —C(NH)NH—$C_2$-$C_{12}$-alkenyl, —C(NH)NH—$C_2$-$C_{12}$-alkenyl, —C(NH)NH—$C_3$-$C_{12}$-cycloalkyl, —C(NH)NH-aryl, —C(NH)NH-heteroaryl, —C(NH)NH-heterocycloalkyl, —S(O)—$C_2$-$C_{12}$alkyl, —S(O)—$C_2$-$C_{12}$-alkenyl, —S(O)—$C_3$-$C_{12}$-cycloalkyl, —S(O)-aryl, —S(O)-heteroaryl, —S(O)-heterocycloalkyl-$SO_2NH_2$, —$SO_2$NH—$C_1$-$C_{12}$-alkyl, —$SO_2$NH—$C_2$-$C_{12}$-alkenyl, —$SO_2$NH—$C_2$-$C_{12}$-alkenyl, —$SO_2$NH—$C_3$-$C_{12}$-cycloalkyl, —$SO_2$NH-aryl, —$SO_2$NH-heteroaryl, —$SO_2$NH-heterocycloalkyl, —$NHSO_2$—$C_1$-$C_{12}$-alkyl, —$NHSO_2$—$C_2$-$C_{12}$-alkenyl, —$NHSO_2$—$C_2$-$C_{12}$-alkenyl, —$NHSO_2$—$C_3$-$C_{12}$-cycloalkyl, —$NHSO_2$-aryl, —$NHSO_2$-heteroaryl, —$NHSO_2$-heterocycloalkyl, —$CH_2NH_2$, —$CH_2SO_2CH_3$, aryl, arylalkyl, heteroaryl, heteroarylalkyl, heterocycloalkyl, —$C_3$-$C_{12}$-cycloalkyl, polyalkoxyalkyl, polyalkoxy, -methoxymethoxy, -methoxyethoxy, —SH, —S—$C_1$-$C_{12}$-alkyl, —S—$C_2$-$C_{12}$-alkenyl, —S—$C_2$-$C_{12}$-alkenyl, —S—$C_3$-$C_{12}$-cycloalkyl, —S-aryl, —S-heteroaryl, —S-heterocycloalkyl, or methylthiomethyl);

$R_1$ is H, alkyl, alkenyl, alkynyl, each containing 0, 1, 2, or 3 heteroatoms selected from O, S, or N; or $R_1$ is aryl, arylalkyl, heteroaryl, heterocyclic, or carbocyclic; wherein $R_1$ may be optionally substituted;

$R_2$ is hydrogen, optionally substituted alkyl (including aralkyl), optionally substituted cycloalkyl, and optionally substituted heterocyclyl; and $R_6$ is hydrogen or optionally substituted alkyl.

In certain embodiments, $R_1$ is phenyl or pyridyl, each of which may be optionally substituted.

In certain further embodiments, $R_1$ is substituted with 0-4 substituents, selected from $N(R_A)(R_A)$, $C(O)NH(R_A)$, alkoxy, and heterocyclic, each of which may be further substituted; wherein each $R_A$ is independently selected from alkyl, and heterocyclic.

In certain further embodiments, $R_1$ is substituted with 0-4 substituents, selected from alkoxy,

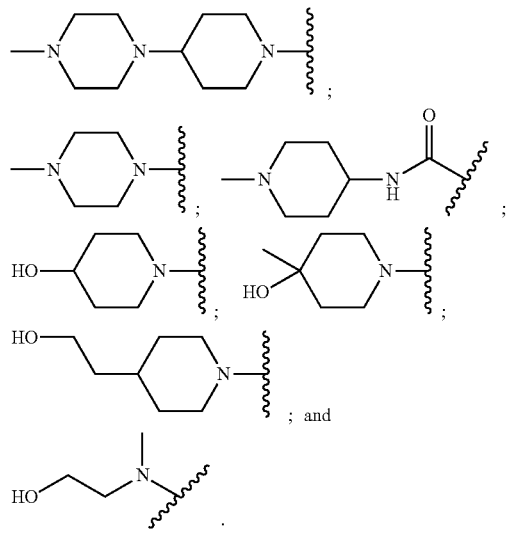

In certain embodiments, $R_2$ is H, methyl, or ethyl.
In certain embodiments, $R_6$ is H.
In certain embodiments, X is H.
In certain embodiments, R' is H.
In certain embodiments, L is absent.
In certain embodiments, A is a single bond.
In another aspect, the invention provides a compound of formula II:

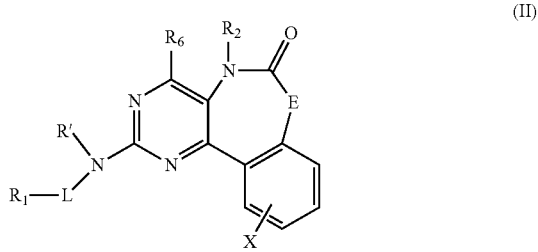

or a pharmaceutically acceptable salt, ester or prodrug thereof,
wherein,
R' is H or alkyl;
L is absent, S, SO, $SO_2$, or CO;
X is an optional substituent as defined for formula I;
E is $NR_2$ or $CHR_2$;
$R_1$ is H, alkyl, alkenyl, alkynyl, each containing 0, 1, 2, or 3 heteroatoms selected from O, S, or N; or $R_1$ is aryl, arylalkyl, heteroaryl, heterocyclic, or carbocyclic; wherein $R_1$ may be optionally substituted;

$R_2$ is, independently for each occurrence, hydrogen, optionally substituted alkyl (including aralkyl), optionally substituted cycloalkyl, and optionally substituted heterocyclyl; and $R_6$ is hydrogen or optionally substituted alkyl.

In certain embodiments, $R_1$ is phenyl or pyridyl, each of which may be optionally substituted.

In certain further embodiments, $R_1$ is substituted with 0-4 substituents, selected from $N(R_A)(R_A)$, $C(O)NH(R_A)$, alkoxy, and heterocyclic, each of which may be further substituted; wherein each $R_A$ is independently selected from alkyl, and heterocyclic.

In certain further embodiments, $R_1$ is substituted with 0-4 substituents, selected from alkoxy,

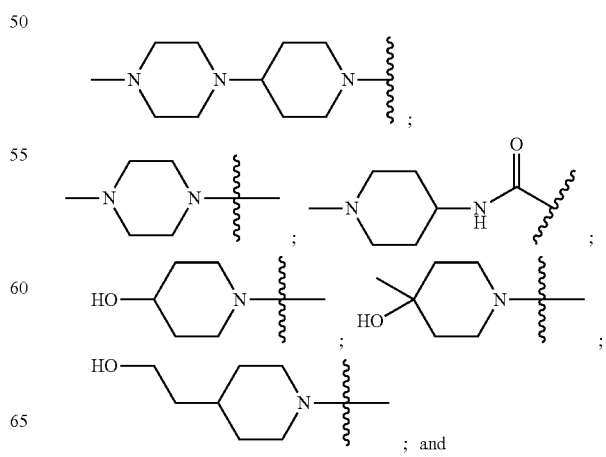

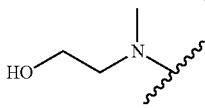

In certain embodiments, E is NR$_2$.

In certain embodiments, R$_2$ is H, methyl, or ethyl. In certain embodiments, each R$_2$ is H, methyl, optionally substituted benzyl, cyclopentyl, or pyranyl. In certain embodiments, if E is NR$_2$, then one R$_2$ is H or methyl, and the other R$_2$ is H, methyl, optionally substituted benzyl, cyclopentyl, or pyranyl. In certain embodiments, the optionally substituted benzyl is 2-chlorobenzyl, 2,4-dichlorobenzyl, 2-chloro, 4-fluorobenzyl, or 2-methylbenzyl.

In certain embodiments, R$_6$ is H.
In certain embodiments, X is H.
In certain embodiments, R' is H.
In certain embodiments, L is absent.

In another aspect, the invention provides a compound of formula III:

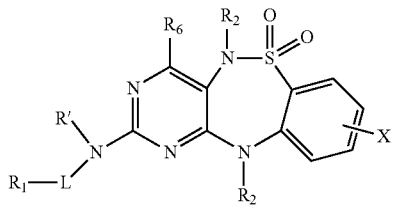

or a pharmaceutically acceptable salt, ester or prodrug thereof,
wherein,
R' is H or alkyl;
L is absent, S, SO, SO$_2$, or CO;
X is an optional substituent as defined for formula I;
R$_1$ is H, alkyl, alkenyl, alkynyl, each containing 0, 1, 2, or 3 heteroatoms selected from O, S, or N; or R$_1$ is aryl, arylalkyl, heteroaryl, heterocyclic, or carbocyclic; wherein R$_1$ may be optionally substituted;
R$_2$ is, independently for each occurrence, hydrogen, optionally substituted alkyl (including aralkyl), optionally substituted cycloalkyl, and optionally substituted heterocyclyl; and
R$_6$ is hydrogen or optionally substituted alkyl.

In certain embodiments, R$_1$ is phenyl or pyridyl, each of which may be optionally substituted.

In certain further embodiments, R$_1$ is substituted with 0-4 substituents, selected from N(R$_A$)(R$_A$), C(O)NH(R$_A$), alkoxy, and heterocyclic, each of which may be further substituted; wherein each R$_A$ is independently selected from alkyl, and heterocyclic.

In certain further embodiments, R$_1$ is substituted with 0-4 substituents, selected from alkoxy,

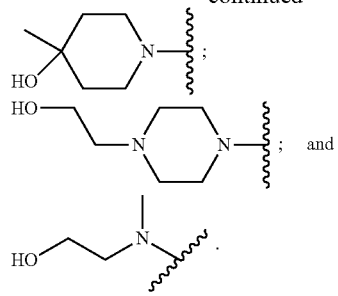

In certain embodiments, R$_2$ is H, methyl, or ethyl.
In certain embodiments, R$_6$ is H.
In certain embodiments, X is H.
In certain embodiments, R' is H.
In certain embodiments, L is absent.

In another aspect, the invention provides a compound of formula IV:

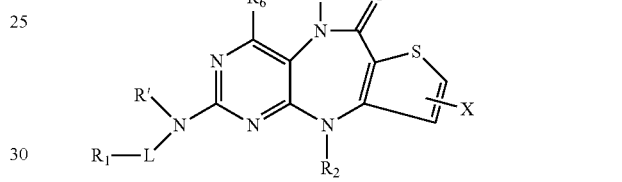

or a pharmaceutically acceptable salt, ester or prodrug thereof,
wherein,
R' is H or alkyl;
L is absent, S, SO, SO$_2$, or CO;
X is an optional substituent as defined for formula I;
R$_1$ is H, alkyl, alkenyl, alkynyl, each containing 0, 1, 2, or 3 heteroatoms selected from O, S, or N; or R$_1$ is aryl, arylalkyl, heteroaryl, heterocyclic, or carbocyclic; wherein R$_1$ may be optionally substituted;
R$_2$ is, independently for each occurrence, hydrogen, optionally substituted alkyl (including aralkyl), optionally substituted cycloalkyl, and optionally substituted heterocyclyl; and
R$_6$ is hydrogen or optionally substituted alkyl.

In certain embodiments, R$_1$ is phenyl or pyridyl, each of which may be optionally substituted.

In certain further embodiments, R$_1$ is substituted with 0-4 substituents, selected from N(R$_A$)(R$_A$), C(O)NH(R$_A$), alkoxy, and heterocyclic, each of which may be further substituted; wherein each R$_A$ is independently selected from alkyl, and heterocyclic.

In certain further embodiments, R$_1$ is substituted with 0-4 substituents, selected from alkoxy,

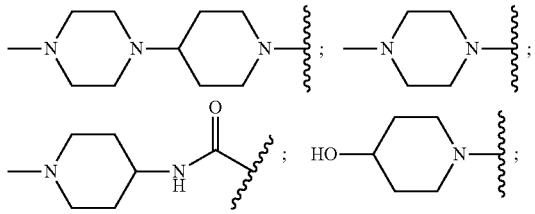

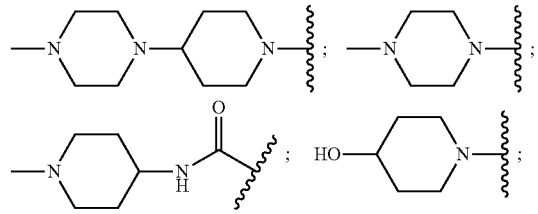

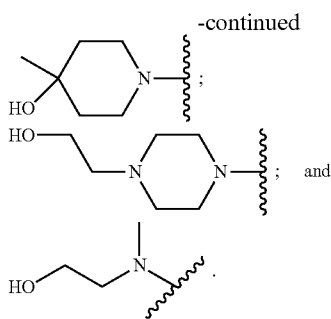

In certain embodiments, $R_2$ is H, methyl, or ethyl.
In certain embodiments, $R_6$ is H.
In certain embodiments, X is H.
In certain embodiments, R' is H.
In certain embodiments, L is absent.

In another aspect, the invention provides a compound of formula V:

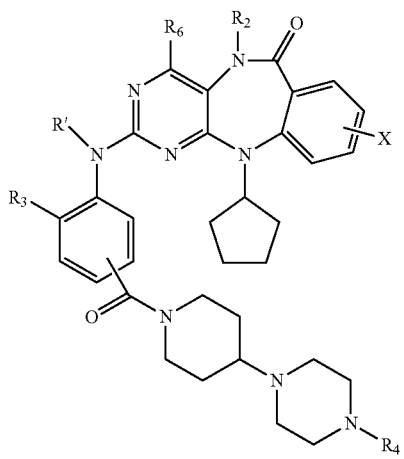

(V)

or a pharmaceutically acceptable salt, ester or prodrug thereof,
wherein,
X is an optional substituent as defined for formula I;
$R_2$ is hydrogen or optionally substituted alkyl;
$R_3$ is —OH or —O-(optionally substituted alkyl);
$R_4$ is hydrogen or optionally substituted alkyl; and
$R_6$ is hydrogen or optionally substituted alkyl.

In certain embodiments, $R_2$ is H, methyl, or ethyl.
$R_3$ is —OCH$_3$ or —OCH$_2$CH$_3$.
In certain embodiments, X is H.
In certain embodiments, R' is H.
In certain embodiments, $R_4$ is methyl or ethyl.

In another aspect, the invention provides a compound of Formula VI:

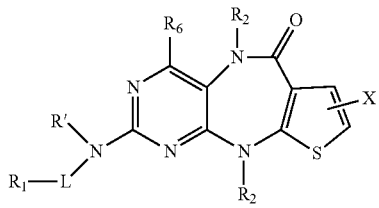

or a pharmaceutically acceptable salt, ester or prodrug thereof,
wherein,
R' is H or alkyl;
L is absent, S, SO, SO$_2$, or CO;
X is an optional substituent as defined for formula I;
$R_1$ is H, alkyl, alkenyl, alkynyl, each containing 0, 1, 2, or 3 heteroatoms selected from O, S, or N; or $R_1$ is aryl, arylalkyl, heteroaryl, heterocyclic, or carbocyclic; wherein $R_1$ may be optionally substituted;
$R_2$ is, independently for each occurrence, hydrogen, optionally substituted alkyl, optionally substituted cycloalkyl, and optionally substituted heterocyclyl; or
two X moieties on adjacent atoms of the thiophene ring can form, together with the atoms to which they are attached, a phenyl ring; and
$R_6$ is hydrogen or optionally substituted alkyl.

In another aspect, the invention provides a compound of Formula VII:

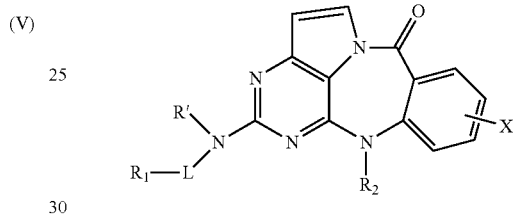

or a pharmaceutically acceptable salt, ester or prodrug thereof,
wherein,
R' is H or alkyl;
L is absent, S, SO, SO$_2$, or CO;
X is an optional substituent as defined for formula I;
$R_1$ is H, alkyl, alkenyl, alkynyl, each containing 0, 1, 2, or 3 heteroatoms selected from, S, or N; or $R_1$ is aryl, arylalkyl, heteroaryl, heterocyclic, or carbocyclic; wherein $R_1$ may be optionally substituted;
$R_2$ is hydrogen, optionally substituted alkyl, optionally substituted cycloalkyl, and optionally substituted heterocyclyl; and
$R_6$ is hydrogen or optionally substituted alkyl.

In another aspect, the invention provides a compound of Formula VIII:

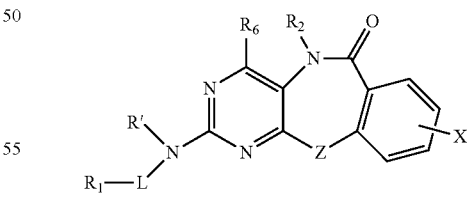

or a pharmaceutically acceptable salt, ester or prodrug thereof,
wherein,
R' is H or alkyl;
L is absent, S, SO, SO$_2$, or CO;
X is an optional substituent as defined for formula I;
Z is O or S;
$R_1$ is H, alkyl, alkenyl, alkynyl, each containing 0, 1, 2, or 3 heteroatoms selected from O, S, or N; or $R_1$ is aryl, arylalkyl, heteroaryl, heterocyclic, or carbocyclic; wherein $R_1$ may be optionally substituted;

$R_2$ is hydrogen, optionally substituted alkyl, optionally substituted cycloalkyl, and optionally substituted heterocyclyl; and $R_6$ is hydrogen or optionally substituted alkyl.

In another aspect, the invention provides a compound of Formula IX:

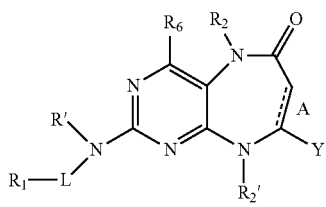

or a pharmaceutically acceptable salt, ester or prodrug thereof,
wherein,
A is a single bond or double bond;
R' is H or alkyl;
L is absent, S, SO, $SO_2$, or CO;
Y is hydrogen, optionally substituted alkyl, optionally substituted cycloalkyl, and optionally substituted heterocyclyl;
$R_1$ is H, alkyl, alkenyl, alkynyl, each containing 0, 1, 2, or 3 heteroatoms selected from O, S, or N; or $R_1$ is aryl, arylalkyl, heteroaryl, heterocyclic, or carbocyclic; wherein $R_1$ may be optionally substituted;
$R_2$ and $R_2$' are each independently hydrogen, optionally substituted alkyl, optionally substituted cycloalkyl, and optionally substituted heterocyclyl;
or Y and $R_2$' can form, together with the atoms to which they are attached, a five-membered ring; and
$R_6$ is hydrogen or optionally substituted alkyl.

In one aspect, the invention provides a compound of formula A:

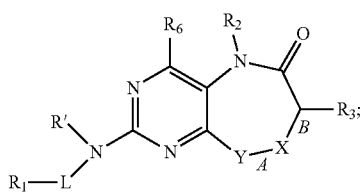

or a pharmaceutically acceptable salt, ester or prodrug thereof,
wherein,
X is $CHR_4$, $CR_4$, NH, $NR_4$ or N;
Y is $NR_5$, N, S, SO, $SO_2$, O, $CHR_5$, or $CR_5$; wherein at least one of X and Y is NH, $NR_4$, $NR_5$, N, S, SO, $SO_2$, or O;
A is a single bond or double bond;
B is a single bond or double bond, wherein both A and B are not double bonds;
R' is H or alkyl;
L is absent, S, SO, $SO_2$, or CO;
$R_1$ is H, alkyl, alkenyl, alkynyl, each containing 0, 1, 2, or 3 heteroatoms selected from O, S, or N; or $R_1$ is aryl, arylalkyl, heteroaryl, heterocyclic, or carbocyclic; wherein $R_1$ may be optionally substituted;

$R_2$ is hydrogen or optionally substituted alkyl;
$R_3$ is hydrogen, alkyl, alkenyl, aryl, arylalkyl, heteroaryl, heterocyclic, or carbocyclic, each of which may be optionally substituted;
$R_4$ is hydrogen, alkyl, alkenyl, aryl, arylalkyl, heteroaryl, heterocyclic, or carbocyclic, each of which may be optionally substituted;
$R_5$ is hydrogen, alkyl, alkenyl, aryl, arylalkyl, heteroaryl, heterocyclic, or carbocyclic, each of which may be optionally substituted;
or $R_3$ and X, together with the atoms to which they are attached, form a 3-8 membered carbocyclic, aryl, heterocyclic, or heteroaryl; each of which is optionally substituted;
or X and Y, together with the atoms to which they are attached, form a 3-8 membered carbocyclic, aryl, heterocyclic, or heteroaryl; each of which is optionally substituted; and
$R_6$ is hydrogen or optionally substituted alkyl.

In another aspect, the invention provides a compound of formula F:

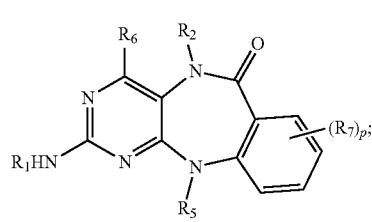

or a pharmaceutically acceptable salt, ester or prodrug thereof,
wherein,
$R^1$ is alkyl, aryl, heteroaryl, heterocyclic, or carbocyclic, wherein R1 may be optionally substituted;
$R^2$ is hydrogen or optionally substituted alkyl;
$R_5$ is hydrogen, optionally substituted alkyl, optionally substituted aralkyl, or optionally substituted carbocyclic; and
$R_6$ is hydrogen or optionally substituted alkyl;
each $R_7$ is independently alkyl, alkenyl, aryl, arylalkyl, heteroaryl, heterocyclic, carbocyclic, alkoxy, NH(alkyl), NH(aryl), N(alkyl)(alkyl), or N(alkyl)(aryl), each of which may be optionally substituted; hal, nitro, or cyano; and
p is 0-4;
or, when p is 2, 3, or 4, two occurrences of $R_7$ may be joined, together with the carbon atoms to which they are attached, to form an aryl or heteroaryl ring (e.g., having 5 or 6 atoms in the aryl or heteroaryl ring), e.g., a fused phenyl ring.

In certain embodiments, $R_1$ is methyl, ethyl, propyl, iso-propyl, butyl, s-butyl, t-butyl, pentyl, hexyl, cyclohexyl, piperidinyl, pyrrolidino, phenyl, 1-naphthyl, 2-naphthyl, pyridyl, pyrimidinyl, pyrazinyl, pyridizinyl, quinolinyl, thienyl, thiazolyl, oxazolyl, isoxazolyl, pyrrolyl, furanyl, isoquinolinyl, imiazolyl, or triazolyl, each of which may be optionally substituted.

In a further embodiment, $R_1$ is phenyl or pyridyl, each of which may be optionally substituted. In a further embodiment, $R_1$ is pyrazolyl. In certain embodiments, $R_1$ is

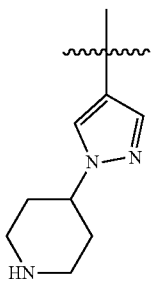

In another embodiment, $R_1$ is substituted with 0-4 substituents, selected from hal, nitro, cyano, hydroxyl, amino, NH(RA), N(RA)(RA), $CO_2H$, C(O)RA, C(O)ORA, C(O)$NH_2$, C(O)NH(RA), C(O)N(RA)(RA), alkyl, aryl, arylalkyl, alkoxy, heteroaryl, heterocyclic, and carbocyclic, each of which may be further substituted; wherein each RA is independently selected from alkyl, carbocyclic, aryl, heteroaryl, and heterocyclic.

In certain embodiments, two occurrences of $R_7$ are joined to form a phenyl ring.

In certain embodiments, the compound is:

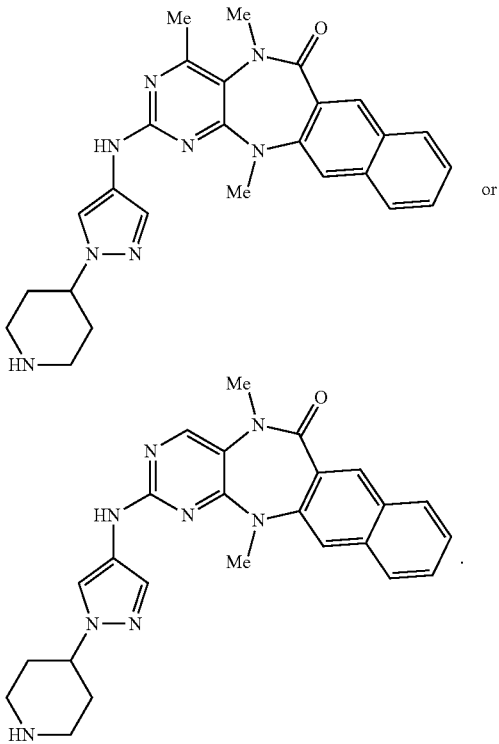

Representative compounds of the invention include, but are not limited to, the following compounds of Tables 1-6, which follow the Examples.

Suitable syntheses for compounds of the invention can be found in the Examples below. In addition, syntheses disclosed, e.g., in U.S. Patent Application Publication No. US-2012-0040961-A1 (the contents of which is incorporated herein by reference), can be used, with appropriate modifcations, to prepare compounds of the invention.

Another embodiment is a method of making a compound of any of the formulae herein using any one, or combination of, reactions delineated herein. The method can include the use of one or more intermediates or chemical reagents delineated herein.

Another aspect is an isotopically labeled compound of any of the formulae delineated herein. Such compounds have one or more isotope atoms which may or may not be radioactive (e.g., $^3H$, $^2H$, $^{14}C$, $^{13}C$, $^{35}S$, $^{32}P$, $^{125}I$, and $^{131}I$) introduced into the compound. Such compounds are useful for drug metabolism studies and diagnostics, as well as therapeutic applications.

A compound of the invention can be prepared as a pharmaceutically acceptable acid addition salt by reacting the free base form of the compound with a pharmaceutically acceptable inorganic or organic acid. Alternatively, a pharmaceutically acceptable base addition salt of a compound of the invention can be prepared by reacting the free acid form of the compound with a pharmaceutically acceptable inorganic or organic base.

Alternatively, the salt forms of the compounds of the invention can be prepared using salts of the starting materials or intermediates.

The free acid or free base forms of the compounds of the invention can be prepared from the corresponding base addition salt or acid addition salt from, respectively. For example a compound of the invention in an acid addition salt form can be converted to the corresponding free base by treating with a suitable base (e.g., ammonium hydroxide solution, sodium hydroxide, and the like). A compound of the invention in a base addition salt form can be converted to the corresponding free acid by treating with a suitable acid (e.g., hydrochloric acid, etc.).

Prodrug derivatives of the compounds of the invention can be prepared by methods known to those of ordinary skill in the art (e.g., for further details see Saulnier et al., (1994), Bioorganic and Medicinal Chemistry Letters, Vol. 4, p. 1985). For example, appropriate prodrugs can be prepared by reacting a non-derivatized compound of the invention with a suitable carbamylating agent (e.g., 1,1-acyloxyalkylcarbanochloridate, para-nitrophenyl carbonate, or the like).

Protected derivatives of the compounds of the invention can be made by means known to those of ordinary skill in the art. A detailed description of techniques applicable to the creation of protecting groups and their removal can be found in T. W. Greene, "Protecting Groups in Organic Chemistry", 3rd edition, John Wiley and Sons, Inc., 1999.

Compounds of the present invention can be conveniently prepared, or formed during the process of the invention, as solvates (e.g., hydrates). Hydrates of compounds of the present invention can be conveniently prepared by recrystallization from an aqueous/organic solvent mixture, using organic solvents such as dioxin, tetrahydrofuran or methanol.

Acids and bases useful in the methods herein are known in the art. Acid catalysts are any acidic chemical, which can be inorganic (e.g., hydrochloric, sulfuric, nitric acids, aluminum trichloride) or organic (e.g., camphorsulfonic acid, p-toluenesulfonic acid, acetic acid, ytterbium triflate) in nature. Acids are useful in either catalytic or stoichiometric amounts to facilitate chemical reactions. Bases are any basic chemical, which can be inorganic (e.g., sodium bicarbonate, potassium hydroxide) or organic (e.g., triethylamine, pyridine) in nature. Bases are useful in either catalytic or stoichiometric amounts to facilitate chemical reactions.

In addition, some of the compounds of this invention have one or more double bonds, or one or more asymmetric centers. Such compounds can occur as racemates, racemic mixtures, single enantiomers, individual diastereomers, diastereomeric mixtures, and cis- or trans- or E- or Z-double isomeric forms, and other stereoisomeric forms that may be defined, in terms of absolute stereochemistry, as (R)- or (S)-, or as (D)- or (L)- for amino acids. All such isomeric forms of these compounds are expressly included in the present invention. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981). The compounds of this invention may also be represented in multiple tautomeric forms, in such instances, the invention expressly includes all tautomeric forms of the compounds described herein (e.g., alkylation of a ring system may result in alkylation at multiple sites, the invention expressly includes all such reaction products). When the compounds described herein contain olefinic double bonds or other centers of geometric asymmetry, and unless specified otherwise, it is intended that the compounds include both E and Z geometric isomers. Likewise, all tautomeric forms are also intended to be included. The configuration of any carbon-carbon double bond appearing herein is selected for convenience only and is not intended to designate a particular configuration unless the text so states; thus a carbon-carbon double bond depicted arbitrarily herein as trans may be cis, trans, or a mixture of the two in any proportion. All such isomeric forms of such compounds are expressly included in the present invention. All crystal forms of the compounds described herein are expressly included in the present invention.

The synthesized compounds can be separated from a reaction mixture and further purified by a method such as column chromatography, high pressure liquid chromatography, or recrystallization. As can be appreciated by the skilled artisan, further methods of synthesizing the compounds of the formulae herein will be evident to those of ordinary skill in the art. Additionally, the various synthetic steps may be performed in an alternate sequence or order to give the desired compounds. In addition, the solvents, temperatures, reaction durations, etc. delineated herein are for purposes of illustration only and one of ordinary skill in the art will recognize that variation of the reaction conditions can produce the desired bridged macrocyclic products of the present invention. Synthetic chemistry transformations and protecting group methodologies (protection and deprotection) useful in synthesizing the compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

The compounds of this invention may be modified by appending various functionalities via any synthetic means delineated herein to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion.

The compounds of the invention are defined herein by their chemical structures and/or chemical names. Where a compound is referred to by both a chemical structure and a chemical name, and the chemical structure and chemical name conflict, the chemical structure is determinative of the compound's identity.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof.

Methods of the Invention

In another aspect, the invention provides a method of treating a disease in a subject comprising administering to the subject a compound, pharmaceutically acceptable salt, ester or prodrug of formulae I-IX (or formulae A or F).

In one embodiment, the invention provides a method wherein the disease is mediated by a kinase selected from a MAP kinase, a mitotic spindle kinase, and a polo kinase.

In another embodiment, the invention provides a method wherein the disease is mediated by a kinase selected from MPS1, ERK5, BMK1, MAPK7, polo kinase 1, 2, 3, or 4, Ack1, Ack2, Abl, DCAMKL1, ABL1, Abl mutants, DCAMKL2, ARK5, BRK, MKNK2, FGFR4, TNK1, PLK1, ULK2, PLK4, PRKD1, PRKD2, PRKD3, ROS1, RPS6KA6, TAOK1, TAOK3, TNK2, Bcr-Abl, GAK, cSrc, TPR-Met, Tie2, MET, FGFR3, Aurora, Axl, Bmx, BTK, c-kit, CHK2, Flt3, MST2, p70S6K, PDGFR, PKB, PKC, Raf, ROCK-II, Rsk1, SGK, TrkA, TrkB and TrkC. In a further embodiment, the kinase is ERK-5, MPS1, or BMK-1. In a further embodiment, the kinase is ERK-5, LRKK2, or EphA2.

In another embodiment, the invention provides a method wherein the disease is cancer or a proliferation disease.

In a further embodiment, the disease is lung, colon, breast, prostate, liver, pancreas, brain, kidney, ovaries, stomach, skin, and bone cancers, gastric, breast, pancreatic cancer, glioma, and hepatocellular carcinoma, papillary renal carcinoma, head and neck squamous cell carcinoma, leukemias, lymphomas, myelomas, and solid tumors.

In another embodiment, the disease is inflammation, arthritis, rheumatoid arthritis, spondylarthropathies, gouty arthritis, osteoarthritis, juvenile arthritis, and other arthritic conditions, systemic lupus erthematosus (SLE), skin-related conditions, psoriasis, eczema, burns, dermatitis, neuroinflammation, allergy, pain, neuropathic pain, fever, pulmonary disorders, lung inflammation, adult respiratory distress syndrome, pulmonary sarcoisosis, asthma, silicosis, chronic pulmonary inflammatory disease, and chronic obstructive pulmonary disease (COPD), cardiovascular disease, arteriosclerosis, myocardial infarction (including post-myocardial infarction indications), thrombosis, congestive heart failure, cardiac reperfusion injury, as well as complications associated with hypertension and/or heart failure such as vascular organ damage, restenosis, cardiomyopathy, stroke including ischemic and hemorrhagic stroke, reperfusion injury, renal reperfusion injury, ischemia including stroke and brain ischemia, and ischemia resulting from cardiac/coronary bypass, neurodegenerative disorders, liver disease and nephritis, gastrointestinal conditions, inflammatory bowel disease, Crohn's disease, gastritis, irritable bowel syndrome, ulcerative colitis, ulcerative diseases, gastric ulcers, viral and bacterial infections, sepsis, septic shock, gram negative sepsis, malaria, meningitis, HIV infection, opportunistic infections, cachexia secondary to infection or malignancy, cachexia secondary to acquired immune deficiency syndrome (AIDS), AIDS, ARC (AIDS related complex), pneumonia, herpes virus, myalgias due to infection, influenza, autoimmune disease, graft vs. host reaction and allograft rejections, treatment of bone resorption diseases, osteoporosis, multiple sclerosis, cancer, leukemia, lymphoma, colorectal cancer, brain cancer, bone cancer, epithelial call-derived neoplasia (epithelial carcinoma), basal cell carcinoma, adenocarcinoma, gastrointestinal cancer, lip cancer, mouth cancer, esophageal cancer, small bowel cancer, stomach cancer, colon cancer, liver cancer, bladder cancer, pancreas cancer, ovarian cancer, cervical cancer, lung cancer, breast cancer, skin cancer, squamus cell and/or basal cell cancers, prostate cancer, renal cell carcinoma, and other known cancers that affect epithelial cells throughout the body, chronic myelogenous leukemia (CML), acute myeloid leukemia (AML) and acute promyelocytic leukemia (APL), angiogenesis including neoplasia, metastasis, central nervous system disorders, central nervous system disorders having an inflammatory or apoptotic component, Alzheimer's disease, Parkinson's disease, Huntington's disease, amyotrophic lateral sclerosis, spinal cord injury, and peripheral neuropathy, Canine B-Cell Lymphoma.

In a further embodiment, the disease is inflammation, arthritis, rheumatoid arthritis, spondylarthropathies, gouty arthritis, osteoarthritis, juvenile arthritis, and other arthritic conditions, systemic lupus erthematosus (SLE), skin-related conditions, psoriasis, eczema, dermatitis, pain, pulmonary disorders, lung inflammation, adult respiratory distress syndrome, pulmonary sarcoisosis, asthma, chronic pulmonary inflammatory disease, and chronic obstructive pulmonary disease (COPD), cardiovascular disease, arteriosclerosis, myocardial infarction (including post-myocardial infarction indications), congestive heart failure, cardiac reperfusion injury, inflammatory bowel disease, Crohn's disease, gastritis, irritable bowel syndrome, leukemia, lymphoma.

In another aspect, the invention provides a method of treating a kinase mediated disorder in a subject comprising: administering to the subject identified as in need thereof a compound, pharmaceutically acceptable salt, ester or prodrug of formulae I-IX (or formulae A or F).

In one embodiment, the compound is an inhibitor of MPS1, ERK5, BMK1, MAPK7, polo kinase 1, 2, 3, or 4, Ack1, Ack2, Abl, DCAMKL1, ABL1, Abl mutants, DCAMKL2, ARK5, BRK, MKNK2, FGFR4, TNK1, PLK1, ULK2, PLK4, PRKD1, PRKD2, PRKD3, ROS1, RPS6KA6, TAOK1, TAOK3, TNK2, Bcr-Abl, GAK, cSrc, TPR-Met, Tie2, MET, FGFR3, Aurora, Axl, Bmx, BTK, c-kit, CHK2, Flt3, MST2, p70S6K, PDGFR, PKB, PKC, Raf, ROCK-H, Rsk1, SGK, TrkA, TrkB or TrkC. In a further embodiment, the compound is an inhibitor of ERK-5, MPS1, or BMK-1. In a further embodiment, the kinase is ERK-5, LRKK2, or EphA2.

In certain embodiments, the subject is administered an additional therapeutic agent.

In a further embodiment, the compound and the additional therapeutic agent are administered simultaneously or sequentially.

In another aspect, the invention provides a method for reducing kinase-dependent cell growth comprising contacting a cell with a kinase inhibitor compound of formulae I-IX (or formulae A or F).

In other aspects, the invention provides a method of inhibiting kinase in a subject identified as in need of such treatment, comprising administering a compound of formulae I-IX (or formulae A or F).

In certain embodiments, the invention provides a method wherein the subject is a human.

In other embodiments, the invention provides a method wherein the kinase inhibitor has a Ki for inhibiting kinase less than about 1 micromolar.

In one embodiment, the invention provides a method of synthesizing a compound of formulae I-IX (or formulae A or F).

Another aspect of this invention provides compounds or compositions that are inhibitors of protein kinases, and thus are useful for the treatment of the diseases, disorders, and conditions, along with other uses described herein. In certain embodiments, these compositions optionally further comprise one or more additional therapeutic agents.

The present invention provides compounds and compositions that are useful as inhibitors of protein kinases. In certain embodiments, the invention provides compounds and compositions that are useful as inhibitors of protein kinases selected from AAK1, ABL1, ABL1(E255K), ABL1 (F317I), ABL1(F317L), ABL1(H396P), ABL1(M351T), ABL1(Q252H), ABL1(T315I), ABL1(Y253F), ABL2, ACVR1, ACVR1B, ACVR2A, ACVR2B, ACVRL1, ADCK3, ADCK4, AKT1, AKT2, AKT3, ALK, AMPK-alpha1, AMPK-alpha2, ANKK1, ARK5, ASK1, ASK2, AURKA, AURKB, AURKC, AXL, BIKE, BLK, BMPR1A, BMPR1B, BMPR2, BMX, BRAF, BRAF(V600E), BRK, BRSK1, BRSK2, BTK, CAMK1, CAMK1D, CAMK1G, CAMK2A, CAMK2D, CAMK2G, CAMK4, CAMKK1, CAMKK2, CDC2L1, CDC2L2, CDK11, CDK2, CDK3, CDK5, CDK7, CDK8, CDK9, CDKL2, CDKL3, CDKL5, CHECK1, CHEK2, CIT, CLK1, CLK2, CLK3, CLK4, CSF1R, CSK, CSNK1A1L, CSNK1D, CSNK1E, CSNK1G1, CSNK1G3, CSNK2A1, CSNK2A2, CTK, DAPK1, DAPK2, DAPK3, DCAMKL1, DCAMKL2, DCAMKL3, DDR1, DDR2, DLK, DMPK, DMPK2, DRAK1, DRAK2, DYRK1A, DYRK1B, DYRK2, EGFR, EGFR (E746-A750DEL), EGFR (G719C), EGFR (G719S), EGFR(L747-E749del, A750P), EGFR(L747-S752del, P753S), EGFR(L747-T751del, Sins), EGFR(L858R), EGFR(L858R, T790M), EGFR(L861Q), EGFR(S752-1759del), EPHAL EPHA2, EPHA3, EPHA4, EPHA5, EPHA6, EPHA7, EPHA8, EPHB1, EPHB2, EPHB3, EPHB4, EPHB6, ERBB2, ERBB3, ERBB4, ERK1, ERK2, ERK3, ERK4, ERK5, ERK8, ERN1, FAK, FER, FES, FGFR1, FGFR2, FGFR3, FGFR3(G697C), FGFR4, FGR, FLT1, FLT3, FLT3(D835H), FLT3(D835Y), FLT3(ITD), FLT3(K663Q), FLT3(N841I), FLT4, FRK, FYN, GAK, GCN2(Kin.Dom.2, S808G), GRK1, GRK4, GRK7, GSK3A, GSK3B, HCK, HIPK1, HIPK2, HIPK3, HIPK4, HPK1, HUNK, ICK, IGF1R, IKK-ALPHA, IKK-BETA, IKK-EPSILON, INSR, INSRR, IRAK1, IRAK3, ITK, JAK1(JH1domain-catalytic), JAK1(JH2domain-pseudokinase), JAK2(JH1domain-catalytic), JAK3(JH1domain-catalytic), JNK1, JNK2, JNK3, KIT, KIT(D816V), KIT(L576P), KIT(V559D), KIT(V559D, T670I), KIT(V559D, V654A), LATS1, LATS2, LCK, LIMK1, LIMK2, LKB1, LOK, LTK, LYN, LZK, MAK, MAP3K1, MAP2K15, MAP3K2, MAP3K3, MAP3K4, MAP4K2, MAP4K3, MAP4K5, MAPKAPK2, MAPKAPK5, MARK1, MARK2, MARK3, MARK4, MAST1, MEK1, MEK2, MEK3, MEK4, MEK6, MELK, MERTK, MET, MET(M1250T), MET(Y1235D), MINK, MKNK1, MKNK2, MLCK, MLK1, MLK2, MLK3, MRCKA, MRCKB, MST1, MST1R, MST2, MST3, MST4, MUSK, MYLK, MYLK2, MYO3A, MYO3B, NDR1, NDR2, NEK1, NEK2, NEK5, NEK6, NEK7, NEK9, NIM1, NLK, OSR1, p38-alpha, p38-beta, p38-delta, p38-gamma, PAK1, PAK2, PAK3, PAK4, PAK6, PAK7, PCTK1, PCTK2, PCTK3, PDGFRA, PDGFRB, PDPK1, PFTAIRE2, PFTK1, PHKG1, PHKG2, PIK3C2B, PIK3C2G, PIK3CA, PIK3CA (C420R), PIK3CA(E542K), PIK3CA(E545A), PIK3CA (E545K), PIK3CA(H1047L), PIK3CA(H1047Y), PIK3CA (M1043I), PIK3CA(Q546K), PIK3CB, PIK3CD, PIK3CG, PIK4CB, PIM1, PIM2, PIM3, PIP5K1A, PIP5K2B, PKAC-ALPHA, PKAC-BETA, PKMYT1, PKN1, PKN2, PLK1, PLK2, PLK3, PLK4, PRKCD, PRKCE, PRKCH, PRKCQ, PRKD1, PRKD3, PRKG1, PRKG2, PRKR, PRKX, PRP4, PYK2, QSK, RAF1, RET, RET(M918T), RET(V804L), RET(V804M), RIOK1, RIOK2, RIOK3, RIPK1, RIPK2, RIPK4, ROCK1, ROCK2, ROS1, RPS6KA1(Kin.Dom. 1-N-terminal), RPS6KA1(Kin. Dom. 2-C-terminal), RPS6KA2(Kin.Dom.1-N-terminal), RPS6KA2(Kin.Dom.2-C-terminal), RPS6KA3(Kin.Dom.1-N-terminal), RPS6KA4 (Kin.Dom.1-N-terminal), RPS6KA4(Kin.Dom.2-C-terminal), RPS6KA5(Kin.Dom.1-N-terminal), RPS6KA5 (Kin.Dom.2-C-terminal), RPS6KA6(Kin.Dom.1-N-terminal), RPS6KA6(Kin.Dom.2-C-terminal), SBK1, SgK085, SgK110, SIK, SIK2, SLK, SNARK, SRC, SRMS, SRPK1, SRPK2, SRPK3, STK16, STK33, STK39, SYK, TAK1, TAO1, TAOK2, TAOK3, TBK1, TEC, TESK1, TGFBR1, TGFBR2, TIE1, TIE2, TLK1, TLK2, TNIK, TNK1, TNK2, TNNI3K, TRKA, TRKB, TRKC, TSSK1B, TTK, TXK, TYK2(JH1domain-catalytic), TYK2 (JH2domain-pseudokinase), TYRO3, ULK1, ULK2, ULK3, VEGFR2, WEE1, WEE2, YANK2, YANK3, YES, YSK1, YSK4, ZAK and ZAP70. In a further embodiment, the kinase is ERK-5, LRKK2, or EphA2.

In some embodiments, the present invention provides compounds and compositions that are useful as inhibitors of protein kinases selected from MPS1, ERK5, BMK1, MAPK7, polo kinase 1, 2, 3, or 4, Ack1, Ack2, Abl, DCAMKL1, ABL1, Abl mutants, DCAMKL2, ARK5, BRK, MKNK2, FGFR4, TNK1, PLK1, ULK2, PLK4, PRKD1, PRKD2, PRKD3, ROS1, RPS6KA6, TAOK1, TAOK3, TNK2, Bcr-Abl, GAK, cSrc, TPR-Met, Tie2, MET, FGFR3, Aurora, Axl, Bmx, BTK, c-kit, CHK2, Flt3, MST2, p70S6K, PDGFR, PKB, PKC, Raf, ROCK-H, Rsk1, SGK, TrkA, TrkB and TrkC. In a further embodiment, the kinase is ERK-5, LRKK2, or EphA2.

As inhibitors of protein kinases, the compounds and compositions of this invention are particularly useful for treating or lessening the severity of a disease, condition, or disorder where a protein kinase is implicated in the disease, condition, or disorder. In one aspect, the present invention provides a method for treating or lessening the severity of a disease, condition, or disorder where a protein kinase is implicated in the disease state. In another aspect, the present invention provides a method for treating or lessening the severity of a kinase disease, condition, or disorder where inhibition of enzymatic activity is implicated in the treatment of the disease. In another aspect, this invention provides a method for treating or lessening the severity of a disease, condition, or disorder with compounds that inhibit enzymatic activity by binding to the protein kinase. Another aspect provides a method for treating or lessening the severity of a kinase disease, condition, or disorder by inhibiting enzymatic activity of the kinase with a protein kinase inhibitor.

In some embodiments, said method is used to treat or prevent a condition selected from autoimmune diseases, inflammatory diseases, proliferative and hyperproliferative diseases, immunologically-mediated diseases, bone diseases, metabolic diseases, neurological and neurodegenerative diseases, cardiovascular diseases, hormone related diseases, allergies, asthma, and Alzheimer's disease. In other embodiments, said condition is selected from a proliferative disorder and a neurodegenerative disorder.

One aspect of this invention provides compounds that are useful for the treatment of diseases, disorders, and conditions characterized by excessive or abonormal cell proliferation.

Such diseases include, a proliferative or hyperproliferative disease, and a neurodegenerative disease. Examples of proliferative and hyperproliferative diseases include, without limitation, cancer. The term "cancer" includes, but is not limited to, the following cancers: breast; ovary; cervix; prostate; testis, genitourinary tract; esophagus; larynx, glioblastoma; neuroblastoma; stomach; skin, keratoacanthoma; lung, epidermoid carcinoma, large cell carcinoma, small cell carcinoma, lung adenocarcinoma; bone; colon; colorectal; adenoma; pancreas, adenocarcinoma; thyroid, follicular carcinoma, undifferentiated carcinoma, papillary carcinoma; seminoma; melanoma; sarcoma; bladder carcinoma; liver carcinoma and biliary passages; kidney carcinoma; myeloid disorders; lymphoid disorders, Hodgkin's, hairy cells; buccal cavity and pharynx (oral), lip, tongue, mouth, pharynx; small intestine; colon-rectum, large intestine, rectum, brain and central nervous system; chronic myeloid leukemia (CML), and leukemia. The term "cancer" includes, but is not limited to, the following cancers: myeloma, lymphoma, or a cancer selected from gastric, renal, or and the following cancers: head and neck, oropharangeal, non-small cell lung cancer (NSCLC), endometrial, hepatocarcinoma, Non-Hodgkins lymphoma, and pulmonary.

In some embodiments, the compounds of this invention are useful for treating cancer, such as colorectal, thyroid, breast, and lung cancer; and myeloproliferative disorders, such as polycythemia vera, thrombocythemia, myeloid metaplasia with myelofibrosis, chronic myelogenous leukemia, chronic myelomonocytic leukemia, hypereosinophilic syndrome, juvenile myelomonocytic leukemia, and systemic mast cell disease.

In some embodiments, the compounds of this invention are useful for treating hematopoietic disorders, in particular, acute-myelogenous leukemia (AMLi), chronic-myelogenous leukemia (CML), acute-promyelocytic leukemia, and acute lymphocytic leukemia (ALL).

Examples of neurodegenerative diseases include, without limitation, Alzheimer's disease.

Another aspect of this invention provides a method for the treatment or lessening the severity of a disease selected from a proliferative or hyperproliferative disease, or a neurodegenerative disease, comprising administering an effective amount of a compound, or a pharmaceutically acceptable composition comprising a compound, to a subject in need thereof.

The present invention provides compounds, compositions and methods for the treatment of kinase related disease, particularly MPS1, ERK5, BMK1, MAPK7, polo kinase 1, 2, 3, or 4, Ack1, Ack2, Abl, DCAMKL1, ABL1, Abl mutants, DCAMKL2, ARK5, BRK, MKNK2, FGFR4, TNK1, PLK1, ULK2, PLK4, PRKD1, PRKD2, PRKD3, ROS1, RPS6KA6, TAOK1, TAOK3, TNK2, Bcr-Abl, GAK, cSrc, TPR-Met, Tie2, MET, FGFR3, Aurora, Axl, Bmx, BTK, c-kit, CHK2, Flt3, MST2, p70S6K, PDGFR, PKB, PKC, Raf, ROCK-H, Rsk1, SGK, TrkA, TrkB and TrkC kinase related diseases. In a further embodiment, the kinase is ERK-5, LRKK2, or EphA2.

Compounds of the invention modulate the activity of kinases and, as such, are useful for treating diseases or disorders in which kinases, contribute to the pathology and/or symptomology of the disease. Examples of kinases that are inhibited by the compounds and compositions described herein and against which the methods described herein are useful include, but are not limited to, MPS1, ERK5, BMK1, MAPK7, polo kinase 1, 2, 3, or 4, Ack1, Ack2, Abl, DCAMKL1, ABL1, Abl mutants, DCAMKL2, ARK5, BRK, MKNK2, FGFR4, TNK1, PLK1, ULK2, PLK4, PRKD1, PRKD2, PRKD3, ROS1, RPS6KA6, TAOK1, TAOK3, TNK2, Bcr-Abl, GAK, cSrc, TPR-Met, Tie2, MET, FGFR3, Aurora, Axl, Bmx, BTK, c-kit, CHK2, Flt3, MST2, p70S6K, PDGFR, PKB, PKC, Raf, ROCK-H, Rsk1, SGK, TrkA, TrkB and TrkC kinases. In a further embodiment, the kinase is ERK-5, LRKK2, or EphA2.

As inhibitors of protein kinases, the compounds and compositions of this invention are also useful in biological samples. One aspect of the invention relates to inhibiting protein kinase activity in a biological sample, which method comprises contacting said biological sample with a compound of the invention or a composition comprising said compound. The term "biological sample", as used herein, means an in vitro or an ex vivo sample, including, without limitation, cell cultures or extracts thereof; biopsied material obtained from a mammal or extracts thereof and blood, saliva, urine, feces, semen, tears, or other body fluids or extracts thereof. Inhibition of protein kinase activity in a biological sample is useful for a variety of purposes that are known to one of skill in the art. Examples of such purposes include, but are not limited to, blood transfusion, organ-transplantation, and biological specimen storage.

Another aspect of this invention relates to the study of protein kinases in biological and pathological phenomena; the study of intracellular signal transduction pathways mediated by such protein kinases; and the comparative evaluation of new protein kinase inhibitors. Examples of such uses include, but are not limited to, biological assays such as enzyme assays and cell-based assays.

The activity of the compounds as protein kinase inhibitors may be assayed in vitro, in vivo or in a cell line. In vitro assays include assays that determine inhibition of either the kinase activity or ATPase activity of the activated kinase. Alternate in vitro assays quantitate the ability of the inhibitor to bind to the protein kinase and may be measured either by radiolabelling the inhibitor prior to binding, isolating the inhibitor/kinase complex and determining the amount of radiolabel bound, or by running a competition experiment where new inhibitors are incubated with the kinase bound to known radioligands. Detailed conditions for assaying a compound utilized in this invention as an inhibitor of various kinases are set forth in the Examples below.

In accordance with the foregoing, the present invention further provides a method for preventing or treating any of the diseases or disorders described above in a subject in need of such treatment, which method comprises administering to said subject a therapeutically effective amount of a compound of the invention or a pharmaceutically acceptable salt thereof. For any of the above uses, the required dosage will vary depending on the mode of administration, the particular condition to be treated and the effect desired.

Pharmaceutical Compositions

In another aspect, the invention provides a pharmaceutical composition comprising a compound of formulae I-IX (or formulae A or F), or a pharmaceutically acceptable ester, salt, or prodrug thereof, together with a pharmaceutically acceptable carrier.

Compounds of the invention can be administered as pharmaceutical compositions by any conventional route, in particular enterally, e.g., orally, e.g., in the form of tablets or capsules, or parenterally, e.g., in the form of injectable solutions or suspensions, topically, e.g., in the form of lotions, gels, ointments or creams, or in a nasal or suppository form. Pharmaceutical compositions comprising a compound of the present invention in free form or in a pharmaceutically acceptable salt form in association with at least one pharmaceutically acceptable carrier or diluent can be manufactured in a conventional manner by mixing, granulating or coating methods. For example, oral compositions can be tablets or gelatin capsules comprising the active ingredient together with a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and or polyvinylpyrrolidone; if desired d) disintegrants, e.g., starches, agar, alginic acid or its sodium salt, or effervescent mixtures; and/or e) absorbents, colorants, flavors and sweeteners. Injectable compositions can be aqueous isotonic solutions or suspensions, and suppositories can be prepared from fatty emulsions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Suitable formulations for transdermal applications include an effective amount of a compound of the present invention with a carrier. A carrier can include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Matrix transdermal formulations may also be used. Suitable formulations for topical application, e.g., to the skin and eyes, are preferably aqueous solutions, ointments, creams or gels well-known in the art. Such may contain solubilizers, stabilizers, tonicity enhancing agents, buffers and preservatives.

Compounds of the invention can be administered in therapeutically effective amounts in combination with one or more therapeutic agents (pharmaceutical combinations). For example, synergistic effects can occur with other immunomodulatory or anti-inflammatory substances, for example when used in combination with cyclosporin, rapamycin, or ascomycin, or immunosuppressant analogues thereof, for example cyclosporin A (CsA), cyclosporin G, FK-506, rapamycin, or comparable compounds, corticosteroids, cyclophosphamide, azathioprine, methotrexate, brequinar, leflunomide, mizoribine, mycophenolic acid, mycophenolate mofetil, 15-deoxyspergualin, immunosuppressant antibodies, especially monoclonal antibodies for leukocyte receptors, for example MHC, CD2, CD3, CD4, CD7, CD25, CD28, B7, CD45, CD58 or their ligands, or other immunomodulatory compounds, such as CTLA41g. Where the compounds of the invention are administered in conjunction with other therapies, dosages of the co-administered compounds will of course vary depending on the type of co-drug employed, on the specific drug employed, on the condition being treated and so forth.

The pharmaceutical compositions of the present invention comprise a therapeutically effective amount of a compound of the present invention formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. The pharmaceutical compositions of this invention can be administered to humans and other animals orally, rectally, parenterally, intracisternally, intravaginally, intraperitoneally, topically (as by powders, ointments, or drops), buccally, or as an oral or nasal spray.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to the methods of treatment of the present invention, disorders are treated or prevented in a subject, such as a human or other animal, by administering to the subject a therapeutically effective amount of a compound of the invention, in such amounts and for such time as is necessary to achieve the desired result. The term "therapeutically effective amount" of a compound of the invention, as used herein, means a sufficient amount of the compound so as to decrease the symptoms of a disorder in a subject. As is well understood in the medical arts a therapeutically effective amount of a compound of this invention will be at a reasonable benefit/risk ratio applicable to any medical treatment.

In general, compounds of the invention will be administered in therapeutically effective amounts via any of the usual and acceptable modes known in the art, either singly or in combination with one or more therapeutic agents. A therapeutically effective amount may vary widely depending on the severity of the disease, the age and relative health of the subject, the potency of the compound used and other factors. In general, satisfactory results are indicated to be obtained systemically at daily dosages of from about 0.03 to 2.5 mg/kg per body weight. An indicated daily dosage in the larger mammal, e.g. humans, is in the range from about 0.5 mg to about 100 mg, conveniently administered, e.g. in divided doses up to four times a day or in retard form. Suitable unit dosage forms for oral administration comprise from ca. 1 to 50 mg active ingredient.

In certain embodiments, a therapeutic amount or dose of the compounds of the present invention may range from about 0.1 mg/Kg to about 500 mg/Kg, alternatively from about 1 to about 50 mg/Kg. In general, treatment regimens according to the present invention comprise administration to a patient in need of such treatment from about 10 mg to about 1000 mg of the compound(s) of this invention per day in single or multiple doses. Therapeutic amounts or doses will also vary depending on route of administration, as well as the possibility of co-usage with other agents.

Upon improvement of a subject's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. The subject may, however, require intermittent treatment on a long-term basis upon any recurrence of disease symptoms.

It will be understood, however, that the total daily usage of the compounds and compositions of the present invention will be decided by the attending physician within the scope of sound medical judgment. The specific inhibitory dose for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The invention also provides for a pharmaceutical combinations, e.g. a kit, comprising a) a first agent which is a compound of the invention as disclosed herein, in free form or in pharmaceutically acceptable salt form, and b) at least one co-agent. The kit can comprise instructions for its administration.

The terms "co-administration" or "combined administration" or the like as utilized herein are meant to encompass administration of the selected therapeutic agents to a single patient, and are intended to include treatment regimens in which the agents are not necessarily administered by the same route of administration or at the same time.

The term "pharmaceutical combination" as used herein means a product that results from the mixing or combining of more than one active ingredient and includes both fixed and non-fixed combinations of the active ingredients. The term "fixed combination" means that the active ingredients, e.g. a compound of the invention and a co-agent, are both administered to a patient simultaneously in the form of a single entity or dosage. The term "non-fixed combination" means that the active ingredients, e.g. a compound of the invention and a co-agent, are both administered to a patient as separate entities either simultaneously, concurrently or sequentially with no specific time limits, wherein such administration provides therapeutically effective levels of the two compounds in the body of the patient. The latter also applies to cocktail therapy, e.g. the administration of three or more active ingredients.

In certain embodiments, these compositions optionally further comprise one or more additional therapeutic agents. For example, chemotherapeutic agents or other antiproliferative agents may be combined with the compounds of this invention to treat proliferative diseases and cancer. Examples of known chemotherapeutic agents include, but are not limited to, Gleevec™, adriamycin, dexamethasone, vincristine, cyclophosphamide, fluorouracil, topotecan, taxol, interferons, and platinum derivatives.

Other examples of agents the compounds of this invention may also be combined with include, without limitation: treatments for Alzheimer's Disease such as Aricept18 and Excelon®; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif®), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-I RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and antiparkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and antiviral agents; agents for treating blood disorders such as corticosteroids, antileukemic agents, and growth factors; and agents for treating immunodeficiency disorders such as gamma globulin. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes, oils such as peanut oil, cottonseed oil; safflower oil; sesame oil; olive oil; corn oil and soybean oil; glycols; such a propylene glycol or polyethylene glycol; esters such as ethyl oleate and ethyl laurate, agar; buffering agents such as magnesium hydroxide and aluminum hydroxide; alginic acid; pyrogen-free water, isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The protein kinase inhibitors or pharmaceutical salts thereof may be formulated into pharmaceutical compositions for administration to animals or humans. These pharmaceutical compositions, which comprise an amount of the protein inhibitor effective to treat or prevent a protein kinase-mediated condition and a pharmaceutically acceptable carrier, are another embodiment of the present invention.

In another aspect, the invention provides a kit comprising a compound capable of inhibiting kinase activity selected from one or more compounds of formulae I-IX (or formulae A or F), and instructions for use in treating cancer.

EXAMPLES

The compounds and processes of the present invention will be better understood in connection with the following examples, which are intended as an illustration only and not to limit the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

The following synthesis examples illustrate suitable methods for preparing compounds of the invention.

Example 1: Synthesis of Thiophene Compounds of Formula IV

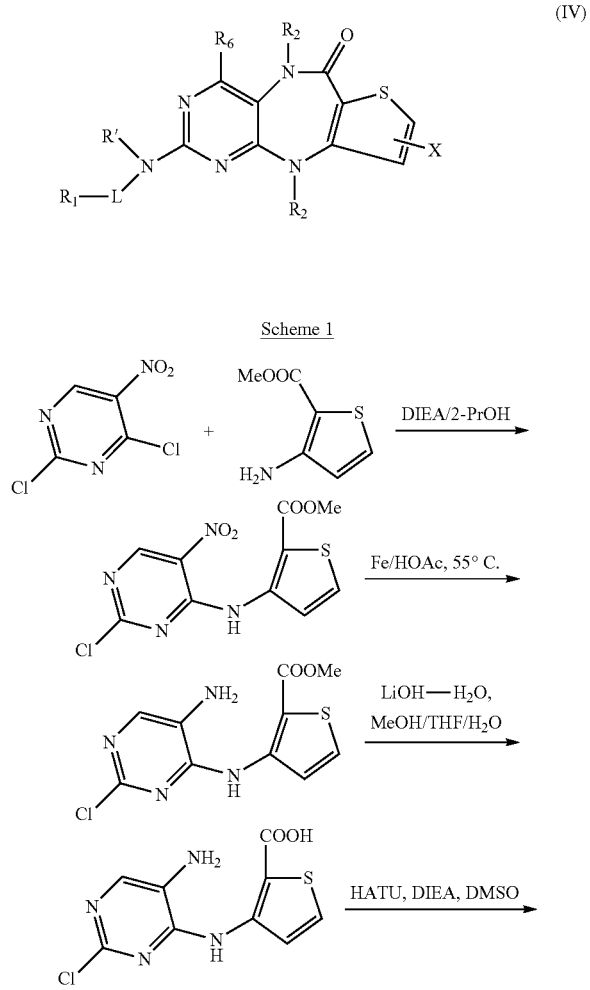

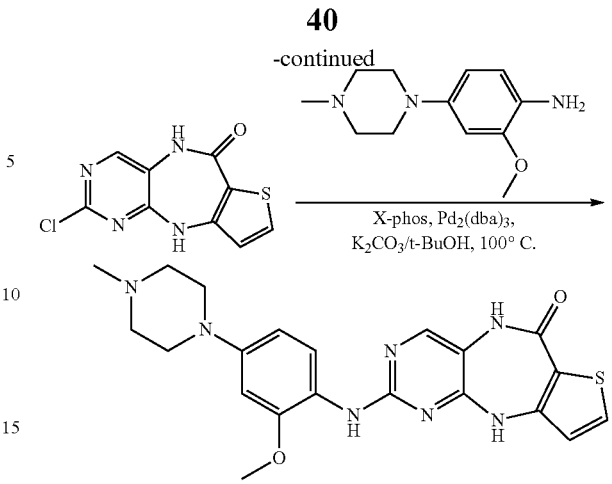

To a stirred solution of methyl 3-aminothiophene-2-carboxylate (2.36 g, 15 mmol) and DIEA (5.22 mL, 30 mmol) in 2-PrOH (60 mL) was added 2,4-dichloro-5-nitropyrimidine (3.78 g, 19.5 mmol) in one portion at room temperature. Then the reaction was stirred at RT. After the reaction complete as monitored by LC-MS, the resulting mixture was diluted with ethyl acetate and washed with water and brine, the organic layer was dried over anhydrous sodium sulfate and concentrated in vacuo. The residue was used for next step directly without further purification.

A mixture of methyl 3-(2-chloro-5-nitropyrimidin-4-ylamino)thiophene-2-carboxylate and iron power (8.4 g, 150 mmol) in acetic acid (220 mL) was heated at 55° C. After the reaction complete, the mixture was concentrated in vacuo. Then the residue was purified by silica-gel column chromatography with methanol and dichloromethane to give methyl 3-(5-amino-2-chloropyrimidin-4-ylamino)thiophene-2-carboxylate (4.2 g, 98%).

To a suspension of methyl 3-(5-amino-2-chloropyrimidin-4-ylamino)thiophene-2-carboxylatein in methanol/tetrahydrofuran (30 mL/30 mL) was added LiOH solution (3.99 g (95 mmol) in 30 mL water) at room temperature. After the reaction complete as monitored by LC-MS, the reaction mixture was concentrated and neutralized with 6 N HCl till PH to 5. The precipitated solid was collected. The aqueous layer was extracted with CHCl3/i-PrOH (4/1) twice. The organic layer was washed with brine and dried over anhydrous sodium sulfate. The solvent was removed in vacuo. This portion of product was combined with the precipitated solid.

A reaction mixture of 3-(5-amino-2-chloropyrimidin-4-ylamino)thiophene-2-carboxylic acid (1.17 g, 4.33 mmol), HATU (2.47 g, 6.5 mmol) and DIEA (2.27 mL, 13 mmol) in 25.0 mL of dimethyl sulfoxide (DMSO) was stirred at room temperature. After the reaction complete as monitored by LC-MS, the solution was poured into ice-water. The precipitated solid was collected and lyophilyzed. The crude product was used in next step without further purification.

A mixture of starting material (25 mg, 0.1 mmol), 2-methoxy-4-(4-methylpiperazin-1-yl)benzenamine (22 mg, 0.1 mmol), X-Phos (4.3 mg), Pd$_2$(dba)$_3$ (5.5 mg) and K$_2$CO$_3$ (41.5 mg, 0.3 mmol) in t-BuOH (1.5 mL) was heated at 100° C. in a seal tube for 4 h. Then the reaction was filtered through celite and eluted with dichloromethane. The solvent was removed in vacuo and the residue was purified by ISCO to afford the title compound (24.7 mg).

Example 2: Synthesis of Sulfone Compounds of Formula III

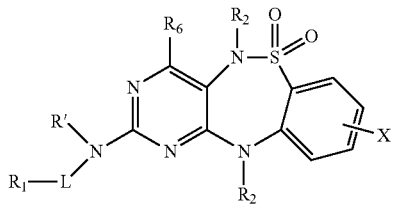

Scheme 2

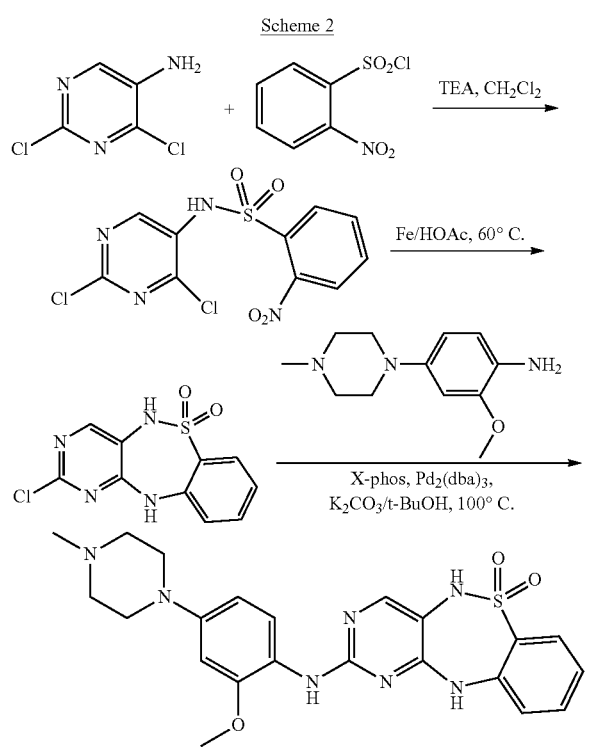

To a stirred solution of 2,4-dichloropyrimidin-5-amine (328 mg, 2.0 mmol) and TEA (0.42 mL, 3.0 mmol) in dichloromethane (6.0 mL) was added 2-nitrobenzene-1-sulfonyl chloride (443 mg, 2.0 mmol) in one portion at 0° C. The reaction mixture was stirred and allowed to approach room temperature. After the reaction complete as monitored by LC-MS, the resulting mixture was diluted with dichloromethane and washed with water and brine, the organic layer was dried over anhydrous sodium sulfate and concentrated in vacuo. The residue was purified by silica gel chromatography with dichloromethane:methanol to give the desired compound N-(2,4-dichloropyrimidin-5-yl)-2-nitrobenzenesulfonamide (359 mg, 52%).

A mixture of N-(2,4-dichloropyrimidin-5-yl)-2-nitrobenzenesulfonamide (190 mg, 0.55 mmol) and iron power (560 mg, 10 mmol) in acetic acid (8 mL) was heated at 60° C. After the reaction complete, the mixture was concentrated in vacuo and poured into ice-water. The precipitated solid was collected and lyophilyzed. The crude product was used in next step without further purification.

A mixture of starting material (28 mg, 0.1 mmol), 2-methoxy-4-(4-methylpiperazin-1-yl)benzenamine (22 mg, 0.1 mmol), X-Phos (4.3 mg), Pd$_2$(dba)$_3$ (5.5 mg) and K$_2$CO$_3$ (41.5 mg, 0.3 mmol) in t-BuOH (1.5 mL) was heated at 100° C. in a seal tube for 4 h. The reaction was then filtered through celite, eluted with dichloromethane, and concentrated in vacuo. The residue was then purified by reverse-phase prep-HPLC to afford the title compound as the TFA salt (7.2 mg, 15%).

Example 3: Synthesis of Tetracyclic Compounds of Formula I

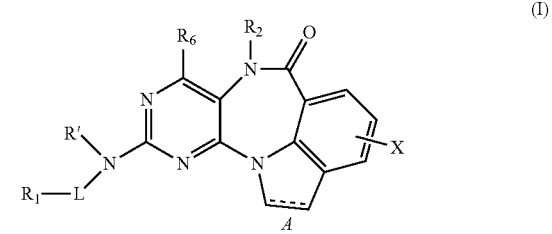

Scheme 3

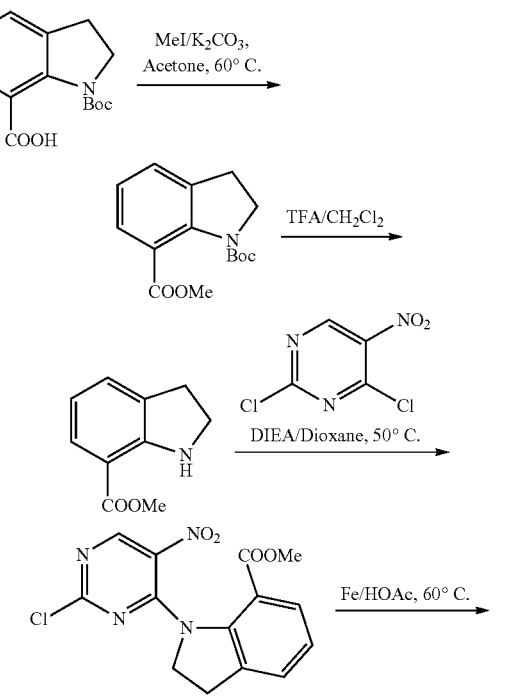

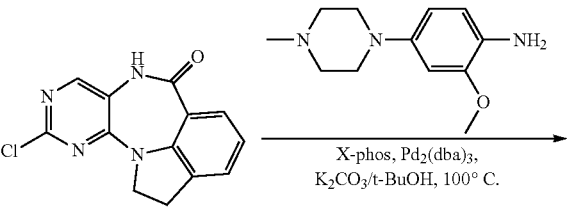

-continued

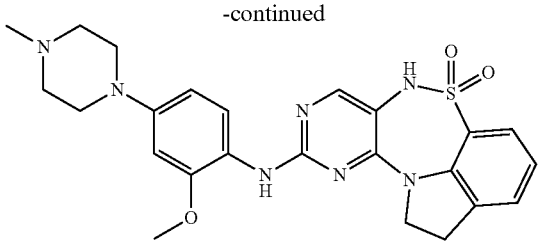

A mixture of 1-(tert-butoxycarbonyl)indoline-7-carboxylic acid (460 mg, 1.75 mmol), MeI (0.22 mL, 3.5 mmol) and potassium carbonate (484 mg, 3.5 mmol) in acetone (20 mL) was heated at 60° C. After the reaction was complete, the reaction mixture was filtered through celite, eluted with dichloromethane and concentrated in vacuo. The residue was purified by silica gel chromatography with hexanes: ethyl acetate to give 1-tert-butyl 7-methyl indoline-1,7-dicarboxylate (390 mg, 80%).

A mixture of 1-tert-butyl 7-methyl indoline-1,7-dicarboxylate (390 mg, 1.41 mmol) and TFA (2.5 mL) in dichloromethane (8 mL) was stirred at room temperature. After the reaction complete as monitored by LC-MS, the mixture was concentrated in vacuo. The residue was dissolved in ethyl acetate and washed with saturated sodium bicarbonate. The organic layer was dried over anhydrous sodium sulfate and concentrated in vacuo. The crude product was used in next step without further purification.

A mixture of methyl 1-indoline-7-carboxylate (244 mg, 1.37 mmol), 2,4-dichloro-5-nitropyrimidine (400 mg, 2.06 mmol) and DIEA (0.72 mL, 4.1 mmol) in dioxane (17 mL) was stirred at 50° C. After the reaction complete as monitored by LC-MS, the resulting mixture was concentrated in vacuo and purified by silica gel chromatography to give methyl 1-(2-chloro-5-nitropyrimidin-4-yl)indoline-7-carboxylate (433 mg, 94%).

A mixture of methyl 1-(2-chloro-5-nitropyrimidin-4-yl)indoline-7-carboxylate (188 mg, 0.69 mmol) and iron power (800 mg, 14.3 mmol) in acetic acid (12 mL) was heated at 55° C. After the reaction complete, the mixture was concentrated in vacuo and poured into ice-water. The precipitated solid was collected and lyophilyzed. The crude product was used in next step without further purification.

A mixture of starting material (27 mg, 0.1 mmol), 2-methoxy-4-(4-methylpiperazin-1-yl)benzenamine (22 mg, 0.1 mmol), X-Phos (4.3 mg), Pd$_2$(dba)$_3$ (5.5 mg) and K$_2$CO$_3$ (41.5 mg, 0.3 mmol) in t-BuOH (1.5 mL) was heated at 100° C. in a seal tube for 4 h. The reaction was then filtered through celite, eluted with dichloromethane, and concentrated in vacuo. The residue was then purified by reverse-phase prep-HPLC to afford the title compound as the TFA salt (21.5 mg, 47%).

Example 4: Synthesis of Compounds of Formula II

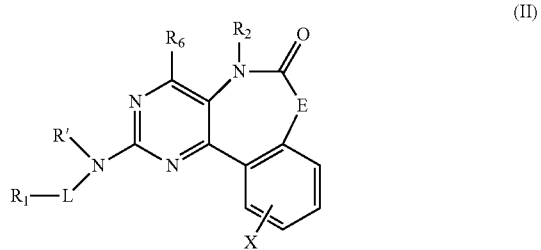

Scheme 4

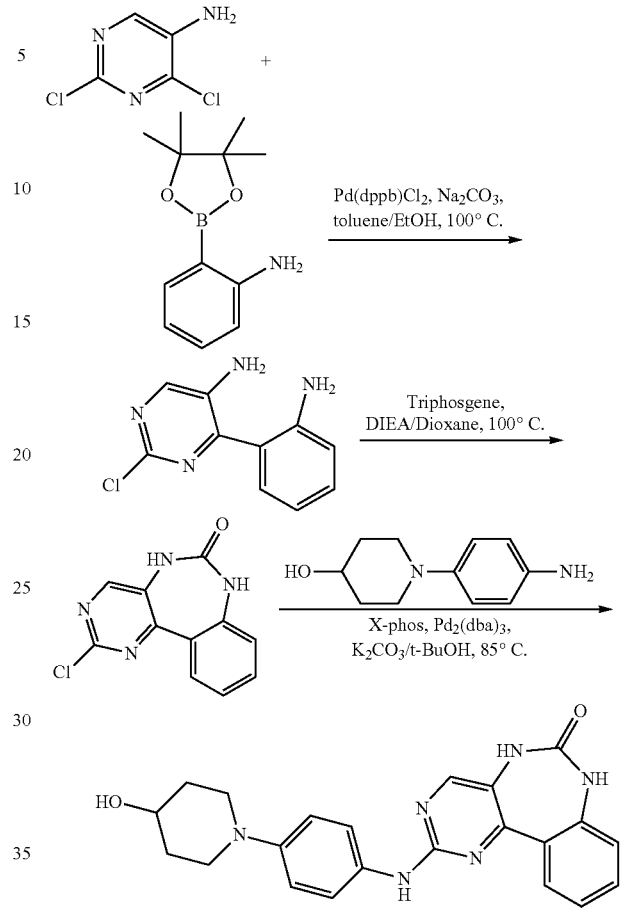

A mixture of 2,4-dichloropyrimidin-5-amine (246 mg, 1.5 mmol), 2-(4,4,5,5-tetramethyl-1,3,2-dioxaborolan-2-yl)benzenamine (219 mg, 1.0 mmol), Pd(dppb)Cl$_2$ (60 mg, 0.1 mmol) and Na$_2$CO$_3$ (4 mL, 1.0 M solution) in toluene/EtOH (2.0 mL/3.0 mL) was heated at 100° C. in a seal tube for 3 h. The reaction was then filtered through celite, eluted with dichloromethane, washed by brine, and concentrated in vacuo. The residue was then purified by silica gel chromatography with 3.5 N ammonia in MeOH solution: dichloromethane to give 4-(2-aminophenyl)-2-chloropyrimidin-5-amine (158 mg, 48%).

To a stirred solution of 4-(2-aminophenyl)-2-chloropyrimidin-5-amine (17 mg, 0.077 mmol) in dioxane (2.5 mL) were added DIEA (0.04 mL) and triphosgene (11 mg, 0.039 mmol) at room temperature. Then the reaction was stirred at 100° C. After the reaction complete as monitored by LC-MS, the solution was poured into ice-water. The precipitated solid was collected and lyophilized. The crude product was used in next step without further purification.

A mixture of starting material (12 mg, 0.05 mmol), 1-(4-aminophenyl)piperidin-4-ol (10 mg, 0.05 mmol), X-Phos (4.3 mg), Pd$_2$(dba)$_3$ (5.5 mg) and K$_2$CO$_3$ (30 mg, 0.22 mmol) in t-BuOH (1.0 mL) was heated at 85° C. in a seal tube for 4 h. The reaction was then filtered through celite, eluted with dichloromethane, and concentrated in vacuo. The residue was then purified by reverse-phase prep-HPLC to afford the title compound as the TFA salt (8.2 mg, 40%).

Example 5: Synthesis of Compounds of Formula V

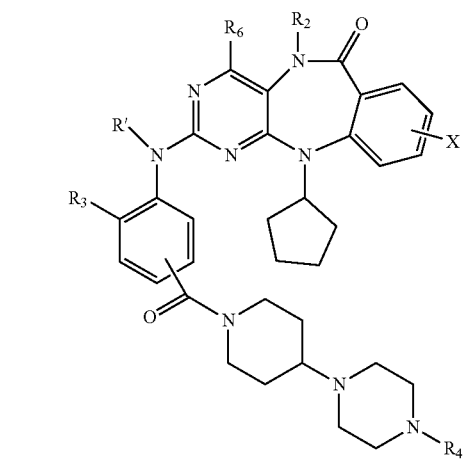

(V)

Scheme 5

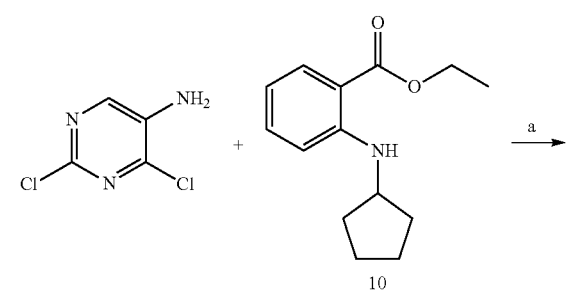

a

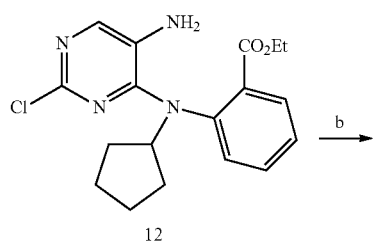

b

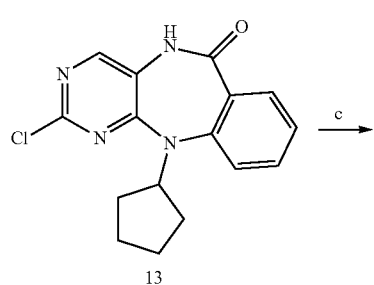

c

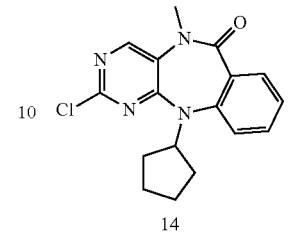

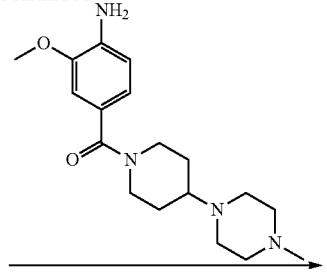

d

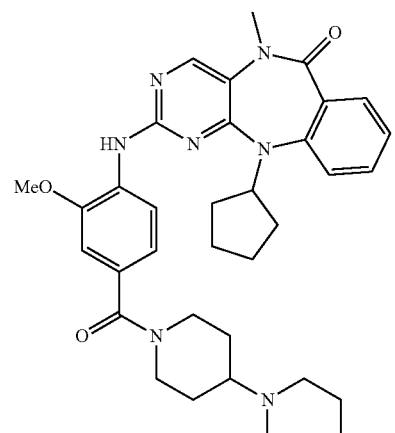

25

<sup>a</sup>Reagents and conditions: (a) 4 N HCl in Dioxane, Dioxane, 60° C.; (b) Fe/HOAc, 60° C.; (c) MeI/NaH, DMA, 0° C.; (d) X-Phos (9% mol), Pd$_2$(dba)$_3$ (6% mol), K$_2$CO$_3$ (3.0 eq.), t-BuOH, 100° C.

Chemistry.

An efficient four-step synthetic route was developed to enable the synthesis of benzo[e]pyrimido-[5,4-b]diazepine-6(11H)-ones. The synthesis of 25 using a modified synthetic procedure is outlined in Scheme 5. First, 2,4-dichloro-5-nitropyrimidine was reacted with N-cyclopentylanthranilic ethyl ester under acidic conditions using 4 N of hydrochloride in dioxane at 60° C. to give the amination product 12 in good yield. Using basic conditions with diisopropylethyl amine, only trace quantities of the amination product 12 were obtained and 2,4-dichloro-5-nitropyrimidine was hydrolyzed completely. We suspect that the substituted reaction under basic condition was hampered by the steric hindrance imposed by the bulky N-cyclopentylanthranilic ethyl ester substrate. We also observed that the yield of the substitution reaction under acidic conditions is higher than that obtained under basic condition when the N-isopropyl anthranilic ethyl ester is used as a substrate. The substitution reaction was followed by iron-mediated reduction of 12 and in situ cyclization in acetic acid at 60° C. to afford the 7-member lactam intermediate 13 in good yield. Compound 25 was obtained via methylation of 13 of the lactam followed by palladium mediated amination of 14 with (4-amino-3-methoxyphenyl)(4-(4-methylpiperazin-1-yl)piperidin-1-yl)methanone.

In more detail:

A mixture of ethyl 2-(cyclopentylamino)benzoate (1.40 g, 6.0 mmol), 4 N HCl in dioxane solution (2.25 mL, 9.0 mmol) and 2,4-dichloro-5-nitropyrimidine (1.74 g, 9.0 mmol) in dioxane (40 mL) was heated at 60° C. for 90 hours. After the reaction was complete as monitored by thin layer chromatography (TLC), the reaction solution was concentrated and the residue was purified by silica-gel column chromatography with ethyl acetate and hexane (1/20, v/v) to give the amination product 12 (1.84 g, 79%). MS (ESI) m/z 391 (M+H)$^+$.

A mixture of compound 12 (1.79 g, 4.59 mmol) and iron powder (2.57 g, 45.9 mmol) in acetic acid (80 mL) was heated at 60° C. for 9 hours. After the reaction was complete as monitored by reverse phase analytical liquid-chromatography electrospray mass spectrometry (LC-MS), the solvent was removed in vacuo. The resulting residue was poured into ice-water which resulted in a solid precipitate that was collected by filtration, washed with water and air dried to give the intermediate 13 (1.21 g, 84%). $^1$H NMR (600 MHz, DMSO-d$_6$) δ 10.48 (s, 1H), 8.18 (s, 1H), 7.57 (d, J=7.2 Hz, 1H), 7.50 (s, 1H), 7.30 (d, J=7.2 Hz, 1H), 7.17 (s, 1H), 4.61 (brs, 1H), 2.30-1.90 (m, 2H), 1.70-1.40 (m, 4H), 1.38-1.20 (m, 2H). MS (ESI) m/z 315 (M+H)$^+$.

To a stirred suspension of compound 13 (314 mg, 1.0 mmol) and MeI (0.13 mL, 2.0 mmol) in dimethyl acetamide (DMA, 10.0 mL) was added NaH (80 mg, 60% suspension in mineral oil) at −10° C. and the reaction was gradually warmed to 0° C. After the reaction was complete as monitored by LC-MS, the solution was poured into ice-water which resulted in a solid precipitate. The precipitate was collected by filtration, washed with water and air dried to give the intermediate 14 (273 mg, 83%). $^1$H NMR (600 MHz, DMSO-d$_6$) δ 8.64 (s, 1H), 7.58 (dd, J=1.8, 7.8 Hz, 1H), 7.49 (t, J=7.8 Hz, 1H), 7.33 (d, J=8.4 Hz, 1H), 7.19 (t, J=7.2 Hz, 1H), 4.68-4.64 (m, 1H), 3.44 (s, 3H), 2.28-2.20 (m, 1H), 2.10-2.02 (m, 1H), 1.64-1.54 (m, 4H), 1.50-1.34 (m, 2H). MS (ESI) m/z 329 (M+H)+.

A mixture of 14 (33 mg, 0.1 mmol), (4-amino-3-methoxyphenyl)(4-(4-methylpiperazin-1-yl)piperidin-1-yl)methanone (33 mg, 0.1 mmol), X-Phos (4.3 mg), Pd$_2$(dba)$_3$ (5.5 mg) and K$_2$CO$_3$ (41.5 mg, 0.3 mmol) in 1.2 mL of t-BuOH was heated at 100° C. in a seal tube for 4 h. Then the reaction was filtered through Celite and eluted with dichloromethane. The dichloromethane was removed in vacuo and the resulting crude product was purified by reverse-phase prep-HPLC using a water (0.05% TFA)/acetonitrile (0.05% TFA) gradient to afford the title compound 25 (35.3 mg, 57%). $^1$H NMR (600 MHz, DMSO-d$_6$) δ 9.53 (s, 1H), 8.44 (s, 1H), 8.20 (d, J=7.8 Hz, 1H), 8.14 (s, 1H), 7.56 (d, J=8.4 Hz, 1H), 7.45 (t, J=7.8 Hz, 1H), 7.28 (d, J=9.0 Hz, 1H), 7.15 (t, J=7.8 Hz, 1H), 6.99 (d, J=8.4 Hz, 1H), 4.68-4.64 (m, 1H), 3.86 (s, 3H), 3.42 (s, 3H), 3.40-3.28 (m, 6H), 3.08-2.90 (m, 5H), 2.76 (s, 3H), 2.60-2.52 (m, 1H), 2.46-2.38 (m, 1H), 2.30-2.27 (m, 1H), 2.09-2.06 (m, 1H), 1.85-1.65 (m, 2H), 1.57-1.52 (m, 4H), 1.50-1.47 (m, 1H), 1.42-1.32 (m, 3H). MS (ESI) m/z 625 (M+H)$^+$.

Example 6: Synthesis of Compounds of Formula VII

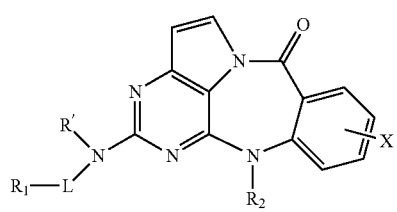

(VII)

Scheme 6

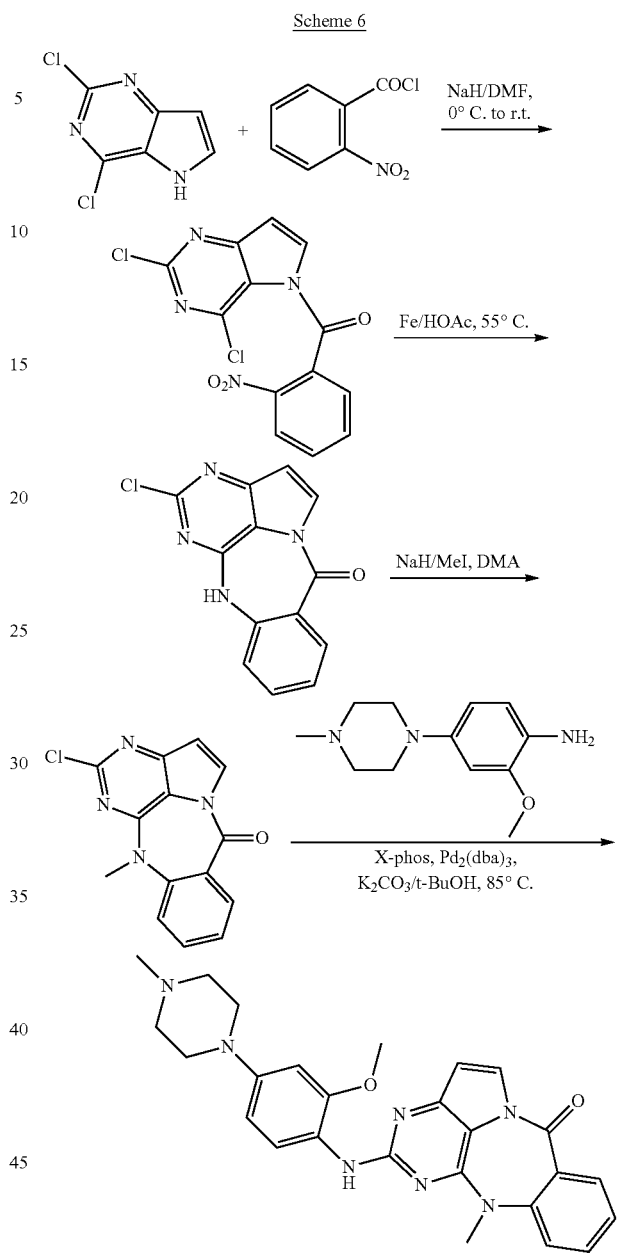

To a stirred solution of 2,4-dichloro-5H-pyrrolo[3,2-d]pyrimidine (1.01 g, 5.4 mmol) in DMF (40 mL) was added sodium hydride (0.43 g, 10.8 mmol) at 0° C. After 15 minutes, 2-nitrobenzoyl chloride (0.864 mL, 6.5 mmol) was added dropwise. The reaction was stirred at 0° C. till the reaction completed as monitored by LC-MS. The reaction was quenched by saturated NH$_4$Cl solution, poured into ice-water. The solid was collected, dried under vacuum and used for next step directly without further purification.

A mixture of (2,4-dichloro-5H-pyrrolo[3,2-d]pyrimidin-5-yl)(2-nitrophenyl)methanone (1.04 g, 3.1 mmol) and iron power (1.8 g, 32.1 mmol) in acetic acid (50 mL) was heated at 55° C. After the reaction complete, the mixture was concentrated in vacuo and poured into ice-water. The precipitated solid was collected and lyophilyzed. The crude product was used in next step without further purification.

To a stirred suspension of 4-chloro-3,5,6,11a-tetraazadibenzo[cd,g]azulen-11(6H)-one (270 mg, 1 mmol) in DMA (8 mL), MeI (0.094 mL, 1.5 mmol) was added. The reaction was stirred at 0° C. till the reaction completed as monitored by LC-MS. Then the reaction was quenched by saturated NH₄Cl solution, poured into ice-water. The precipitated solid was collected. The aqueous layer was extracted with ethyl acetate. The organic layer was washed with brine and dried over anhydrous sodium sulfate. The solvent was removed in vacuo. This portion of product was combined with the precipitated solid and was purified by silica gel chromatography to give the desired compound (210 mg, 74%).

A mixture of starting material (29 mg, 0.1 mmol), 2-methoxy-4-(4-methylpiperazin-1-yl)benzenamine (22 mg, 0.1 mmol), X-Phos (4.3 mg), Pd₂(dba)₃ (5.5 mg) and K₂CO₃ (41.5 mg, 0.3 mmol) in t-BuOH (1.5 mL) was heated at 85° C. in a seal tube for 1.5h. Then the reaction was filtered through celite and eluted with dichloromethane. The solvent was removed in vacuo and the residue was purified by ISCO to afford the title compound (8.1 mg).

Example 7: Synthesis of Compounds of Formula VIII

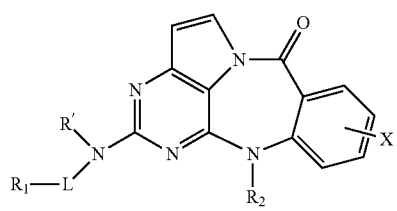
(VIII)

Scheme 7

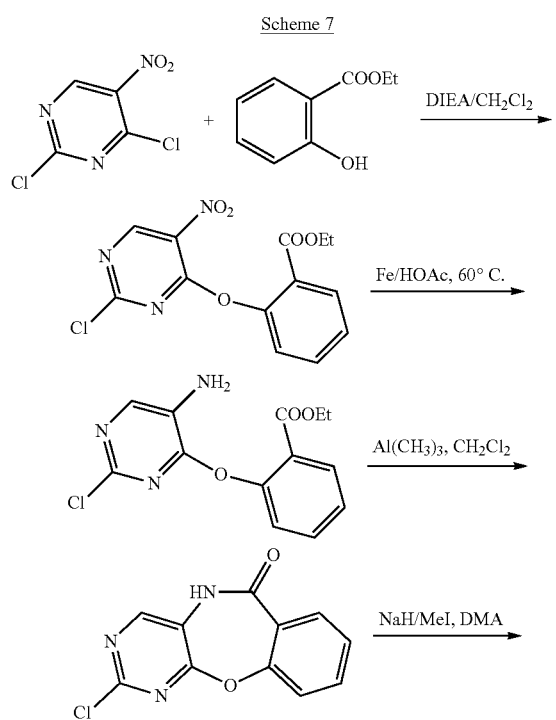

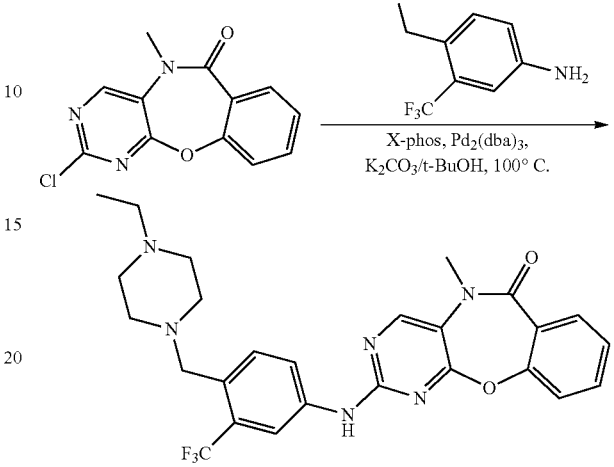

A reaction mixture of 2,4-dichloro-5-nitropyrimidine (2.91 g, 65 mmol), ethyl 2-hydroxybenzoate (1.66 g, 10 mmol) and DIEA (3.5 mL, 20 mmol) in dichloromethane (45 mL) was stirred at 0° C. till the reaction completed as monitored by LC-MS. The reaction was diluted with ethyl acetate and washed with water and brine, the organic layer was dried over anhydrous sodium sulfate, concentrated in vacuo and used for next step directly without further purification.

A mixture of ethyl 2-((2-chloro-5-nitropyrimidin-4-yl)oxy)benzoate (3.2 g, 10 mmol) and iron power (5.6 g, 100 mmol) in acetic acid (140 mL) was heated at 60° C. After the reaction complete, the mixture was concentrated in vacuo and poured into ice-water. The precipitated solid was collected and lyophilyzed. The crude product was used in next step without further purification.

To a stirred solution of ethyl 2-((5-amino-2-chloropyrimidin-4-yl)oxy)benzoate (1.47 g, 5.0 mmol) in CH₂Cl₂ (50 mL) was added Al(CH₃)₃ solution (0.15 mmol) at 0° C. The reaction mixture was heated to 45° C. slowly. When the reaction completed as monitored by LC-MS, it was cooled to 0° C. and quenched by addition of 1N HCl. The mixture was concentrated in vacuo and poured into ice-water. The precipitated solid was collected and lyophilyzed. The crude product was used in next step without further purification.

To a stirred suspension of 2-chlorobenzo[f]pyrimido[4,5-b][1,4]oxazepin-6(5H)-one (247 mg, 1 mmol) in DMA (10 mL), MeI (0.08 mL, 1.5 mmol) was added. The reaction was stirred at −10° C. till the reaction completed as monitored by LC-MS. Then the reaction was quenched by saturated NH₄Cl solution, poured into ice-water. The precipitated solid was collected. The aqueous layer was extracted with ethyl acetate. The organic layer was washed with brine and dried over anhydrous sodium sulfate. The solvent was removed in vacuo. This portion of product was combined with the precipitated solid and was purified by silica gel chromatography to give the desired compound.

A mixture of starting material (29 mg, 0.1 mmol), 4-((4-ethylpiperazin-1-yl)methyl)-3-(trifluoromethyl)aniline (29 mg, 0.1 mmol), X-Phos (4.3 mg), Pd₂(dba)₃ (5.5 mg) and K₂CO₃ (41.5 mg, 0.3 mmol) in t-BuOH (1.5 mL) was heated at 100° C. in a seal tube for 4 h. Then the reaction was filtered through celite and eluted with dichloromethane. The solvent was removed in vacuo and the residue was purified by HPLC to afford the title compound (26.3 mg).

Example 8: Synthesis of Additional Compounds

Scheme 8. Synthesis of 4,5,13-trimethyl-2-((1-(piperidin-4-yl)-1H-pyrazol-4-yl)amino)-5,13-dihydro-6H-naphtho[2,3-e]pyrimido[5,4-b][1,4]diazepin-6-one (HTH-01-015)[a]

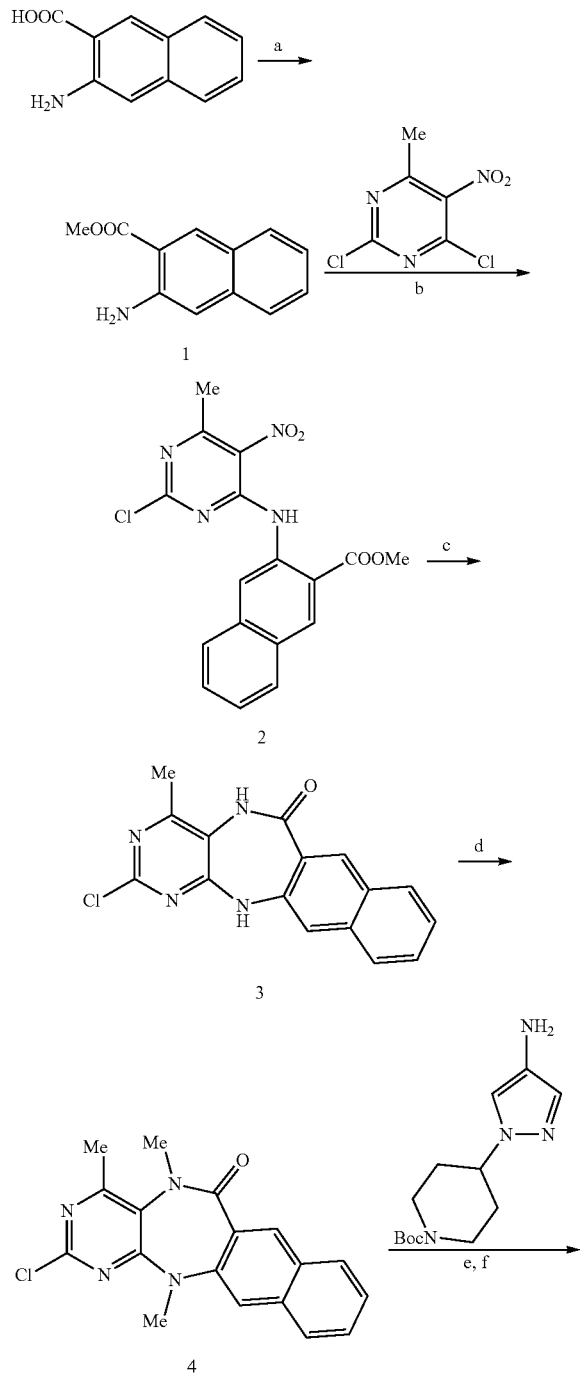

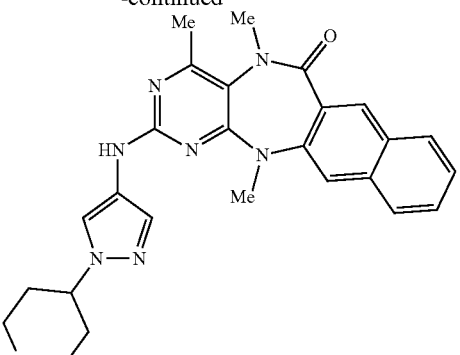

5, HTH-01-015

[a]Reagents and conditions: (a) TMSCH$_2$N$_2$ (1.2 eq.), MeOH/Toluene (1:4), 0° C.; (b) DIEA (2.0 eq), 2-Propanol; (c) Fe (14.5 eq.), HOAc, 60° C.; (d) MeI (5.0 eq.), NaH (3.6 eq.), DMA, 0° C.; (e) X-Phos (20% mol), Pd$_2$(dba)$_3$ (10% mol), K$_2$CO$_3$ (3.0 eq.), t-BuOH 85° C.; (f) TFA (50 eq), DCM.

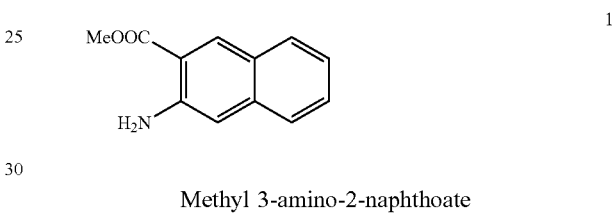

Methyl 3-amino-2-naphthoate

To a solution of 3-amino-2-naphthoic acid (562 mg, 3.0 mmol, 1.0 eq) in methanol/toluene (1:4, 10 mL) was added 2.0 M of TMSCH$_2$N$_2$ solution in hexane (1.8 mL, 3.6 mmol, 1.2 eq) at 0° C. The reaction was stirred overnight at rt. Next day, the reaction was quenched with excess acetic acid until no bubbling was seen. The mixture was directly concentrated in vacuo. The residue was purified by silica-gel column chromatography with ethyl acetate and hexane (0%-25% gradient, v/v) to give compound 1 (500 mg, 83%). $^1$H NMR (400 MHz, MeOD) δ 8.46 (s, 1H), 7.70 (d, J=8.2 Hz, 1H), 7.51 (d, J=8.2 Hz, 1H), 7.37 (ddd, J=8.2, 6.8, 1.2 Hz, 1H), 7.15 (ddd, J=8.2, 6.8, 1.2 Hz, 1H), 7.05 (s, 1H), 3.93 (s, 3H). MS (ESI) calcd for [C$_{12}$H$_{12}$NO$_2$]$^+$: 202; found 202.

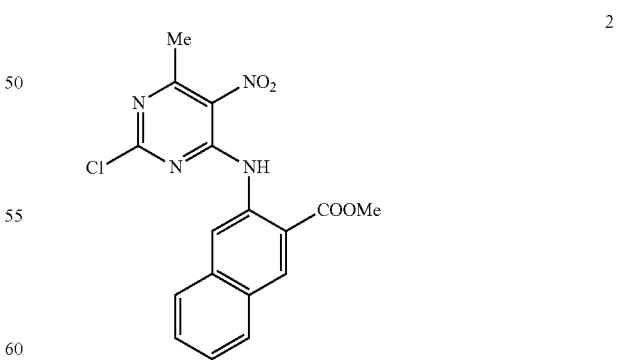

Methyl 3-((2-chloro-6-methyl-5-nitropyrimidin-4-yl)amino)-2-naphthoate

A mixture of compound 1 (480 mg, 2.4 mmol, 1.0 eq), N,N-diisopropylethylamine (DIEA) (0.83 mL, 4.8 mmol, 2.0 eq) and 2,4-dichloro-6-methyl-5-nitropyrimidine (0.76 g, 3.6 mmol, 1.5 eq) in 2-propanol (43 mL) was stirred at rt overnight. The product crashed out of 2-propanol, and was collected by filtration and dried in vacuo. The crude compound 2 (0.79 g, 88%) was used for the next step without further purification. $^1$H NMR (400 MHz, CDCl$_3$) δ 12.04 (s, 1H), 8.94 (s, 1H), 8.68 (s, 1H), 7.89 (d, J=8.2 Hz, 2H), 7.63 (ddd, J=8.2, 7.0, 1.2 Hz, 1H), 7.51 (ddd, J=8.2, 7.0, 1.2 Hz, 1H), 4.05 (s, 3H), 2.73 (s, 3H). MS (ESI) calcd for $[C_{17}H_{14}ClN_4O_4]^+$: 373; found 373.

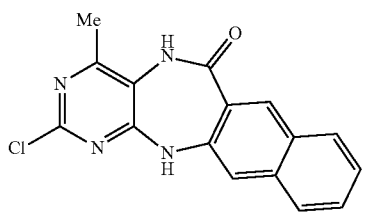

2-chloro-4-methyl-5,13-dihydro-6H-naphtho[2,3-e]pyrimido[5,4-b][1,4]diazepin-6-one To a solution of compound 2 (0.79 g, 2.1 mmol, 1.0 eq) in acetic acid (90 mL) was added iron powder (1.7 g, 30.4 mmol, 14.5 eq). The reaction was stirred at 60° C. overnight. After the reaction was complete as monitored by reverse phase analytical liquid-chromatography electrospray mass spectrometry (LC-MS), the solvent was removed in vacuo. The resulting residue was poured into ice water and stirred, which resulted in a solid precipitate that was collected by filtration, washed with water and air dried to give compound 3 (0.64 g, 98%). $^1$H NMR (400 MHz, CDCl$_3$) δ 8.63 (s, 1H), 7.85 (d, J=8.2 Hz, 1H), 7.68 (d, J=8.2 Hz, 1H), 7.54 (ddd, J=8.2, 7.0, 1.4 Hz, 1H), 7.42 (ddd, J=8.2, 7.0, 1.2 Hz, 1H), 7.17 (s, 1H), 7.15 (s, 1H), 6.88 (s, 1H), 2.52 (s, 3H). MS (ESI) calcd for $[C_{16}H_{12}ClN_4O]^+$: 311; found 311.

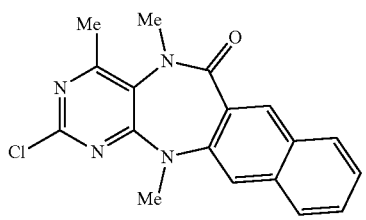

2-chloro-4,5,13-trimethyl-5,13-dihydro-6H-naphtho[2,3-e]pyrimido[5,4-b][1,4]diazepin-6-one To a stirred suspension of compound 3 (0.64 g, 2.1 mmol, 1.0 eq) and MeI (0.64 mL, 10.3 mmol, 5.0 eq) in dimethyl acetamide (DMA, 20.0 mL) was added NaH (300 mg, 60% suspension in mineral oil, 3.6 eq) at 0° C. After the reaction was complete as monitored by LC-MS, the solution was poured into ice water, which resulted in a solid precipitate. The precipitate was collected by filtration, washed with water and air dried to give the crude product. The crude product was purified by silica-gel column chromatography with ethyl acetate and hexane (0%-80% gradient, v/v) to give compound 4 (67 mg, 10%). $^1$H NMR (400 MHz, MeOD) δ 8.30 (s, 1H), 7.88 (d, J=8.2 Hz, 1H), 7.84 (d, J=8.2 Hz, 1H), 7.61 (s, 1H), 7.54 (ddd, J=8.2, 7.0, 1.2 Hz, 1H), 7.45 (ddd, J=8.2, 7.0, 1.2 Hz, 1H), 3.51 (s, 3H), 3.37 (s, 3H), 2.48 (s, 3H). MS (ESI) calcd for $[C_{18}H_{16}ClN_4O]^+$: 339; found 339.

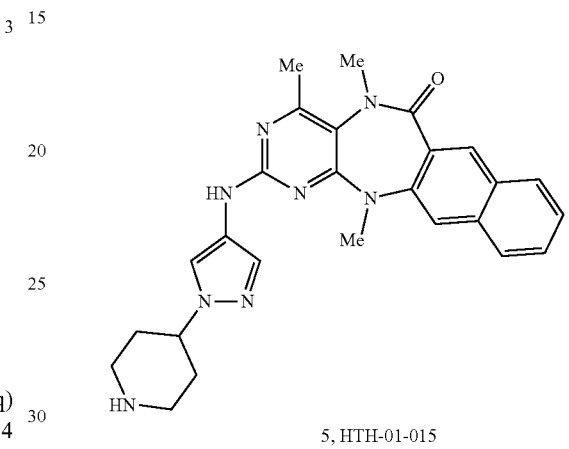

5, HTH-01-015

4,5,13-trimethyl-2-((1-(piperidin-4-yl)-1H-pyrazol-4-yl)amino)-5,13-dihydro-6H-naphtho[2,3-e]pyrimido[5,4-b][1,4]diazepin-6-one A mixture of 4 (34 mg, 0.1 mmol, 1.0 eq), tert-butyl 4-(4-amino-1H-pyrazol-1-yl)piperidine-1-carboxylate (27 mg, 0.1 mmol, 1.0 eq), X-Phos (8.6 mg, 20%), Pd$_2$(dba)$_3$ (11 mg, 10%) and K$_2$CO$_3$ (41.5 mg, 0.3 mmol) in 1.2 mL of t-BuOH was heated at 85° C. in a sealed tube for 3.5 h. The reaction was then filtered through celite and eluted with dichloromethane (DCM). The DCM was removed in vacuo. The resulting crude product was stirred with trifluoroacetic acid (TFA, 0.38 mL, 5 mmol, 50 eq) in DCM (2 mL) at rt overnight to afford Boc deprotection. The solvent was removed in vacuo. The residue was purified by reverse-phase prep-HPLC using a water (0.05% TFA)/methanol (0.05% TFA) gradient to afford the title compound HTH-01-015 as TFA salt (18 mg, yield: 31%). $^1$H NMR (400 MHz, DMSO-d$_6$) δ 9.72-9.40 (br, 1H), 8.74-8.61 (br, 1H), 8.54-8.37 (br, 1H), 8.29 (s, 1H), 7.97 (d, J=8.2 Hz, 1H), 7.92 (s, 1H), 7.88 (d, J=8.2 Hz, 1H), 7.67 (s, 1H), 7.60 (s, 1H), 7.56 (ddd, J=8.2, 7.0, 1.2 Hz, 1H), 7.46 (ddd, J=8.2, 7.0, 1.2 Hz, 1H), 4.54-4.41 (br, 1H), 3.54-3.38 (br, 5H), 3.27 (s, 3H), 3.17-3.02 (br, 2H), 2.33 (s, 3H), 2.26-2.04 (br, 4H). MS (ESI) calcd for $[C_{26}H_{29}N_8O^+]^+$: 469; found 469.

XMD18-42 and XMD17-51 were synthesized following similar strategies as shown in Scheme 8.

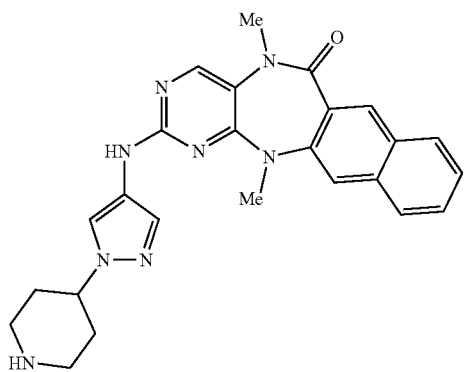

XMD18-42

5,13-dimethyl-2-((1-(piperidin-4-yl)-1H-pyrazol-4-yl)amino)-5,13-dihydro-6H-naphtho[2,3-e]pyrimido[5,4-b][1,4]diazepin-6-one $^1$H NMR (400 MHz, DMSO-d$_6$) δ 9.77-9.44 (br, 1H), 9.18-8.96 (br, 2H), 8.39 (s, 1H), 8.33 (s, 1H), 7.98 (d, J=8.2 Hz, 1H), 7.95 (s, 1H), 7.91 (d, J=8.2 Hz, 1H), 7.75 (s, 1H), 7.60 (s, 1H), 7.57 (t, J=8.2 Hz, 1H), 7.46 (t, J=8.2 Hz, 1H), 4.56-4.43 (br, 1H), 3.55-3.47 (br, 3H), 3.45 (s, 3H), 3.43-3.34 (br, 2H), 3.13-2.99 (br, 2H), 2.27-2.09 (br, 4H). MS (ESI) calcd for [C$_{25}$H$_{27}$N$_8$O$^+$]$^+$: 455; found 455.

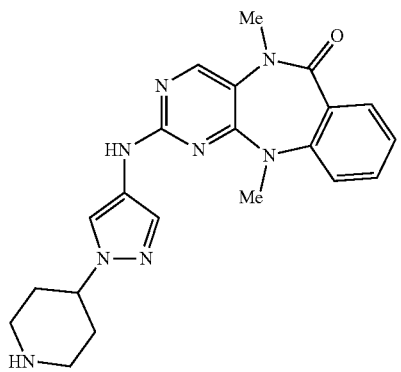

XMD17-51

5,11-dimethyl-2-((1-(piperidin-4-yl)-1H-pyrazol-4-yl)amino)-5,11-dihydro-6H-benzo[e]pyrimido[5,4-b][1,4]diazepin-6-one $^1$H NMR (400 MHz, DMSO-d$_6$) δ 9.77-9.60 (br, 1H), 9.16-8.94 (br, 2H), 8.35 (s, 1H), 7.93 (s, 1H), 7.68 (dd, J=7.9, 1.8 Hz, 1H), 7.58 (s, 1H), 7.51 (td, J=7.9, 1.8 Hz, 1H), 7.28 (d, J=7.9 Hz, 1H), 7.18 (t, J=7.9 Hz, 1H), 4.52-4.44 (br, 1H), 3.42-3.34 (br, 5H), 3.38 (s, 3H), 3.10-3.00 (br, 2H), 2.21-2.12 (br, 4H). MS (ESI) calcd for [C$_{21}$H$_{25}$N$_8$O$^+$]$^+$: 405; found 405.

XMD18-83 was synthesized following similar strategies as shown in Scheme 8.

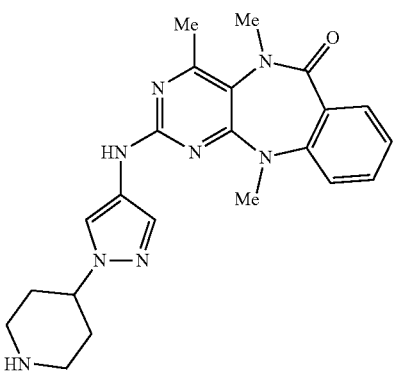

XMD18-83

4,5,11-trimethyl-2-((1-(piperidin-4-yl)-1H-pyrazol-4-yl)amino)-5,11-dihydro-6H-benzo[e]pyrimido[5,4-b][1,4]diazepin-6-one $^1$H NMR (600 MHz, DMSO-d$_6$) δ 9.66-9.34 (br, 1H), 8.73-8.62 (br, 1H), 8.53-8.38 (br, 1H), 7.89 (s, 1H), 7.63 (dd, J=7.8, 1.5 Hz, 1H), 7.56 (s, 1H), 7.45 (td, J=7.8, 1.5 Hz, 1H), 7.20 (d, J=7.8 Hz, 1H), 7.14 (t, J=7.8 Hz, 1H), 4.45 (m, 1H), 3.42-3.28 (br, 5H), 3.18 (s, 3H), 3.06 (m, 2H), 2.29 (s, 3H), 2.20-2.12 (br, 2H), 2.12-2.03 (br, 2H). MS (ESI) calcd for [C$_{22}$H$_{27}$N$_8$O]$^+$: 419; found 419.

TABLE 1

Compounds of the invention

| Compound ID | Structure | Spectroscopy |
|---|---|---|
| JWE-089 | 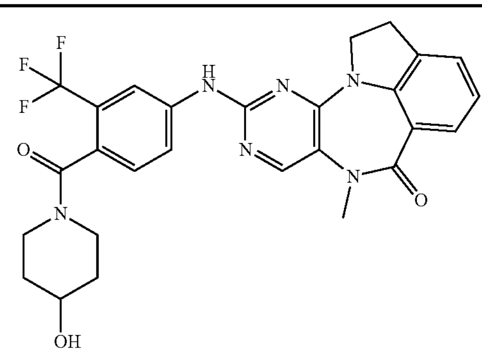 | |

TABLE 1-continued

Compounds of the invention

| Compound ID | Structure | Spectroscopy |
|---|---|---|
| XMD16-34 | 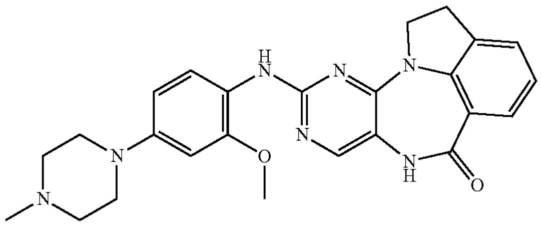 [SMILES: COc1cc(N2CCN(C)CC2)ccc1Nc1ncc2c(n1)N1CCc3cccc(c31)C(=O)N2] | |
| XMD16-39 | 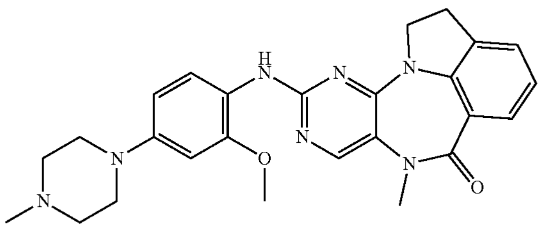 [SMILES: COc1cc(N2CCN(C)CC2)ccc1Nc1ncc2c(n1)N1CCc3cccc(c31)C(=O)N2C] | |
| XMD16-43 | 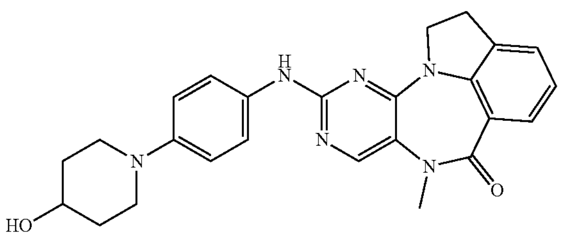 [SMILES: CN1C(=O)c2cccc3c2N(CC3)c2nc(Nc3ccc(N4CCC(O)CC4)cc3)ncc21] | |
| XMD16-44 | 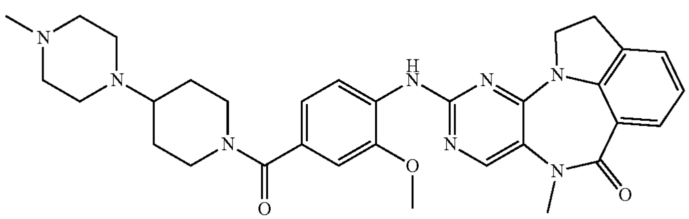 [SMILES: COc1cc(C(=O)N2CCC(N3CCN(C)CC3)CC2)ccc1Nc1ncc2c(n1)N1CCc3cccc(c31)C(=O)N2C] | |
| XMD16-45 | 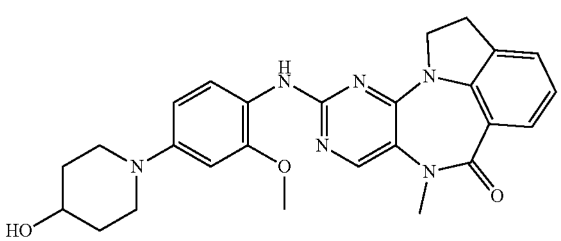 [SMILES: COc1cc(N2CCC(O)CC2)ccc1Nc1ncc2c(n1)N1CCc3cccc(c31)C(=O)N2C] | |
| XMD16-46 | 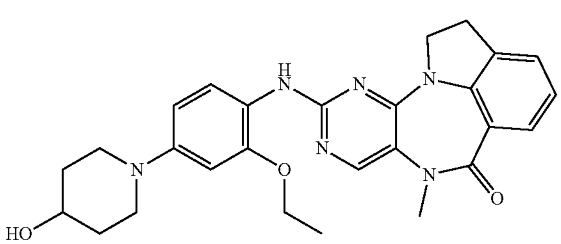 [SMILES: CCOc1cc(N2CCC(O)CC2)ccc1Nc1ncc2c(n1)N1CCc3cccc(c31)C(=O)N2C] | |

TABLE 1-continued

Compounds of the invention

| Compound ID | Structure | Spectroscopy |
|---|---|---|
| XMD16-58 | 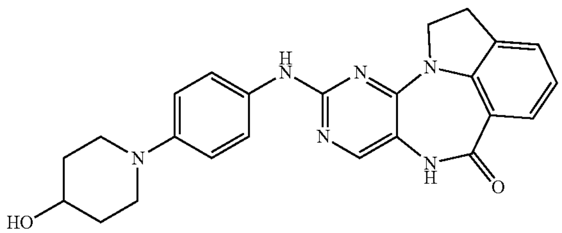 [SMILES: O=C1Nc2cnc(Nc3ccc(N4CCC(O)CC4)cc3)nc2N2CCc3cccc1c32] | |
| XMD16-85 | 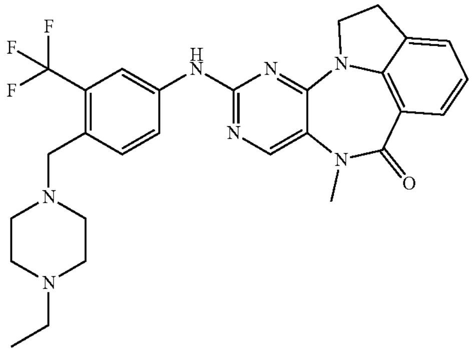 [SMILES: CCN1CCN(Cc2ccc(Nc3ncc4c(n3)N3CCc5cccc(c53)C(=O)N4C)cc2C(F)(F)F)CC1] | |

TABLE 2

Compounds of the invention

| Compound ID | Structure | EphA2 Activity (% Inhibition at 10 micromolar) |
|---|---|---|
| JWF-039 | 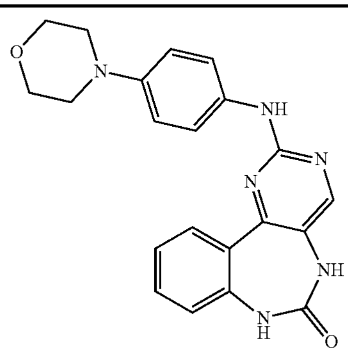 | 358 |
| JWF-040 | 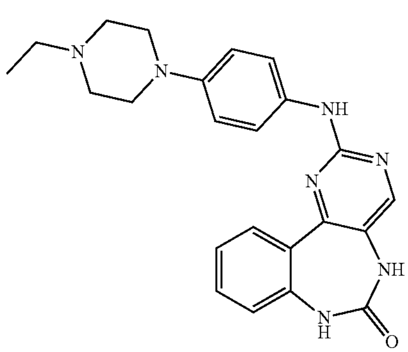 [SMILES: CCN1CCN(c2ccc(Nc3ncc4c(n3)-c3ccccc3NC(=O)N4)cc2)CC1] | 51.9 |

TABLE 2-continued
Compounds of the invention
| Compound ID | Structure | EphA2 Activity (% Inhibition at 10 micromolar) |
|---|---|---|
| JWF-041 | 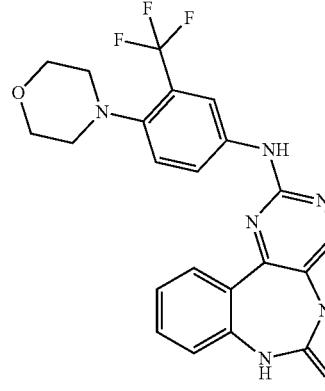 | 4850 |
| JWF-042 | 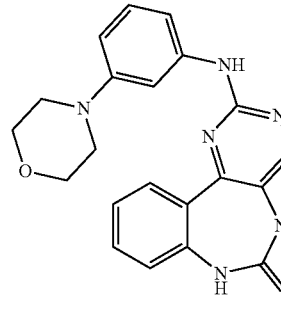 | 170 |
| JWF-043 | 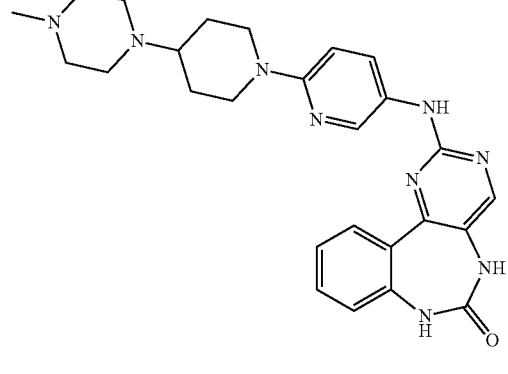 | 113 |
| JWF-044 | 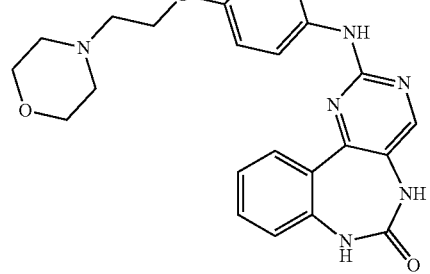 | 118 |

TABLE 2-continued
Compounds of the invention
| Compound ID | Structure | EphA2 Activity (% Inhibition at 10 micromolar) |
|---|---|---|
| JWF-045 | 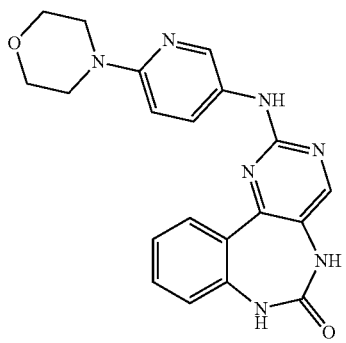 [SMILES: O=C1Nc2ccccc2-c2nc(Nc3ccc(N4CCOCC4)nc3)ncc2N1] | 162 |
| JWF-046 | 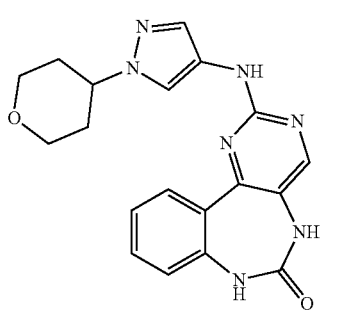 [SMILES: O=C1Nc2ccccc2-c2nc(Nc3cnn(C4CCOCC4)c3)ncc2N1] | 17.4 |
| JWF-050 | 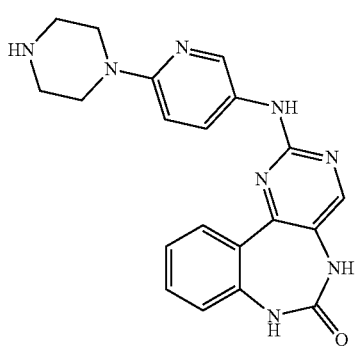 [SMILES: O=C1Nc2ccccc2-c2nc(Nc3ccc(N4CCNCC4)nc3)ncc2N1] | EphA2: 323 |
| JWF-051 | 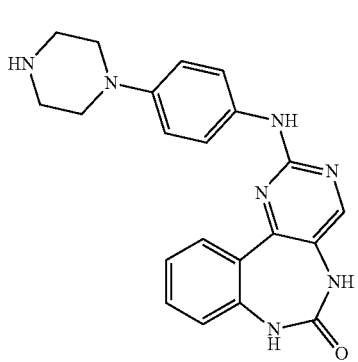 [SMILES: O=C1Nc2ccccc2-c2nc(Nc3ccc(N4CCNCC4)cc3)ncc2N1] | EphA2: 39.5 |

TABLE 2-continued
Compounds of the invention
| Compound ID | Structure | EphA2 Activity (% Inhibition at 10 micromolar) |
|---|---|---|
| JWF-052 | 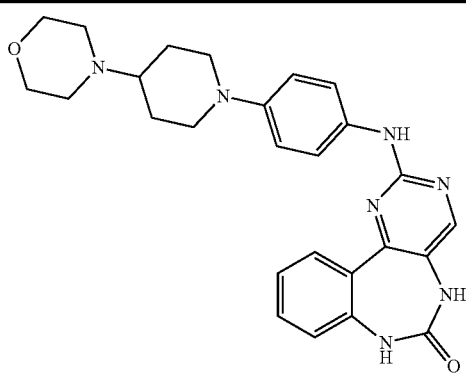 | EphA2: 127 |
| JWF-056 | 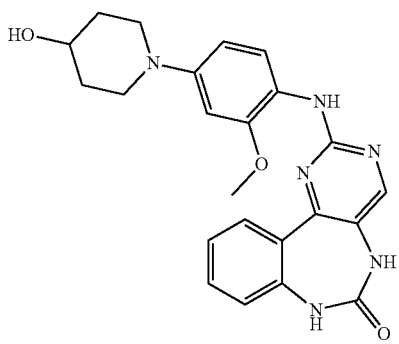 [SMILES: COc1cc(N2CCC(O)CC2)ccc1Nc1ncc2c(n1)-c1ccccc1NC(=O)N2] | 1810 |
| JWF-057 | 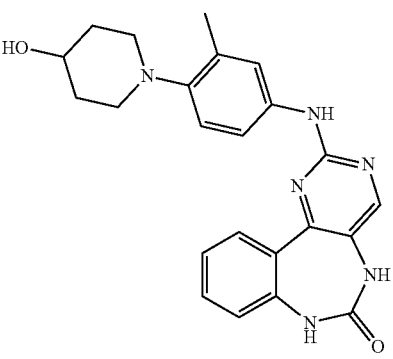 [SMILES: Cc1cc(Nc2ncc3c(n2)-c2ccccc2NC(=O)N3)ccc1N1CCC(O)CC1] | 1.97 |
| JWF-060 | 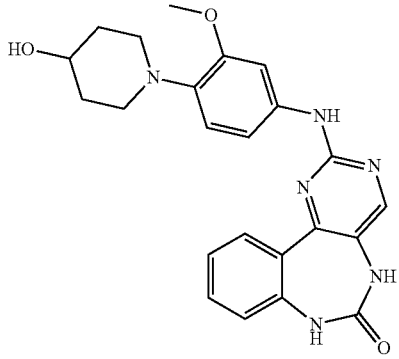 [SMILES: COc1cc(Nc2ncc3c(n2)-c2ccccc2NC(=O)N3)ccc1N1CCC(O)CC1] | 24.0 |

TABLE 2-continued

Compounds of the invention

| Compound ID | Structure | EphA2 Activity (% Inhibition at 10 micromolar) |
|---|---|---|
| XMD16-95 | 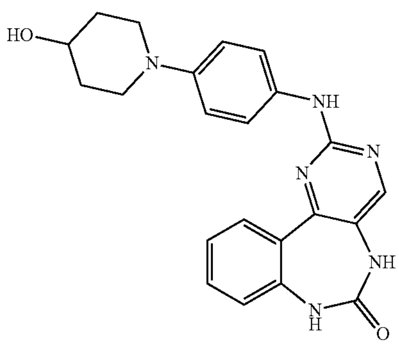 [SMILES: O=C1Nc2ccccc2-c2nc(Nc3ccc(N4CCC(O)CC4)cc3)ncc2N1] | 21.6 |
| XMD16-120 | 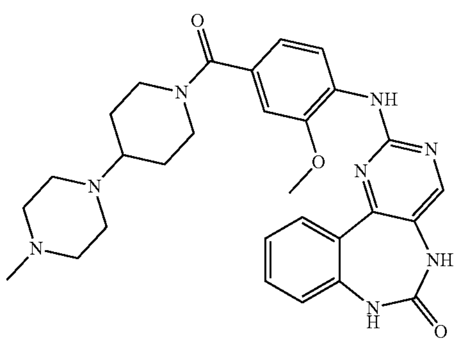 [SMILES: COc1cc(C(=O)N2CCC(N3CCN(C)CC3)CC2)ccc1Nc1ncc2c(n1)-c1ccccc1NC(=O)N2] | |
| XMD16-101-1 | 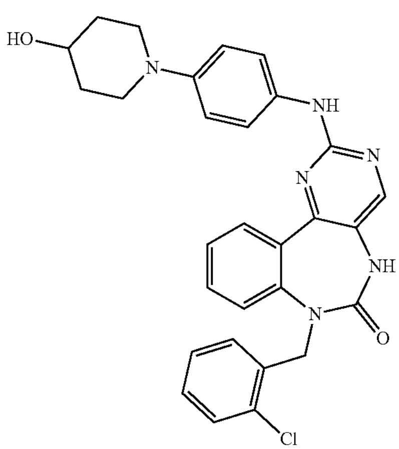 [SMILES: O=C1Nc2cnc(Nc3ccc(N4CCC(O)CC4)cc3)nc2-c2ccccc2N1Cc1ccccc1Cl] | |

TABLE 2-continued

Compounds of the invention

| Compound ID | Structure | EphA2 Activity (% Inhibition at 10 micromolar) |
|---|---|---|
| XMD16-101-2 | 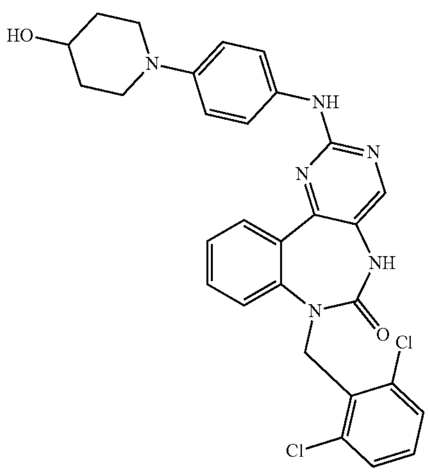 [SMILES: O=C1Nc2cnc(Nc3ccc(N4CCC(O)CC4)cc3)nc2-c2ccccc2N1Cc1c(Cl)cccc1Cl] | |
| XMD16-117 | 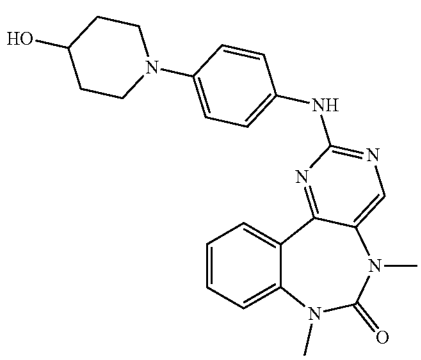 [SMILES: CN1C(=O)N(C)c2cnc(Nc3ccc(N4CCC(O)CC4)cc3)nc2-c2ccccc21] | |
| XMD16-118 | 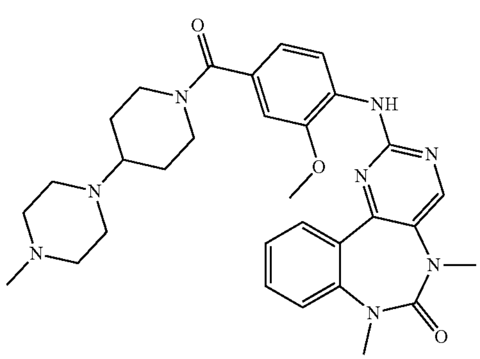 | |

TABLE 2-continued
Compounds of the invention
| Compound ID | Structure | EphA2 Activity (% Inhibition at 10 micromolar) |
|---|---|---|
| XMD16-121 | 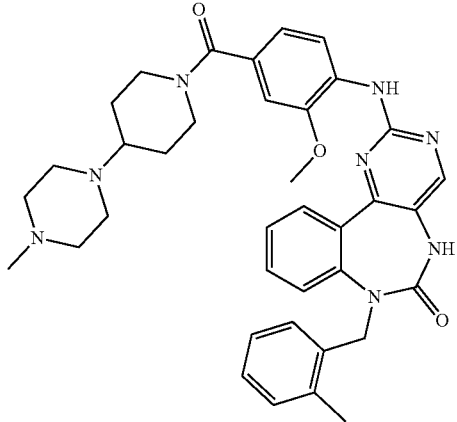 [SMILES: COc1cc(C(=O)N2CCC(N3CCN(C)CC3)CC2)ccc1Nc1ncc2c(n1)-c1ccccc1N(Cc1ccccc1C)C(=O)N2] | |
| XMD16-125 | 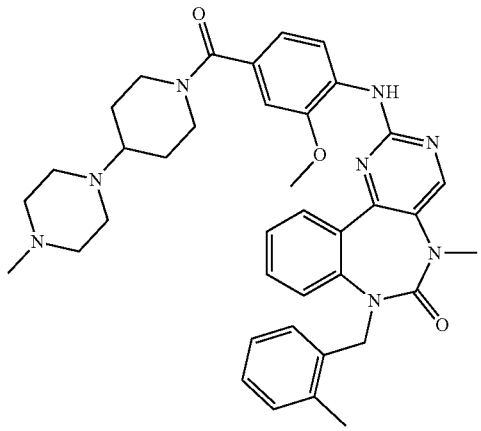 | |
| XMD16-122-1 | 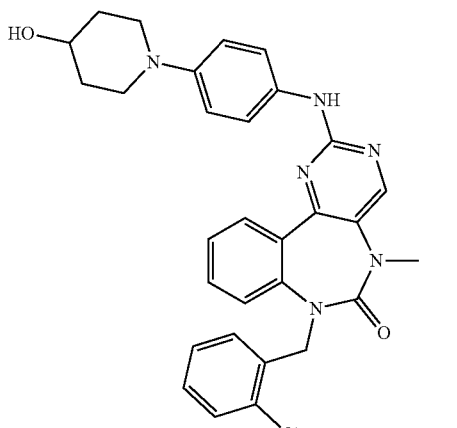 | |

TABLE 2-continued

Compounds of the invention

| Compound ID | Structure | EphA2 Activity (% Inhibition at 10 micromolar) |
|---|---|---|
| XMD16-122-2 | 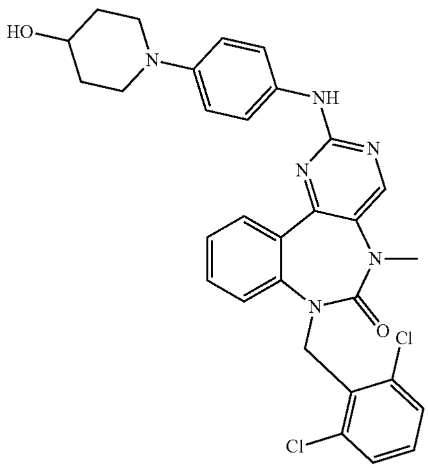 [SMILES: CN1C(=O)N(Cc2c(Cl)cccc2Cl)c2ccccc2-c2nc(Nc3ccc(N4CCC(O)CC4)cc3)ncc21] | |
| XMD16-127 | 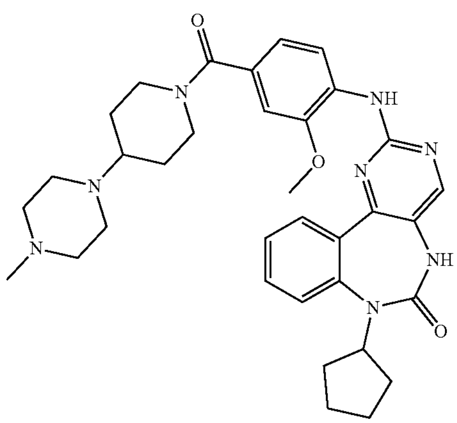 [SMILES: COc1cc(C(=O)N2CCC(N3CCN(C)CC3)CC2)ccc1Nc1ncc2c(n1)-c1ccccc1N(C1CCCC1)C(=O)N2] | −1.1, −10.5 |
| XMD16-128 | 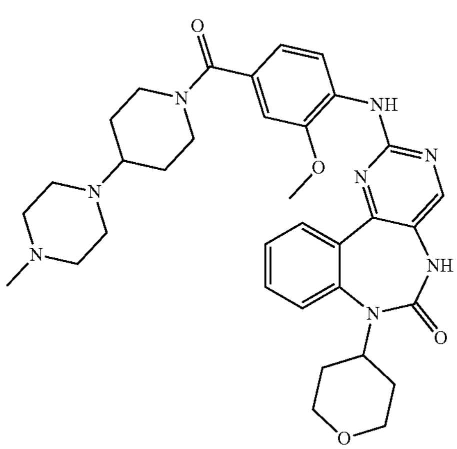 [SMILES: COc1cc(C(=O)N2CCC(N3CCN(C)CC3)CC2)ccc1Nc1ncc2c(n1)-c1ccccc1N(C1CCOCC1)C(=O)N2] | −5.1, −8.2 |

TABLE 2-continued
Compounds of the invention
| Compound ID | Structure | EphA2 Activity (% Inhibition at 10 micromolar) |
|---|---|---|
| AB-1-9 | 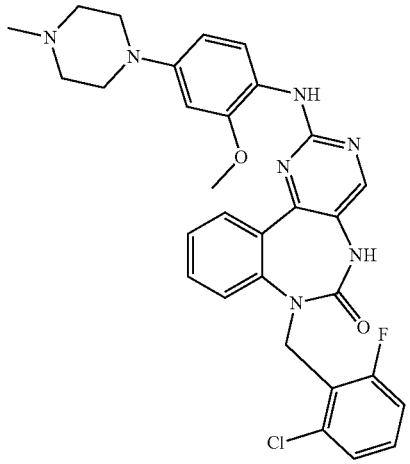 [SMILES: COc1cc(N2CCN(C)CC2)ccc1Nc1ncc2c(n1)-c1ccccc1N(Cc1c(F)cccc1Cl)C(=O)N2] | |
| AB-1-15 | 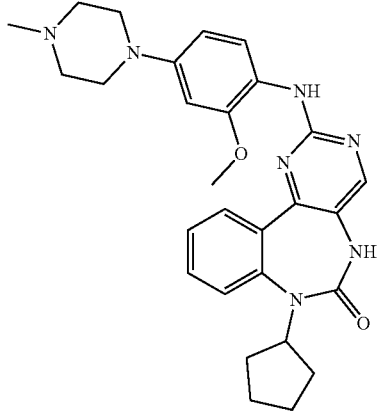 [SMILES: COc1cc(N2CCN(C)CC2)ccc1Nc1ncc2c(n1)-c1ccccc1N(C1CCCC1)C(=O)N2] | |
| AB-1-16 | 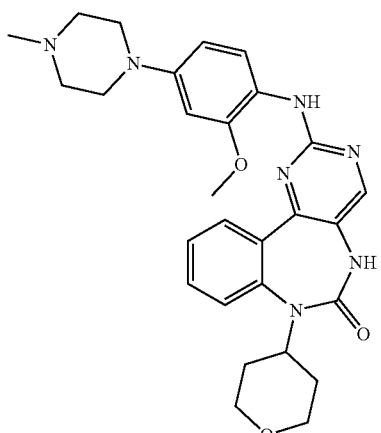 | |

TABLE 2-continued

Compounds of the invention

| Compound ID | Structure | EphA2 Activity (% Inhibition at 10 micromolar) |
|---|---|---|
| AB-1-17 | 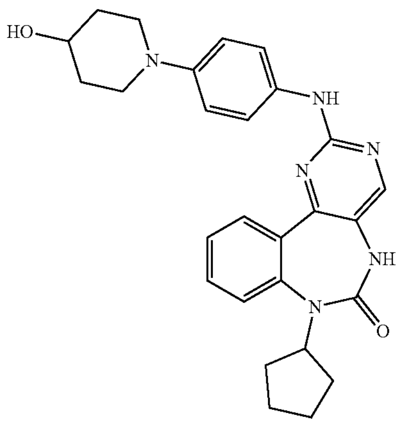 [SMILES: O=C1Nc2cnc(Nc3ccc(N4CCC(O)CC4)cc3)nc2-c2ccccc2N1C1CCCC1] | |
| AB-1-24 | 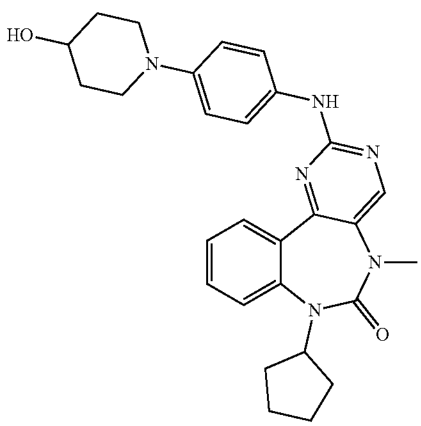 [SMILES: CN1C(=O)N(C2CCCC2)c2ccccc2-c2nc(Nc3ccc(N4CCC(O)CC4)cc3)ncc21] | |
| AB-1-25 | 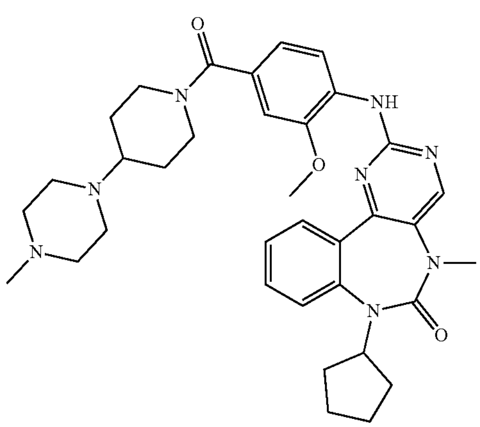 | |

TABLE 2-continued

Compounds of the invention

| Compound ID | Structure | EphA2 Activity (% Inhibition at 10 micromolar) |
|---|---|---|
| XMD16-117 | 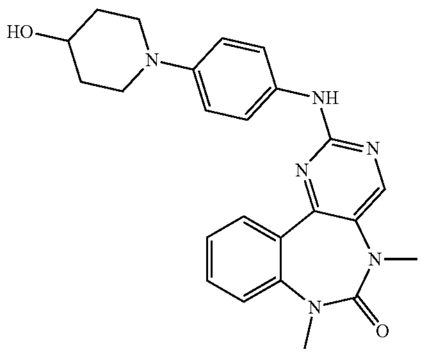 [SMILES: CN1C(=O)N(C)c2cnc(Nc3ccc(N4CCC(O)CC4)cc3)nc2-c2ccccc21] | |
| XMD16-118 | 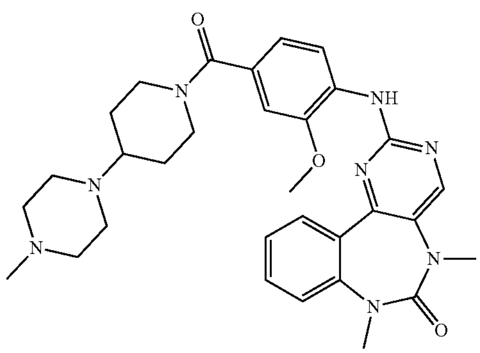 | |
| XMD16-123-1 | 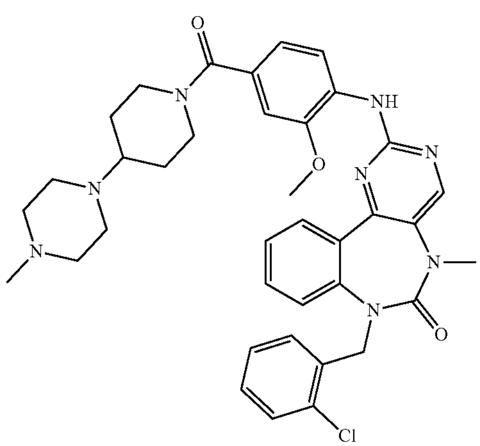 | |

TABLE 2-continued

Compounds of the invention

| Compound ID | Structure | EphA2 Activity (% Inhibition at 10 micromolar) |
|---|---|---|
| XMD16-123-2 | 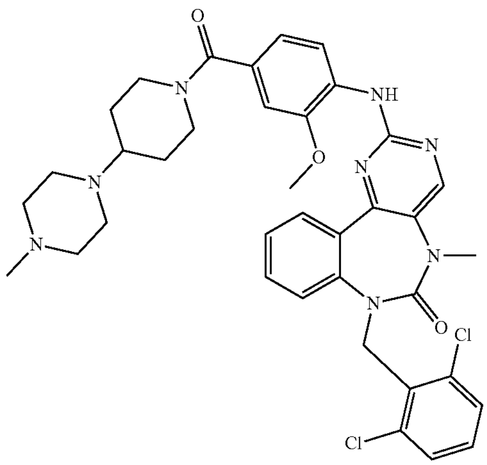 [SMILES: COc1cc(C(=O)N2CCC(N3CCN(C)CC3)CC2)ccc1Nc1ncc2c(n1)-c1ccccc1N(Cc1c(Cl)cccc1Cl)C(=O)N2C] | |
| XMD16-124 | 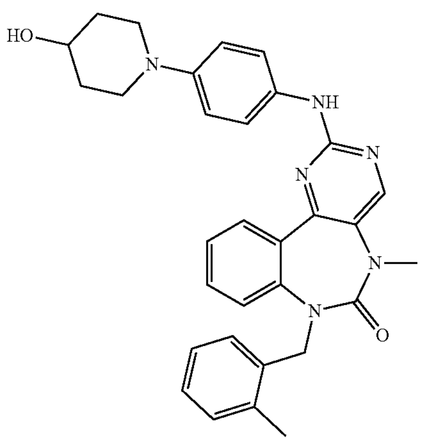 [SMILES: Cc1ccccc1CN1C(=O)N(C)c2cnc(Nc3ccc(N4CCC(O)CC4)cc3)nc2-c2ccccc21] | |

TABLE 3

Compounds of the invention

| Compound ID | Structure | Spectroscopy |
|---|---|---|
| XMD15-118 | 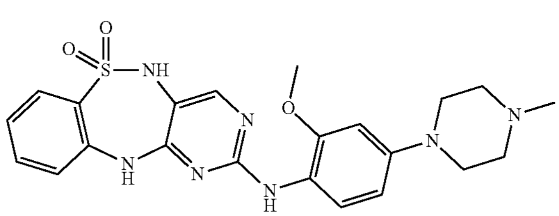 [SMILES: COc1cc(N2CCN(C)CC2)ccc1Nc1ncc2c(n1)Nc1ccccc1S(=O)(=O)N2] | |

TABLE 3-continued

Compounds of the invention

| Compound ID | Structure | Spectroscopy |
|---|---|---|
| XMD15-119 | 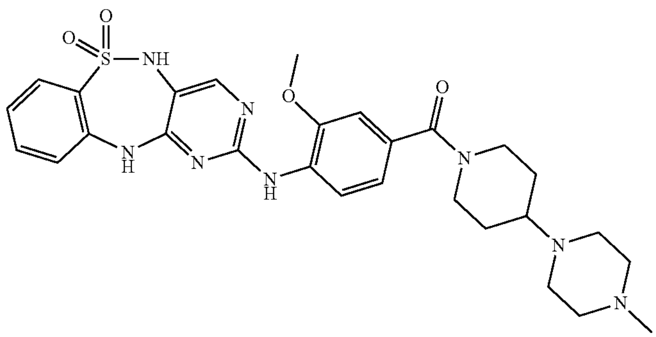 [SMILES: COc1cc(C(=O)N2CCC(N3CCN(C)CC3)CC2)ccc1Nc1ncc2c(n1)Nc1ccccc1S(=O)(=O)N2] | |
| XMD15-128 | 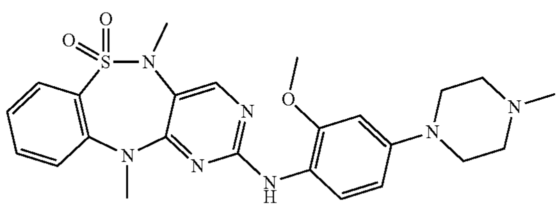 [SMILES: COc1cc(N2CCN(C)CC2)ccc1Nc1ncc2c(n1)N(C)c1ccccc1S(=O)(=O)N2C] | |
| XMD15-129 | 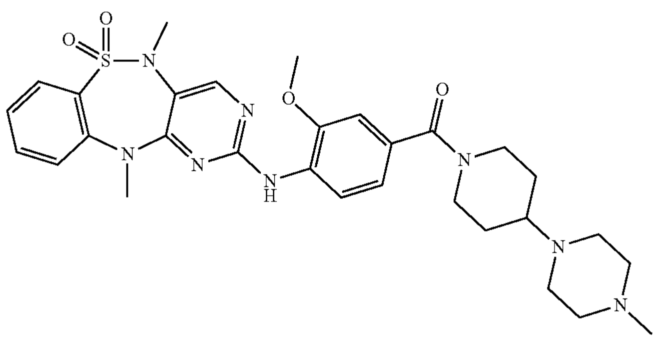 [SMILES: COc1cc(C(=O)N2CCC(N3CCN(C)CC3)CC2)ccc1Nc1ncc2c(n1)N(C)c1ccccc1S(=O)(=O)N2C] | |
| XMD16-86 | 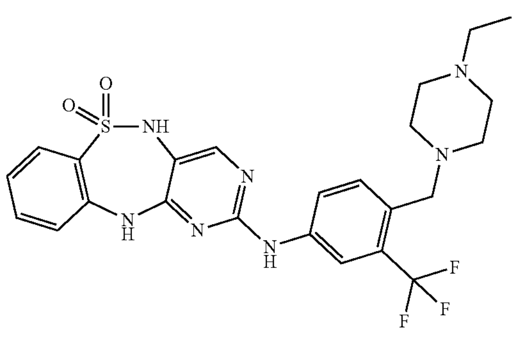 [SMILES: CCN1CCN(Cc2ccc(Nc3ncc4c(n3)Nc3ccccc3S(=O)(=O)N4)cc2C(F)(F)F)CC1] | |
| XMD16-35 | 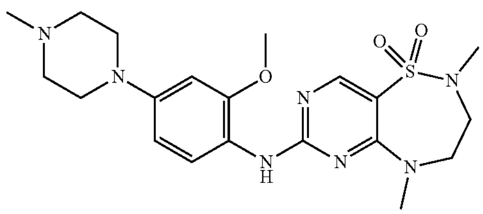 | |

TABLE 3-continued

Compounds of the invention

| Compound ID | Structure | Spectroscopy |
|---|---|---|
| XMD16-41 | 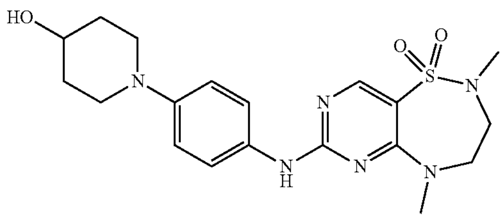 [SMILES: CN1CCN(C)S(=O)(=O)c2cnc(Nc3ccc(N4CCC(O)CC4)cc3)nc21] | |

TABLE 4

Compounds of the invention

| Compound ID | Structure | Spectroscopy |
|---|---|---|
| XMD15-143 | 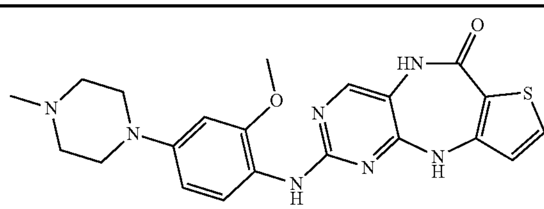 | |
| XMD15-144 | 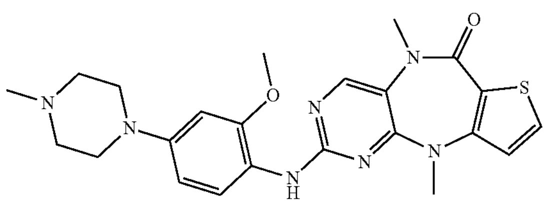 [SMILES: COc1cc(N2CCN(C)CC2)ccc1Nc1ncc2c(n1)N(C)c1ccsc1C(=O)N2C] | |
| XMD15-145 | 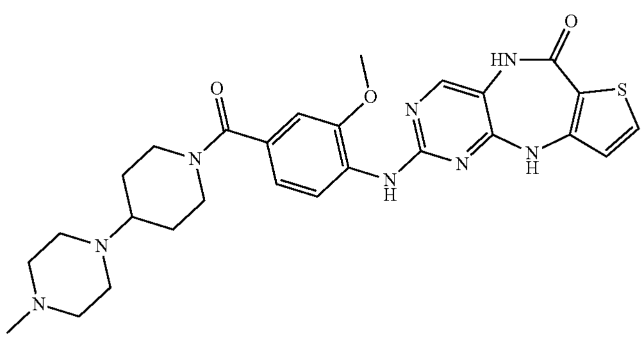 [SMILES: COc1cc(C(=O)N2CCC(N3CCN(C)CC3)CC2)ccc1Nc1ncc2c(n1)Nc1ccsc1C(=O)N2] | |
| XMD15-146 | 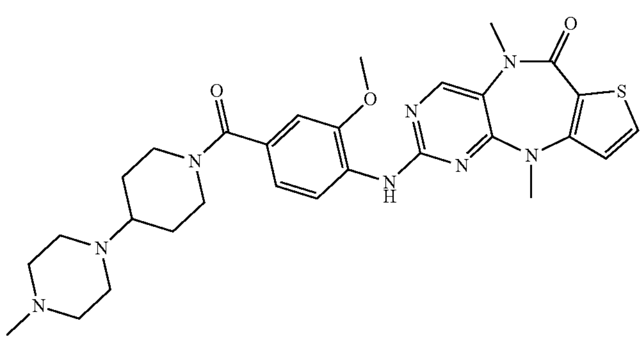 [SMILES: COc1cc(C(=O)N2CCC(N3CCN(C)CC3)CC2)ccc1Nc1ncc2c(n1)N(C)c1ccsc1C(=O)N2C] | |

TABLE 4-continued

Compounds of the invention

| Compound ID | Structure | Spectroscopy |
|---|---|---|
| XMD16-91 | 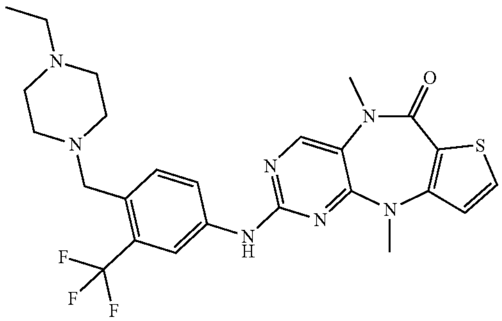 [SMILES: CCN1CCN(Cc2ccc(Nc3ncc4c(n3)N(C)c3ccsc3C(=O)N4C)cc2C(F)(F)F)CC1] | |

TABLE 5

Compounds of the Invention

| Compound ID | Structure | Spectroscopy |
|---|---|---|
| XMD16-12 | 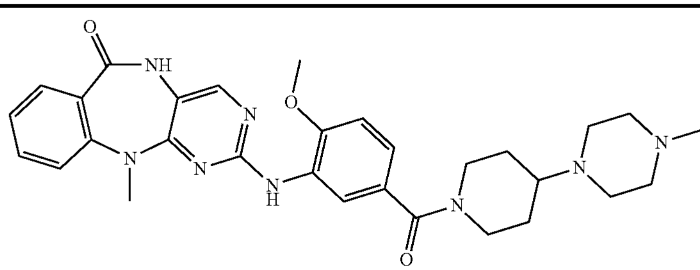 | |
| XMD16-4 | 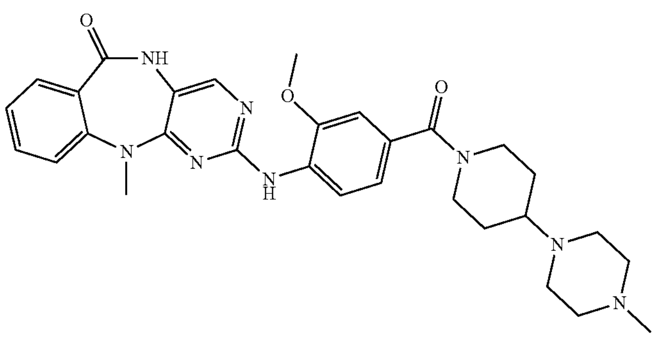 [SMILES: COc1cc(C(=O)N2CCC(N3CCN(C)CC3)CC2)ccc1Nc1ncc2c(n1)N(C)c1ccccc1C(=O)N2] | |
| XMD17-109 (Compound 26) | 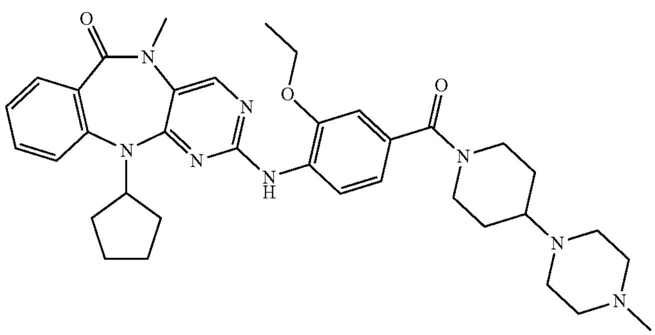 [SMILES: CCOc1cc(C(=O)N2CCC(N3CCN(C)CC3)CC2)ccc1Nc1ncc2c(n1)N(C1CCCC1)c1ccccc1C(=O)N2C] | |

TABLE 5-continued

Compounds of the Invention

| Compound ID | Structure | Spectroscopy |
|---|---|---|
| XMD17-121 | 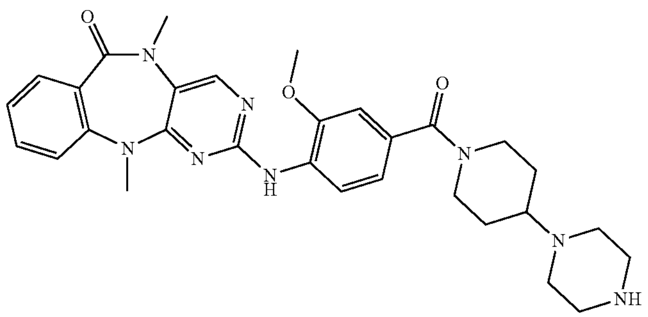 [SMILES: COc1cc(C(=O)N2CCC(N3CCNCC3)CC2)ccc1Nc1ncc2c(n1)N(C)c1ccccc1C(=O)N2C] | |
| XMD17-133 | 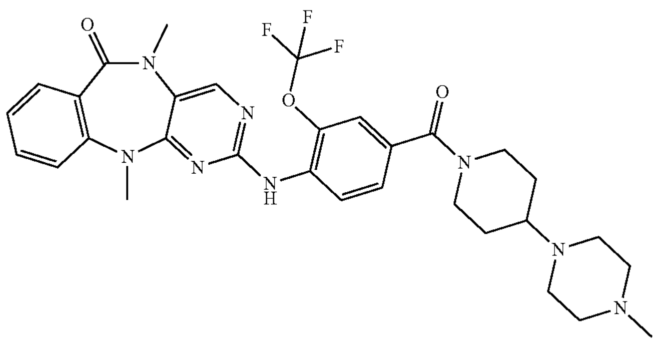 [SMILES: CN1CCN(C2CCN(C(=O)c3ccc(Nc4ncc5c(n4)N(C)c4ccccc4C(=O)N5C)c(OC(F)(F)F)c3)CC2)CC1] | |
| XMD17-26 (Compound 25) | 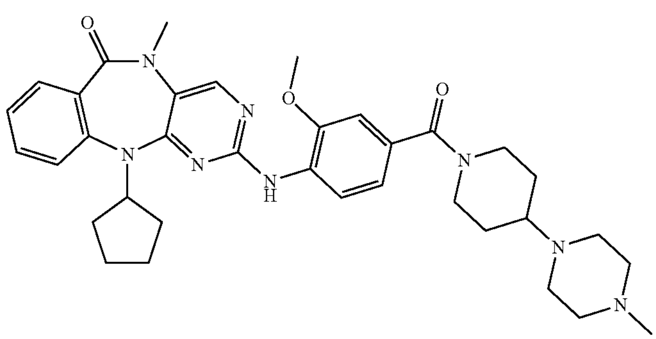 [SMILES: COc1cc(C(=O)N2CCC(N3CCN(C)CC3)CC2)ccc1Nc1ncc2c(n1)N(C1CCCC1)c1ccccc1C(=O)N2C] | |
| XMD17-27 | 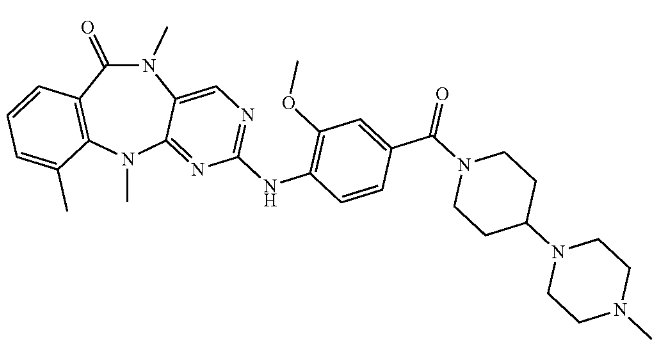 [SMILES: COc1cc(C(=O)N2CCC(N3CCN(C)CC3)CC2)ccc1Nc1ncc2c(n1)N(C)c1c(C)cccc1C(=O)N2C] | |

TABLE 5-continued
Compounds of the Invention
| Compound ID | Structure | Spectroscopy |
|---|---|---|
| XMD17-28 | 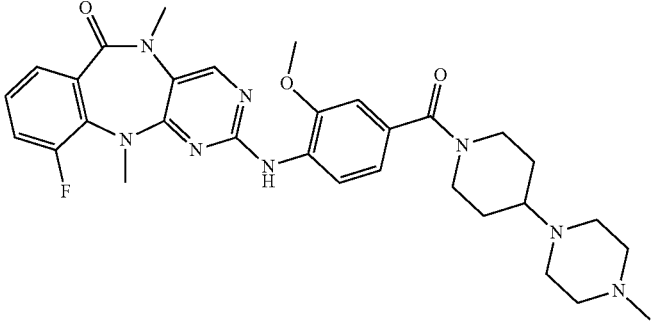 | |
TABLE 6
Additional Compounds of the Invention
| Compound ID | Structure | Spectroscopy |
|---|---|---|
| XMD11-85a | 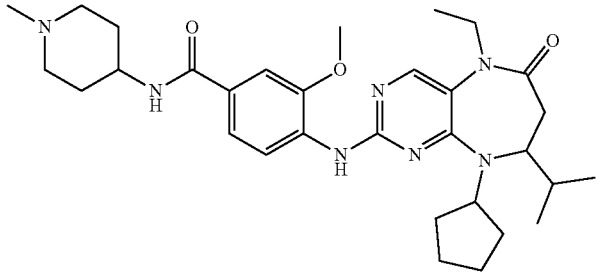 [SMILES: CCN1C(=O)CC(C(C)C)N(C2CCCC2)c2nc(Nc3ccc(C(=O)NC4CCN(C)CC4)cc3OC)ncc21] | |
| XMD11-85b | 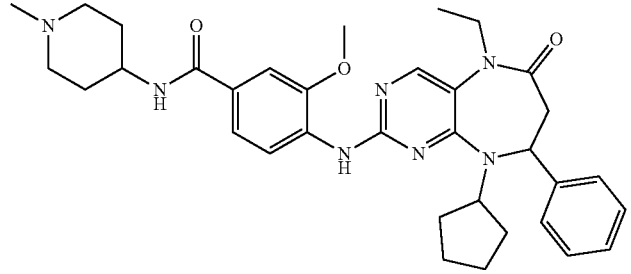 [SMILES: CCN1C(=O)CC(c2ccccc2)N(C2CCCC2)c2nc(Nc3ccc(C(=O)NC4CCN(C)CC4)cc3OC)ncc21] | |
| XMD11-85g | 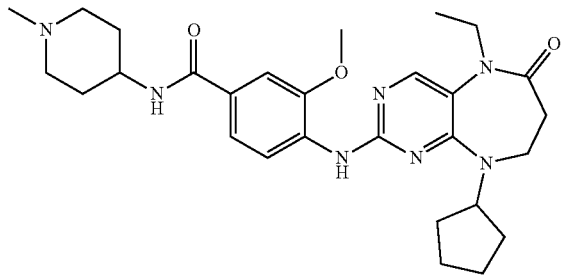 [SMILES: CCN1C(=O)CCN(C2CCCC2)c2nc(Nc3ccc(C(=O)NC4CCN(C)CC4)cc3OC)ncc21] | |

TABLE 6-continued
Additional Compounds of the Invention
| Compound ID | Structure | Spectroscopy |
|---|---|---|
| XMD11-85h | 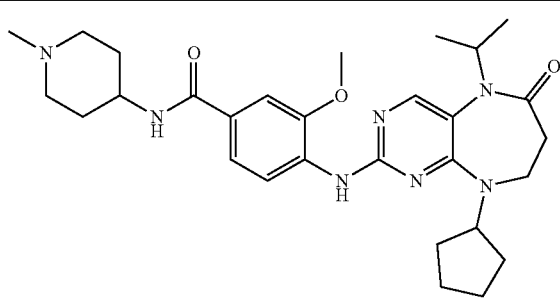 | |
| XMD11-85c | 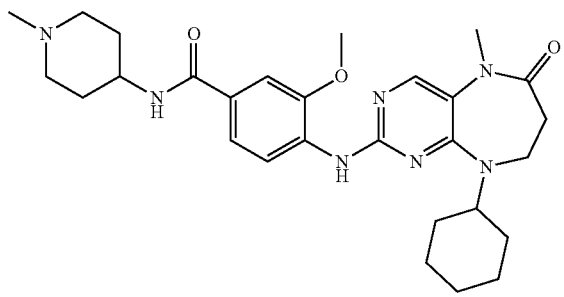 [SMILES: COc1cc(C(=O)NC2CCN(C)CC2)ccc1Nc1ncc2c(n1)N(C1CCCCC1)CCC(=O)N2C] | |
| XMD11-85d | 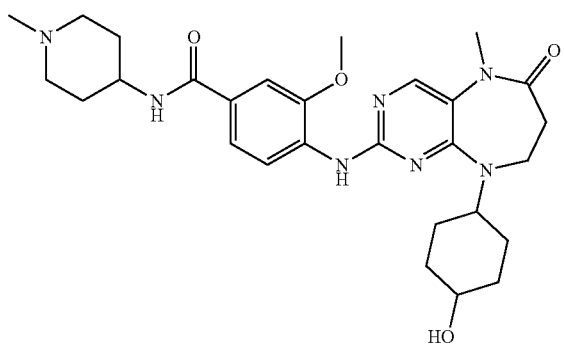 [SMILES: COc1cc(C(=O)NC2CCN(C)CC2)ccc1Nc1ncc2c(n1)N(C1CCC(O)CC1)CCC(=O)N2C] | |
| XMD11-85e | 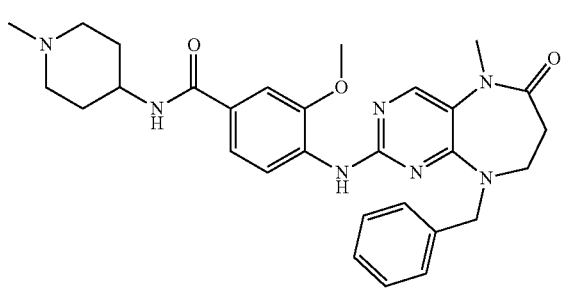 [SMILES: COc1cc(C(=O)NC2CCN(C)CC2)ccc1Nc1ncc2c(n1)N(Cc1ccccc1)CCC(=O)N2C] | |

TABLE 6-continued

Additional Compounds of the Invention

| Compound ID | Structure | Spectroscopy |
|---|---|---|
| XMD11-85f | 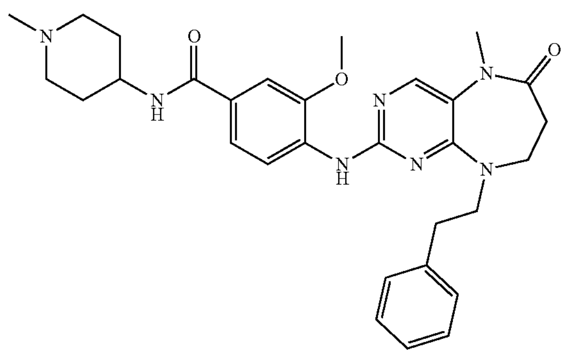 [SMILES: COc1cc(C(=O)NC2CCN(C)CC2)ccc1Nc1ncc2c(n1)N(CCc1ccccc1)CCC(=O)N2C] | |
| DLW-1-138-1 | 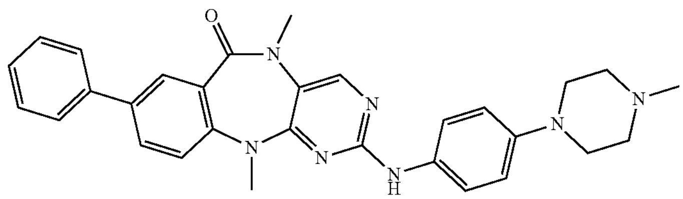 [SMILES: CN1CCN(c2ccc(Nc3ncc4c(n3)N(C)c3ccc(-c5ccccc5)cc3C(=O)N4C)cc2)CC1] | |
| DLW-1-142-1 | 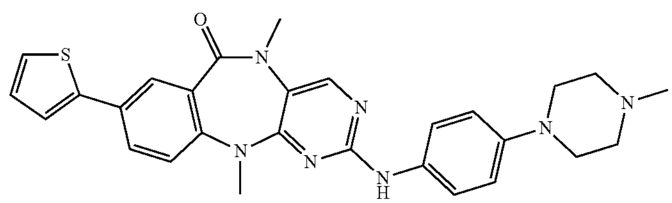 [SMILES: CN1CCN(c2ccc(Nc3ncc4c(n3)N(C)c3ccc(-c5cccs5)cc3C(=O)N4C)cc2)CC1] | |
| XMD-16-87 | 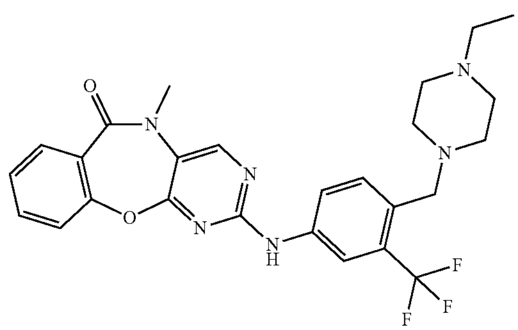 | |
| XMD-16-88 | 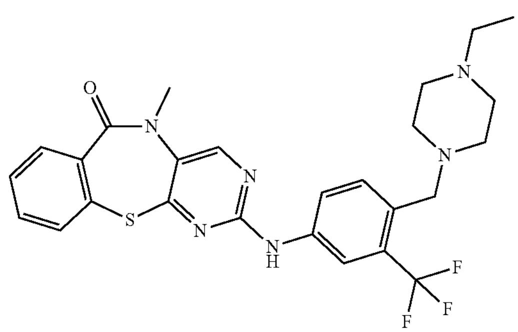 [SMILES: CCN1CCN(Cc2ccc(Nc3ncc4c(n3)Oc3ccccc3C(=O)N4C)cc2C(F)(F)F)CC1] | |

TABLE 6-continued

Additional Compounds of the Invention

| Compound ID | Structure | Spectroscopy |
|---|---|---|
| XMD-16-90 | 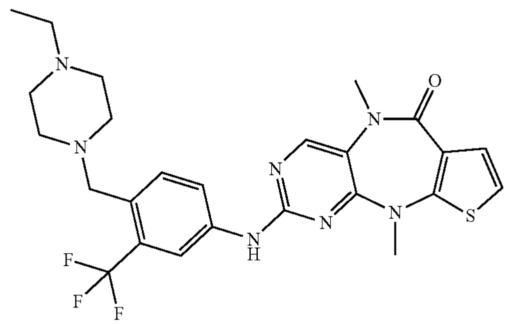 [SMILES: CCN1CCN(Cc2ccc(Nc3ncc4c(n3)N(C)c3sccc3C(=O)N4C)cc2C(F)(F)F)CC1] | |
| DLW-01-080-01 | 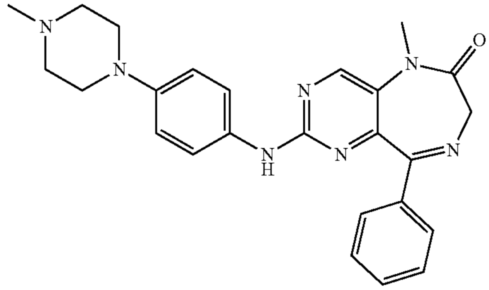 [SMILES: CN1CCN(c2ccc(Nc3ncc4c(n3)C(c3ccccc3)=NCC(=O)N4C)cc2)CC1] | |
| XMD17-62 | 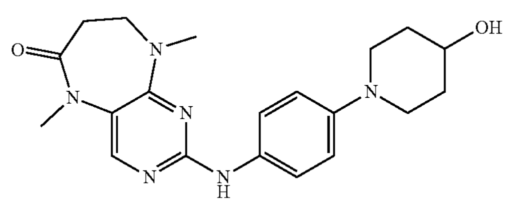 [SMILES: CN1CCC(=O)N(C)c2cnc(Nc3ccc(N4CCC(O)CC4)cc3)nc21] | |
| XMD17-63 | 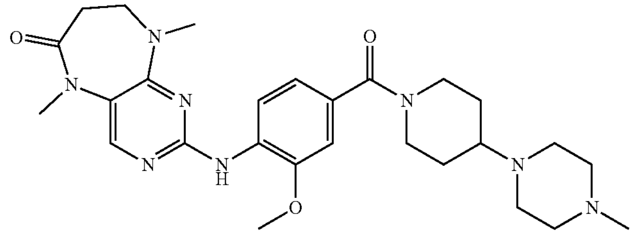 [SMILES: COc1cc(C(=O)N2CCC(N3CCN(C)CC3)CC2)ccc1Nc1ncc2c(n1)N(C)CCC(=O)N2C] | |
| XMD17-87 | 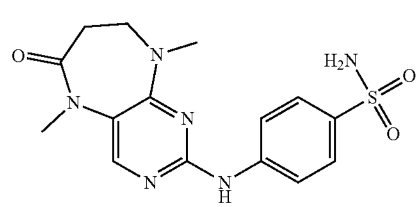 [SMILES: CN1CCC(=O)N(C)c2cnc(Nc3ccc(S(N)(=O)=O)cc3)nc21] | |

TABLE 6-continued

Additional Compounds of the Invention

| Compound ID | Structure | Spectroscopy |
|---|---|---|
| XMD8-81-1 | 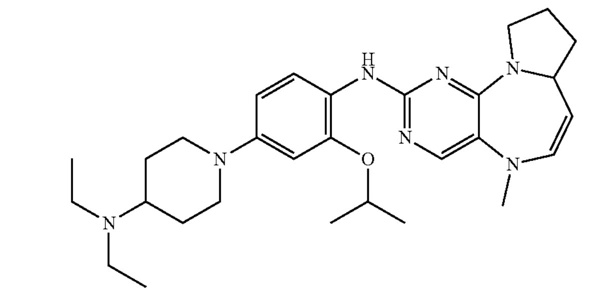 [SMILES: CCN(CC)C1CCN(c2ccc(Nc3ncc4c(n3)N3CCCC3C=CN4C)c(OC(C)C)c2)CC1] | |
| XMD17-73 | 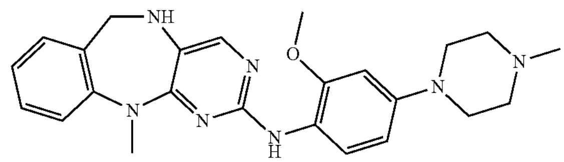 [SMILES: COc1cc(N2CCN(C)CC2)ccc1Nc1ncc2c(n1)N(C)c1ccccc1CN2] | |
| XMD18-19 | 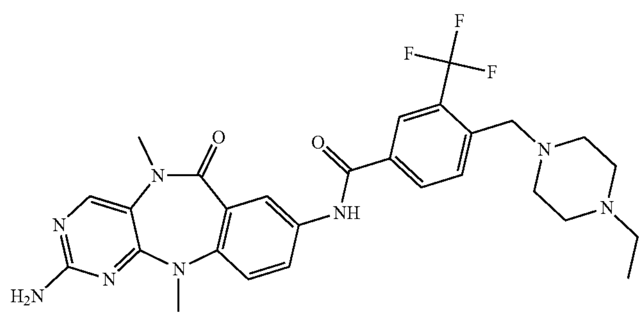 [SMILES: CCN1CCN(Cc2ccc(C(=O)Nc3ccc4c(c3)C(=O)N(C)c3cnc(N)nc3N4C)cc2C(F)(F)F)CC1] | |
| XMD18-29 | 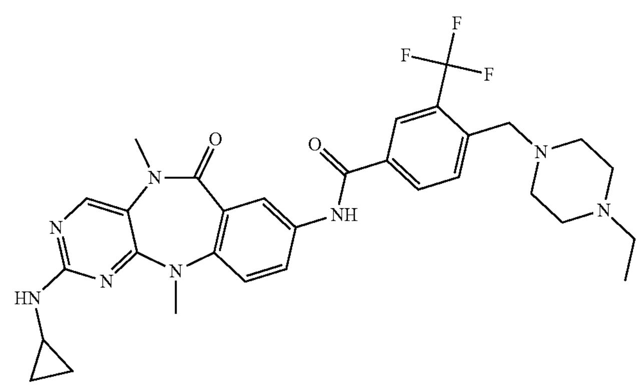 [SMILES: CCN1CCN(Cc2ccc(C(=O)Nc3ccc4c(c3)C(=O)N(C)c3cnc(NC5CC5)nc3N4C)cc2C(F)(F)F)CC1] | |
| XMD18-30 | 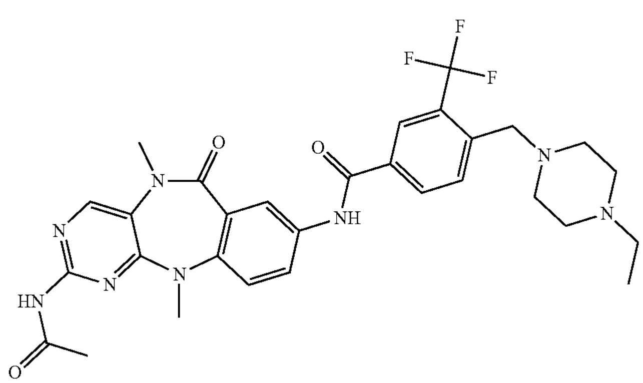 [SMILES: CCN1CCN(Cc2ccc(C(=O)Nc3ccc4c(c3)C(=O)N(C)c3cnc(NC(C)=O)nc3N4C)cc2C(F)(F)F)CC1] | |

TABLE 6-continued

Additional Compounds of the Invention

| Compound ID | Structure | Spectroscopy |
|---|---|---|
| XMD18-31 | 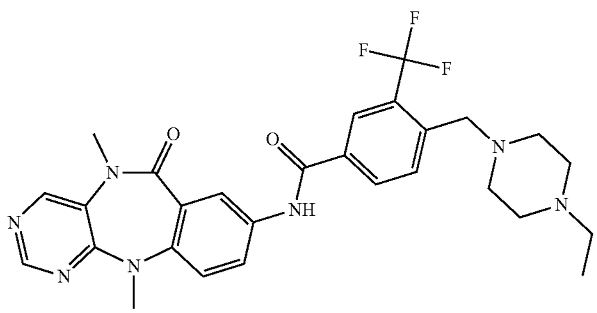 [SMILES: CCN1CCN(Cc2ccc(C(=O)Nc3ccc4c(c3)C(=O)N(C)c3cncnc3N4C)cc2C(F)(F)F)CC1] | |
| XMD18-33 | 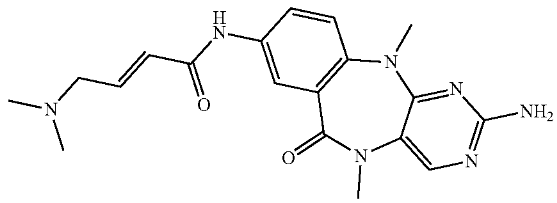 [SMILES: CN(C)C/C=C/C(=O)Nc1ccc2c(c1)C(=O)N(C)c1cnc(N)nc1N2C] | |
| XMD18-34 | 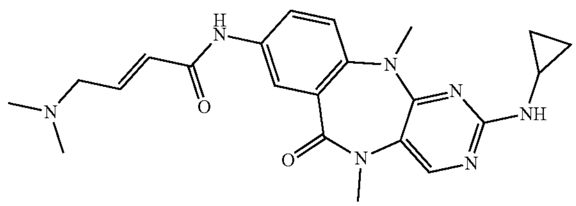 [SMILES: CN(C)C/C=C/C(=O)Nc1ccc2c(c1)C(=O)N(C)c1cnc(NC3CC3)nc1N2C] | |
| XMD18-36 | 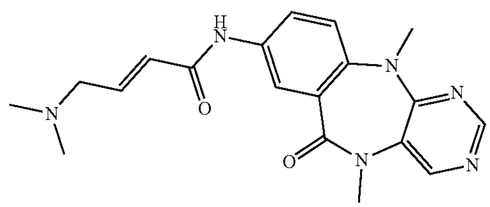 [SMILES: CN(C)C/C=C/C(=O)Nc1ccc2c(c1)C(=O)N(C)c1cncnc1N2C] | |
| XMD18-41 | 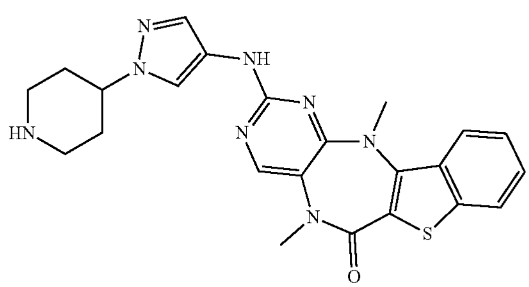 [SMILES: CN1C(=O)c2sc3ccccc3c2N(C)c2nc(Nc3cnn(C4CCNCC4)c3)ncc21] | |
| XMD18-42 | 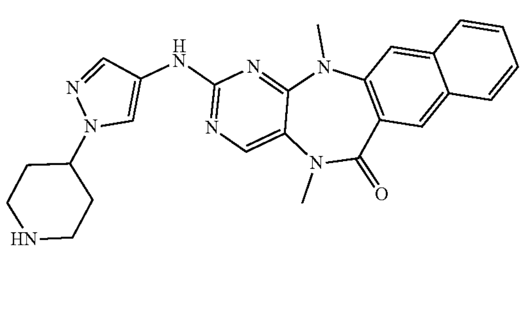 [SMILES: CN1C(=O)c2cc3ccccc3cc2N(C)c2nc(Nc3cnn(C4CCNCC4)c3)ncc21] | |

US 10,787,461 B2
103                                                                                                        104
TABLE 6-continued
Additional Compounds of the Invention
| Compound ID | Structure | Spectroscopy |
|---|---|---|
| XMD18-47 | 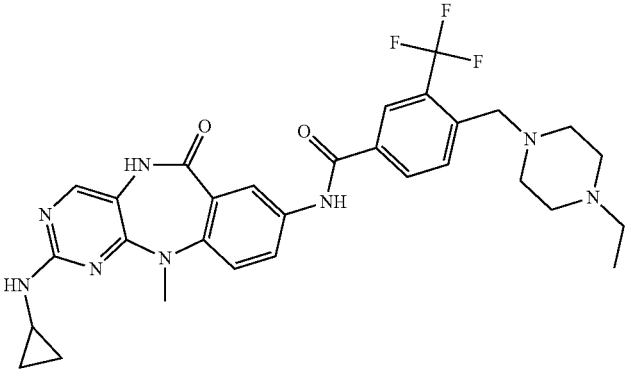 [SMILES: CCN1CCN(Cc2ccc(C(=O)Nc3ccc4c(c3)C(=O)Nc3cnc(NC5CC5)nc3N4C)cc2C(F)(F)F)CC1] | |
| XMD18-48 | 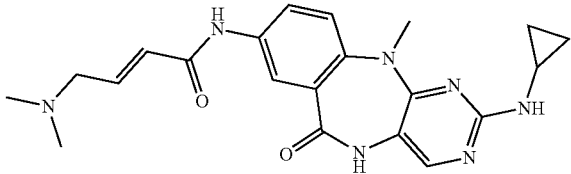 [SMILES: CN(C)C/C=C/C(=O)Nc1ccc2c(c1)C(=O)Nc1cnc(NC3CC3)nc1N2C] | |
| XMD16-61 | 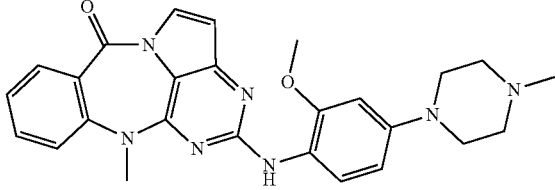 [SMILES: COc1cc(N2CCN(C)CC2)ccc1Nc1nc2c3c(ccn3C(=O)c3ccccc3N2C)n1] | |
| XMD16-62 | 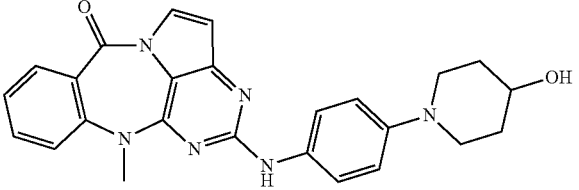 [SMILES: CN1c2ccccc2C(=O)n2ccc3nc(Nc4ccc(N5CCC(O)CC5)cc4)nc1c32] | |
| XMD16-63 | 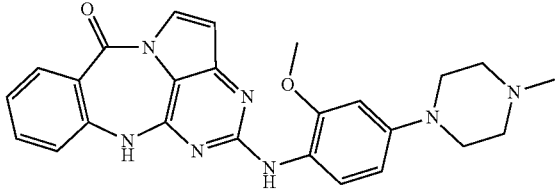 [SMILES: COc1cc(N2CCN(C)CC2)ccc1Nc1nc2c3c(ccn3C(=O)c3ccccc3N2)n1] | |
| XMD16-64 | 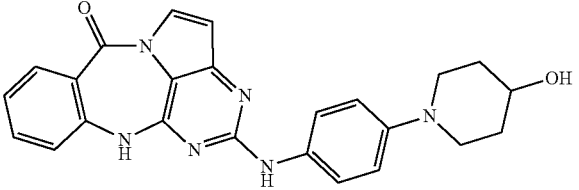 [SMILES: O=C1c2ccccc2Nc2nc(Nc3ccc(N4CCC(O)CC4)cc3)nc3ccn1c23] | |

TABLE 6-continued
Additional Compounds of the Invention
| Compound ID | Structure | Spectroscopy |
|---|---|---|
| XMD17-60 | 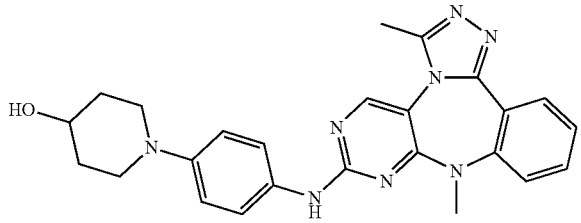 [SMILES: Cc1nnc2n1-c1cnc(Nc3ccc(N4CCC(O)CC4)cc3)nc1N(C)c1ccccc1-2] | |
| XMD17-61 | 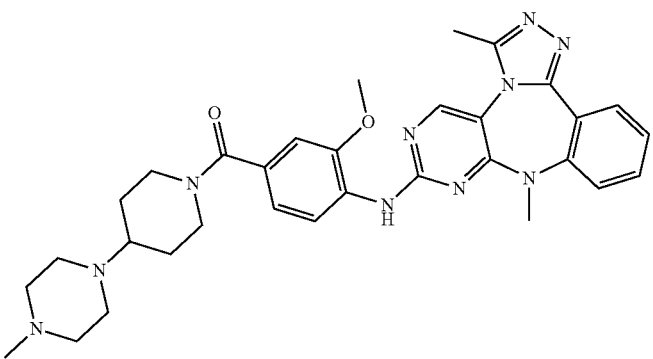 [SMILES: COc1cc(C(=O)N2CCC(N3CCN(C)CC3)CC2)ccc1Nc1ncc2c(n1)N(C)c1ccccc1-c1nnc(C)n1-2] | |
| HG-8-110-01 | 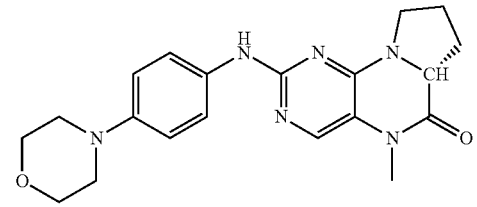 [SMILES: CN1C(=O)[C@H]2CCCN2c2nc(Nc3ccc(N4CCOCC4)cc3)ncc21] | |
| HG-8-112-01 | 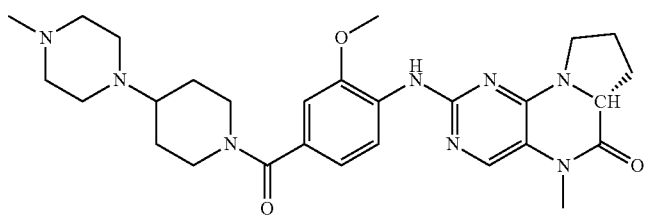 [SMILES: COc1cc(C(=O)N2CCC(N3CCN(C)CC3)CC2)ccc1Nc1ncc2c(n1)N1CCC[C@@H]1C(=O)N2C] | |
| HG-8-112-03 | 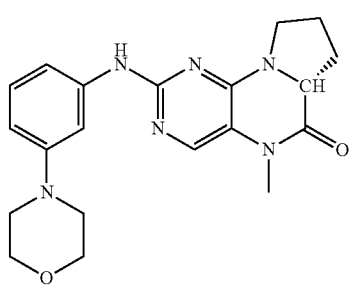 [SMILES: CN1C(=O)[C@H]2CCCN2c2nc(Nc3cccc(N4CCOCC4)c3)ncc21] | |

TABLE 6-continued

Additional Compounds of the Invention

| Compound ID | Structure | Spectroscopy |
|---|---|---|
| HG-8-126-01 | 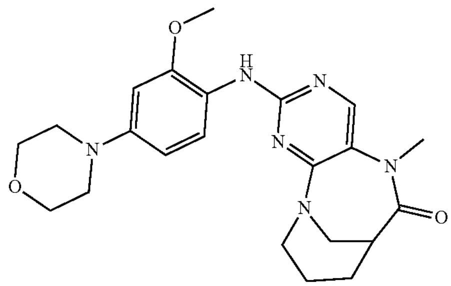 [SMILES: COc1cc(N2CCOCC2)ccc1Nc1ncc2c(n1)N1CCCC(C1)C(=O)N2C] | |
| HG-8-127-01 | 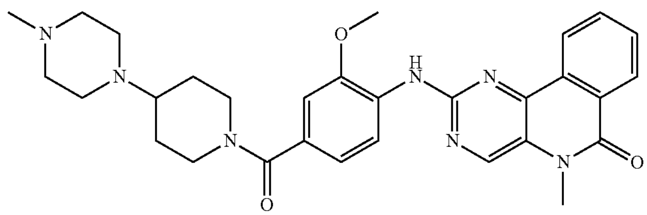 [SMILES: COc1cc(C(=O)N2CCC(N3CCN(C)CC3)CC2)ccc1Nc1ncc2c(n1)c1ccccc1c(=O)n2C] | |
| HG-8-137-01 | 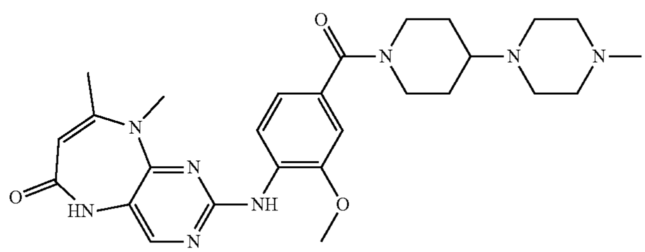 [SMILES: COc1cc(C(=O)N2CCC(N3CCN(C)CC3)CC2)ccc1Nc1ncc2c(n1)N(C)C(C)=CC(=O)N2] | |
| HG-8-137-03 | 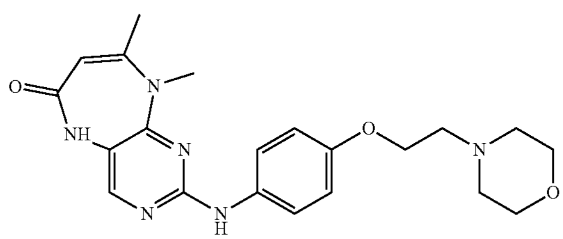 [SMILES: CC1=CC(=O)Nc2cnc(Nc3ccc(OCCN4CCOCC4)cc3)nc2N1C] | |
| HG-8-138-01 | 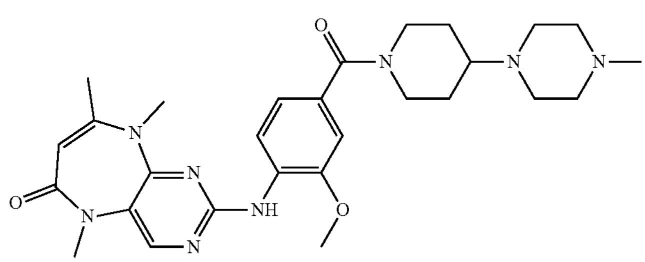 [SMILES: COc1cc(C(=O)N2CCC(N3CCN(C)CC3)CC2)ccc1Nc1ncc2c(n1)N(C)C(C)=CC(=O)N2C] | |
| HG-8-138-03 | 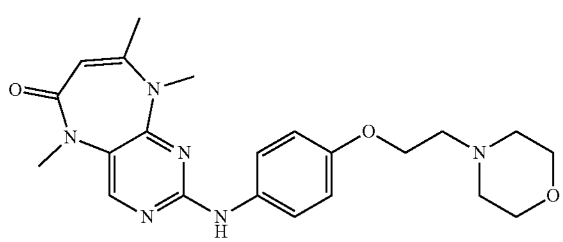 [SMILES: CC1=CC(=O)N(C)c2cnc(Nc3ccc(OCCN4CCOCC4)cc3)nc2N1C] | |

TABLE 6-continued

Additional Compounds of the Invention

| Compound ID | Structure | Spectroscopy |
|---|---|---|
| HG-9-43-01 | 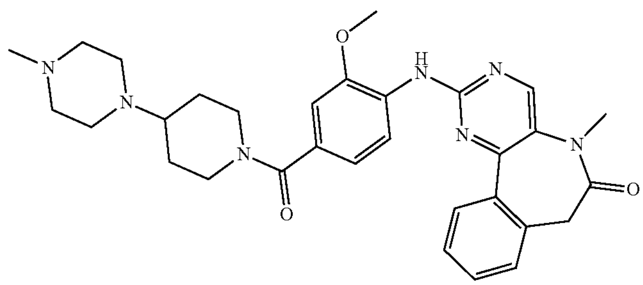 [SMILES: COc1cc(C(=O)N2CCC(N3CCN(C)CC3)CC2)ccc1Nc1ncc2c(n1)-c1ccccc1CC(=O)N2C] | |
| DLW-01-117-01 | 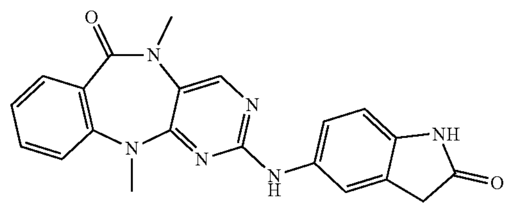 [SMILES: CN1C(=O)c2ccccc2N(C)c2nc(Nc3ccc4c(c3)CC(=O)N4)ncc21] | |
| DLW-01-124-01 | 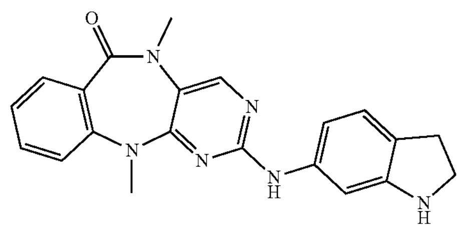 [SMILES: CN1C(=O)c2ccccc2N(C)c2nc(Nc3ccc4c(c3)NCC4)ncc21] | |
| JWE-035 | 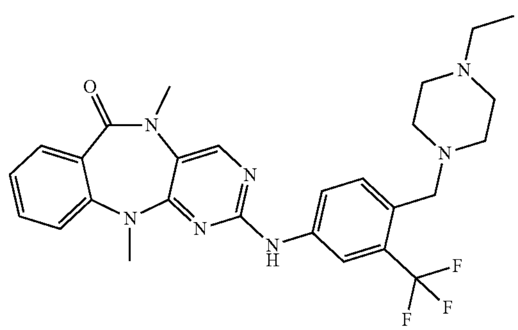 [SMILES: CCN1CCN(Cc2ccc(Nc3ncc4c(n3)N(C)c3ccccc3C(=O)N4C)cc2C(F)(F)F)CC1] | |
| JWE-036 | 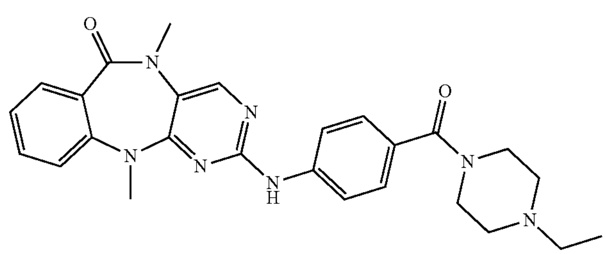 [SMILES: CCN1CCN(C(=O)c2ccc(Nc3ncc4c(n3)N(C)c3ccccc3C(=O)N4C)cc2)CC1] | |
| JWE-037 | 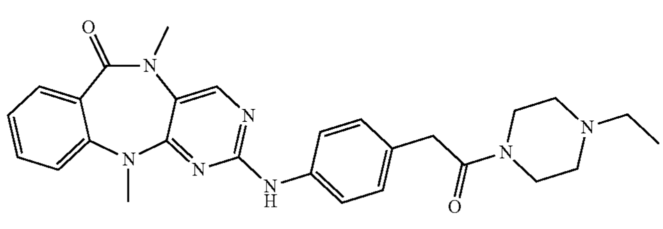 [SMILES: CCN1CCN(C(=O)Cc2ccc(Nc3ncc4c(n3)N(C)c3ccccc3C(=O)N4C)cc2)CC1] | |

TABLE 6-continued
Additional Compounds of the Invention
| Compound ID | Structure | Spectroscopy |
|---|---|---|
| JWE-038 | 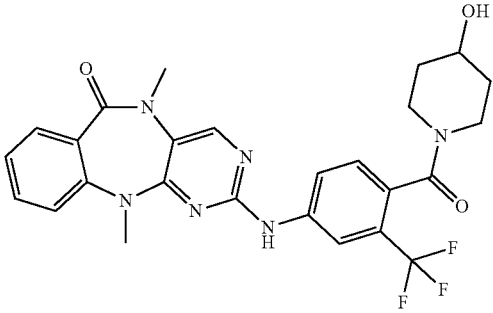 [SMILES: CN1C(=O)c2ccccc2N(C)c2nc(Nc3ccc(C(=O)N4CCC(O)CC4)c(C(F)(F)F)c3)ncc21] | |
| JWE-041 | 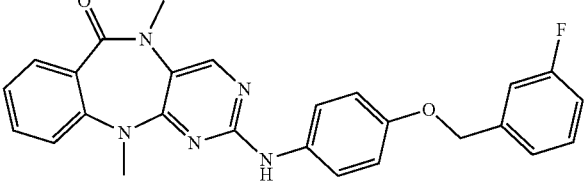 | |
| JWE-042 | 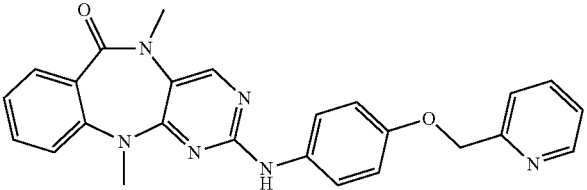 [SMILES: CN1C(=O)c2ccccc2N(C)c2nc(Nc3ccc(OCc4ccccn4)cc3)ncc21] | |
| JWE-043 | 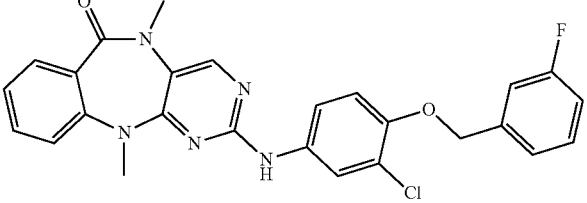 | |
| JWE-044 | 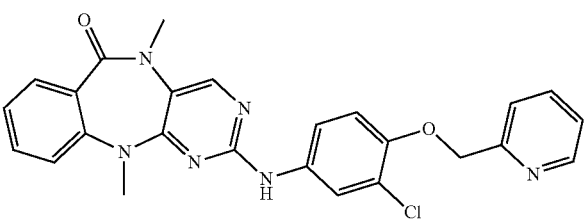 [SMILES: CN1C(=O)c2ccccc2N(C)c2nc(Nc3ccc(OCc4ccccn4)c(Cl)c3)ncc21] | |
| JWE-045 | 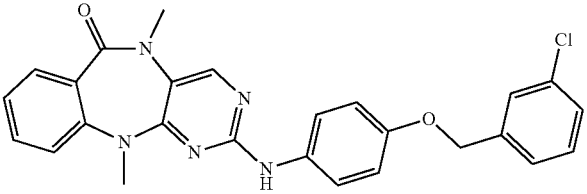 | |

TABLE 6-continued

Additional Compounds of the Invention

| Compound ID | Structure | Spectroscopy |
|---|---|---|
| JWE-067 | 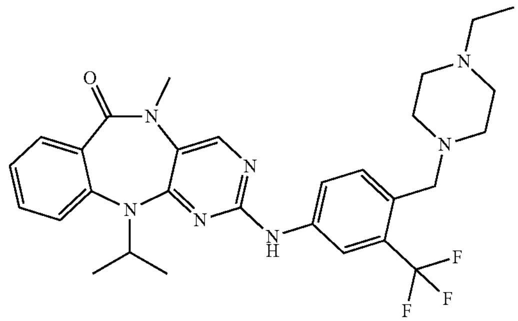 [SMILES: CCN1CCN(Cc2ccc(Nc3ncc4c(n3)N(C(C)C)c3ccccc3C(=O)N4C)cc2C(F)(F)F)CC1] | |
| JWE-068 | 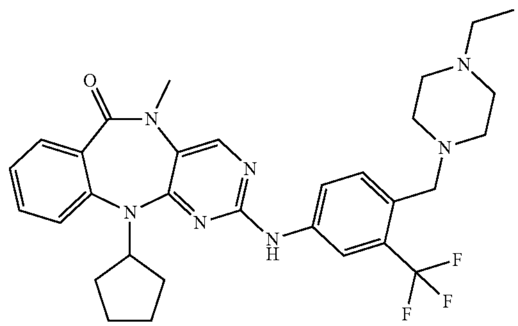 [SMILES: CCN1CCN(Cc2ccc(Nc3ncc4c(n3)N(C3CCCC3)c3ccccc3C(=O)N4C)cc2C(F)(F)F)CC1] | |
| JWE-071 | 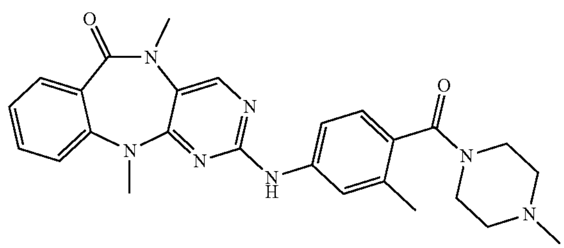 [SMILES: Cc1cc(Nc2ncc3c(n2)N(C)c2ccccc2C(=O)N3C)ccc1C(=O)N1CCN(C)CC1] | |
| JWE-094 | 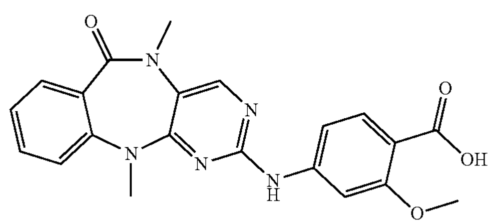 [SMILES: COc1cc(Nc2ncc3c(n2)N(C)c2ccccc2C(=O)N3C)ccc1C(=O)O] | |
| XMD12-54 | 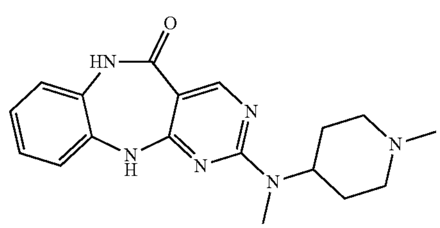 [SMILES: CN1CCC(N(C)c2ncc3c(n2)Nc2ccccc2NC3=O)CC1] | |
| XMD16-10 | 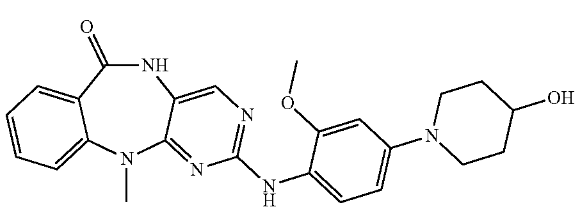 [SMILES: COc1cc(N2CCC(O)CC2)ccc1Nc1ncc2c(n1)N(C)c1ccccc1C(=O)N2] | |

TABLE 6-continued
Additional Compounds of the Invention
| Compound ID | Structure | Spectroscopy |
|---|---|---|
| XMD16-12 | 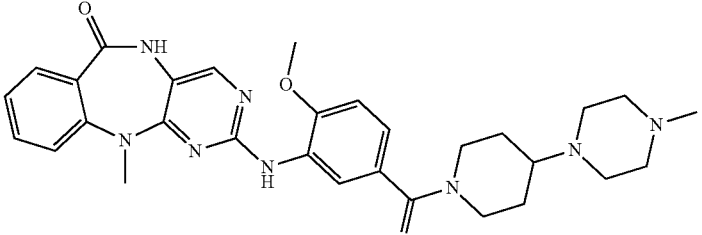 | |
| XMD16-116 | 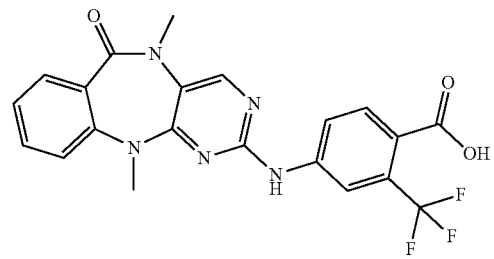 [SMILES: CN1C(=O)c2ccccc2N(C)c2nc(Nc3ccc(C(=O)O)c(C(F)(F)F)c3)ncc21] | |
| XMD16-13 | 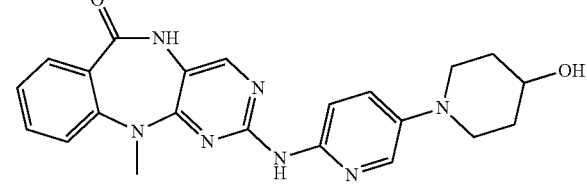 | |
| XMD16-144 | 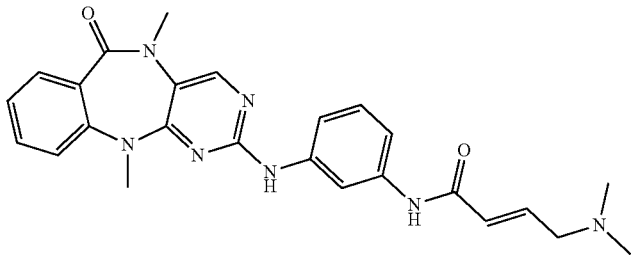 [SMILES: CN(C)C/C=C/C(=O)Nc1cccc(Nc2ncc3c(n2)N(C)c2ccccc2C(=O)N3C)c1] | |
| XMD16-145 | 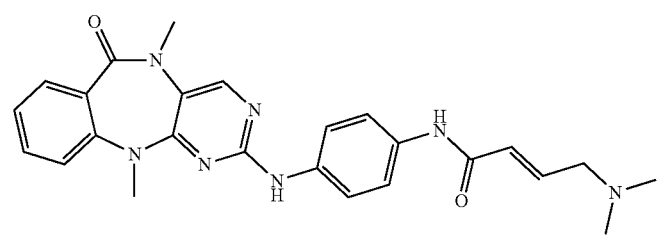 [SMILES: CN(C)C/C=C/C(=O)Nc1ccc(Nc2ncc3c(n2)N(C)c2ccccc2C(=O)N3C)cc1] | |
| XMD16-146 | 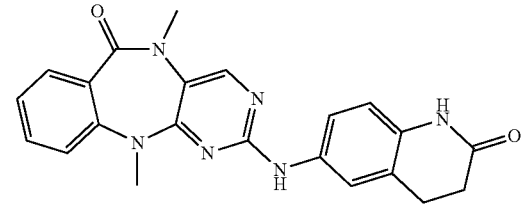 [SMILES: CN1C(=O)c2ccccc2N(C)c2nc(Nc3ccc4c(c3)CCC(=O)N4)ncc21] | |

TABLE 6-continued
Additional Compounds of the Invention
| Compound ID | Structure | Spectroscopy |
|---|---|---|
| XMD16-4 | 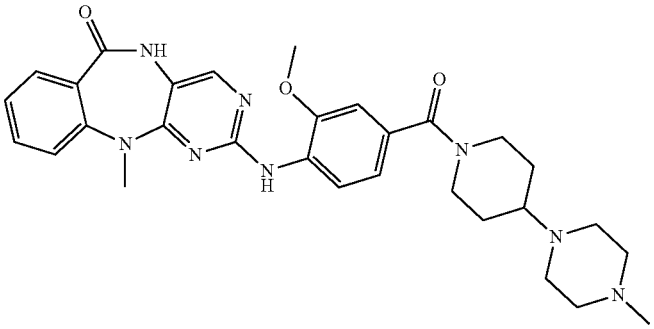 [SMILES: COc1cc(C(=O)N2CCC(N3CCN(C)CC3)CC2)ccc1Nc1ncc2c(n1)N(C)c1ccccc1C(=O)N2] | |
| XMD16-47 | 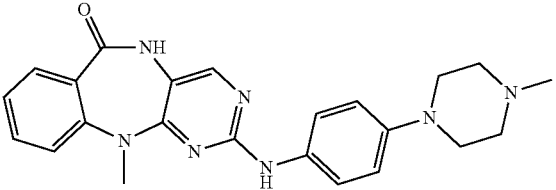 [SMILES: CN1CCN(c2ccc(Nc3ncc4c(n3)N(C)c3ccccc3C(=O)N4)cc2)CC1] | |
| XMD16-48 | 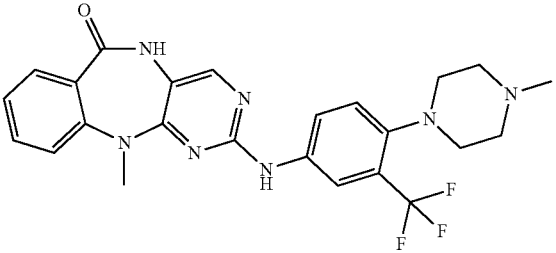 [SMILES: CN1CCN(c2ccc(Nc3ncc4c(n3)N(C)c3ccccc3C(=O)N4)cc2C(F)(F)F)CC1] | |
| XMD16-5 | 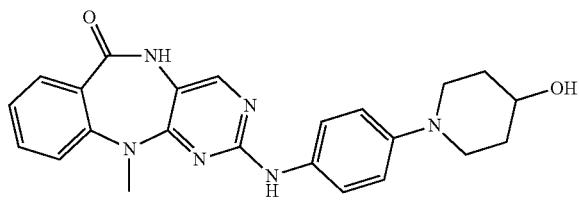 [SMILES: CN1c2ccccc2C(=O)Nc2cnc(Nc3ccc(N4CCC(O)CC4)cc3)nc21] | |
| XMD16-54 | 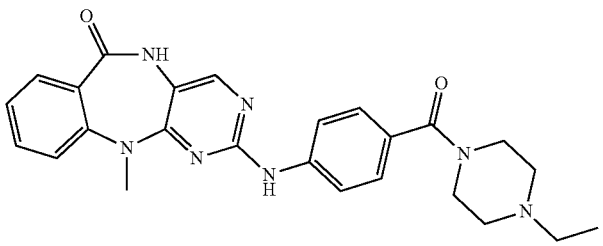 [SMILES: CCN1CCN(C(=O)c2ccc(Nc3ncc4c(n3)N(C)c3ccccc3C(=O)N4)cc2)CC1] | |
| XMD16-55 | 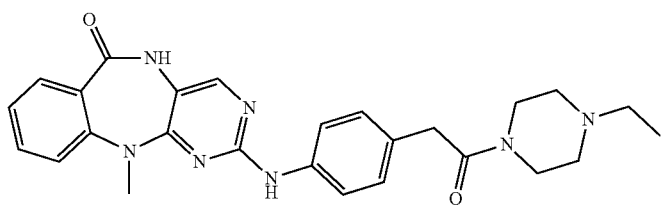 [SMILES: CCN1CCN(C(=O)Cc2ccc(Nc3ncc4c(n3)N(C)c3ccccc3C(=O)N4)cc2)CC1] | |

TABLE 6-continued

Additional Compounds of the Invention

| Compound ID | Structure | Spectroscopy |
|---|---|---|
| XMD16-56 | 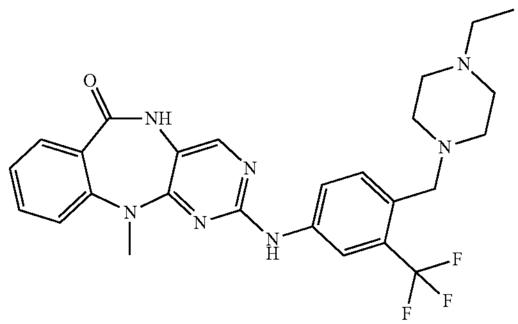 [SMILES: CCN1CCN(Cc2ccc(Nc3ncc4c(n3)N(C)c3ccccc3C(=O)N4)cc2C(F)(F)F)CC1] | |
| XMD16-67 | 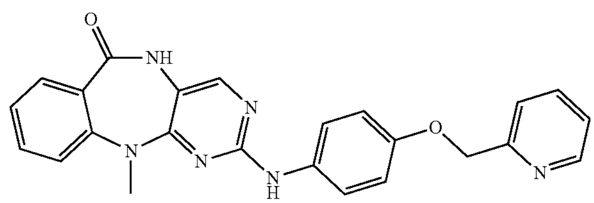 [SMILES: CN1c2ccccc2C(=O)Nc2cnc(Nc3ccc(OCc4ccccn4)cc3)nc21] | |
| XMD16-68 | 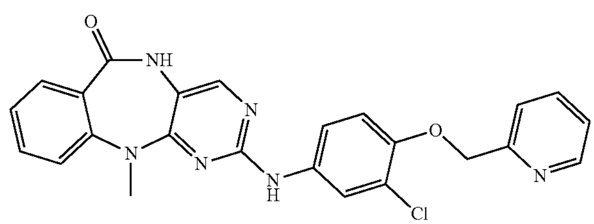 [SMILES: CN1c2ccccc2C(=O)Nc2cnc(Nc3ccc(OCc4ccccn4)c(Cl)c3)nc21] | |
| XMD17-1 | 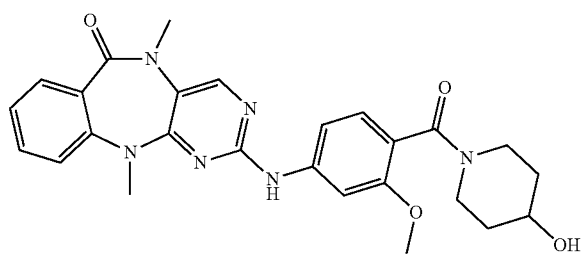 [SMILES: COc1cc(Nc2ncc3c(n2)N(C)c2ccccc2C(=O)N3C)ccc1C(=O)N1CCC(O)CC1] | |
| XMD17-109 | 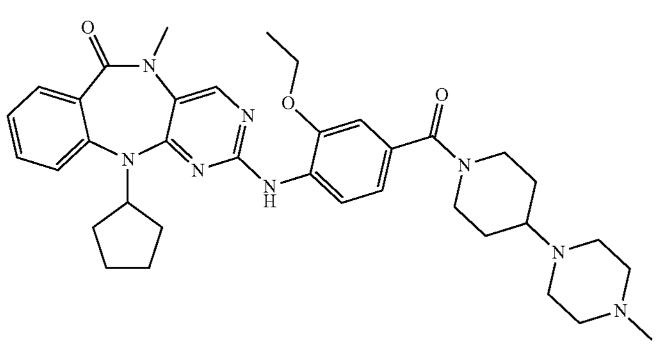 [SMILES: CCOc1cc(C(=O)N2CCC(N3CCN(C)CC3)CC2)ccc1Nc1ncc2c(n1)N(C1CCCC1)c1ccccc1C(=O)N2C] | |

TABLE 6-continued

Additional Compounds of the Invention

| Compound ID | Structure | Spectroscopy |
|---|---|---|
| XMD17-121 | 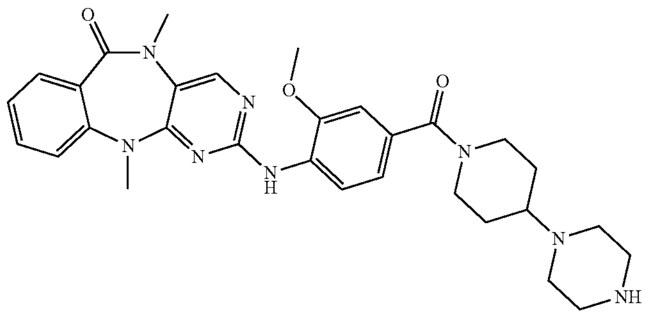 [SMILES: COc1cc(C(=O)N2CCC(N3CCNCC3)CC2)ccc1Nc1ncc2c(n1)N(C)c1ccccc1C(=O)N2C] | |
| XMD17-122 | 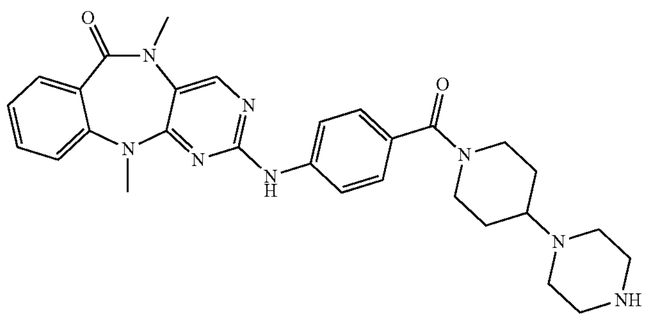 [SMILES: CN1C(=O)c2ccccc2N(C)c2nc(Nc3ccc(C(=O)N4CCC(N5CCNCC5)CC4)cc3)ncc21] | |
| XMD17-123 | 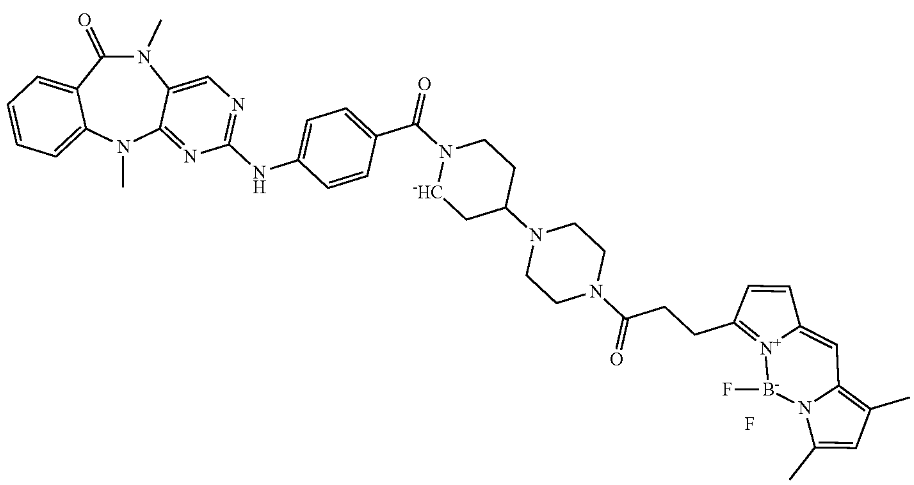 | |
| XMD17-124 | 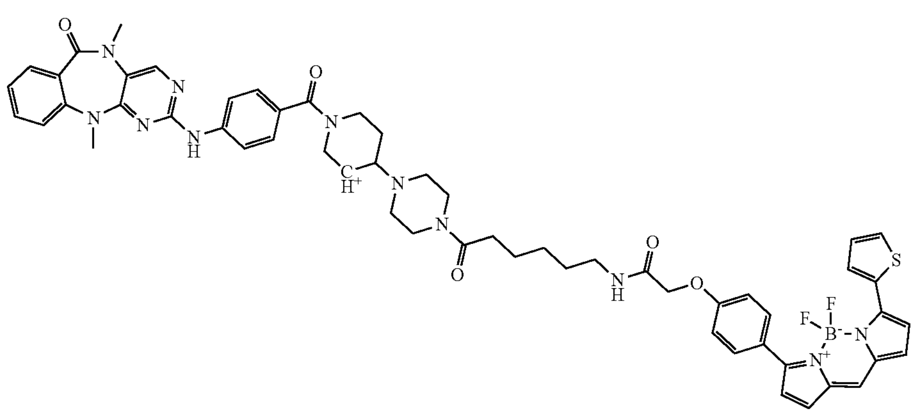 | |

TABLE 6-continued

Additional Compounds of the Invention

| Compound ID | Structure | Spectroscopy |
|---|---|---|
| XMD17-133 | 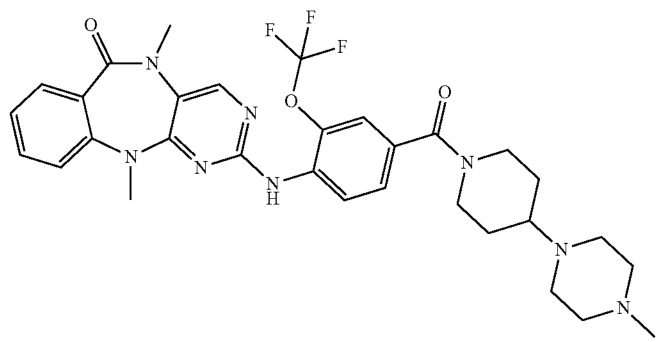 [SMILES: CN1CCN(C2CCN(C(=O)c3ccc(Nc4ncc5c(n4)N(C)c4ccccc4C(=O)N5C)c(OC(F)(F)F)c3)CC2)CC1] | |
| XMD17-134 | 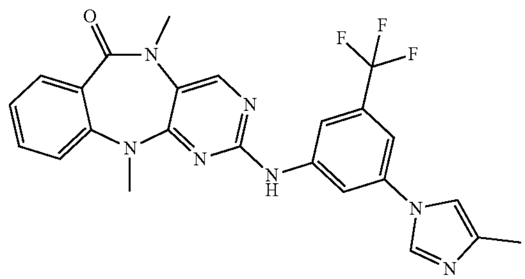 [SMILES: Cc1cn(-c2cc(Nc3ncc4c(n3)N(C)c3ccccc3C(=O)N4C)cc(C(F)(F)F)c2)cn1] | |
| XMD17-137 | 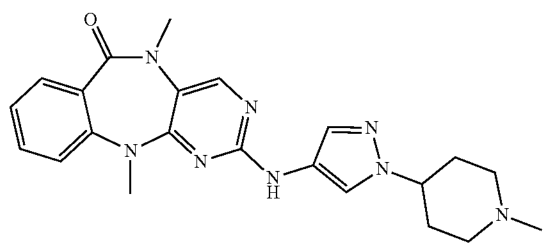 [SMILES: CN1CCC(n2cc(Nc3ncc4c(n3)N(C)c3ccccc3C(=O)N4C)cn2)CC1] | |
| XMD17-139 | 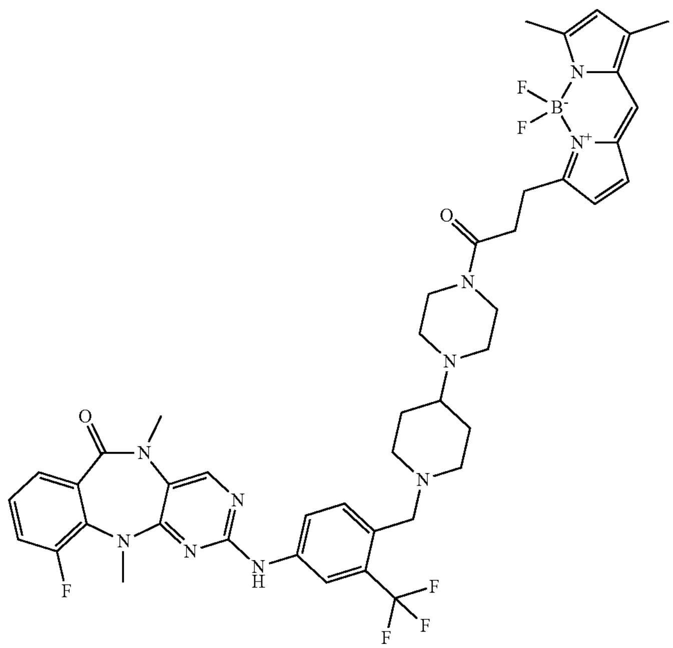 [SMILES: Cc1cc(C)n2c1C=C1C=CC(CCC(=O)N3CCN(C4CCN(Cc5ccc(Nc6ncc7c(n6)N(C)c6c(F)cccc6C(=O)N7C)cc5C(F)(F)F)CC4)CC3)=[N+]1[B-]2(F)F] | |

125

126

TABLE 6-continued

Additional Compounds of the Invention

| Compound ID | Structure | Spectroscopy |
|---|---|---|
| XMD17-140 | 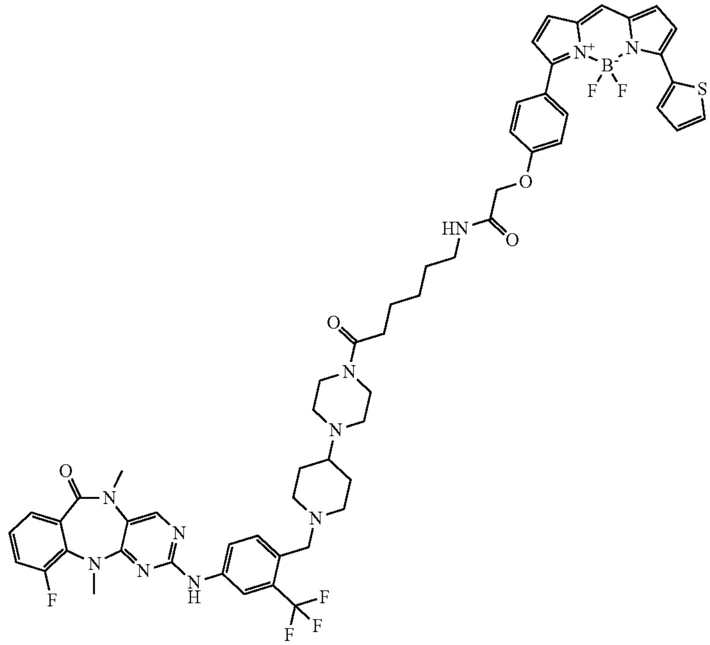 [SMILES: CN1C(=O)c2cccc(F)c2N(C)c2nc(Nc3ccc(CN4CCC(N5CCN(C(=O)CCCCCNC(=O)COc6ccc(C7=[N+]8C(=Cc9ccc(-c%10cccs%10)n9[B-]8(F)F)C=C7)cc6)CC5)CC4)c(C(F)(F)F)c3)ncc21] | |
| XMD17-141 | 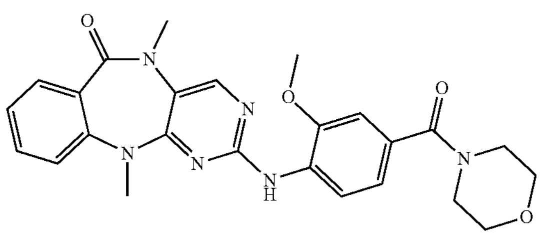 [SMILES: COc1cc(C(=O)N2CCOCC2)ccc1Nc1ncc2c(n1)N(C)c1ccccc1C(=O)N2C] | |
| XMD17-16 | 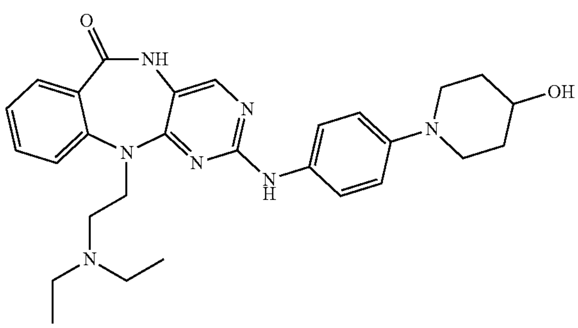 [SMILES: CCN(CC)CCN1c2ccccc2C(=O)Nc2cnc(Nc3ccc(N4CCC(O)CC4)cc3)nc21] | |
| XMD17-26 | 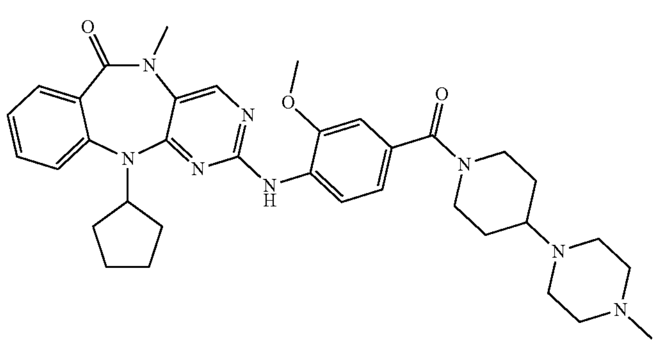 [SMILES: COc1cc(C(=O)N2CCC(N3CCN(C)CC3)CC2)ccc1Nc1ncc2c(n1)N(C1CCCC1)c1ccccc1C(=O)N2C] | |

TABLE 6-continued

Additional Compounds of the Invention

| Compound ID | Structure | Spectroscopy |
|---|---|---|
| XMD17-27 | 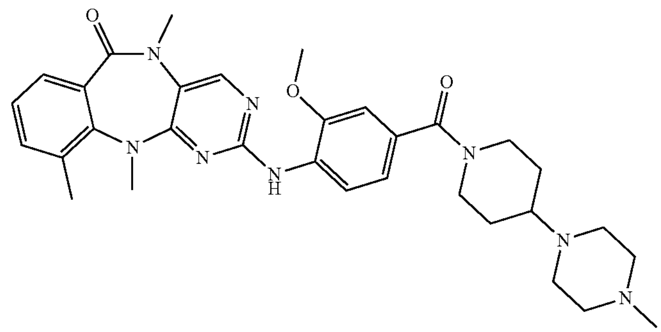 [SMILES: COc1cc(C(=O)N2CCC(N3CCN(C)CC3)CC2)ccc1Nc1ncc2c(n1)N(C)c1c(C)cccc1C(=O)N2C] | |
| XMD17-28 | 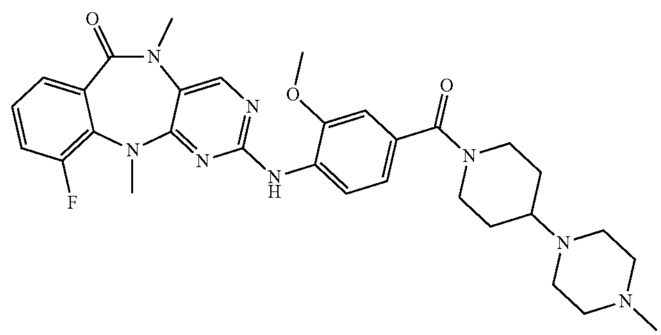 | |
| XMD17-35 | 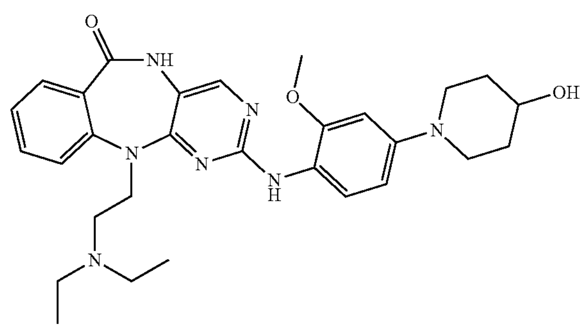 [SMILES: CCN(CC)CCN1c2ccccc2C(=O)Nc2cnc(Nc3ccc(N4CCC(O)CC4)cc3OC)nc21] | |
| XMD17-37 | 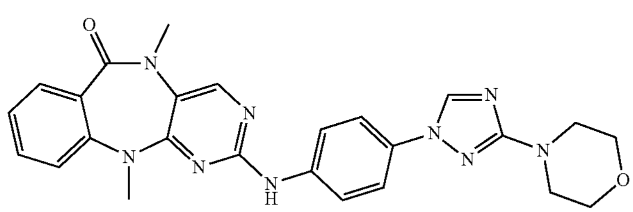 [SMILES: CN1C(=O)c2ccccc2N(C)c2nc(Nc3ccc(-n4cnc(N5CCOCC5)n4)cc3)ncc21] | |
| XMD17-38 | 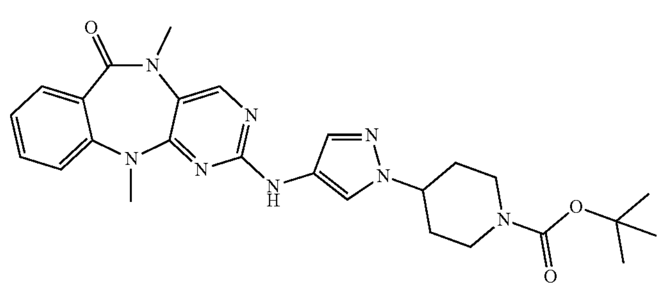 [SMILES: CN1C(=O)c2ccccc2N(C)c2nc(Nc3cnn(C4CCN(C(=O)OC(C)(C)C)CC4)c3)ncc21] | |

TABLE 6-continued
Additional Compounds of the Invention
| Compound ID | Structure | Spectroscopy |
|---|---|---|
| XMD17-51 | 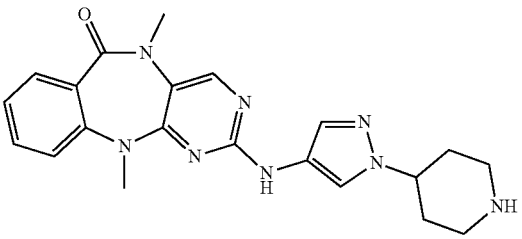 [SMILES: CN1C(=O)c2ccccc2N(C)c2nc(Nc3cnn(C4CCNCC4)c3)ncc21] | |
| XMD17-78 | 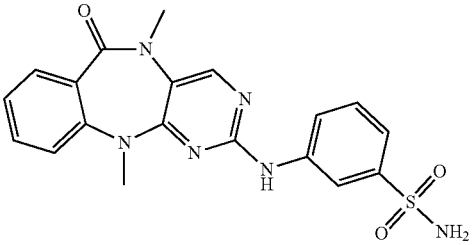 [SMILES: CN1C(=O)c2ccccc2N(C)c2nc(Nc3cccc(S(N)(=O)=O)c3)ncc21] | |
| XMD17-81 | 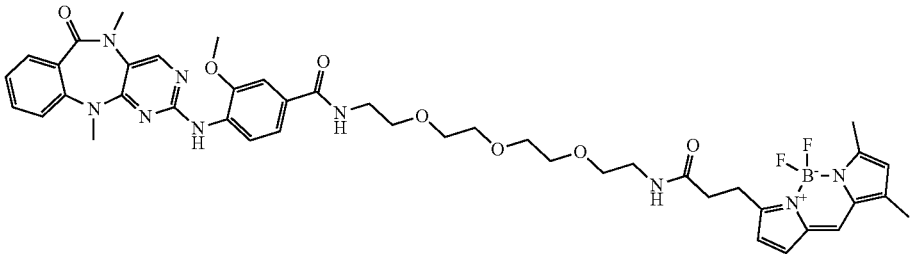 [SMILES: COc1cc(C(=O)NCCOCCOCCOCCNC(=O)CCC2=[N+]3C(=Cc4c(C)cc(C)n4[B-]3(F)F)C=C2)ccc1Nc1ncc2c(n1)N(C)c1ccccc1C(=O)N2C] | |
| XMD17-85 | 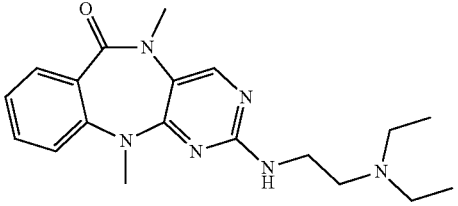 [SMILES: CCN(CC)CCNc1ncc2c(n1)N(C)c1ccccc1C(=O)N2C] | |
| XMD17-86 | 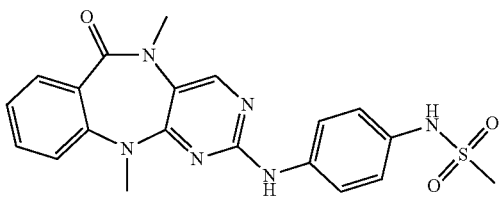 [SMILES: CN1C(=O)c2ccccc2N(C)c2nc(Nc3ccc(NS(C)(=O)=O)cc3)ncc21] | |
| XMD17-88 | 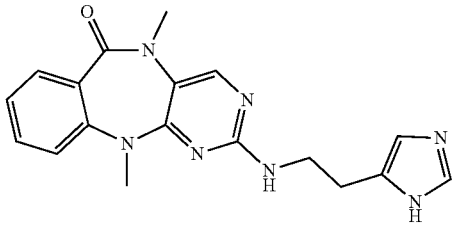 [SMILES: CN1C(=O)c2ccccc2N(C)c2nc(NCCc3cnc[nH]3)ncc21] | |

TABLE 6-continued

Additional Compounds of the Invention

| Compound ID | Structure | Spectroscopy |
|---|---|---|
| XMD17-89 | 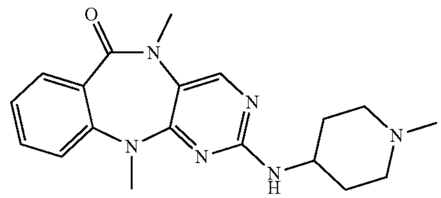 [SMILES: CN1CCC(Nc2ncc3c(n2)N(C)c2ccccc2C(=O)N3C)CC1] | |
| DLW-01-122-01 | 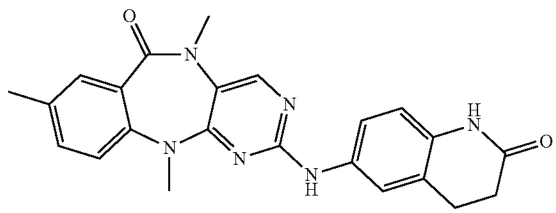 [SMILES: Cc1ccc2c(c1)C(=O)N(C)c1cnc(Nc3ccc4c(c3)CCC(=O)N4)nc1N2C] | |
| DLW-01-125-01 | 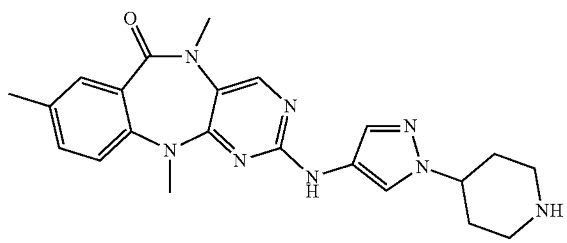 [SMILES: Cc1ccc2c(c1)C(=O)N(C)c1cnc(Nc3cnn(C4CCNCC4)c3)nc1N2C] | |
| XMD17-75 | 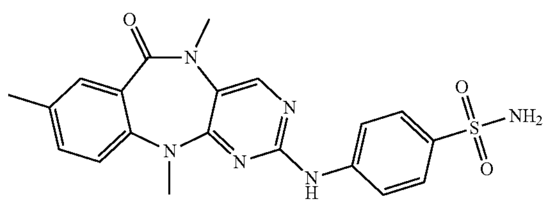 [SMILES: Cc1ccc2c(c1)C(=O)N(C)c1cnc(Nc3ccc(S(N)(=O)=O)cc3)nc1N2C] | |
| XMD17-77 | 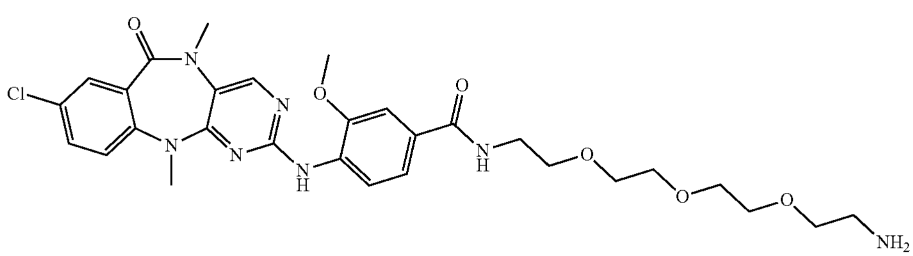 [SMILES: COc1cc(C(=O)NCCOCCOCCOCCN)ccc1Nc1ncc2c(n1)N(C)c1ccc(Cl)cc1C(=O)N2C] | |
| XMD17-79 | 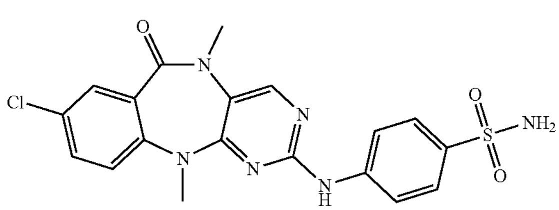 [SMILES: CN1C(=O)c2cc(Cl)ccc2N(C)c2nc(Nc3ccc(S(N)(=O)=O)cc3)ncc21] | |

133 134
TABLE 6-continued
Additional Compounds of the Invention
| Compound ID | Structure | Spectroscopy |
|---|---|---|
| DLW-01-126-01 | 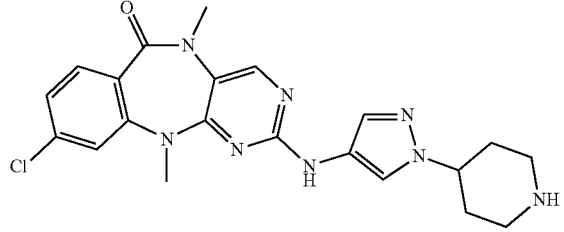 [SMILES: CN1C(=O)c2ccc(Cl)cc2N(C)c2nc(Nc3cnn(C4CCNCC4)c3)ncc21] | |
| XMD17-82 | 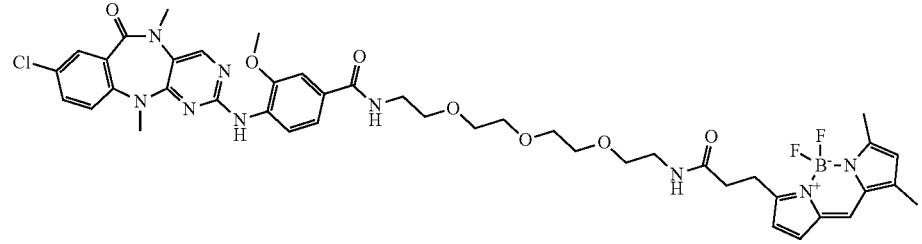 [SMILES: COc1cc(C(=O)NCCOCCOCCOCCNC(=O)CCC2=[N+]3C(=Cc4c(C)cc(C)n4[B-]3(F)F)C=C2)ccc1Nc1ncc2c(n1)N(C)c1ccc(Cl)cc1C(=O)N2C] | |
| DLW-01-111-01 | 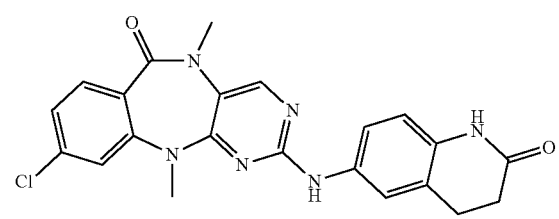 [SMILES: CN1C(=O)c2ccc(Cl)cc2N(C)c2nc(Nc3ccc4c(c3)CCC(=O)N4)ncc21] | |
| DLW-1-141-1 | 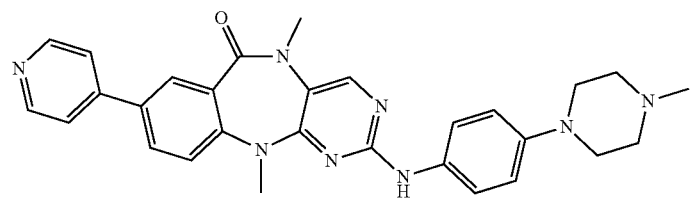 [SMILES: CN1CCN(c2ccc(Nc3ncc4c(n3)N(C)c3ccc(-c5ccncc5)cc3C(=O)N4C)cc2)CC1] | |
| DLW-1-138-1 | 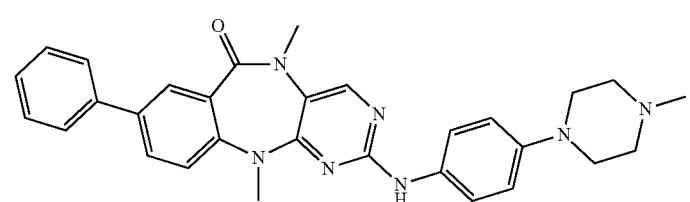 | |
| DLW-1-142-1 | 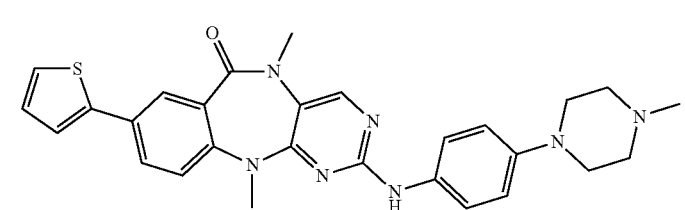 | |
| XMD11-138 | 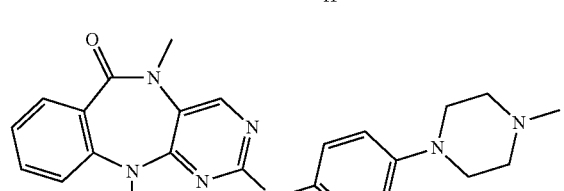 | |

TABLE 6-continued

Additional Compounds of the Invention

| Compound ID | Structure | Spectroscopy |
|---|---|---|
| XMD11-139 | 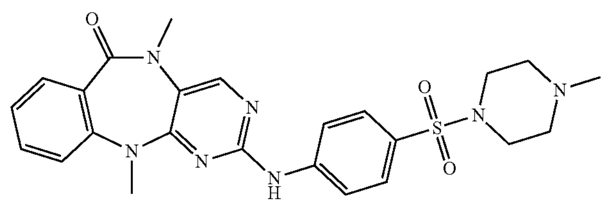 [SMILES: CN1CCN(S(=O)(=O)c2ccc(Nc3ncc4c(n3)N(C)c3ccccc3C(=O)N4C)cc2)CC1] | |
| XMD11-140 | 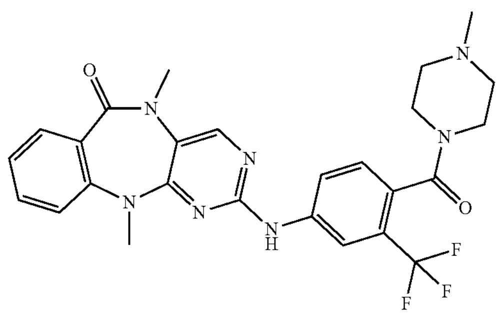 [SMILES: CN1CCN(C(=O)c2ccc(Nc3ncc4c(n3)N(C)c3ccccc3C(=O)N4C)cc2C(F)(F)F)CC1] | |
| XMD11-141 | 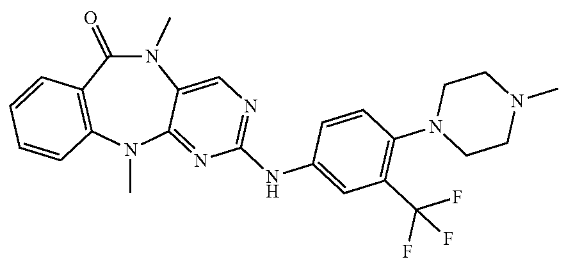 [SMILES: CN1CCN(c2ccc(Nc3ncc4c(n3)N(C)c3ccccc3C(=O)N4C)cc2C(F)(F)F)CC1] | |
| XMD12-1 | 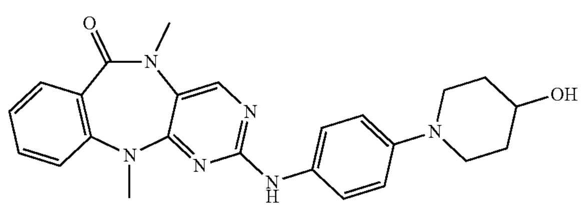 [SMILES: CN1C(=O)c2ccccc2N(C)c2nc(Nc3ccc(N4CCC(O)CC4)cc3)ncc21] | |
| XMD12-129 | 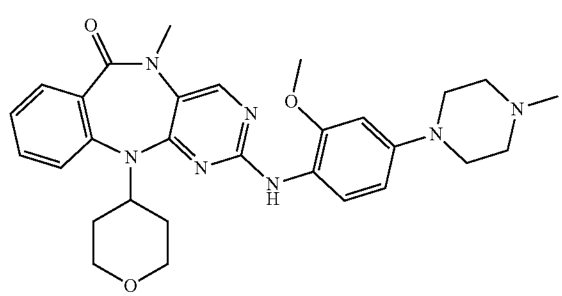 [SMILES: COc1cc(N2CCN(C)CC2)ccc1Nc1ncc2c(n1)N(C1CCOCC1)c1ccccc1C(=O)N2C] | |

TABLE 6-continued

Additional Compounds of the Invention

| Compound ID | Structure | Spectroscopy |
|---|---|---|
| XMD12-130 | 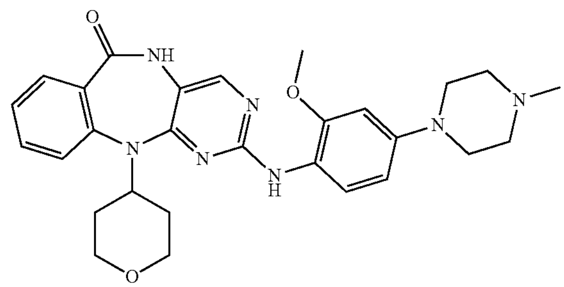 [SMILES: COc1cc(N2CCN(C)CC2)ccc1Nc1ncc2c(n1)N(C1CCOCC1)c1ccccc1C(=O)N2] | |
| XMD12-2 | 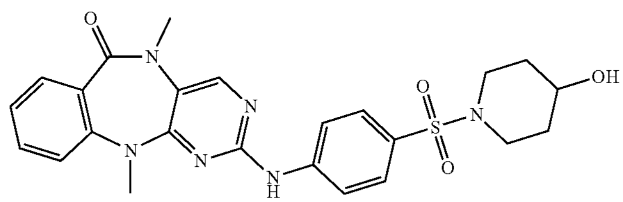 [SMILES: CN1C(=O)c2ccccc2N(C)c2nc(Nc3ccc(S(=O)(=O)N4CCC(O)CC4)cc3)ncc21] | |
| XMD12-3-1 | 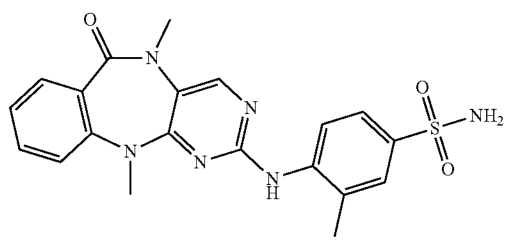 [SMILES: Cc1cc(S(N)(=O)=O)ccc1Nc1ncc2c(n1)N(C)c1ccccc1C(=O)N2C] | |
| XMD12-3-2 | 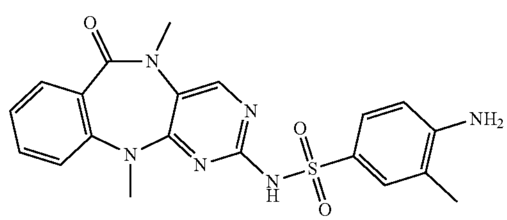 [SMILES: Cc1cc(S(=O)(=O)Nc2ncc3c(n2)N(C)c2ccccc2C(=O)N3C)ccc1N] | |
| XMD12-43a | 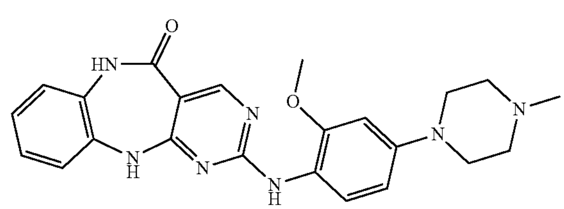 [SMILES: COc1cc(N2CCN(C)CC2)ccc1Nc1ncc2c(n1)Nc1ccccc1NC2=O] | |
| XMD12-51 | 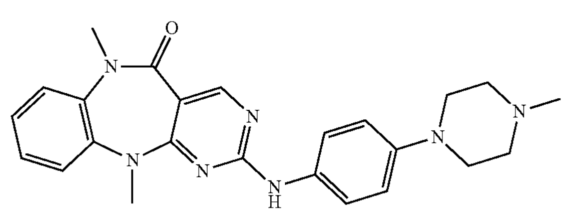 [SMILES: CN1CCN(c2ccc(Nc3ncc4c(n3)N(C)c3ccccc3N(C)C4=O)cc2)CC1] | |

TABLE 6-continued
Additional Compounds of the Invention
| Compound ID | Structure | Spectroscopy |
|---|---|---|
| XMD12-52 | 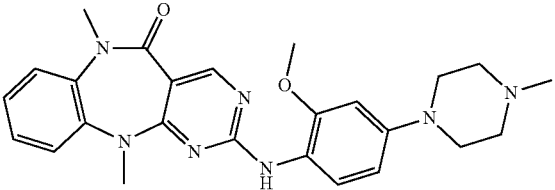 [SMILES: COc1cc(N2CCN(C)CC2)ccc1Nc1ncc2c(n1)N(C)c1ccccc1N(C)C2=O] | |
| XMD12-53 | 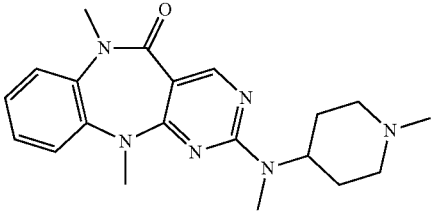 [SMILES: CN1CCC(N(C)c2ncc3c(n2)N(C)c2ccccc2N(C)C3=O)CC1] | |
| XMD12-54 | 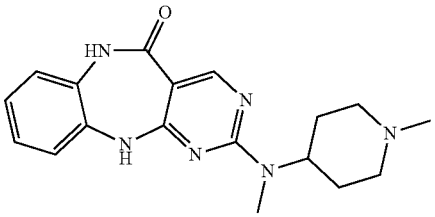 [SMILES: CN1CCC(N(C)c2ncc3c(n2)Nc2ccccc2NC3=O)CC1] | |
| XMD12-55 | 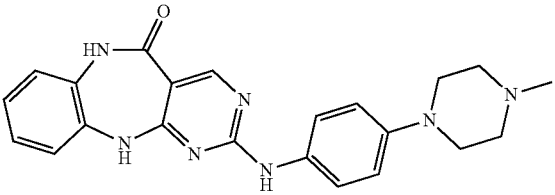 [SMILES: CN1CCN(c2ccc(Nc3ncc4c(n3)Nc3ccccc3NC4=O)cc2)CC1] | |
| XMD12-68 | 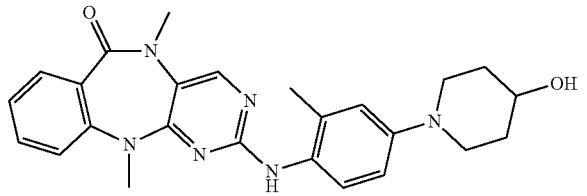 [SMILES: Cc1cc(N2CCC(O)CC2)ccc1Nc1ncc2c(n1)N(C)c1ccccc1C(=O)N2C] | |
| XMD12-69 | 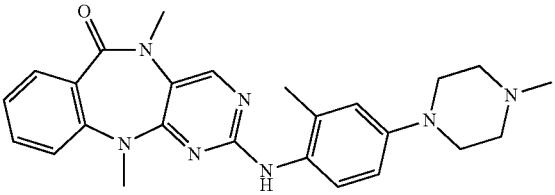 [SMILES: Cc1cc(N2CCN(C)CC2)ccc1Nc1ncc2c(n1)N(C)c1ccccc1C(=O)N2C] | |
| XMD12-70-2 | 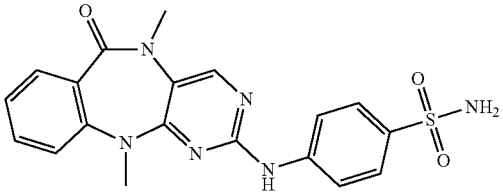 [SMILES: CN1C(=O)c2ccccc2N(C)c2nc(Nc3ccc(S(N)(=O)=O)cc3)ncc21] | |

141    142
TABLE 6-continued
Additional Compounds of the Invention
| Compound ID | Structure | Spectroscopy |
|---|---|---|
| XMD13-137 | 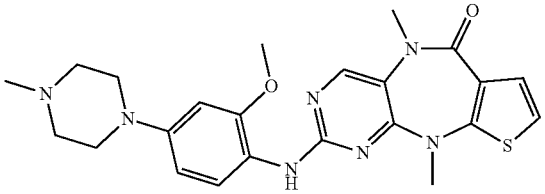 [SMILES: COc1cc(N2CCN(C)CC2)ccc1Nc1ncc2c(n1)N(C)c1sccc1C(=O)N2C] | |
| XMD13-37 | 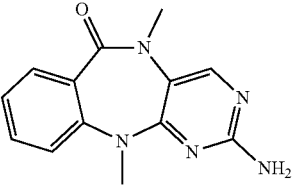 [SMILES: CN1C(=O)c2ccccc2N(C)c2nc(N)ncc21] | |
| XMD13-42 | 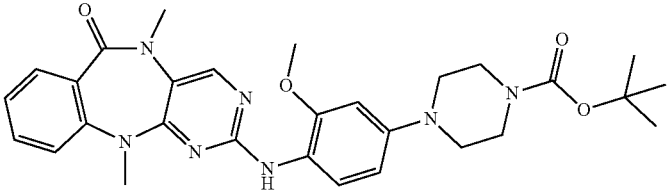 [SMILES: COc1cc(N2CCN(C(=O)OC(C)(C)C)CC2)ccc1Nc1ncc2c(n1)N(C)c1ccccc1C(=O)N2C] | |
| XMD13-43 | 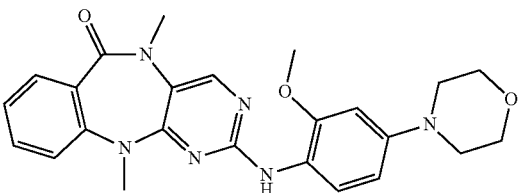 [SMILES: COc1cc(N2CCOCC2)ccc1Nc1ncc2c(n1)N(C)c1ccccc1C(=O)N2C] | |
| XMD13-44 | 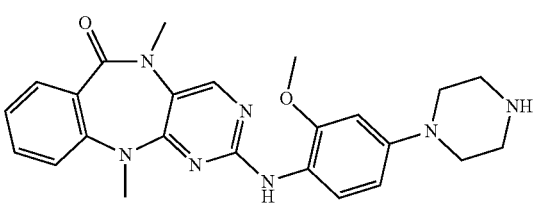 [SMILES: COc1cc(N2CCNCC2)ccc1Nc1ncc2c(n1)N(C)c1ccccc1C(=O)N2C] | |
| XMD13-65 | 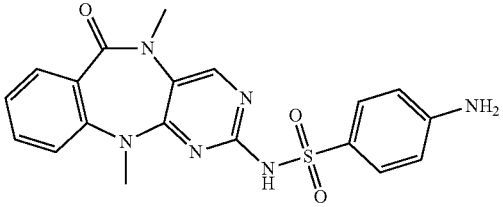 [SMILES: CN1C(=O)c2ccccc2N(C)c2nc(NS(=O)(=O)c3ccc(N)cc3)ncc21] | |
| XMD13-66 | 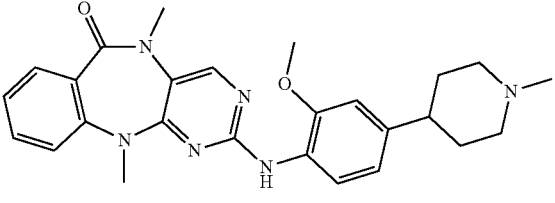 [SMILES: COc1cc(C2CCN(C)CC2)ccc1Nc1ncc2c(n1)N(C)c1ccccc1C(=O)N2C] | |

TABLE 6-continued
Additional Compounds of the Invention
| Compound ID | Structure | Spectroscopy |
|---|---|---|
| XMD13-93 | 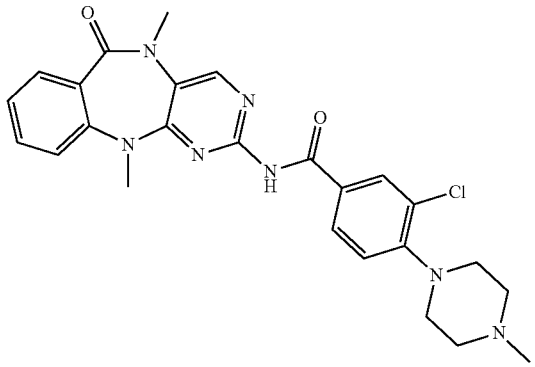 [SMILES: CN1CCN(c2ccc(C(=O)Nc3ncc4c(n3)N(C)c3ccccc3C(=O)N4C)cc2Cl)CC1] | |
| XMD13-98 | 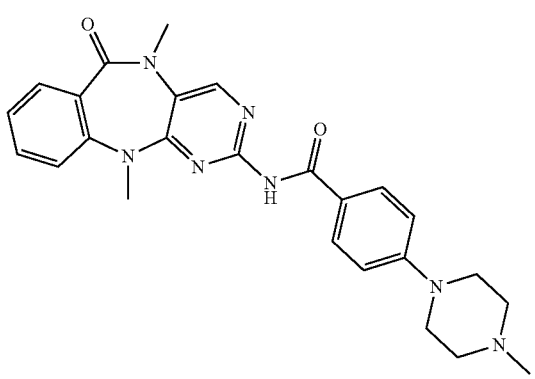 [SMILES: CN1CCN(c2ccc(C(=O)Nc3ncc4c(n3)N(C)c3ccccc3C(=O)N4C)cc2)CC1] | |
| XMD15-69 | 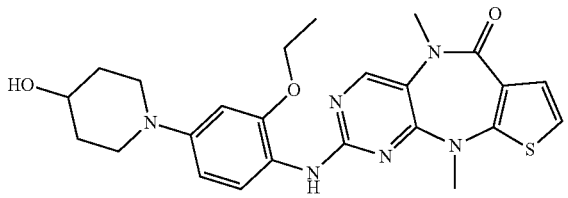 [SMILES: CCOc1cc(N2CCC(O)CC2)ccc1Nc1ncc2c(n1)N(C)c1sccc1C(=O)N2C] | |
| XMD16-11 | 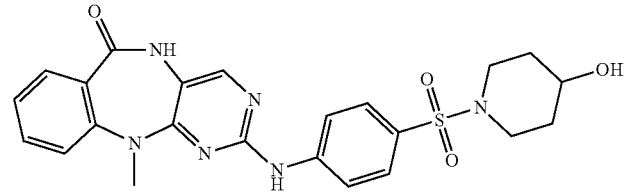 [SMILES: CN1c2ccccc2C(=O)Nc2cnc(Nc3ccc(S(=O)(=O)N4CCC(O)CC4)cc3)nc21] | |
| XMD16-91 | 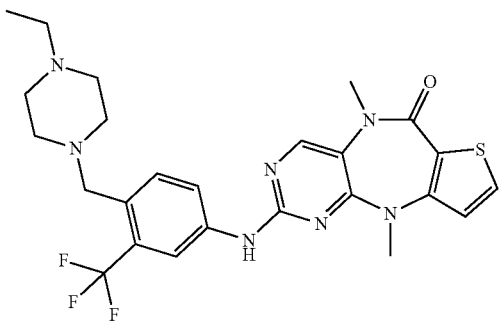 [SMILES: CCN1CCN(Cc2ccc(Nc3ncc4c(n3)N(C)c3ccsc3C(=O)N4C)cc2C(F)(F)F)CC1] | |

TABLE 6-continued

Additional Compounds of the Invention

| Compound ID | Structure | Spectroscopy |
|---|---|---|
| HG-9-75-06 | 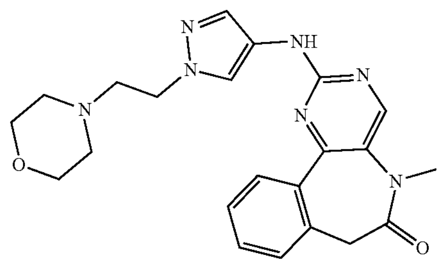 [SMILES: CN1C(=O)Cc2ccccc2-c2nc(Nc3cnn(CCN4CCOCC4)c3)ncc21] | |
| HG-9-135-01 | 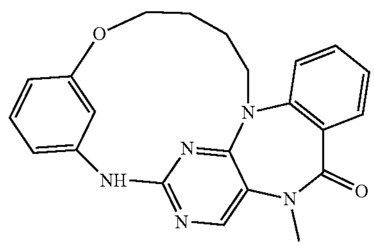 [SMILES: CN1C(=O)c2ccccc2N2CCCCOc3cccc(c3)Nc3ncc1c2n3] | |
| HG-9-129-01a | 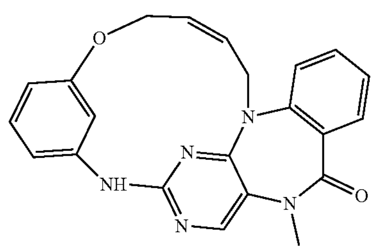 [SMILES: CN1C(=O)c2ccccc2N2C/C=C\COc3cccc(c3)Nc3ncc1c2n3] | |
| HG-10-66-01 | 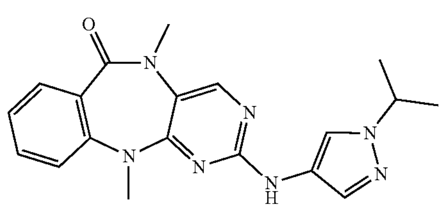 [SMILES: CC(C)n1cc(Nc2ncc3c(n2)N(C)c2ccccc2C(=O)N3C)cn1] | |
| HG-10-67-01 | 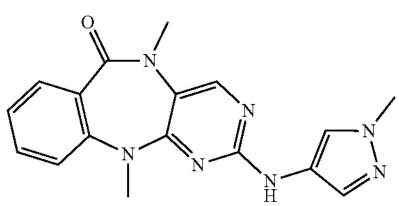 [SMILES: CN1C(=O)c2ccccc2N(C)c2nc(Nc3cnn(C)c3)ncc21] | |
| HG-10-67-02 | 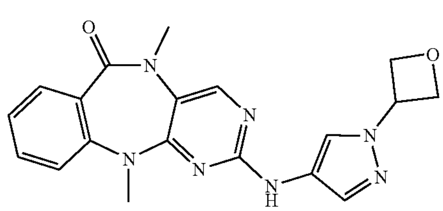 [SMILES: CN1C(=O)c2ccccc2N(C)c2nc(Nc3cnn(C4COC4)c3)ncc21] | |

TABLE 6-continued

Additional Compounds of the Invention

| Compound ID | Structure | Spectroscopy |
|---|---|---|
| HG-10-67-03 | 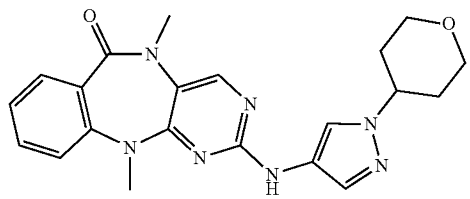 [SMILES: CN1C(=O)c2ccccc2N(C)c2nc(Nc3cnn(C4CCOCC4)c3)ncc21] | |
| HG-10-68-01 | 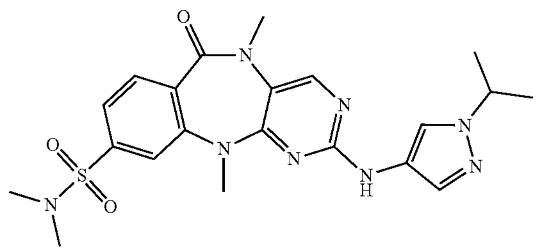 [SMILES: CC(C)n1cc(Nc2ncc3c(n2)N(C)c2cc(S(=O)(=O)N(C)C)ccc2C(=O)N3C)cn1] | |
| HG-10-69-01 | 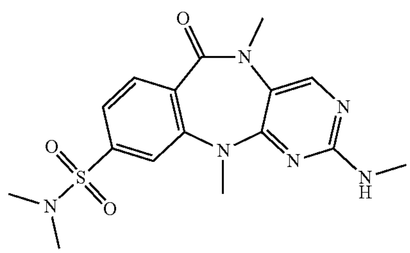 | |
| HG-10-75-01 | 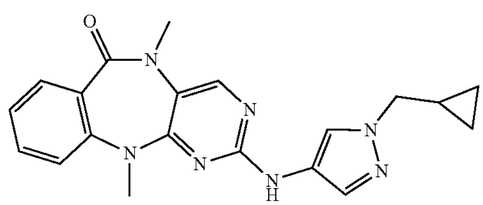 [SMILES: CN1C(=O)c2ccccc2N(C)c2nc(Nc3cnn(CC4CC4)c3)ncc21] | |
| HG-10-75-02 | 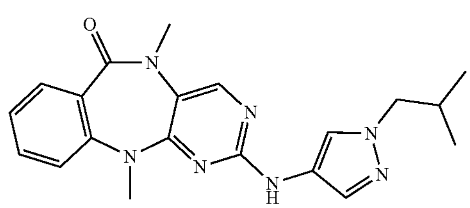 [SMILES: CC(C)Cn1cc(Nc2ncc3c(n2)N(C)c2ccccc2C(=O)N3C)cn1] | |
| XMD7-126 | 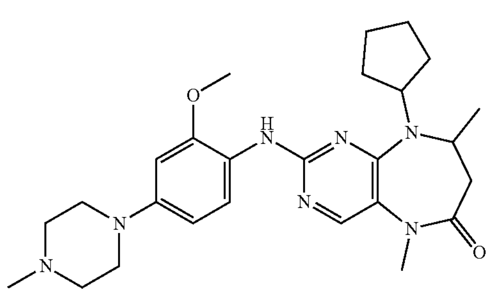 [SMILES: COc1cc(N2CCN(C)CC2)ccc1Nc1ncc2c(n1)N(C1CCCC1)C(C)CC(=O)N2C] | |

TABLE 6-continued

Additional Compounds of the Invention

| Compound ID | Structure | Spectroscopy |
|---|---|---|
| XMD7-126 | 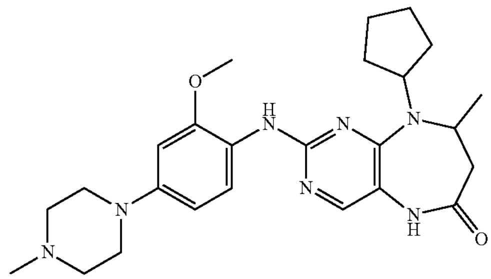 [SMILES: COc1cc(N2CCN(C)CC2)ccc1Nc1ncc2c(n1)N(C1CCCC1)C(C)CC(=O)N2] | |
| XMD7-127 | 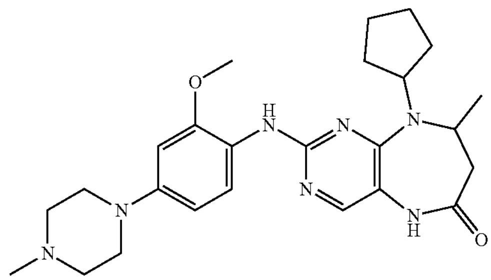 [SMILES: COc1cc(N2CCN(C)CC2)ccc1Nc1ncc2c(n1)N(C1CCCC1)C(C)CC(=O)N2] | |
| XMD8-75 | 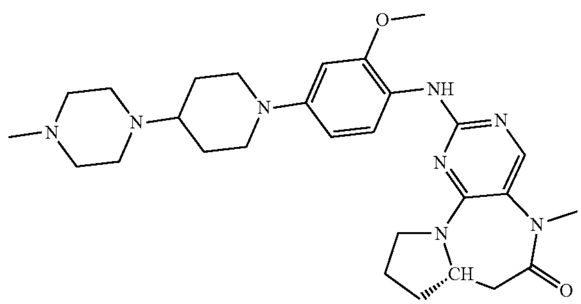 | |
| XMD8-76 | 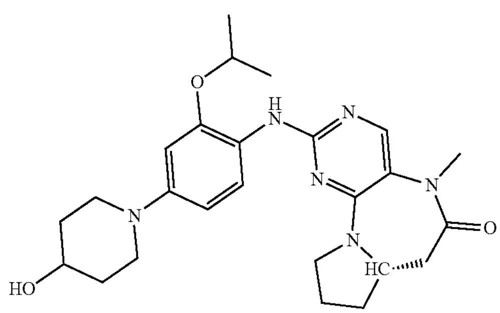 [SMILES: CC(C)Oc1cc(N2CCC(O)CC2)ccc1Nc1ncc2c(n1)N1CCC[C@H]1CC(=O)N2C] | |
| XMD8-81 | 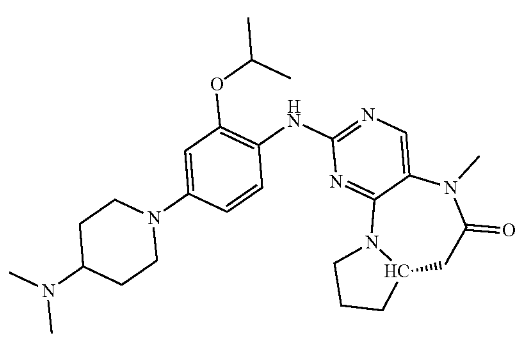 [SMILES: CC(C)Oc1cc(N2CCC(N(C)C)CC2)ccc1Nc1ncc2c(n1)N1CCC[C@H]1CC(=O)N2C] | |

TABLE 6-continued
Additional Compounds of the Invention
| Compound ID | Structure | Spectroscopy |
|---|---|---|
| XMD8-87 | 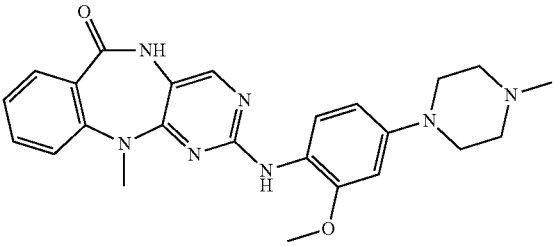 [SMILES: COc1cc(N2CCN(C)CC2)ccc1Nc1ncc2c(n1)N(C)c1ccccc1C(=O)N2] | |
| XMD8-91 | 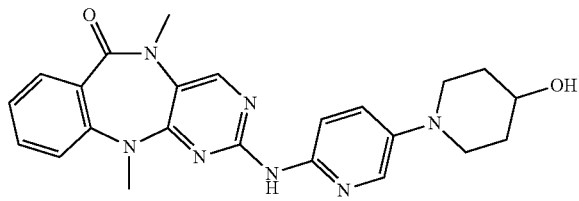 [SMILES: CN1C(=O)c2ccccc2N(C)c2nc(Nc3ccc(N4CCC(O)CC4)cn3)ncc21] | |
| XMD8-96 | 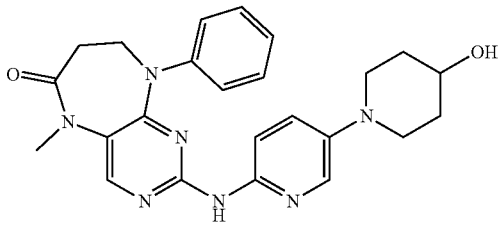 [SMILES: CN1C(=O)CCN(c2ccccc2)c2nc(Nc3ccc(N4CCC(O)CC4)cn3)ncc21] | |
| XMD8-97 | 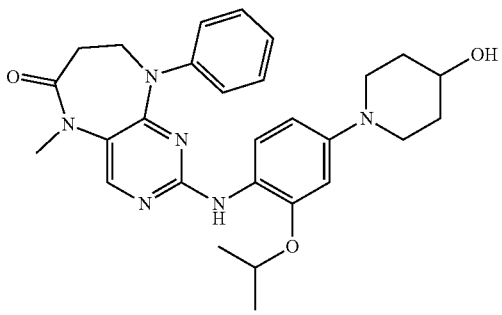 [SMILES: CC(C)Oc1cc(N2CCC(O)CC2)ccc1Nc1ncc2c(n1)N(c1ccccc1)CCC(=O)N2C] | |
| XMD8-98 | 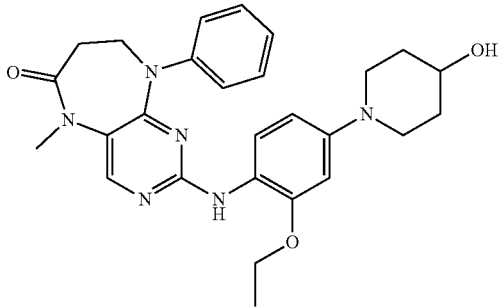 [SMILES: CCOc1cc(N2CCC(O)CC2)ccc1Nc1ncc2c(n1)N(c1ccccc1)CCC(=O)N2C] | |

TABLE 6-continued

Additional Compounds of the Invention

| Compound ID | Structure | Spectroscopy |
|---|---|---|
| XMD9-18 | 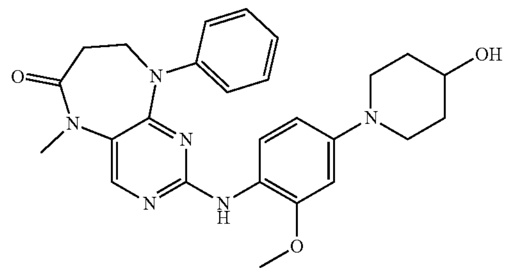 [SMILES: COc1cc(N2CCC(O)CC2)ccc1Nc1ncc2c(n1)N(c1ccccc1)CCC(=O)N2C] | |
| XMD9-21 | 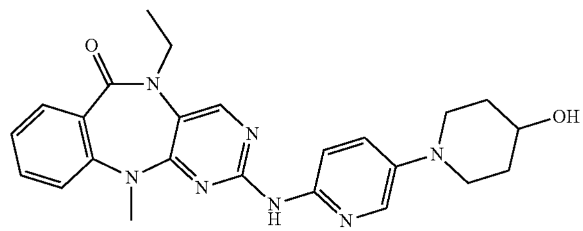 [SMILES: CCN1C(=O)c2ccccc2N(C)c2nc(Nc3ccc(N4CCC(O)CC4)cn3)ncc21] | |
| XMD10-124 | 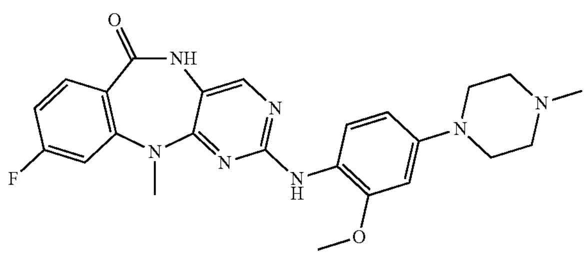 [SMILES: COc1cc(N2CCN(C)CC2)ccc1Nc1ncc2c(n1)N(C)c1cc(F)ccc1C(=O)N2] | |
| XMD10-127 | 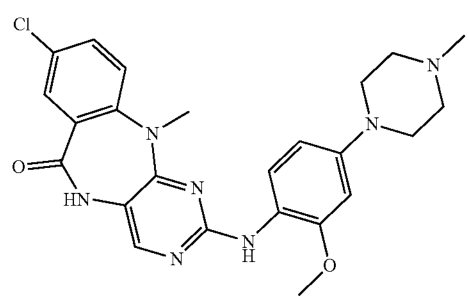 [SMILES: COc1cc(N2CCN(C)CC2)ccc1Nc1ncc2c(n1)N(C)c1ccc(Cl)cc1C(=O)N2] | |
| XMD10-129 | 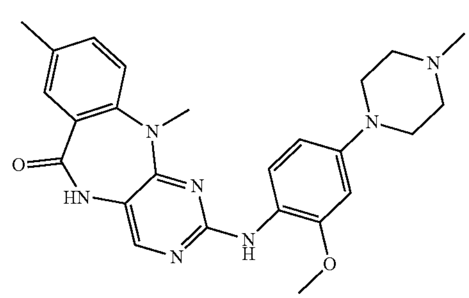 [SMILES: COc1cc(N2CCN(C)CC2)ccc1Nc1ncc2c(n1)N(C)c1ccc(C)cc1C(=O)N2] | |

TABLE 6-continued

Additional Compounds of the Invention

| Compound ID | Structure | Spectroscopy |
|---|---|---|
| XMD11-48 | 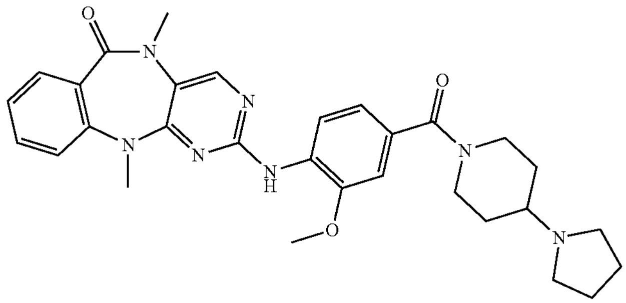 [SMILES: COc1cc(C(=O)N2CCC(N3CCCC3)CC2)ccc1Nc1ncc2c(n1)N(C)c1ccccc1C(=O)N2C] | |
| XMD11-55 | 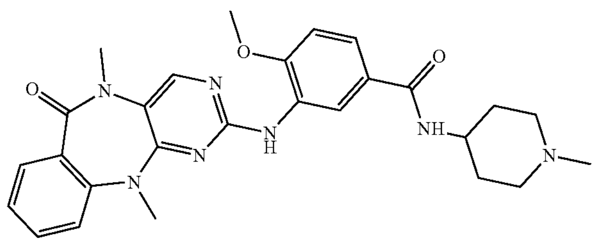 [SMILES: COc1ccc(C(=O)NC2CCN(C)CC2)cc1Nc1ncc2c(n1)N(C)c1ccccc1C(=O)N2C] | |
| XMD11-56 | 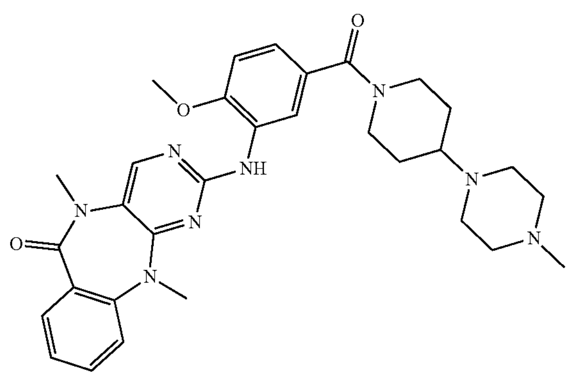 [SMILES: COc1ccc(C(=O)N2CCC(N3CCN(C)CC3)CC2)cc1Nc1ncc2c(n1)N(C)c1ccccc1C(=O)N2C] | |
| XMD11-58 | 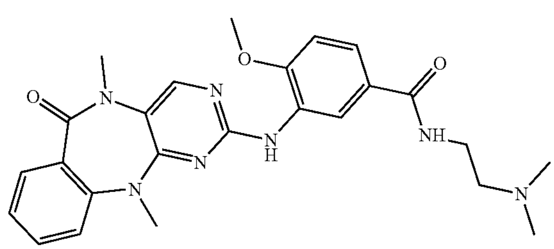 [SMILES: COc1ccc(C(=O)NCCN(C)C)cc1Nc1ncc2c(n1)N(C)c1ccccc1C(=O)N2C] | |
| XMD17-87 | 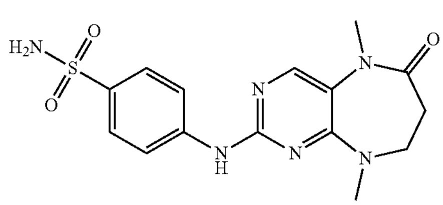 [SMILES: CN1CCC(=O)N(C)c2cnc(Nc3ccc(S(N)(=O)=O)cc3)nc21] | |

TABLE 6-continued

Additional Compounds of the Invention

| Compound ID | Structure | Spectroscopy |
|---|---|---|
| XMD17-67 | 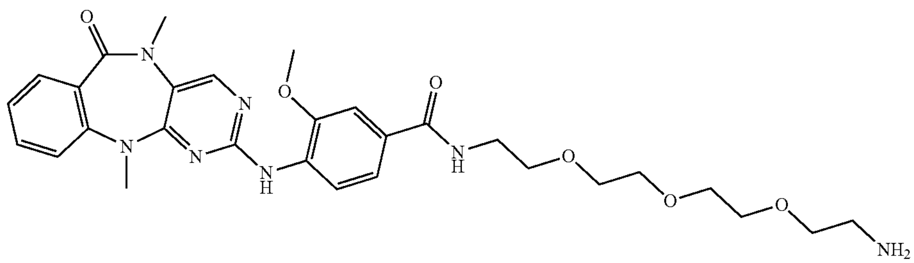 [SMILES: COc1cc(C(=O)NCCOCCOCCOCCN)ccc1Nc1ncc2c(n1)N(C)c1ccccc1C(=O)N2C] | |
| HG9-27-02 | 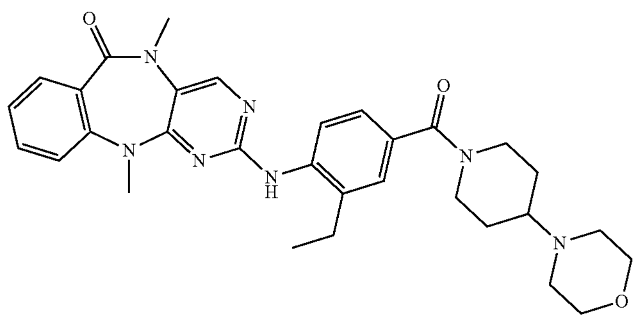 [SMILES: CCc1cc(C(=O)N2CCC(N3CCOCC3)CC2)ccc1Nc1ncc2c(n1)N(C)c1ccccc1C(=O)N2C] | |
| HG8-140-02 | 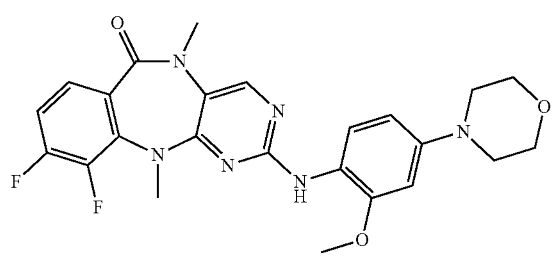 [SMILES: COc1cc(N2CCOCC2)ccc1Nc1ncc2c(n1)N(C)c1c(ccc(F)c1F)C(=O)N2C] | |
| HG8-111-01 | 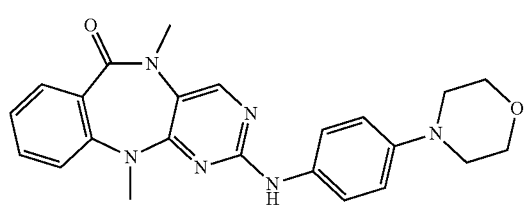 [SMILES: CN1C(=O)c2ccccc2N(C)c2nc(Nc3ccc(N4CCOCC4)cc3)ncc21] | |
| HG8-111-02 | 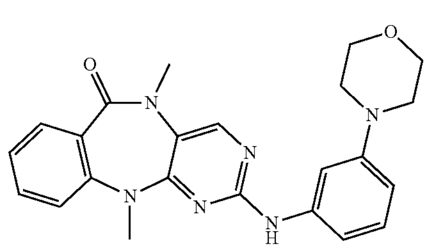 [SMILES: CN1C(=O)c2ccccc2N(C)c2nc(Nc3cccc(N4CCOCC4)c3)ncc21] | |

TABLE 6-continued

Additional Compounds of the Invention

| Compound ID | Structure | Spectroscopy |
|---|---|---|
| HG9-29-01 | 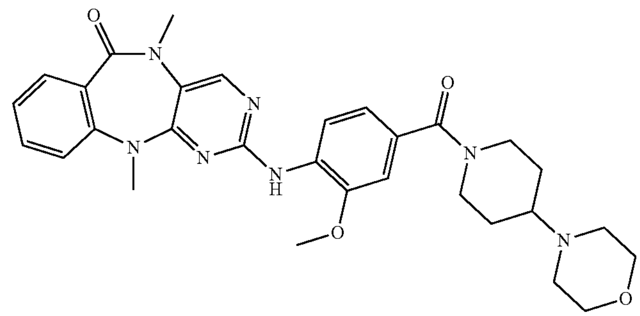 [SMILES: CCc1cc(C(=O)N2CCC(N3CCOCC3)CC2)ccc1Nc1ncc2c(n1)N(C)c1ccccc1C(=O)N2C] | |
| HG9-27-02 | 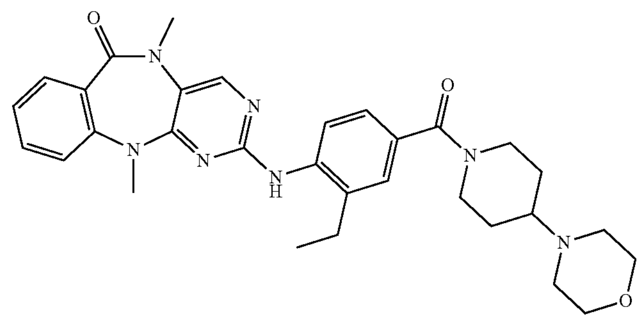 | |
| HG9-29-02 | 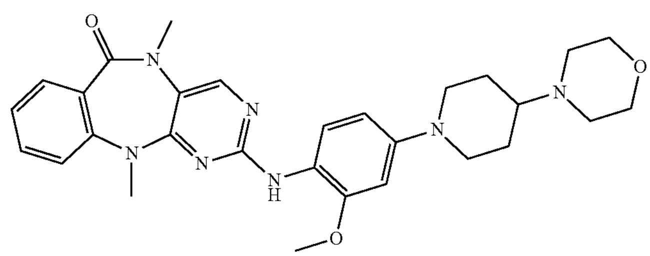 | |
| HG9-29-03 | 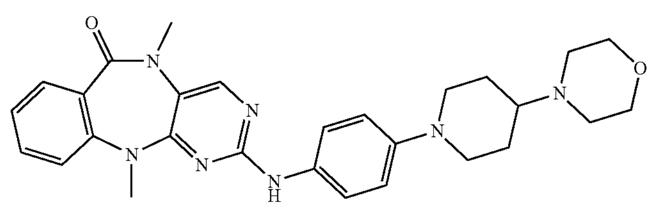 | |
| HG9-29-04 | 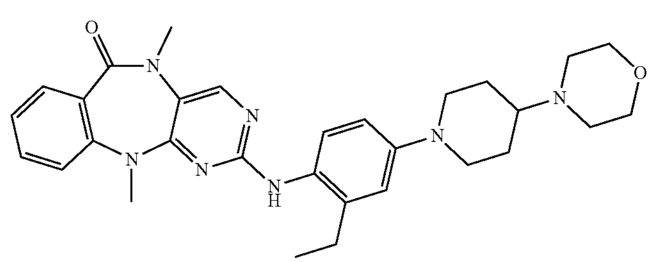 [SMILES: COc1cc(N2CCC(N3CCOCC3)CC2)ccc1Nc1ncc2c(n1)N(C)c1ccccc1C(=O)N2C] | |

TABLE 6-continued

Additional Compounds of the Invention

| Compound ID | Structure | Spectroscopy |
|---|---|---|
| HG9-29-05 | 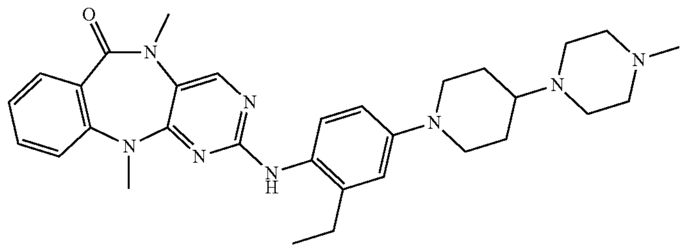 [SMILES: CCc1cc(N2CCC(N3CCN(C)CC3)CC2)ccc1Nc1ncc2c(n1)N(C)c1ccccc1C(=O)N2C] | |
| HG9-48-01 | 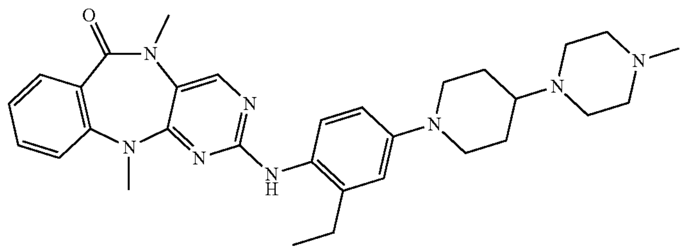 [SMILES: CCc1cc(N2CCC(N3CCN(C)CC3)CC2)ccc1Nc1ncc2c(n1)N(C)c1ccccc1C(=O)N2C] | |
| HG9-95-01 | 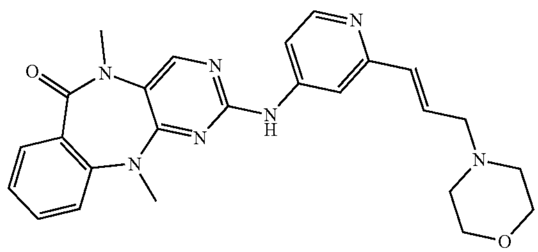 [SMILES: CN1C(=O)c2ccccc2N(C)c2nc(Nc3ccnc(/C=C/CN4CCOCC4)c3)ncc21] | |
| HG9-95-02 | 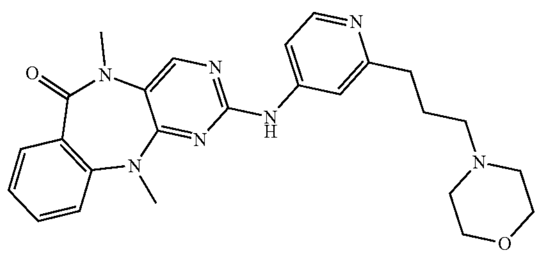 [SMILES: CN1C(=O)c2ccccc2N(C)c2nc(Nc3ccnc(CCCN4CCOCC4)c3)ncc21] | |
| HG9123-01 | 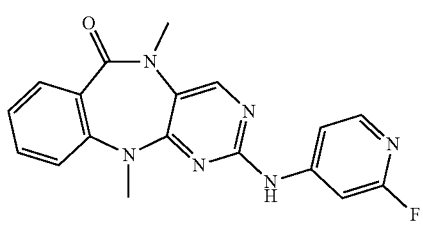 [SMILES: CN1C(=O)c2ccccc2N(C)c2nc(Nc3ccnc(F)c3)ncc21] | |
| HG9123-02 | 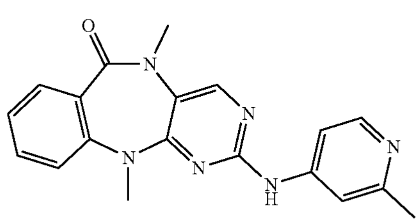 [SMILES: Cc1cc(Nc2ncc3c(n2)N(C)c2ccccc2C(=O)N3C)ccn1] | |

TABLE 6-continued

Additional Compounds of the Invention

| Compound ID | Structure | Spectroscopy |
|---|---|---|
| HG9123-03 | 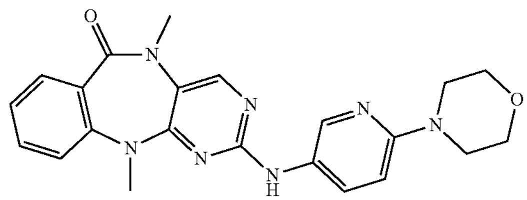 [SMILES: CN1C(=O)c2ccccc2N(C)c2nc(Nc3ccc(N4CCOCC4)nc3)ncc21] | |
| HG9123-04 | 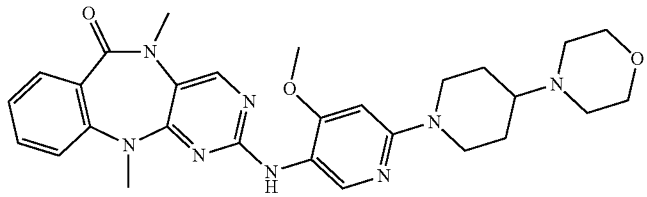 [SMILES: COc1cc(N2CCC(N3CCOCC3)CC2)ncc1Nc1ncc2c(n1)N(C)c1ccccc1C(=O)N2C] | |
| | 2-((2-(1H-imidazol-5-yl)ethyl)amino)-5,11-dimethyl-5H-benzo[e]pyrimido[5,4-b][1,4]-diazepin-6(11H)-one (9) | $^1$H NMR (600 MHz, CD$_3$OD) δ 8.07 (s, 1H), 7.70 (dd, J = 1.8, 7.8 Hz, 1H), 7.65 (s, 1H), 7.46 (dt, J = 1.8, 7.8 Hz, 1H), 7.16 (d, J = 8.4 Hz, 1H), 7.13 (t, J = 7.8 Hz, 1H), 6.86 (s, 1H), 3.61 (t, J = 7.2 Hz, 2H), 3.41 (s, 3H), 3.31 (s, 3H), 2.88 (t, J = 7.2 Hz, 2H). MS (ESI) m/z 350 (M + H)$^+$. |
| | 5,11-dimethyl-2-((1-methylpiperidin-4-yl)amino)-5H-benzo[e]pyrimido[5,4-b][1,4]-diazepin-6(11H)-one (10) | $^1$H NMR (600 MHz, CD$_3$OD) δ 8.14 (s, 1H), 7.78 (d, J = 7.8 Hz, 1H), 7.56 (t, J = 7.8 Hz, 1H) 7.28-7.24 (m, 2H), 4.16 (brs, 1H), 3.62 (d, J = 12.0 Hz, 2H), 3.47 (s, 3H), 3.44 (s, 3H), 3.20 (t, J = 12.6 Hz, 2H), 2.91 (s, 3H), 2.34 (d, J = 13.2 Hz, 2H), 1.87 (q, J = 13.2 Hz, 2H). MS (ESI) m/z 353 (M + H)$^+$. |

TABLE 6-continued

Additional Compounds of the Invention

| Compound ID | Structure | Spectroscopy |
|---|---|---|
| | 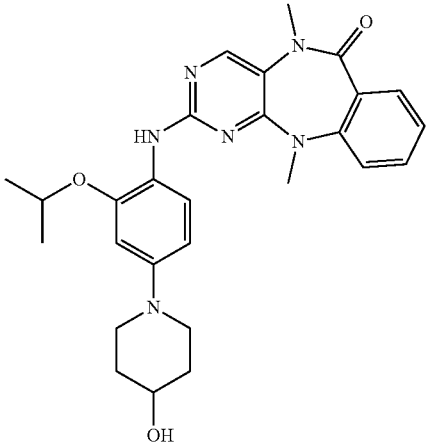  2-((4-(4-hydroxypiperidin-1-yl)-2-isopropoxyphenyl)amino)-5,11-dimethyl-5H-benzo[e]pyrimido[5,4-b][1,4]diazepin-6(11H)-one | $^1$H NMR (600 MHz, CD$_3$OD) δ 8.17 (s, 1H), 8.12 (d, J = 9.0 Hz, 1H), 7.71 (dd, J = 1.2, 7.8 Hz, 1H), 7.45 (dt, J = 1.8, 7.8 Hz, 1H), 7.17 (d, J = 8.4 Hz, 1H), 7.13 (t, J = 7.8 Hz, 1H), 6.67 (d, J = 2.4 Hz, 1H), 6.60 (dd, J = 3.0, 9.0 Hz, 1H), 4.64-4.60 (m, 1H), 3.74-3.70 (m, 1H), 3.48-3.44 (m, 2H), 3.43 (s, 3H), 3.36 (s, 3H), 2.84-2.80 (m, 2H), 1.97-1.95 (m, 2H), 1.69-1.63 (m, 2H), 1.33 (d, J = 6.6 Hz, 6H). MS (ESI) m/z 489 (M + H)$^+$. |
| | 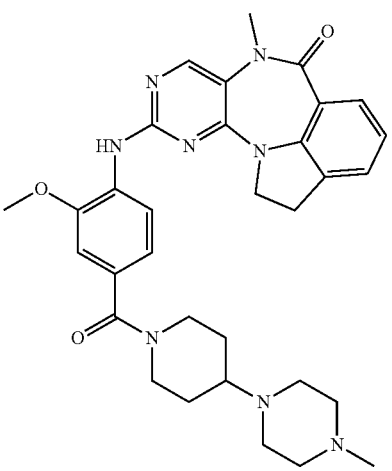  2-((2-methoxy-4-(4-(4-methylpiperazin-1-yl)piperidine-1-carbonyl)phenyl)amino)-5-methyl-10,11-dihydropyrimido[4′,5′:2,3][1,4]diazepino[6,7,1-hi]indol-6(5H)-one (24) | 1H NMR (600 MHz, CD3OD) δ 8.11 (d, J = 8.4 Hz, 1H), 7.99 (s, 1H), 7.88 (d, J = 7.2 Hz, 1H), 7.44 (dd, J = 1.2, 7.8 Hz, 1H), 7.16 (d, J = 1.2 Hz, 1H), 7.14-7.11 (m, 2H), 4.70 (brs, 1H), 4.39 (t, J = 8.4 Hz, 2H), 3.96 (s, 3H), 3.55-3.45 (m, 4H), 3.41 (s, 3H), 3.40-3.32 (m, 6H), 3.25-3.21 (m, 4H), 2.65 (s, 3H), 2.20-1.95 (m, 2H), 1.75-1.65 (m, 2H). MS (ESI) m/z 583 (M + H)+. |

TABLE 6-continued

Additional Compounds of the Invention

| Compound ID | Structure | Spectroscopy |
|---|---|---|
|  | 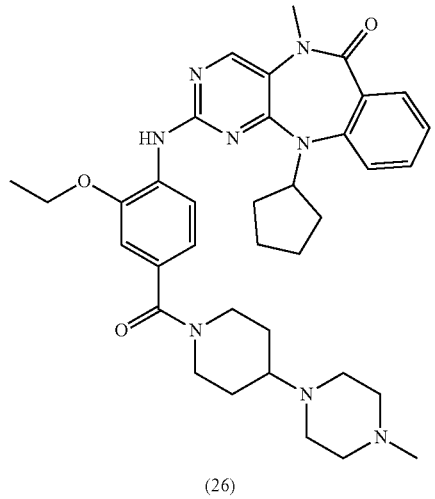<br>(26)<br>11-cyclopentyl-2-((2-ethoxy-4-(4-(4-methylpiperazin-1-yl)piperidine-1-carbonyl)-phenyl)amino)-5-methyl-5H-benzo[e]pyrimido[5,4-b][1,4]diazepin-6(11H)-one | 1H NMR (600 MHz, CD3OD) δ 8.49 (d, J = 8.4 Hz, 1H), 8.36 (s, 1H), 7.64 (dd, J = 1.8, 7.8 Hz, 1H), 7.48-7.45 (m, 1H), 7.27 (d, J = 8.4 Hz, 1H), 7.18 (t, J = 7.8 Hz, 1H), 7.08-7.07 (m, 2H), 4.82-4.78 (m, 1H), 4.19 (q, J = 7.2 Hz, 2H), 3.55-3.48 (m, 9H), 3.45-3.30 (m, 6H), 3.29-3.25 (m, 2H), 2.93 (s, 3H), 2.36-2.33 (m, 1H), 2.15-2.10 (m, 3H), 1.70-1.57 (m, 6H), 1.56-1.54 (m, 1H), 1.47 (t, J = 7.2 Hz, 3H). MS (ESI) m/z 639 (M + H)+. |
| XMD18-83 | 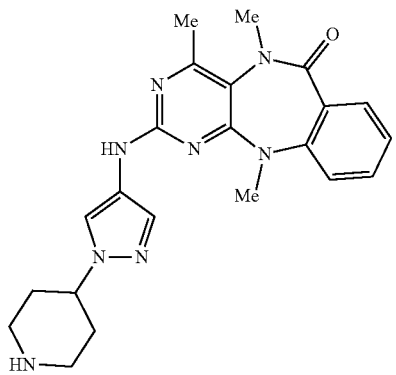 [SMILES: Cc1nc(Nc2cnn(C3CCNCC3)c2)nc2c1N(C)C(=O)c1ccccc1N2C]<br>4,5,11-trimethyl-2-((1-(piperidin-4-yl)-1H-pyrazol-4-yl)amino)-5,11-dihydro-6H-benzo[e]pyrimido[5,4-b][1,4]diazepin-6-one |  |

TABLE 6-continued

Additional Compounds of the Invention

| Compound ID | Structure | Spectroscopy |
|---|---|---|
| HTH-01-015 | 4,5,13-trimethyl-2-((1-(1-(piperidin-4-yl)-1H-pyrazol-4-yl)amino)-5,13-dihydro-6H-naphtho[2,3-e]pyrimido[5,4-b][1,4]diazepin-6-one | |

Example 9: Mps1 (TTK) Cellular Assay—Mitotic Escape Assay

Hela (or U2OS cells) were plated at roughly 30-35% cell density. After 24 hours the medium* was removed and fresh medium supplemented with 2.5 mM thymidine was added to arrest cells at the G1/S transition. After 24 hours in thymidine block the medium was removed, the cells were washed 3× with PBS and replaced with medium supplemented with 330 nM nocodazole (Noc). The cells were incubated with nocodazole for 16-18 hours to produce a mitotic arrest. The medium was then removed carefully and replaced with medium supplemented with 330 nM nocodazole and test compound at the desired concentration (with the final concentration of DMSO below 0.2%). After 2 hours, the cells were harvested, lysed in RIPA buffer, and the levels of cyclin B or phosphorylated Histone 3 (Ser10) determined by western blotting. Alternatively, cells were treated on coverslips, fixed, and phosphorylated Histone 3 levels determined by immunofluorescence.

*Hela/U2OS medium—Dulbecco's Modified Eagle's Medium (DMEM, Sigma), 10% fetal bovine serum, 1% penicillin/streptomycin

Example 10: Plk1 Cellular Assay—Mitotic Arrest Assay

Hela cells were plated at roughly 80% cell density on poly-lysine coated glass coverslips. After 24 hours the medium* was removed and fresh medium supplemented with test compounds was added. Twenty-four hours post-treatment the medium was removed, the coverslips were washed once with phosphate-buffered saline (PBS), pH 7.4 and the cells fixed for 10 minutes at room temperature using the following fixative solution: 100 mM K-Pipes, pH 6.8, 10 mM EGTA, 1 mM $MgCl_2$, 0.2% Triton X-100, 3% formaldehyde. The coverslips were washed 3× with Tris-buffered saline solution (50 mM Tris-HCl pH 7.4, 150 mM NaCl) containing 0.1% Triton X-100 (TBST). The samples were blocked using 2% bovine serum albumin (BSA) in TBST. The samples were then incubated with a phosphorylation-specific antibody against histone 3 (phospho H3) serine-10 (Upstate, 1:500-1:1000) in blocking solution. Cells can also optionally be stained for tubulin as well using appropriate antibodies. After a 2-hr. incubation at room temperature (or 4° C. overnight), the samples were washed 3× with TBST. The samples were then incubated with an appropriate secondary antibody in blocking solution for 1-2 hrs at room temperature (or 4° C. overnight). The samples were washed 3× with TBST and then incubated with Hoechst 33342 stain (Invitrogen, 1:1000-1:2000) in TBST for 15 minutes at room temperature. The samples were washed 3× with TBST and mounted onto glass slides using Prolong Gold Antifade Reagent (Invitrogen).

*Hela/U2OS medium—Dulbecco's Modified Eagle's Medium (DMEM, Sigma), 10% fetal bovine serum, 1% penicillin/streptomycin

Example 11: In Vitro Mps1 Kinase Assay—Invitrogen Mps1 (TTK) LanthaScreen Activity Assay Kinase reactions were carried out at room temperature with the following components: 1× kinase reaction buffer, 5 μg/mL (40 nM) Mps1 kinase, 200 nM AF-647 E4Y substrate, and 1 μM ATP ($K_{m,app}$<1 μM). After one hour a preparation of EDTA (20 mM) and Eu-PY20 Tb-labeled antibody (4 nM) in TR-FRET dilution buffer was added. The final concentration of EDTA and Eu-PY20 in the reaction mixture is 10 mM and 2 nM respectively. The reaction mixture was incubated at room temperature for 30 minutes before being read on a plate reader configured for LanthaScreen™ TR-FRET. Kinase reactions were run over several concentrations of inhibitor to obtain dose-dependent curves.

Example 12: Kinase Selectivity Analysis

Figure 3A:
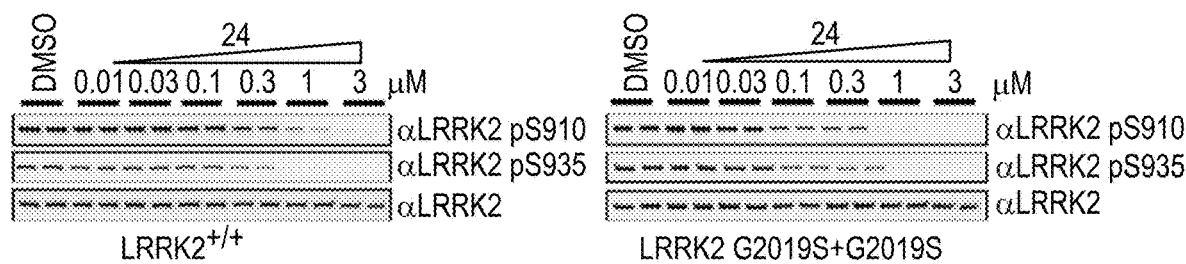
FIG. 3A-FIG. 3B. Compound 24 effectively inhibits endogenously expressed LRRK2, but compound 26 does not. Endogenous LRRK2 from EBV immortalized human lymphoblastoid cells from a control subject and a Parkinson's disease patient homozygous for the LRRK2[G2019S] mutation. After treatment of the cells with DMSO or the indicated concentration of compound 24 (or 26) for 90 min, cell lysates were subjected to immunoblot analysis with the purified indicated antibody for western analysis. Immunoblots were performed in duplicate, and results were representative of at least two independent experiments.
Figure 3B:
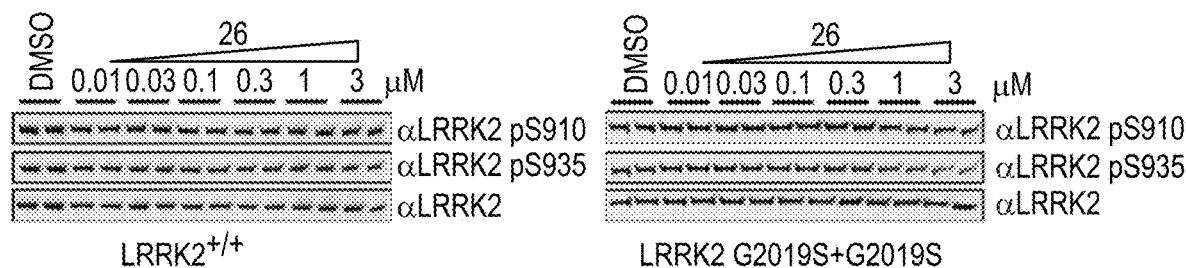

The SAR exploration of the benzo[e]pyrimido-[5,4-b]diazepine-6(11H)-one scaffold led to the discovery of the relatively LRRK2 selective inhibitor 24 and ERK5 selective inhibitor 26 (FIG. 1). The structural features of N-methyl substitution at lactam position ($R^2$), the 2-ethoxy group of 4-amide substituted aniline, N-cyclopentyl substitution (X) and no substituent ($R^4$=H) on the aryl ring of anthranilic acid were essential to achieve potent cellular inhibitory activity against ERK5 and high specificity (FIG. 1, highlighted in red). The linkage ($R^6$) of indoline-7-carboxylic group exhibited improved LRRK2 selectivity exemplifying by compound 24 (FIG. 1, highlighted in blue). The introduction of amide functional group at the 4-position of 2-anilino moiety is favorable for both ERK5 and LRRK2. The substituent at the ortho-position of 2-anilino moiety ($R^5$) and the linkage group (X) are key structural features to separate the SAR of the benzo[e]pyrimido-[5,4-b]diazepine-6(11H)-ones for ERK5 and LRRK2 (FIG. 3A and FIG. 3B). Certain pyrimidine derivatives, (4-((5-chloro-4-(methylamino)pyrimidin-2-yl)amino)-3-methoxyphenyl)(morpholino)methanone (HG-10-102-01) and 2-arylmethyloxy-5-subtitutent-N-arylbenzamide (GSK2578215A) have been reported that are potent LRRK2 inhibitors and that do not inhibit ERK5.

Cellular LRRK2 Inhibitory Effect of Compound 24 and 26.

Figure 2A:
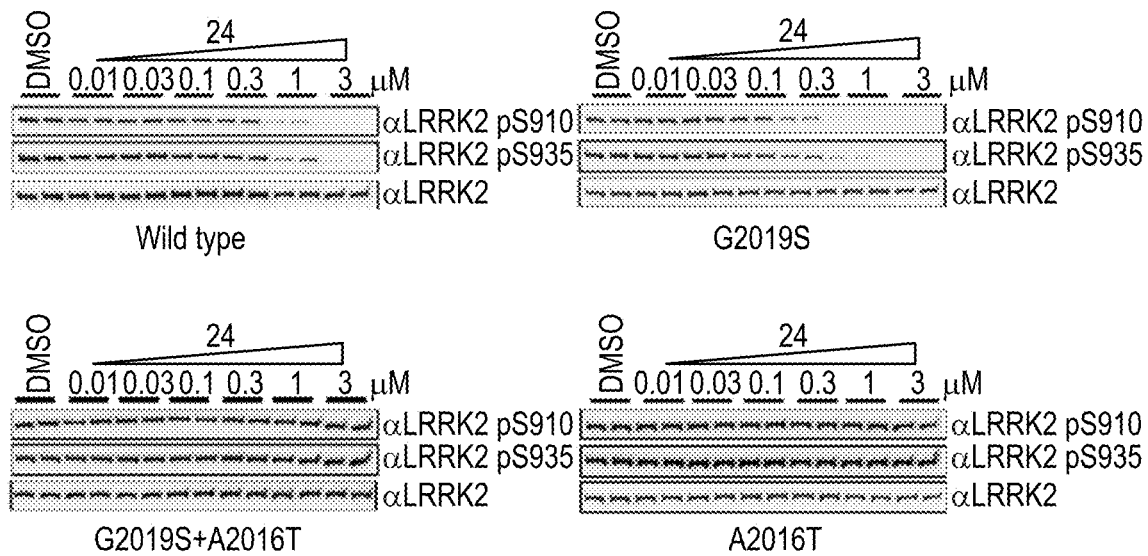
FIG. 2A-FIG. 2B. Compound 24 inhibits LRRK2 in cells, but 26 does not.
Figure 2B:
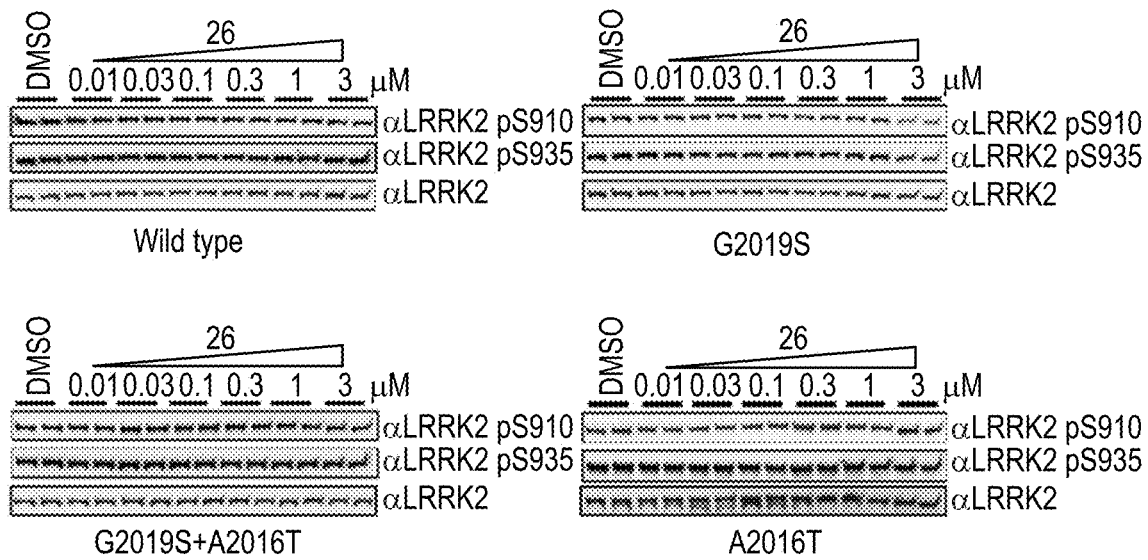

We examined the abilities of compounds 24 and 26 to inhibit LRRK2 in a cellular context. As there are no validated direct phosphorylation substrates of LRRK2, we monitored phosphorylation of Ser910 and Ser935, two residues whose phosphorylation is known to be dependent upon LRRK2 kinase activity (FIG. 2A and FIG. 2B). Compound 24 induced a dose-dependent inhibition of Ser910 and Ser935 phosphorylation in both wild-type LRRK2 and LRRK2[G2019S]stably transfected HEK293 cells (FIG. 2A). Significant reduction on the level of phosphrylation of resides Ser910 and Ser935 was observed at 1-3 µM of 24 for wild-type LRRK2 and at slightly lower doses for LRRK2 [G2019S] (FIG. 2A), which is approximately the same potency relative to LRRK2-IN-1. Compound 24 had no effect on the phosphorylation of Ser910 and Ser935 at a concentration of up to 3 µM in the drug-resistant LRRK2 [G2019S+A2016T] and LRRK2[A2016T] mutants (FIG. 2A), revealing that 24 has the same activity profile compared to LRRK2-IN-1. Consistent with the biochemical results, compound 26 didn't show any inhibitory effect against LRRK2 at a concentration of up to 3 µM in this cellular context (FIG. 2B).

We next examined the effects of compounds 24 and 26 on endogenously expressed LRRK2 in human lymphoblastoid cells derived from a control and Parkinson's disease patient homozygous for the LRRK2[G2019S] mutation (FIG. 3A-FIG. 3B). We found that increasing doses of 24 led to similar reduction on the levels of phosphorylation of endogenous LRKK2 at Ser910 and Ser935, as was observed in HEK293 cells stably expressing wild-type LRRK2 or LRRK2[G2019S] (compare FIG. 2A to FIG. 3A). Moreover, 24 was also more potent against LRRK2[G2019S] mutant than wild type LRRK2, which is consistent with the trend we observed in HEK293 cells. Similarly, compound 26 didn't show inhibitory effects on endogenous LRRK2 (compare FIG. 2B to FIG. 3B). Taken together, compound 24 is as potent LRRK2 inhibitor as LRRK2-IN-1 and worked both in vitro and in cells and with improved selectivity towards LRRK2. Compound 26 is a ERK5 specific inhibitor, which has at least 30-fold cellular selectivity for ERK5 relative to LRRK2 and should not inhibit LRRK2 when used at 1 µM concentrations.

We assessed the selectivity of this scaffold using the KINOMEscan methodology across a near comprehensive panel of 442 kinases. Compounds 24, 25 and 26 were screened at a concentration of 10 µM which revealed a highly selective profile for this inhibitor class. The structure of Compound 24 is shown below:

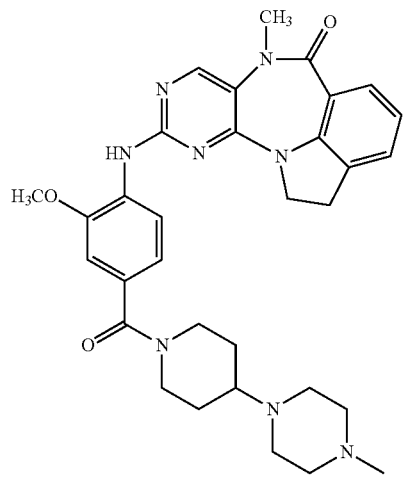 [SMILES: COc1cc(C(=O)N2CCC(N3CCN(C)CC3)CC2)ccc1Nc1ncc2c(n1)N1CCc3cccc(c31)C(=O)N2C]

Compound 24.

Compound 26 having ortho-ethoxy aniline demonstrated outstanding selectivity with a KINOMEscan selectivity score of $S_{10}$ of 0.007 (3/442), and only interactions with ERK5, doublecortin and CaM kinase-like 2 (DCAMKL2) and polo-like kinase 4 (PLK4) were detected. Compound 25 having ortho-methoxy aniline exhibited a $S_{10}$ of 0.018 (8/442). These results revealed that the ortho-substituent could serve as the selectivity handle. Compared with our previously reported ERK5 inhibitor, XMD8-92 (11, $S_{10}$=0.012, 5/402), compound 26 represents a further improvement in selectivity. Compound 24 exhibited the same KINOMEscan selectivity score of $S_{10}$ of 0.036 (16/442) as that of our previous LRRK2 inhibitor (LRRK2-IN-1), while being more selective for LRRK2 over ERK5. Compounds 25 and 26 were also profiled against selected panels of kinases in HeLa and PC3 cell lysates using a chemical proteomics approach, KiNativ. These results revealed that only ERK5 (ERK5) was inhibited with higher than 90% activity at a concentration of 10 µM for both 25 and 26, which further confirmed their highly selective profiles.

Figure 4C:
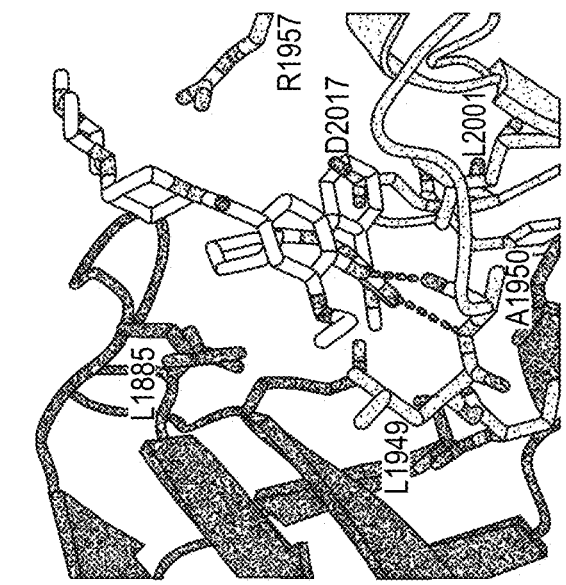
FIG. 4A, FIG. 4B, and FIG. 4C. Docking model of 26 bound to LRRK2 from three different viewing angles. The N-terminal lobe of the LRRK2 model is shown in pink, and the C-terminal lobe in green. 26 is shown in yellow.
Figure 4B:
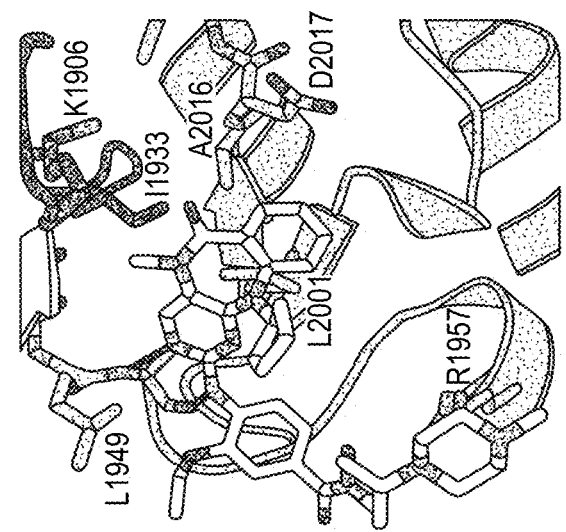
Figure 4A:
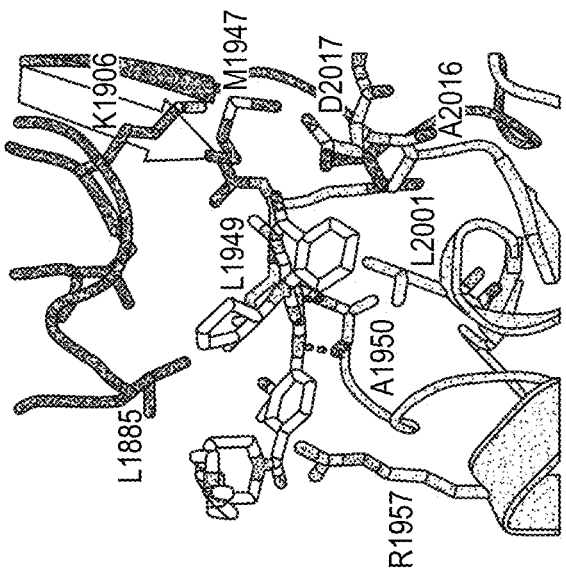

To better understand the SAR for LRRK2, we performed a molecular modeling study using Glide based upon the recently reported crystal structure of Roco kinase (PDB accession code: 4F1T) (FIG. 4A, FIG. 4B, and FIG. 4C). This model allows explanation of some of the SAR that we observed. Overall 26 is predicted to bind to LRRK2 in a manner analogous to what has been observed for a structural analogue, Mps1-IN-2, bound to TTK: The tricyclic core of the compound curves around Leu2001 in the base of the ATP binding site, forming two hydrogen bonds with the hinge region at Ala1950, while the piperidin-piperazine goes towards the solvent region (FIG. 4A). The cyclopentyl group points towards the glycine rich loop, against Leu1885, and would appear to force the tricyclic ring towards the base of the ATP binding site.

The SAR suggests that the phenyl ring of the 2-amino moiety has important interactions, as alternative substituents lost activity to LRRK2 and ERK5, and in the model this moiety would bind against the hinge region. The decrease in LRRK2 affinity caused by N-substitution with increasing size up to cyclopentyl may be because the tricycling ring is forced into a less favourable contact with Ala2016 as the N-substituent makes contact with the glycine-rich loop at Leu1885. The same contacts with Ala2016 and nearby residues would explain why substitution of the anthranilic acid may result in weaker binding. Ortho-substitution of the aniline with increasingly large groups (ethyl, isopropyl) resulted in decreased affinity for LRRK2. Since this group would bind adjacent to Leu1949 (FIG. 4B, FIG. 4C) only conformations with the additional carbons pointing away from Leu1949 would be favourable, resulting in increasingly unfavourable entropy as the substituent goes from methoxy to ethoxy to isopropoxyl.

The key active site residues in this discussion above are either conserved in ERK5 (Leu1949, Leu2001) or conservatively substituted (Leu1885, Ala2016, Met1947). We have recently determined a crystal structure of ERK5 bound to 25 which confirms the both the binding model for 26 with LRRK2 and the SAR explanation.

Conclusions

The new chemo-type of benzo[e]pyrimido-[5,4-b]diazepine-6(11H)-one represents a privileged scaffold for developing ERK5 and LRRK2 kinase inhibitors. Comprehensive SAR exploration led to the identification of the key structural features to separate the SAR of this scaffold for ERK5 and LRRK2. Compound 24 is as potent a LRRK2 inhibitor as LRRK2-IN-1, and worked both in vitro and in cells and with improved selectivity towards LRRK2. Compound 26 represents the most selective and potent ERK5 inhibitor we have developed so far. Given the outstanding specificity and excellent cellular efficacy, 26 could serve as a versatile tool to further probe ERK5 biology. The benzo[e]pyrimido-[5,4-b]diazepine-6(11H)-ones with excellent selectivity, favorable pharmacokinetic parameters, and great efficacy in xenograft tumor models can serve as a privileged template to develop therapeutic agents targeting ERK5.

ERK5 Autophosphorylation Assay.

HeLa cells were serum starved overnight followed by treatment with inhibitors for one hour. Cells were then stimulated with EGF (20 ng/mL) for 17 min and harvested in RIPA buffer (1×PBS, 1% NP40, 0.5% sodium deoxycholate, 0.1% SDS, 0.1 mg/ml PMSF and 1 mM sodium orthovanadate). Proteins from total cell lysates were resolved by 6% sodium dodecyl sulfate (SDS)-poly-acrylamide gel electrophoresis (PAGE), transferred to nitrocellulose membrane, blocked in 5% nonfat milk, and blotted with anti-ERK5 antibody.

Baculovirus Expression of Active ERK5 and Purification.

pFastBAC vector encoding N-terminal hexahistidine-tagged human ERK5 and HA-tagged human MEK1-DD (constitutively active) were used to generate recombinant baculovirus using the Bac-to-Bac system (Invitrogen). *Spodoptera frugiperda* 21 cells (1.5×10$^6$/ml) were infected at a multiplicity of infection of 6 with a mix of both baculovirus and harvested 72 h post-infection. Pelleted cells were lysed in ice-cold lysis buffer (50 mM Tris/HCl, pH 7.5, 1 mM EGTA, 1 mM EDTA, 1 mM sodium orthovanadate, 10 mM sodium β-glycerophosphate, 50 mM NaF, 5 mM sodium pyrophosphate, 0.27 M sucrose, 1 mM benzamidine, 2 mM phenylmethanesulphonylfluoride (PMSF) and 1% Triton X-100), lysed in one round of freeze/thawing, sonicated (4×20 s) and centrifuged at 25,000 g fro 30 min. His-tagged ERK5 was purified as described for His-tagged BRSK1,[37] using 5 ml Ni-NTA-agarose resin (Qiagen) followed by gel filtration chromatography on Superdex 200HR column on an AKTA system (GE Healthcare). Active ERK5 was purified with yields of ~5 mg/L of infected cells, and was greater than 90% homogeneous as judged by densitometric scanning of Coomassie Blue-stained SDS/PAGE gels.

ERK5 Kinase Activity In Vitro Assay.

Kinase activity was determined in an assay volume of 40 µl in kinase buffer (50 mM Tris-HCl, pH 7.5, 0.1 mM EGTA, 1 mM 2-mercaptoethanol) containing 200 ng of pure active ERK5 and the indicated amount of inhibitor. Reaction started by adding 10 mM magnesium acetate, and 50 µM [γ-$^{32}$P]-ATP (500 cpm/pmol) and 250 µM PIMtide (ARK-KRRHPSGPPTA) as substrates. Assays were carried out for 20 min at 30° C., terminated by applying the reaction mixture onto p81 paper and the incorporated radioactivity measured as described previously.

Adaptor Kinase Assay of LRRK2 [G2019S].

In vitro kinase assays were conducted at Invitrogen (Madison, Wis.) using the SelectScreen Kinase Profiling Service.

LRRK2 Cellular Assay.

Reagents and General methods. Tissue-culture reagents were from Life Technologies. Protein G Sepharose was from Amersham. DNA constructs used for transfection were purified from *Escherichia coli* DH5α using Qiagen or Invitrogen plasmid Maxi kits according to the manufacturer's protocol. All DNA constructs were verified by DNA sequencing, which was performed by The Sequencing Service, School of Life Sciences, University of Dundee, Scotland, U.K., using DYEnamic ET terminator chemistry (Amersham Biosciences) on Applied Biosystems automated DNA sequencers.

Cell culture, treatments and cell lysis. HEK293 was cultured in DMEM (Dulbecco's Modified Eagle's medium) supplemented with 10% FBS (fetal bovine serum), 2 mM glutamine and 1× penicillin/streptomycin solution. Lymphoblastoid cell lines were generated by EBV (Epstein-Barr virus) transformation of B lymphocytes using standard methods (European Collection of Cell Cultures). Cell-line ANK is derived from a 47-year-old individual homozygous for the LRRK2[G2019S] mutation who presented with Parkinson's disease. Cell-line AHE is derived from a 31-year-old individual, lacking mutation at the LRRK2 Gly$^{2019}$ residue, and presented with no disease. Human lymphoblastoid cells were maintained in RPMI 1640 with 10% FBS, 2 mM glutamine, 1× penicillin/streptomycin solution and were maintained at cell density of 0.3×10$^6$-2×10$^6$ cells per ml. Epstein-Barr virus immortalized primary human lymphoblastoid cells from one control subject and one Parkinson's disease patient homozygous for the LRRK2 [G2019S] mutation were kindly provided by Alastair Reith (GSK) and have been described previously. For inhibitor experiments, compounds were dissolved in DMSO and utilized at the indicated concentrations. The concentration of DMSO in the culture media did not exceed 1%. Following treatment, cells were washed once with phosphate buffered saline (PBS) buffer and lysed with lysis buffer (50 mM Tris/HCl, pH 7.5, 1 mM EGTA, 1 mM EDTA, 1 mM sodium orthovanadate, 10 mM sodium β-glycerophosphate, 50 mM NaF, 5 mM sodium pyrophosphate, 0.27 M sucrose, 1 mM benzamidine, 2 mM phenylmethanesulphonylfluoride (PMSF) and 1% Triton X-100). When not used immediately, all lysate supernatants were snap-frozen in liquid nitrogen and stored at −80° C. until use. Protein concentrations were determined following centrifugation of the lysate at 16,000×g at 4° C. for 20 minutes using the Bradford method with BSA as the standard. Transient transfection of HEK 293 cells was performed using the polyethyleneimine (PEI) method.

Immunoblot Procedures.

Cell lysates from human lymphoblastoid cells and GFP-LRRK2 expressing stable cell lines were eluted in 65 µl 2×LDS sample buffer (Invitrogen) with final concentration of 1 µg/µl. Following heating at 70° C. for 10 min, 15 µl aliquots were resolved on 8% SDS polyacrylamide gels and transferred to nitrocellulose membranes for detection of LRRK2 phosphorylated at Ser910, LRRK2 phosphorylated at Ser935 and total LRRK2, using purified rabbit monoclonal antibodies (LRRK2 phospho-serine 910 clone, LRRK2 phospho-serine 935 clone and LRRK2 100-500 clone) in PBS with 0.1% sodium azide (Epitomics). Immunoblot films were scanned on an Epson 4990 scanner, and images were managed with Adobe Photoshop.

Molecular Docking Study

A molecular docking study to elucidate the interaction between the inhibitors with the LRRK2 kinase domain was performed. First, we constructed the homology model structure of the LRRK2 kinase domain. We used a crystal structure of Roco kinase (PDB accession code: 4F1T). Sequence alignment of LRRK2 and template proteins was generated using the Discovery Studio 3.5 package (http://www.accelrys.com). A 3D model structure of LRRK2 was built by using the Modeller in Discovery Studio 3.5 package and was further refined by using the CHARMM force field. Second, compounds 25 and 26 were built using Maestro build panel and minimized using the Impact module of Maestro in the Schrödinger suite program. The LRRK2 structure was minimized using the Protein Preparation Wizard by applying an OPLS force field. For the grid generation, the binding site was defined as the centroid of the ATP binding site. Ligand docking into the active site of LRRK2 was carried out using the Schrödinger docking program, Glide. The best-docked poses were selected as the lowest Glide score. The molecular graphics for the inhibitor binding pocket and refined docking models were generated using PyMol package (http://www.pymol.org).

Example 13: In Vitro EphA2 Kinase Assay—Invitrogen EphA2 Z'-LYTE Activity Assay

EphA2 kinase assays were performed according to the methods described in Z'-LYTE® Screening Protocol and Assay Conditions at the Life Technologies website (available at http://www.invitrogen.com).

Western Analysis XMD16-95 Inhibition of EphA2 Kinase Activity In Vivo:

A375 cells were treated with EphrinA2 (100 ng/mL) (R&D systems, Cat No. 7856-A2-050) for 15 minutes, and test compounds were added to cell culture for 60 minutes treatment. Standard western analysis was performed to monitor the EphA2 phosphorylation (Y594) (antibody from Cell Signaling Technology, Cat. No. 3970) status.

The activity of certain compounds of Formula II against EphA2 and other kinases is shown in Table 7.

TABLE 7

| ActivX | |
|---|---|
| EphA1 | 8.5 |
| EphA2 | 9.3 |
| EphA2 | 10.5 |
| EphA7 | 15.3 |
| EphB2 | 2.5 |
| EphB4 | 6.8 |

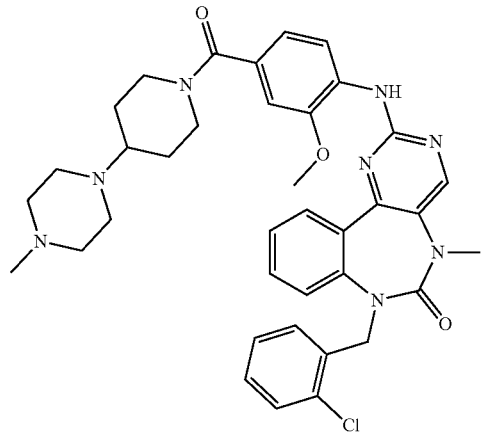

XMD-16-123-1

| | |
|---|---|
| EphA1 | −19.4 |
| EphA2 | 0.9 |
| EphA2 | 1.6 |
| EphA7 | −7.9 |
| EphB2 | 0.9 |
| EphB4 | −14.6 |

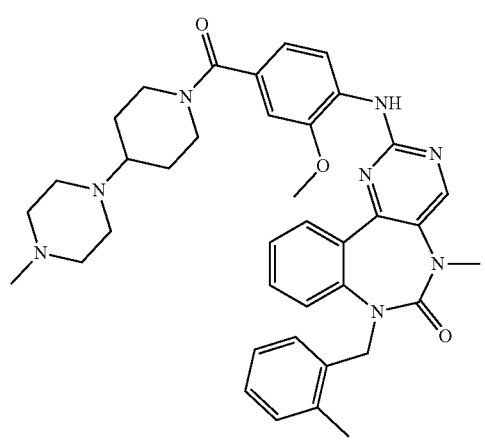

XMD16-125

TABLE 7-continued
| | |
|---|---|
| EphA1 | −2.6 |
| EphA2 | 5.3 |
| EphA2 | −4.4 |
| EphA7 | 2.3 |
| EphB2 | 12.2 |
| EphB4 | 15.9 |
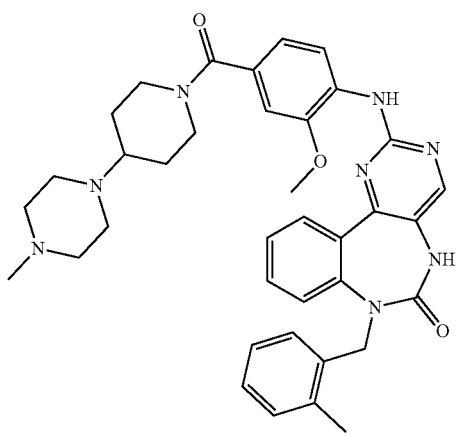
XMD16-121
| | |
|---|---|
| EphA1 | 1.9 |
| EphA2 | −10.5 |
| EphA2 | −1.1 |
| EphA7 | 1.7 |
| EphB2 | 2 |
| EphB4 | 6.6 |
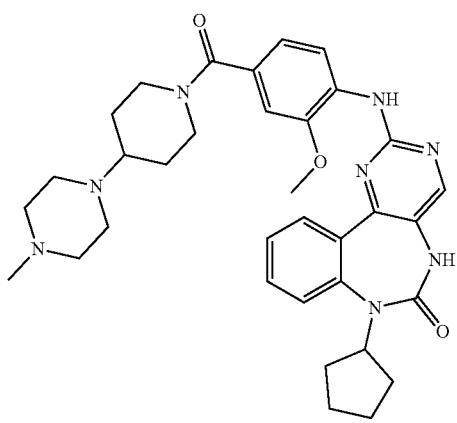
XMD16-127
| | |
|---|---|
| EphA1 | −2.1 |
| EphA2 | −5.1 |
| EphA2 | −8.2 |
| EphA7 | −15.4 |
| EphB2 | 4.5 |
| EphB4 | −13.7 |
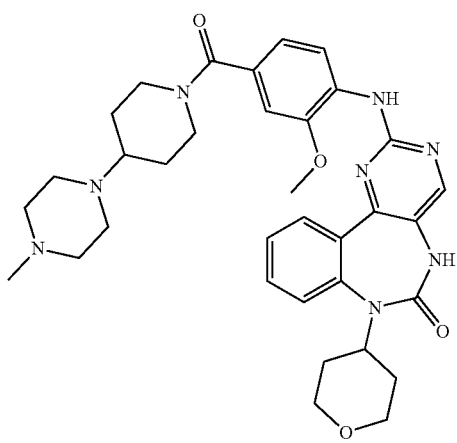
XMD16-128

TABLE 7-continued
| EphA1 | −12.9 |
| EphA2 | 3.9 |
| EphA2 | −8.3 |
| EphA7 | −17.1 |
| EphB2 | −20.9 |
| EphB4 | −22.3 |
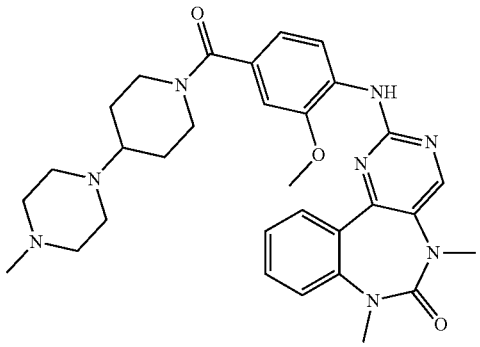
XMD16-118
| EphA1 | 49.2 |
| EphA2 | 41.1 |
| EphA2 | 44.1 |
| EphA7 | 14.7 |
| EphB2 | 60.1 |
| EphB4 | 72.5 |
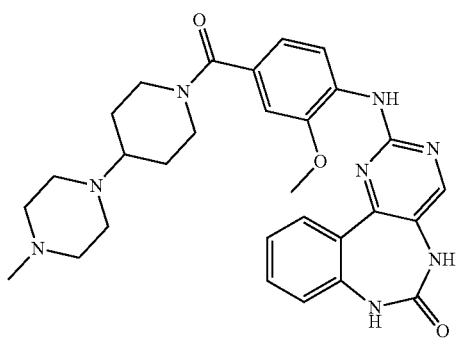
XMD16-120
| EphA1 | 35.6 |
| EphA2 | 10.5 |
| EphA2 | 41.7 |
| EphA7 | −35.6 |
| EphB2 | −10.8 |
| EphB4 | 10 |
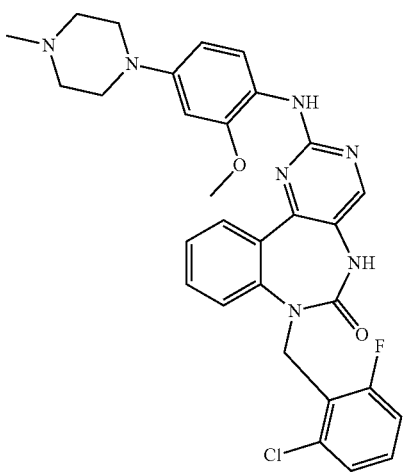
AB-1-9

TABLE 7-continued
| EphA1 | 1.2 |
| EphA2 | −8.8 |
| EphA2 | −5 |
| EphA7 | 2.3 |
| EphB2 | 5.2 |
| EphB4 | −2.4 |
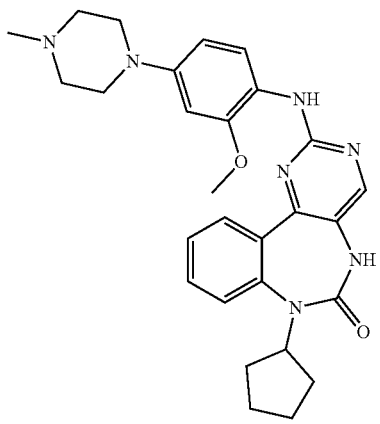
AB-1-15
| EphA1 | 18 |
| EphA2 | −6.8 |
| EphA2 | −1.8 |
| EphA7 | 2.8 |
| EphB2 | 7 |
| EphB4 | 10.7 |
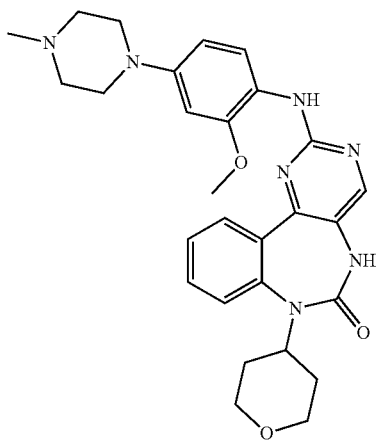
AB-1-16
| EphA1 | 22.3 |
| EphA2 | 16 |
| EphA2 | 8.2 |
| EphA7 | −1.4 |
| EphB2 | 6.1 |
| EphB4 | 3.9 |
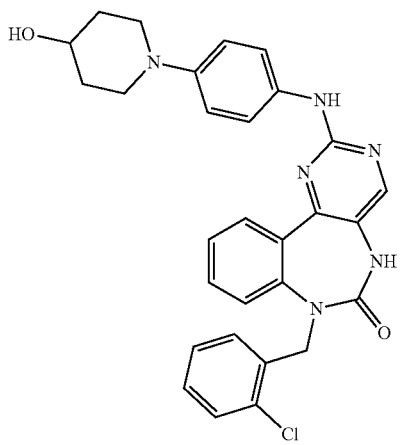
XMD16-101-1

TABLE 7-continued
| | |
|---|---|
| EphA1 | 9.1 |
| EphA2 | 8.1 |
| EphA2 | 1.9 |
| EphA7 | −11.4 |
| EphB2 | 0.6 |
| EphB4 | −1.1 |
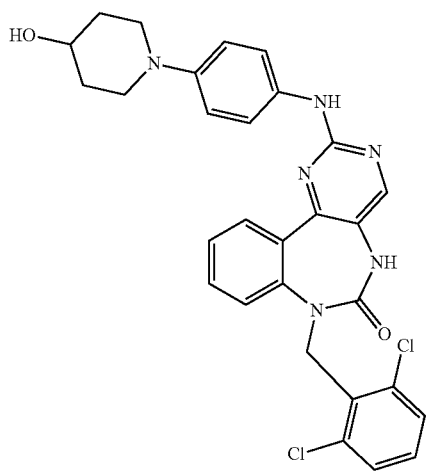
XMD16-101-2
| | |
|---|---|
| EphA1 | 56.8 |
| EphA2 | 33 |
| EphA2 | 30.8 |
| EphA7 | 3.4 |
| EphB2 | 21.5 |
| EphB4 | 39.8 |
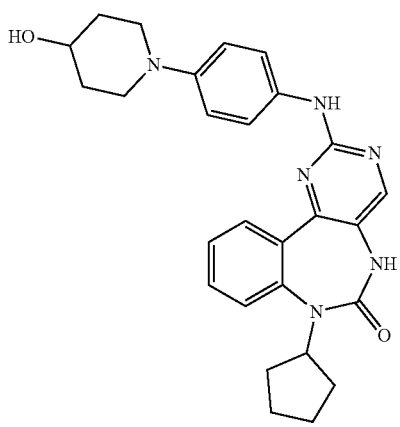
AB-1-17
| | |
|---|---|
| EphA1 | 89.1 |
| EphA2 | 91.7 |
| EphA2 | 76.6 |
| EphA7 | 80.7 |
| EphB2 | 97.2 |
| EphB4 | 95.7 |
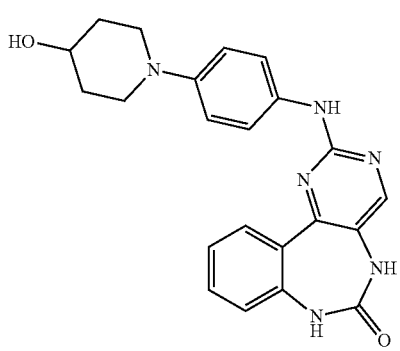
XMD16-95

TABLE 7-continued
| EphA1 | -12.8 |
| EphA2 | 6.2 |
| EphA2 | -2.7 |
| EphA1 | -8.3 |
| EphB2 | -13 |
| EphB4 | -4.3 |
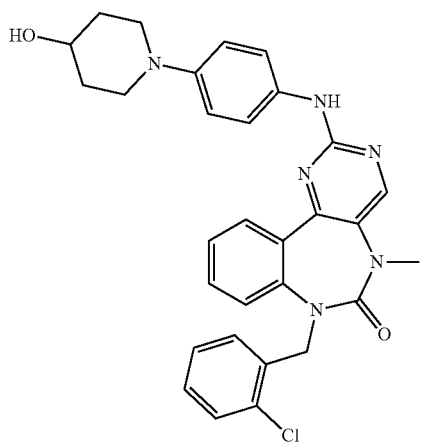
XMD16-122-1
| EphA1 | -4.5 |
| EphA2 | -2.5 |
| EphA2 | -11.3 |
| EphA7 | 0.5 |
| EphB2 | -5.5 |
| EphB4 | 2 |
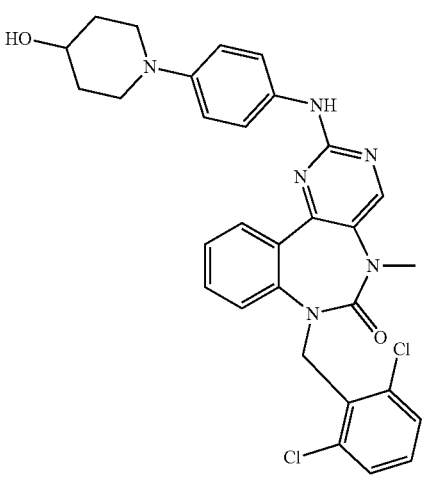
XMD16-122-2
| EphA1 | -4.7 |
| EphA2 | 5.8 |
| EphA2 | -18.4 |
| EphA7 | 4.3 |
| EphB2 | 18.3 |
| EphB4 | -17.3 |
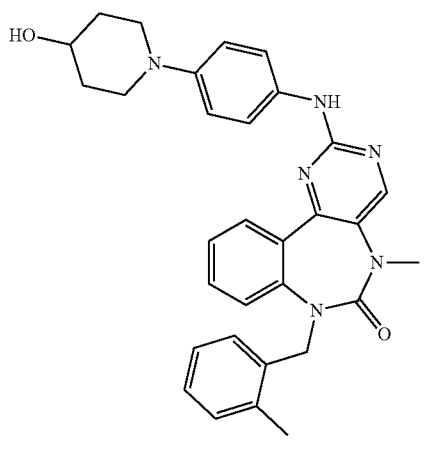
XMD16-124

TABLE 7-continued
| | |
|---|---|
| EphA1 | 28.6 |
| EphA2 | 5.2 |
| EphA2 | 4.9 |
| EphA7 | 12.1 |
| EphB2 | 6.8 |
| EphB4 | 7.4 |
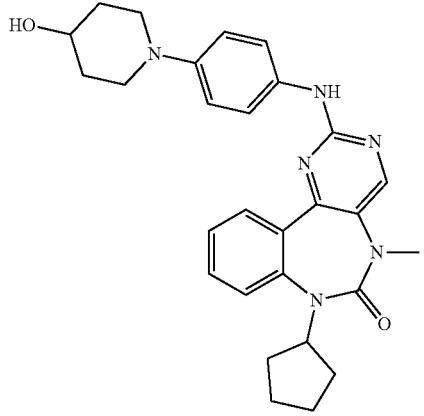
AB-1-24
| | |
|---|---|
| EphA1 | 13.6 |
| EphA2 | 6.8 |
| EphA2 | 9 |
| EphA7 | 5 |
| EphB2 | 19.8 |
| EphB4 | 6.2 |
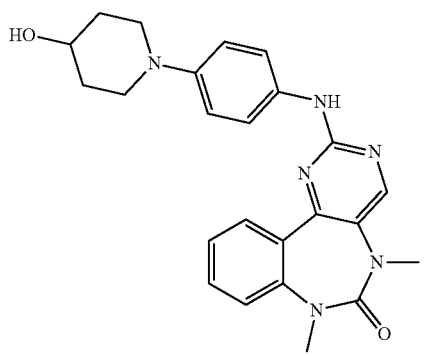
XMD16-117
Ambit
| | |
|---|---|
| EPHA1 | 69 |
| EPHA2 | 100 |
| EPHA3 | 47 |
| EPHA4 | 84 |
| EPHA5 | 91 |
| EPHA6 | 92 |
| EPHA7 | 100 |
| EPHA8 | 100 |
| EPHB1 | 91 |
| EPHB2 | 100 |
| EPHB3 | 93 |
| EPHB4 | 91 |
| EPHB6 | 20 |
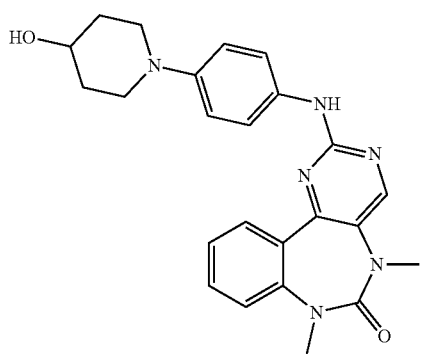
XMD16-117

TABLE 7-continued

| | |
|---|---|
| EPHA1 | 81 |
| EPHA2 | 93 |
| EPHA3 | 77 |
| EPHA4 | 89 |
| EPHA5 | 90 |
| EPHA6 | 100 |
| EPHA7 | 100 |
| EPHA8 | 100 |
| EPHB1 | 84 |
| EPHB2 | 100 |
| EPHB3 | 93 |
| EPHB4 | 99 |
| EPHB6 | 78 |

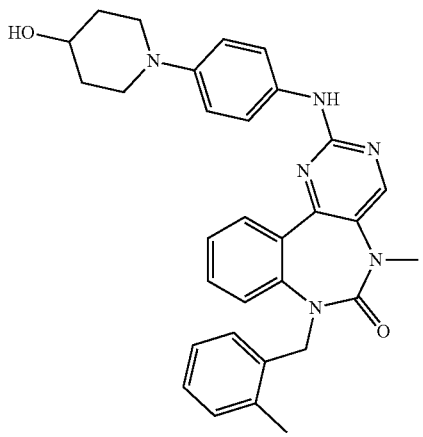

XMD16-124

INCORPORATION BY REFERENCE

The contents of all references (including literature references, issued patents, published patent applications, and co-pending patent applications) cited throughout this application are hereby expressly incorporated herein in their entireties by reference. Unless otherwise defined, all technical and scientific terms used herein are accorded the meaning commonly known to one with ordinary skill in the art.

EQUIVALENTS

Those skilled in the art will recognize, or be able to ascertain using no more than routine experimentation, many equivalents of the specific embodiments of the invention described herein. Such equivalents are intended with be encompassed by the following claims.

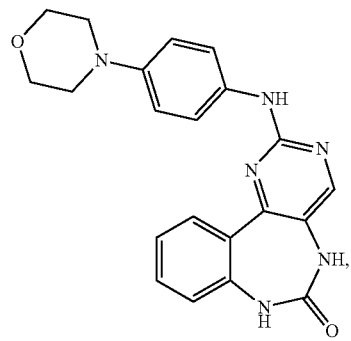

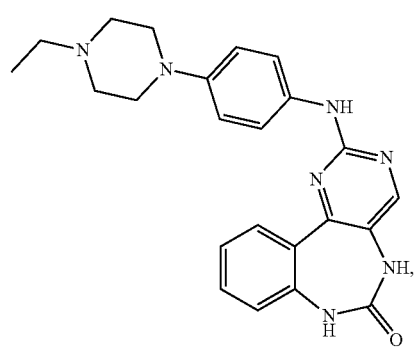

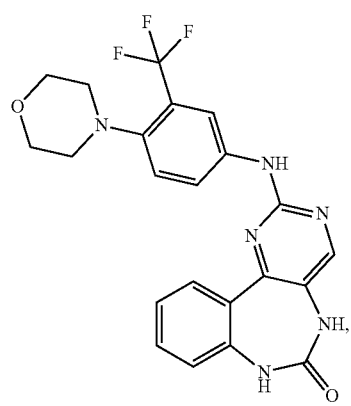

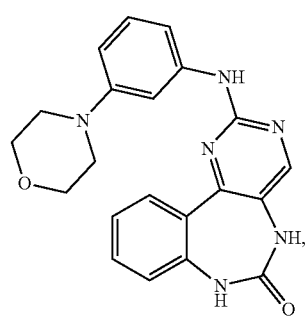

193
-continued
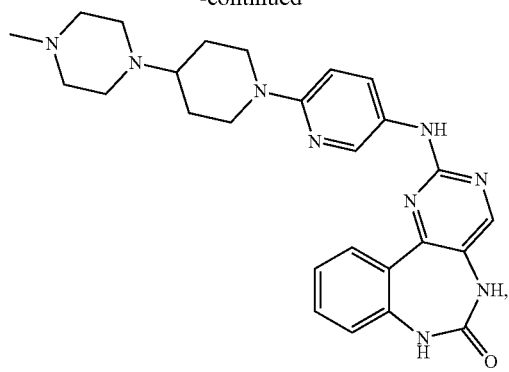
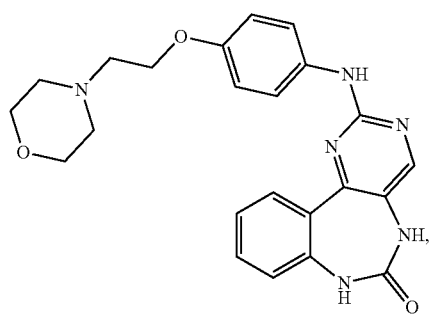
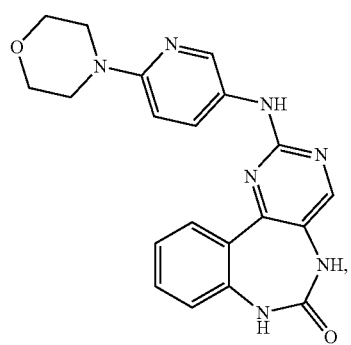
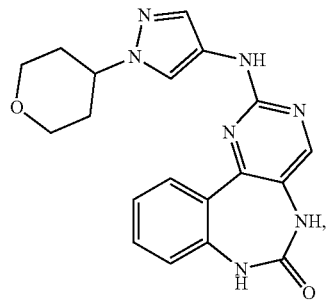
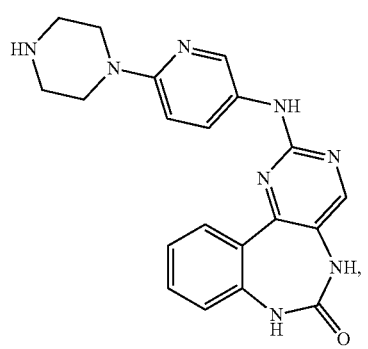
194
-continued
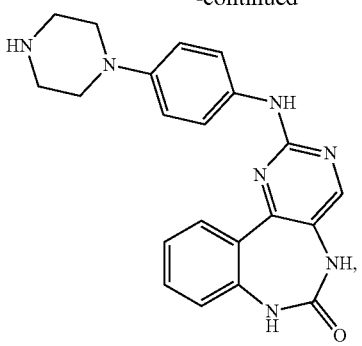
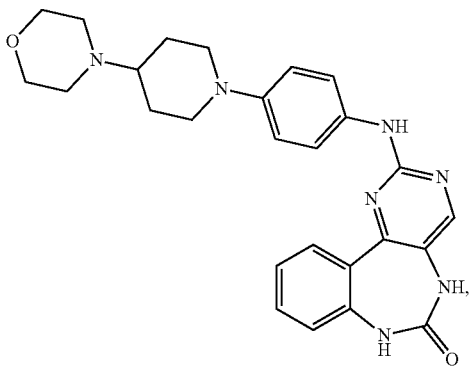
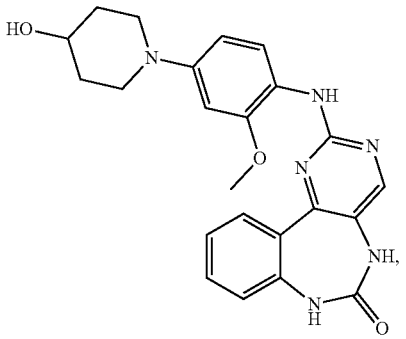
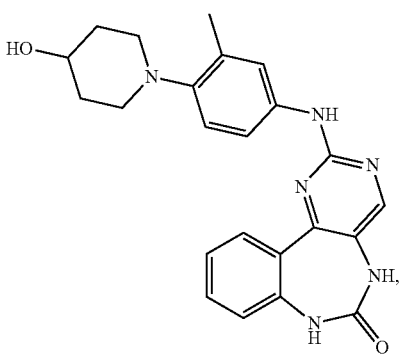

195
-continued
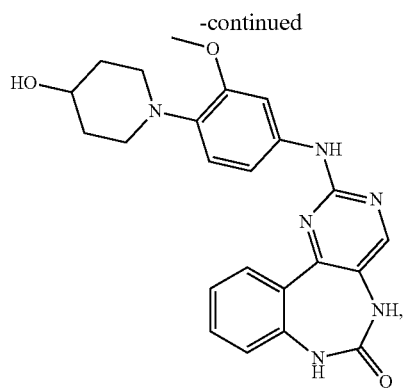
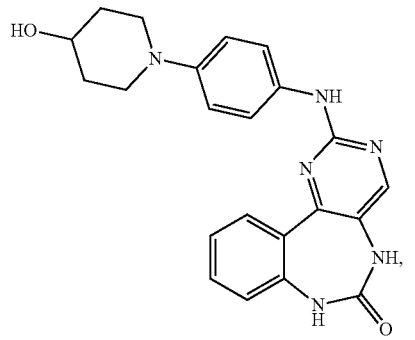
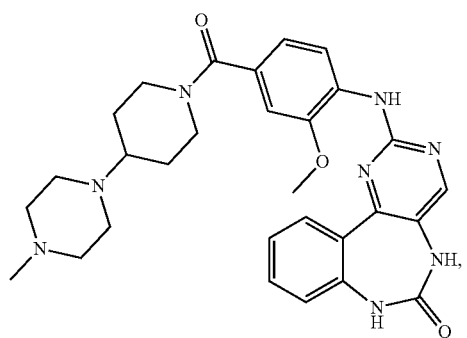
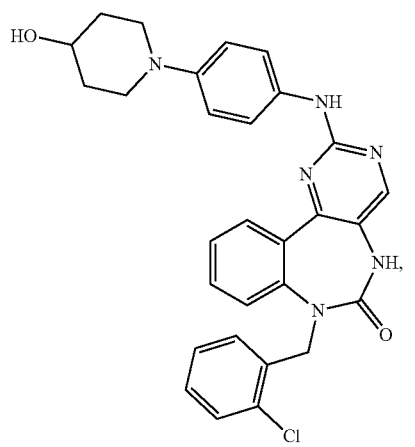
196
-continued
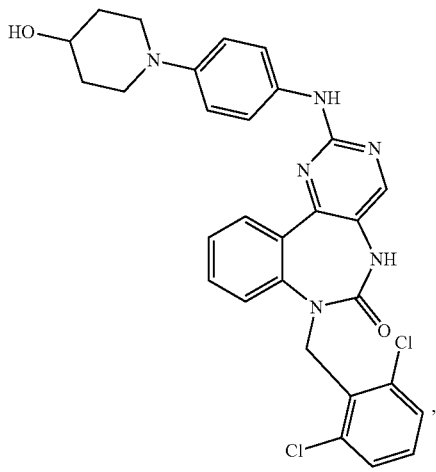
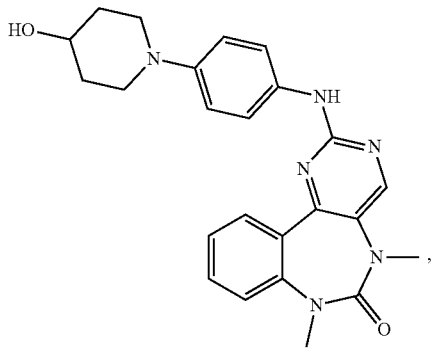
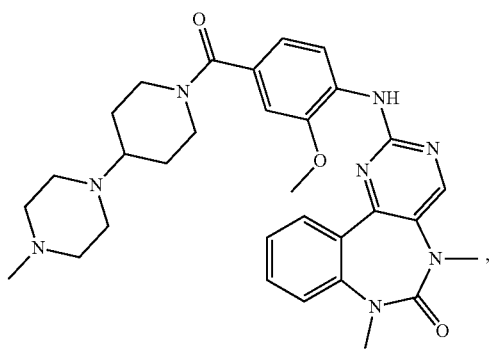
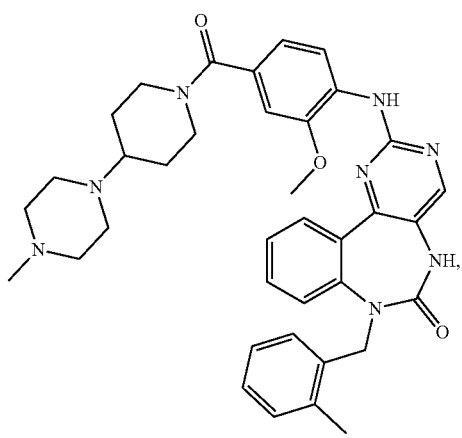

197
-continued
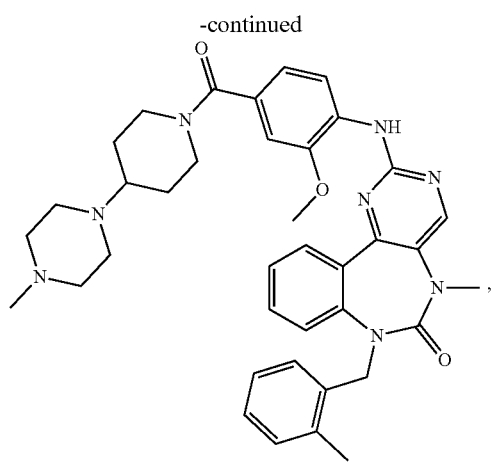
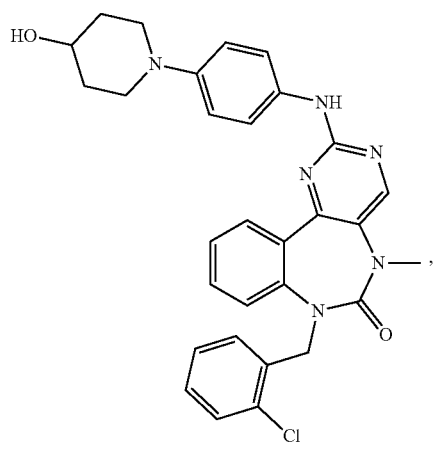
198
-continued
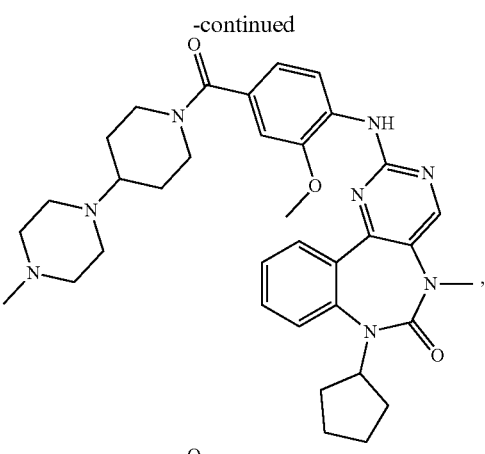
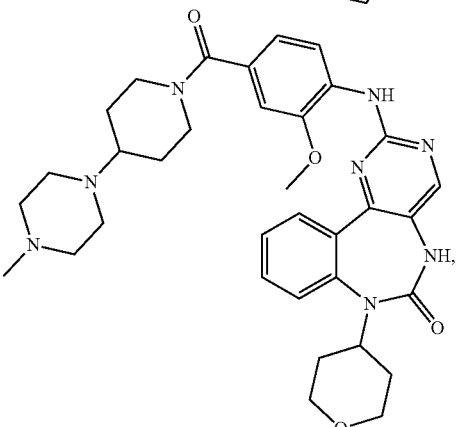
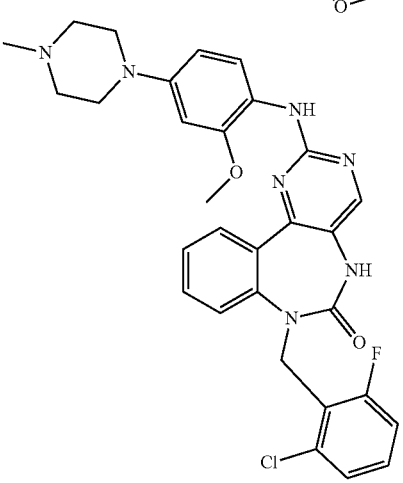
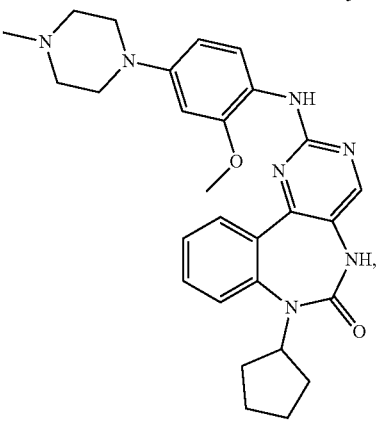

199
-continued
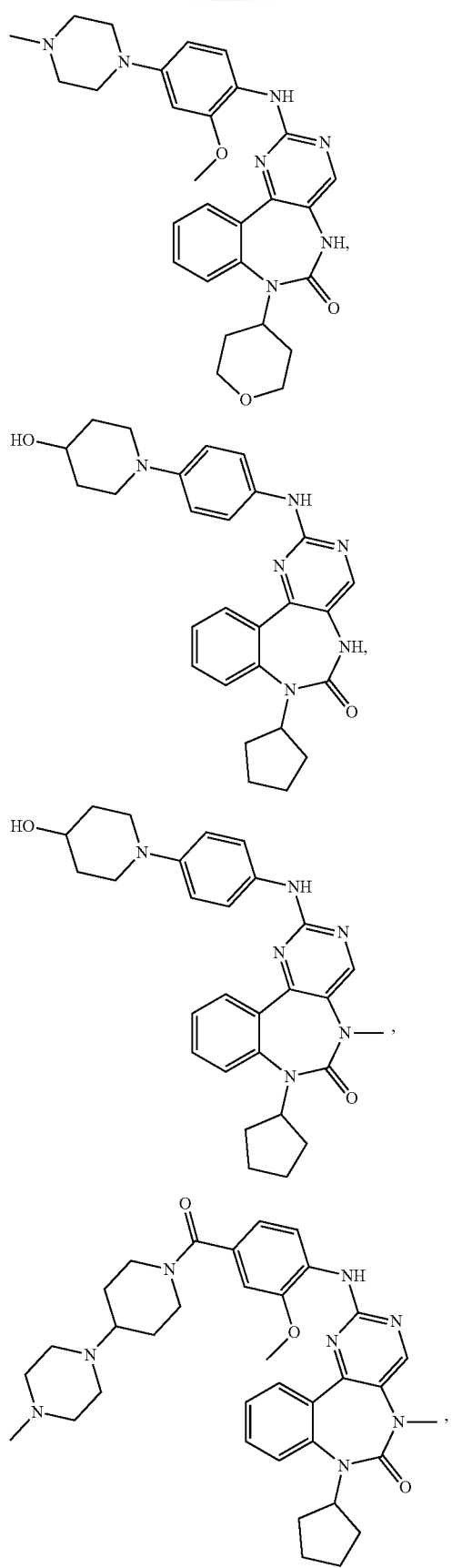
200
-continued
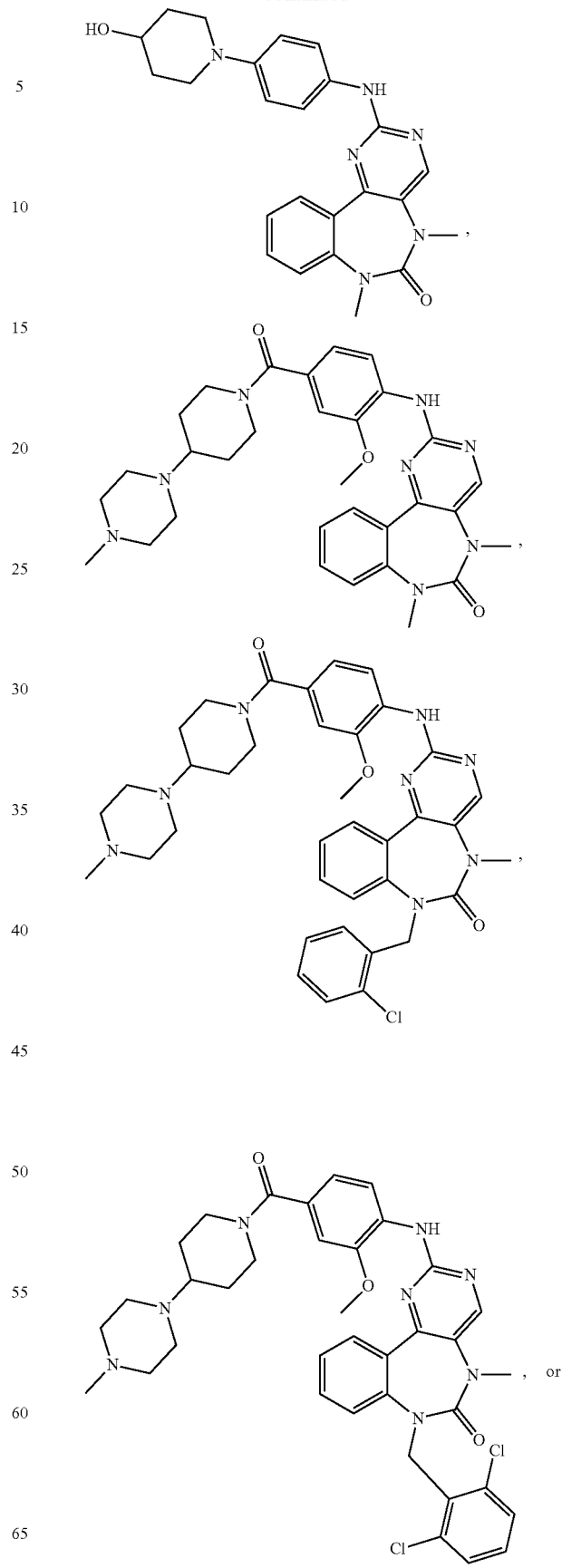

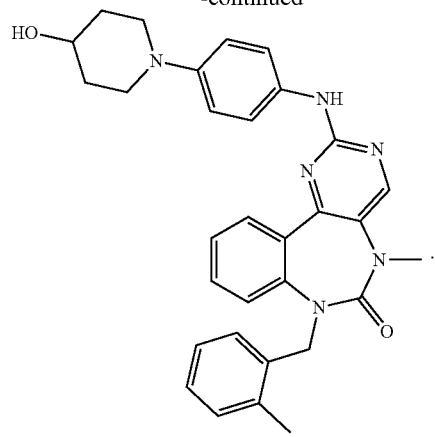

What is claimed:
1. A compound of formula II:

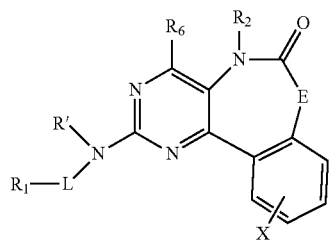

or a pharmaceutically acceptable salt thereof,
wherein,
R' is H or alkyl;
L is absent, S, SO, $SO_2$, or CO;
X is an optional substituent;
E is $NR_2$ or $CHR_2$;
$R_1$ is H, alkyl, alkenyl, alkynyl, each containing 0, 1, 2, or 3 heteroatoms selected from O, S, or N; or $R_1$ is aryl, arylalkyl, heteroaryl, heterocyclic, or carbocyclic; wherein $R_1$ may be optionally substituted;

$R_2$ is, independently for each occurrence, hydrogen, optionally substituted alkyl, optionally substituted cycloalkyl, and optionally substituted heterocyclyl; and
$R_6$ is hydrogen or optionally substituted alkyl,
wherein optional substituents are selected from the group consisting of:
—F, —Cl, —Br, —I,
—OH, protected hydroxy,
—$NO_2$, —CN,
—$NH_2$, protected amino, —NH—$C_1$-$C_{12}$-alkyl, —NH—$C_2$-$C_{12}$-alkenyl, —NH—$C_2$-$C_{12}$-alkenyl, —NH—$C_3$-$C_{12}$-cycloalkyl, —NH-aryl, —NH-heteroaryl, —NH-heterocycloalkyl, -dialkylamino, -diarylamino, -diheteroarylamino,
—O—$C_1$-$C_{12}$-alkyl, —O—$C_2$-$C_{12}$-alkenyl, —O—$C_2$-$C_{12}$-alkenyl, —O—$C_3$-$C_{12}$-cycloalkyl, —O-aryl, —O-heteroaryl, —O-heterocycloalkyl,
—C(O)— $C_1$-$C_{12}$-alkyl, —C(O)— $C_2$-$C_{12}$-alkenyl, —C(O)— $C_2$-$C_{12}$-alkenyl, —C(O)—$C_3$-$C_{12}$-cycloalkyl, —C(O)-aryl, —C(O)-heteroaryl, —C(O)-heterocycloalkyl,
—$CONH_2$, —CONH— $C_1$-$C_{12}$-alkyl, —CONH— $C_2$-$C_{12}$-alkenyl, —CONH— $C_2$-$C_{12}$-alkenyl, —CONH—$C_3$-$C_{12}$-cycloalkyl, —CONH-aryl, —CONH-heteroaryl, —CONH-heterocycloalkyl, —$OCO_2$— $C_1$-$C_{12}$-alkyl, —$OCO_2$—$C_2$-$C_{12}$-alkenyl, —$OCO_2$— $C_2$-$C_{12}$-alkenyl, —$OCO_2$—$C_3$-$C_{12}$-cycloalkyl, —$OCO_2$-aryl, —$OCO_2$-heteroaryl, —$OCO_2$-heterocycloalkyl, —$OCONH_2$, —OCONH— $C_1$-$C_{12}$-alkyl, —OCONH— $C_2$-$C_{12}$-alkenyl, —OCONH—$C_2$-$C_{12}$-alkenyl, —OCONH—$C_3$-$C_{12}$-cycloalkyl, —OCONH-aryl, —OCONH— heteroaryl, —OCONH— heterocycloalkyl, —NHC(O)— $C_1$-$C_{12}$-alkyl, —NHC(O)— $C_2$-$C_{12}$-alkenyl, —NHC(O)—$C_2$-$C_{12}$-alkenyl, —NHC(O)—$C_3$-$C_{12}$-cycloalkyl, —NHC(O)-aryl, —NHC(O)-heteroaryl, —NHC(O)-heterocycloalkyl, —$NHCO_2$— $C_1$-$C_{12}$-alkyl, —$NHCO_2$— $C_2$-$C_{12}$-alkenyl, —$NHCO_2$— $C_2$-$C_{12}$-alkenyl, —$NHCO_2$— $C_3$-$C_{12}$-cycloalkyl, —$NHCO_2$-aryl, —$NHCO_2$-heteroaryl, —$NHCO_2$-heterocycloalkyl, —NHC(O)$NH_2$, —NHC(O)NH— $C_1$-$C_{12}$-alkyl, —NHC(O)NH— $C_2$-$C_{12}$-alkenyl, —NHC(O)NH—$C_2$-$C_{12}$-alkenyl, —NHC(O)NH—$C_3$-$C_{12}$-cycloalkyl, —NHC(O)NH-aryl, —NHC(O)NH-heteroaryl, —NHC(O)NH-heterocycloalkyl, NHC(S)$NH_2$, —NHC(S)NH— $C_1$-$C_{12}$-alkyl, —NHC(S)NH— $C_2$-$C_{12}$-alkenyl, —NHC(S)NH—$C_2$-$C_{12}$-alkenyl, —NHC(S)NH—$C_3$-$C_{12}$-cycloalkyl, —NHC(S)NH-aryl, —NHC(S)NH-heteroaryl, —NHC(S)NH-heterocycloalkyl, —NHC(NH)$NH_2$, —NHC(NH)NH— $C_1$-$C_{12}$-alkyl, —NHC(NH)

NH—C₂-C₁₂-alkenyl, —NHC(NH)NH—C₂-C₁₂-alkenyl, —NHC(NH)NH—C₃-C₁₂-cycloalkyl, —NHC(NH)NH-aryl, —NHC(NH)NH-heteroaryl, —NHC(NH)NH-heterocycloalkyl, —NHC(NH)—C₁-C₁₂-alkyl, —NHC(NH)—C₂-C₁₂-alkenyl, —NHC(NH)—C₂-C₁₂-alkenyl, —NHC(NH)—C₃-C₁₂-cycloalkyl, —NHC(NH)-aryl, —NHC(NH)-heteroaryl, —NHC(NH)-heterocycloalkyl, —C(NH)NH—C₁-C₁₂-alkyl, —C(NH)NH—C₂-C₁₂-alkenyl, —C(NH)NH—C₂-C₁₂-alkenyl, —C(NH)NH—C₃-C₁₂-cycloalkyl, —C(NH)NH-aryl, —C(NH)NH-heteroaryl, —C(NH)NH-heterocycloalkyl, —S(O)—C₁-C₁₂-alkyl,—S(O)—C₂-C₁₂-alkenyl,—S(O)—C₂-C₁₂-alkenyl,—S(O)—C₃-C₁₂-cycloalkyl,—S(O)-aryl,—S(O)-heteroaryl,—S(O)-heterocycloalkyl-SO₂NH₂, —SO₂NH—C₁-C₁₂-alkyl, —SO₂NH—C₂-C₁₂-alkenyl, —SO₂NH—C₂-C₁₂-alkenyl, —SO₂NH—C₃-C₁₂-cycloalkyl, —SO₂NH—aryl, —SO₂NH—heteroaryl, —SO₂NH—heterocycloalkyl, —NHSO₂—C₁-C₁₂-alkyl, —NHSO₂—C₂-C₁₂-alkenyl,—NHSO₂—C₂-C₁₂-alkenyl, —NHSO₂—C₃-C₁₂-cycloalkyl, —NHSO₂-aryl, —NHSO₂-heteroaryl, —NHSO₂-heterocycloalkyl, —CH₂NH₂, —CH₂SO₂CH₃, -aryl, -arylalkyl, -heteroaryl, -heteroarylalkyl, -heterocycloalkyl, —C₃-C₁₂-cycloalkyl, polyalkoxyalkyl, polyalkoxy, -methoxymethoxy, -methoxyethoxy, —SH, —S—C₁-C₁₂-alkyl, —S—C₂-C₁₂-alkenyl, —S—C₂-C₁₂-alkenyl, —S—C₃-C₁₂-cycloalkyl, —S-aryl, —S-heteroaryl, —S-heterocycloalkyl, and methylthiomethyl.

2. The compound of claim 1, wherein R₁ is phenyl or pyridyl, each of which may be optionally substituted.

3. The compound of claim 1, wherein R₁ is substituted with 0-4 substituents, selected from N(R_A)(R_A), C(O)NH(R_A), alkoxy, and heterocyclic, each of which may be further substituted; wherein each R_A is independently selected from alkyl, and heterocyclic.

4. The compound of claim 3, wherein R₁ is substituted with 0-4 substituents, selected from alkoxy,

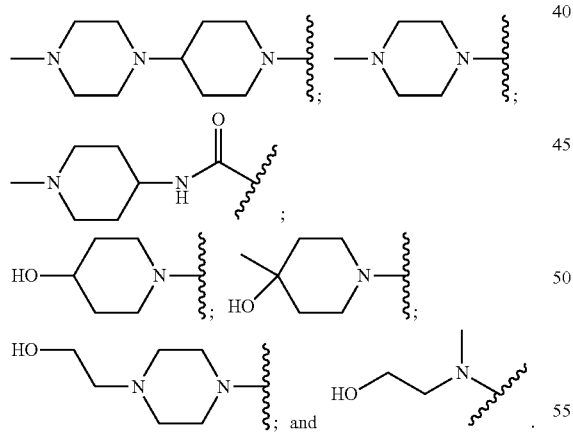

5. The compound of claim 1, wherein R₂ is H, methyl, or ethyl.
6. The compound of claim 1, wherein R₆ is H.
7. The compound of claim 1, wherein x is H.
8. The compound of claim 1, wherein R' is H.
9. The compound of claim 1, wherein L is absent.
10. The compound of claim 1, wherein E is NR₂.
11. A pharmaceutical composition comprising a compound of claim 1, or a pharmaceutically acceptable salt thereof, together with a pharmaceutically acceptable carrier.

12. The compound of claim 1, which is: